(12) United States Patent
Culbert et al.

(10) Patent No.: US 10,716,880 B2
(45) Date of Patent: Jul. 21, 2020

(54) SYSTEMS AND METHODS FOR ASPIRATION AND MONITORING

(71) Applicant: INCUVATE, LLC, Irvine, CA (US)

(72) Inventors: Bradley S. Culbert, Mission Viejo, CA (US); David M. Look, Newport Beach, CA (US); Gary Carlson, Aliso Viejo, CA (US)

(73) Assignee: Incuvate, LLC, Irvine, CA (US)

( * ) Notice: Subject to any disclaimer, the term of this patent is extended or adjusted under 35 U.S.C. 154(b) by 0 days.

(21) Appl. No.: 16/440,955

(22) Filed: Jun. 13, 2019

(65) Prior Publication Data

US 2019/0381223 A1    Dec. 19, 2019

Related U.S. Application Data

(60) Provisional application No. 62/685,659, filed on Jun. 15, 2018, provisional application No. 62/733,618, (Continued)

(51) Int. Cl.
*A61M 1/00* (2006.01)
*A61B 17/3203* (2006.01)
(Continued)

(52) U.S. Cl.
CPC ..... *A61M 1/0025* (2014.02); *A61B 17/32037* (2013.01); *A61M 1/0056* (2013.01); (Continued)

(58) Field of Classification Search
CPC .............. A61M 1/0025; A61M 1/0058; A61M 1/0064; A61M 1/0084; A61M 25/007; (Continued)

(56) References Cited

U.S. PATENT DOCUMENTS

| 4,690,672 A | 9/1987 | Veltrup |
| 4,702,733 A | 10/1987 | Wright et al. |

(Continued)

FOREIGN PATENT DOCUMENTS

| DE | 3387858 C2 | 9/1986 |
| EP | 0529902 A2 | 3/1993 |

(Continued)

OTHER PUBLICATIONS

PCT International Search Report and Written Opinion for PCT/US2019/037259, Applicant: Incuvate, LLC, Forms PCT/ISA/220, 210, and 237 dated Sep. 5, 2019 (9 pages).

*Primary Examiner* — Brandy S Lee
*Assistant Examiner* — Nidah M Hussain
(74) *Attorney, Agent, or Firm* — Blair Walker IP Services, LLC

(57) ABSTRACT

A system for aspiration includes an aspiration catheter including an elongate shaft including an aspiration lumen, and an open distal end, an extension tube, the lumen of the extension tube configured to be hydraulically coupled to the aspiration lumen, a peristaltic pump configured for driving fluid through the extension tube, a compressible portion disposed between the distal end and the proximal end of the extension tube, the compressible portion configured to be coupled to the peristaltic pump, such that operation of the peristaltic pump drives fluid from the aspiration lumen from the distal end of the extension tube to the proximal end of the extension tube, and a controller configured to receive a first signal from the first sensor and configured to vary the operation of the peristaltic pump based at least in part on a first signal received from a first sensor coupled to the aspiration lumen or extension tube related to a change in the characteristic of flow.

30 Claims, 47 Drawing Sheets

Related U.S. Application Data filed on Sep. 19, 2018, provisional application No. 62/744,576, filed on Oct. 11, 2018, provisional application No. 62/749,647, filed on Oct. 23, 2018, provisional application No. 62/755,475, filed on Nov. 3, 2018, provisional application No. 62/769,527, filed on Nov. 19, 2018.

(51) Int. Cl.
 *A61M 25/00* (2006.01)
 *A61B 17/22* (2006.01)

(52) U.S. Cl.
 CPC ........ *A61M 1/0062* (2013.01); *A61M 1/0084* (2013.01); *A61M 25/007* (2013.01); *A61B 2017/22079* (2013.01); *A61M 2205/3317* (2013.01); *A61M 2205/3331* (2013.01); *A61M 2205/3375* (2013.01)

(58) Field of Classification Search
 CPC ............ A61M 25/0026; A61M 1/0023; A61M 25/0068; A61M 5/1723; A61M 2027/004; A61B 1/126; A61B 17/32037
 USPC .......................................................... 604/67
 See application file for complete search history.

(56) References Cited

U.S. PATENT DOCUMENTS

| | | | |
|---|---|---|---|
| 4,770,654 A | 9/1988 | Rogers et al. | |
| 4,886,507 A | 12/1989 | Patton et al. | |
| 4,998,914 A | 3/1991 | Wiest et al. | |
| 5,091,656 A * | 2/1992 | Gahn | A61C 1/0023 200/86.5 |
| 5,129,887 A | 7/1992 | Euteneuer et al. | |
| 5,242,404 A | 9/1993 | Conley et al. | |
| 5,254,085 A | 10/1993 | Cleveland, Jr. | |
| RE34,566 E | 3/1994 | Sjostrom et al. | |
| 5,403,276 A | 4/1995 | Schechter et al. | |
| 5,429,601 A | 7/1995 | Conley et al. | |
| 5,478,331 A | 12/1995 | Heflin et al. | |
| 5,496,267 A | 3/1996 | Drasler et al. | |
| 5,520,638 A | 5/1996 | O'Quinn et al. | |
| 5,556,378 A | 9/1996 | Storz et al. | |
| 5,605,545 A | 2/1997 | Nowosielski et al. | |
| 5,626,563 A | 5/1997 | Dodge et al. | |
| 5,810,770 A | 9/1998 | Chin et al. | |
| 6,059,745 A | 5/2000 | Gelbfish | |
| 6,350,253 B1 * | 2/2002 | Deniega | A61M 25/0074 604/164.02 |
| 6,375,635 B1 | 4/2002 | Moutafis et al. | |
| 6,558,366 B1 | 5/2003 | Drasler et al. | |
| 6,615,835 B1 | 9/2003 | Cise et al. | |
| 6,926,726 B2 | 8/2005 | Drasler et al. | |
| 6,945,951 B1 | 9/2005 | Bonnette et al. | |
| 6,984,239 B1 * | 1/2006 | Drasler | A61B 17/32037 604/22 |
| 7,842,055 B2 | 11/2010 | Pintor et al. | |
| 7,935,077 B2 | 5/2011 | Thor et al. | |
| 8,353,858 B2 | 1/2013 | Kozak et al. | |
| 8,398,581 B2 | 3/2013 | Panotopoulos | |
| 8,932,321 B1 | 1/2015 | Janardhan et al. | |
| 8,998,843 B2 | 4/2015 | Bonnette et al. | |
| 9,238,122 B2 | 1/2016 | Malhi et al. | |
| 9,239,049 B2 * | 1/2016 | Jarnagin | F04B 43/1284 |
| 9,248,221 B2 | 2/2016 | Look et al. | |
| 9,254,144 B2 | 2/2016 | Nguyen et al. | |
| 9,402,938 B2 | 8/2016 | Aklog et al. | |
| 9,433,427 B2 | 9/2016 | Look et al. | |
| 9,510,854 B2 | 12/2016 | Mallaby | |
| 9,586,023 B2 | 3/2017 | Bonnette et al. | |
| 9,597,480 B2 | 3/2017 | Purdy et al. | |
| 9,662,137 B2 | 5/2017 | Jenson et al. | |
| 9,775,964 B2 | 10/2017 | Eubanks et al. | |
| 9,782,195 B2 | 10/2017 | Mactaggart et al. | |
| 9,833,257 B2 | 12/2017 | Bonnette et al. | |
| 9,883,877 B2 | 2/2018 | Look et al. | |
| 9,925,315 B2 | 3/2018 | Eubanks et al. | |
| 10,064,643 B2 | 9/2018 | Malhi et al. | |
| 10,226,263 B2 | 3/2019 | Look et al. | |
| 2003/0236488 A1 | 12/2003 | Novak | |
| 2004/0030281 A1 | 2/2004 | Goble et al. | |
| 2004/0082915 A1 | 4/2004 | Kadan | |
| 2004/0133149 A1 | 7/2004 | Haischmann et al. | |
| 2006/0064051 A1 | 3/2006 | Gross | |
| 2007/0225739 A1 | 9/2007 | Pintor et al. | |
| 2008/0108960 A1 | 5/2008 | Shapland et al. | |
| 2008/0243054 A1 * | 10/2008 | Mollstam | A61M 3/0216 604/31 |
| 2008/0294008 A1 * | 11/2008 | Toyama | A61B 1/015 600/139 |
| 2010/0069937 A1 * | 3/2010 | Seto | A61B 7/32037 606/167 |
| 2010/0191178 A1 | 7/2010 | Ross et al. | |
| 2011/0106004 A1 * | 5/2011 | Eubanks | A61M 5/14232 604/35 |
| 2012/0277665 A1 | 11/2012 | Tachoire et al. | |
| 2015/0025446 A1 | 1/2015 | Jacobson et al. | |
| 2017/0056032 A1 | 3/2017 | Look et al. | |
| 2017/0079672 A1 | 3/2017 | Quick | |
| 2017/0100142 A1 | 4/2017 | Look et al. | |
| 2017/0172603 A1 | 6/2017 | Bonnette et al. | |
| 2017/0265885 A1 | 9/2017 | Bonnette et al. | |
| 2017/0281204 A1 | 10/2017 | Garrison et al. | |
| 2017/0290598 A1 | 10/2017 | Culbert et al. | |
| 2018/0042623 A1 * | 2/2018 | Batiste | A61B 17/22 |
| 2018/0078119 A1 * | 3/2018 | Krimsky | A61B 1/00085 |
| 2018/0207397 A1 | 7/2018 | Look et al. | |
| 2018/0214172 A1 | 8/2018 | Donnelly et al. | |
| 2018/0235648 A1 | 8/2018 | Wilke et al. | |

FOREIGN PATENT DOCUMENTS

| | | |
|---|---|---|
| EP | 2859902 A1 | 4/2015 |
| GB | 2260622 A | 4/1993 |
| WO | WO8600534 A1 | 1/1986 |
| WO | WO0219928 A2 | 3/2002 |
| WO | WO2008042987 A2 | 4/2008 |
| WO | WO2008121481 A1 | 10/2008 |
| WO | WO2010117919 A1 | 10/2010 |
| WO | WO2013188297 A1 | 12/2013 |

* cited by examiner

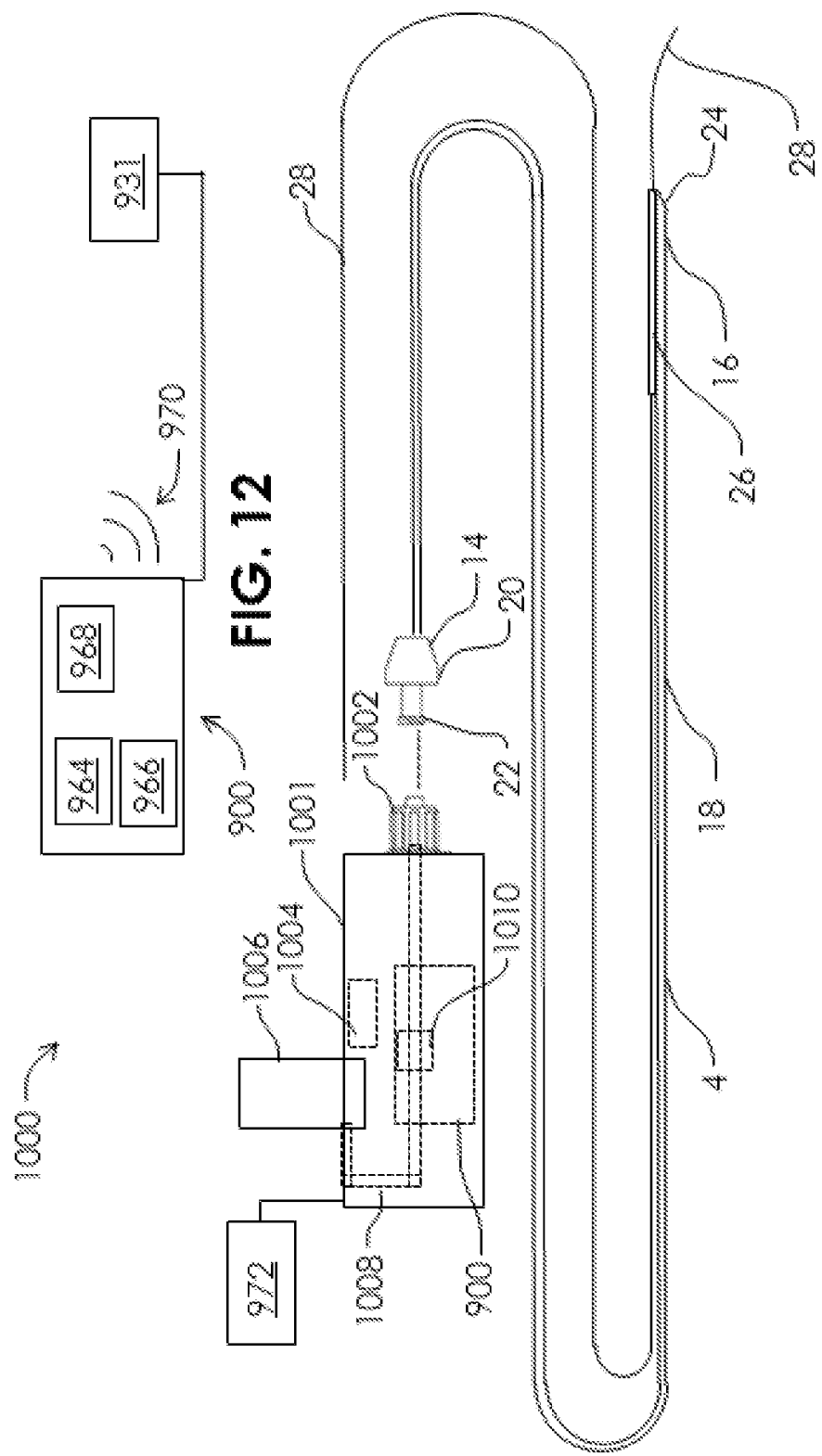

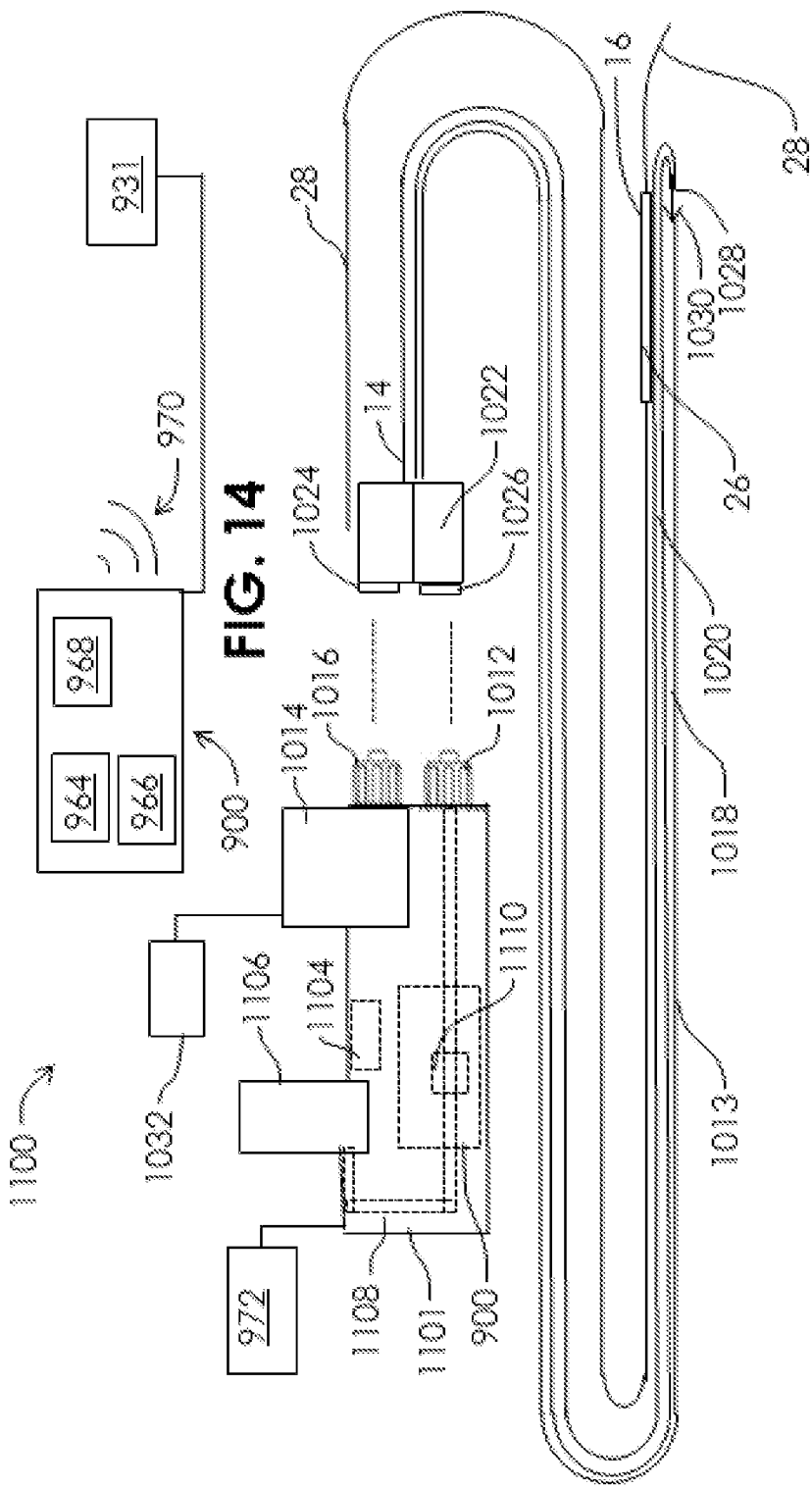

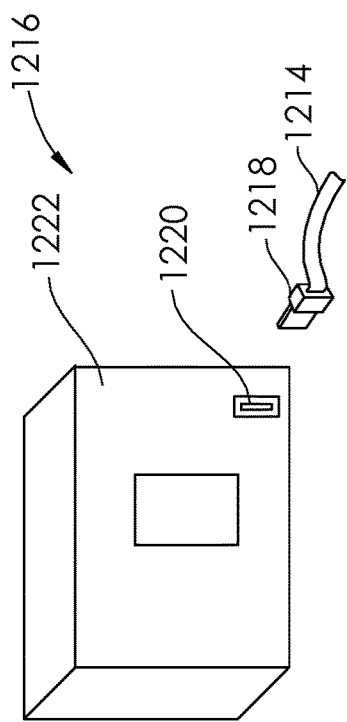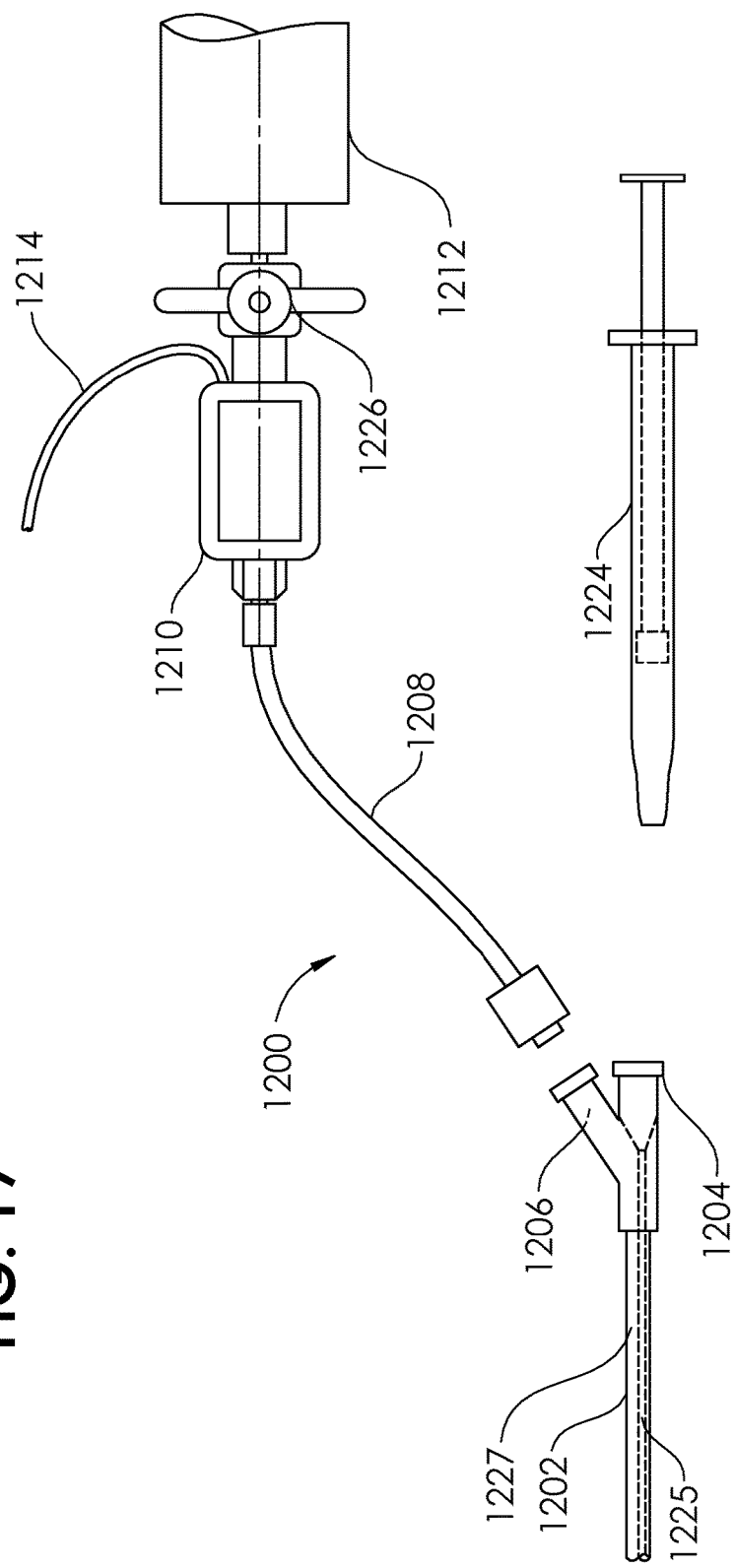

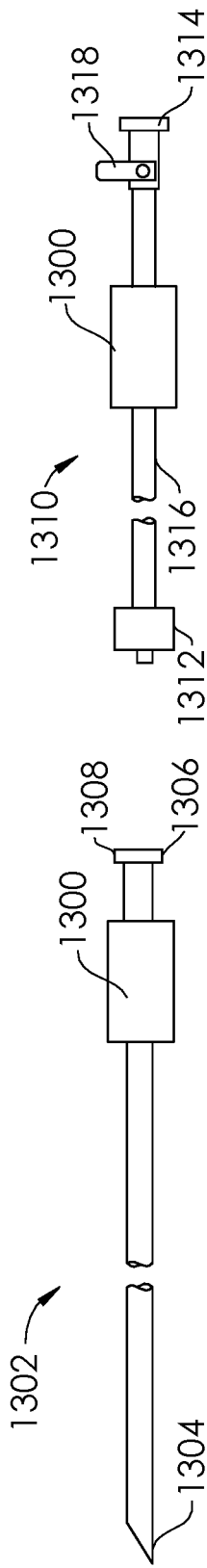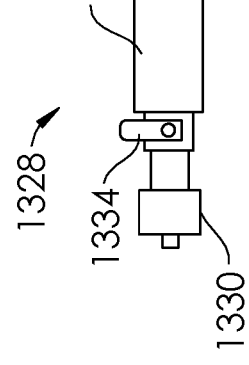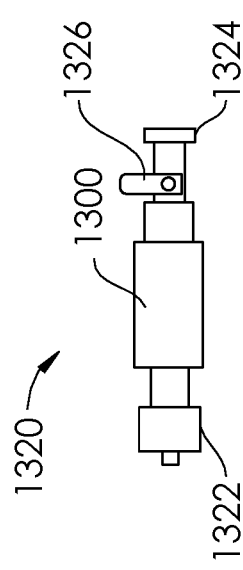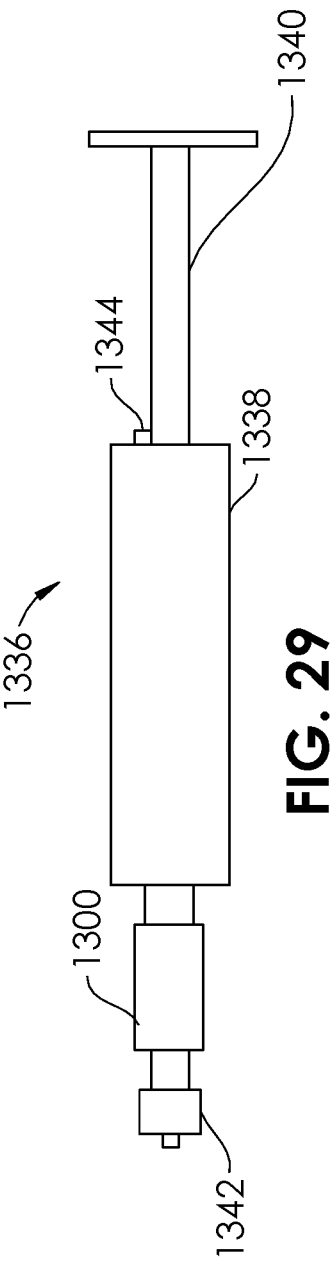
FIG. 25
FIG. 26
FIG. 27
FIG. 28
FIG. 29

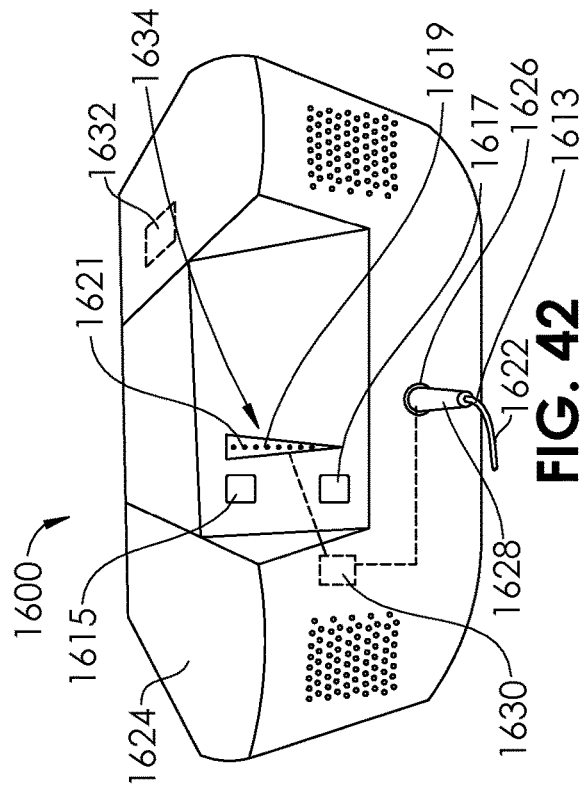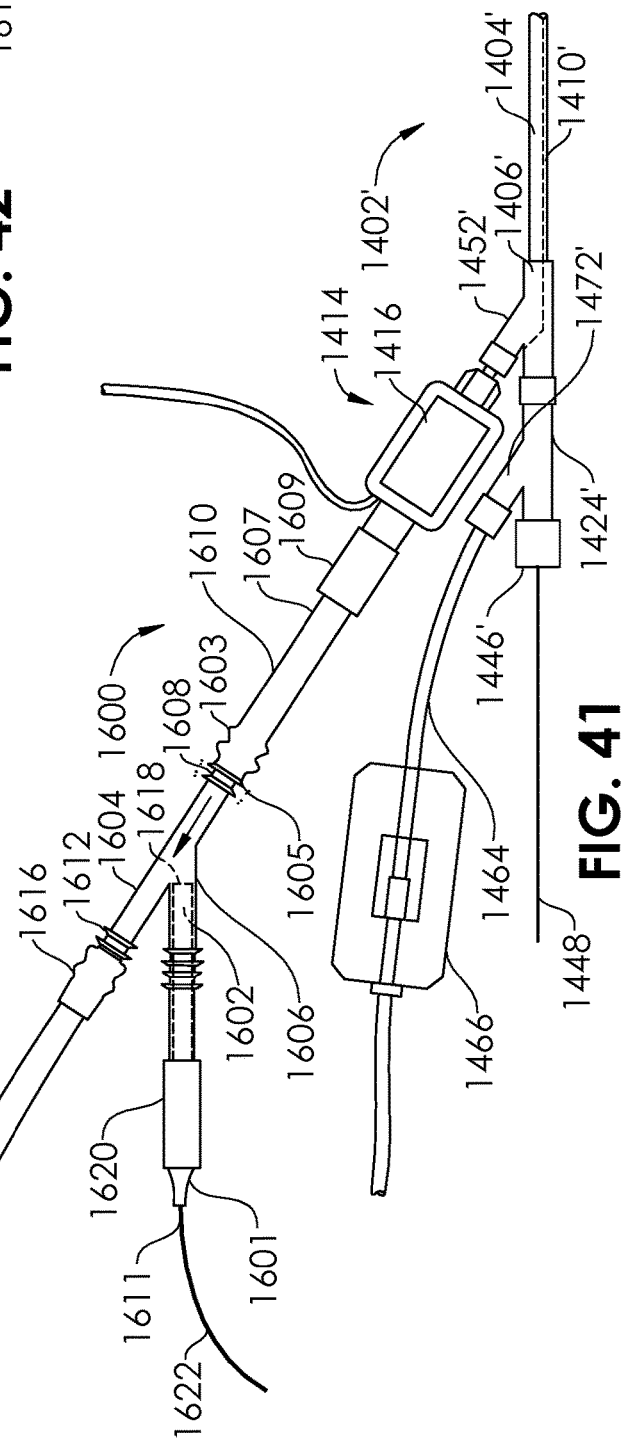

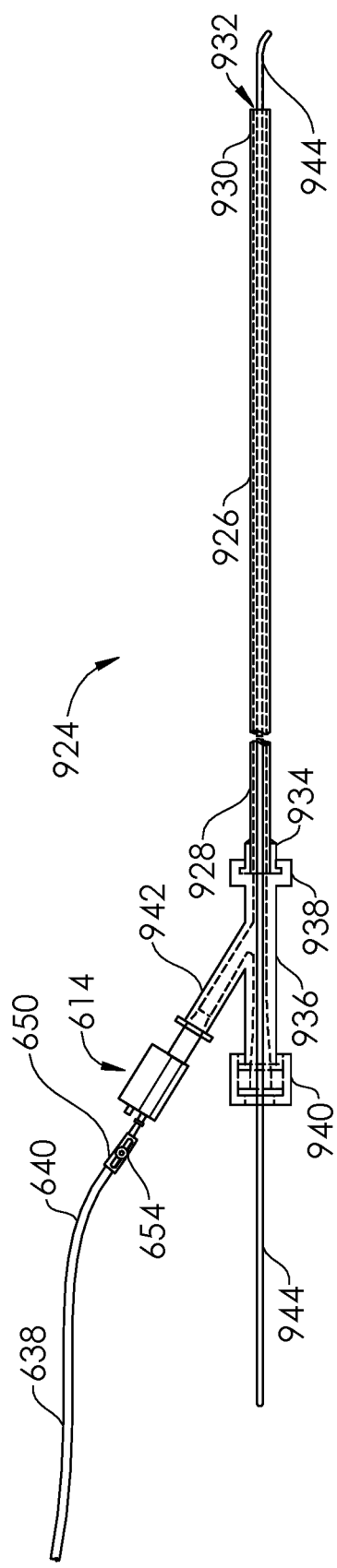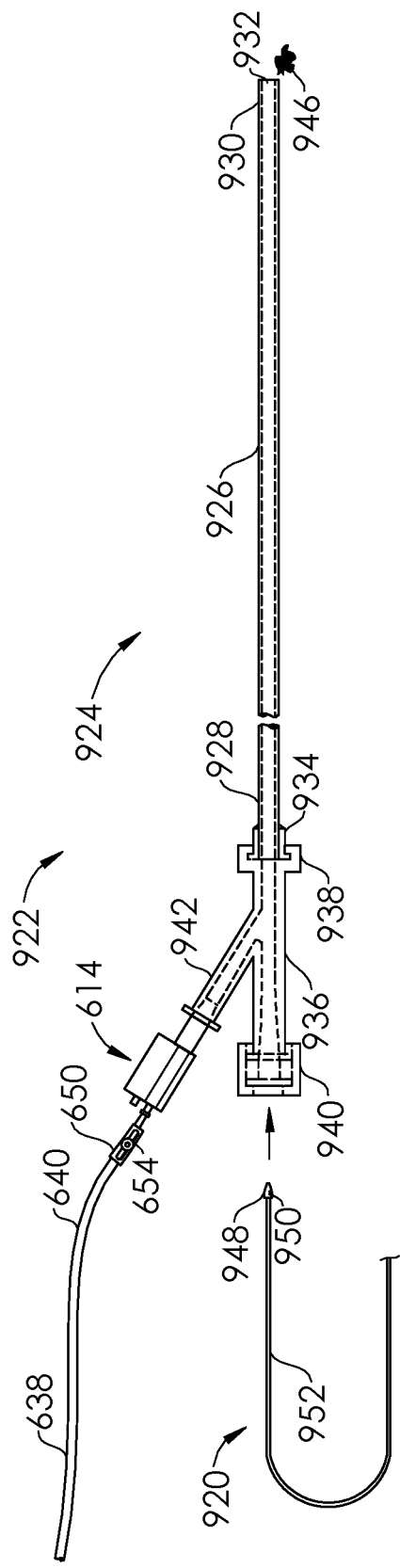

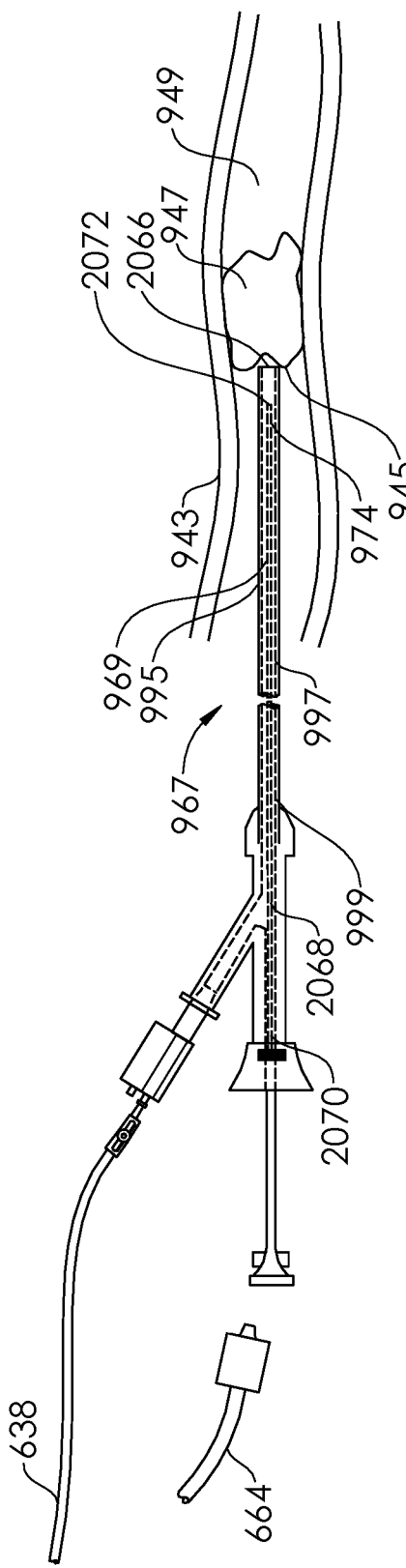
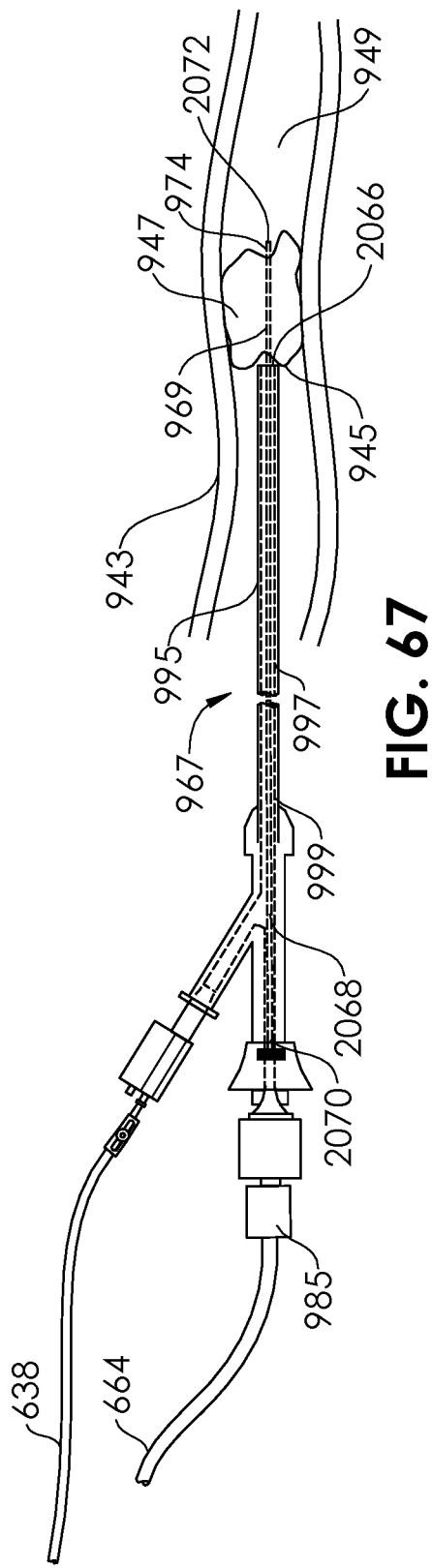

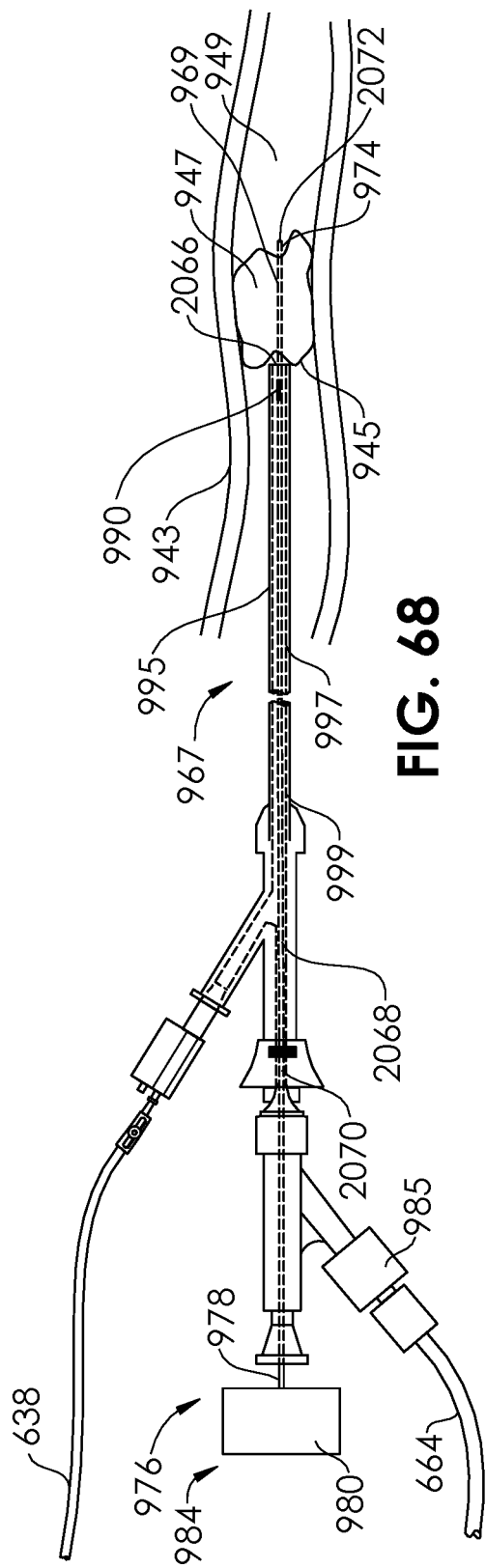
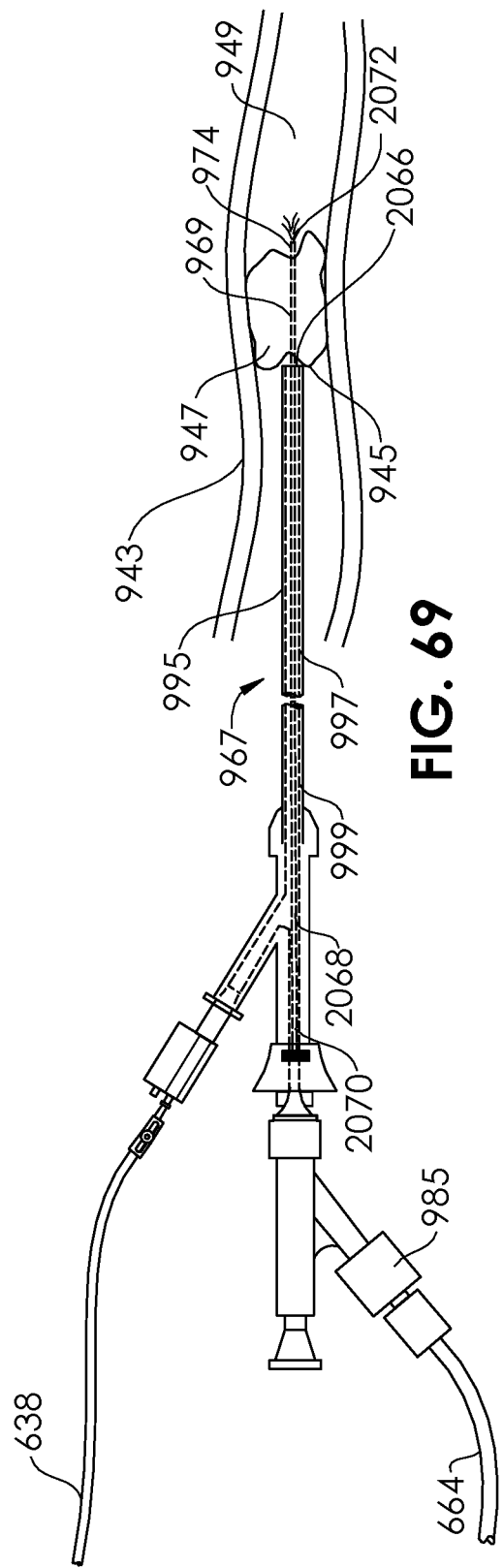

SYSTEMS AND METHODS FOR ASPIRATION AND MONITORING

INCORPORATION BY REFERENCE TO ANY PRIORITY APPLICATIONS

This application claims the benefit of priority to U.S. Provisional Patent Application No. 62/685,659, filed on Jun. 15, 2018, U.S. Provisional Patent Application No. 62/733,618, filed on Sep. 19, 2018, U.S. Provisional Patent Application No. 62/744,576, filed on Oct. 11, 2018, U.S. Provisional Patent Application No. 62/749,647, filed on Oct. 23, 2018, U.S. Provisional Patent Application No. 62/755,475, filed on Nov. 3, 2018, and U.S. Provisional Patent Application No. 62/769,527, filed on Nov. 19, 2018, all of which are herein incorporated by reference in their entirety for all purposes. Priority is claimed pursuant to 35 U.S.C. § 119.

BACKGROUND OF THE INVENTION

Field of the Invention

The field of the invention generally relates to an aspiration system for removing, by aspiration, undesired matter such as a thrombus from a fluid carrying cavity, duct, sinus, or lumen of the body, such as a blood vessel, including a vessel in the brain, or in any space in the body, whether intended to carry fluid or not.

Description of the Related Art

A treatment method for removing undesired matter such as thrombus from a blood vessel of a patient involves use of an aspiration catheter having elongate shaft formed with an aspiration lumen extending therein. An aspiration catheter may also include a guidewire lumen for placement of a guidewire, which is used to guide the aspiration catheter to a target site in the body. By applying a vacuum or negative pressure to a proximal end of the aspiration lumen, for example, with a syringe having a hub that is connected to the proximal end of the aspiration catheter, the matter can be aspirated into an aspiration port at the distal end of the aspiration catheter, into the aspiration lumen, and thus be removed from the patient.

SUMMARY OF THE INVENTION

In one embodiment of the present disclosure, a system for catheter-based aspiration includes an aspiration catheter including an elongate shaft configured for placement within a blood vessel of a subject, the shaft including an aspiration lumen having a proximal end and an open distal end, an extension tube having a distal end and a proximal end and a lumen extending therebetween, the lumen of the extension tube configured to be hydraulically coupled to the aspiration lumen of the aspiration catheter, a peristaltic pump configured for driving fluid through the extension tube and including a pump base having a pressure shoe, and a rotatable head, the rotatable head including two or more compression elements arrayed therearound, a compressible tubular portion disposed between the distal end and the proximal end of the extension tube, the compressible tubular portion configured to be coupled to the pressure shoe and the rotatable head of the peristaltic pump, such that operation of the peristaltic pump causes the rotatable head to rotate such that the two or more compression elements drive fluid from the aspiration lumen of the aspiration catheter through the extension tube from the distal end of the extension tube to the proximal end of the extension tube, a first sensor configured to measure a characteristic of flow through at least one of the aspiration lumen or the lumen of the extension tube, and a controller configured to receive a first signal from the first sensor and configured to vary the operation of the peristaltic pump based at least in part on the first signal received from the first sensor related to a change in the characteristic of flow. A "characteristic of flow" may include a pressure, a flow rate, a flow velocity, or a variation or disturbance in any of these. A "characteristic of flow" may even be a laminar or turbulent condition, or a change between them.

In another embodiment of the present disclosure a method for performing a thrombectomy procedure includes providing an aspiration catheter including an elongate shaft configured for placement within a blood vessel of a subject, the shaft having an aspiration lumen and an injection lumen, the aspiration lumen having an open distal end and a proximal end, the injection lumen extending within the aspiration lumen and having a distal end and a proximal end, the distal end of the injection lumen located within the aspiration lumen near the open distal end of the aspiration lumen, the aspiration catheter further including an orifice at the distal end of the injection lumen configured to create one or more jets when pressurized fluid is injected through the injection lumen, placing at least a distal portion of the elongate shaft into a blood vessel of the subject, placing an extension tube having a distal end and a proximal end and a lumen extending therebetween, the extension tube configured to be hydraulically coupled to the aspiration lumen of the aspiration catheter, within a roller pump such that a compressible portion of the extension tube disposed between the distal end and the proximal end of the extension tube is engageable by two or more rollers of a rotatable head of the roller pump, injecting pressurized fluid through the injection lumen of the aspiration catheter from the proximal end to the distal end such that it passes through the orifice into the aspiration lumen, thereby causing some body fluid to enter into the aspiration lumen of the aspiration catheter, and operating the roller pump such that body fluid forced into the aspiration lumen of the aspiration catheter is caused to transit through the extension tube from the distal end of the extension tube to the proximal end of the extension tube.

In still another embodiment of the present disclosure, a system for catheter aspiration includes an aspiration catheter including an elongate shaft configured for placement within a blood vessel of a subject, the shaft having an aspiration lumen and an injection lumen, the aspiration lumen having an open distal end and a proximal end, the injection lumen extending within the aspiration lumen and having a distal end and a proximal end, the distal end of the injection lumen located within the aspiration lumen near the open distal end of the aspiration lumen, an orifice at the distal end of the injection lumen configured to create one or more jets when pressurized fluid is injected through the injection lumen, an extension tube having a distal end and a proximal end and a lumen extending therebetween, the distal end of the extension tube configured to be hydraulically coupled to the aspiration lumen of the aspiration catheter, the extension tube further having a compressible portion disposed between the distal end and the proximal end of the extension tube, the compressible portion configured for placement within a peristaltic pump, such that operation of the peristaltic pump causes fluid from the aspiration lumen of the aspiration catheter to transit through the extension tube from the distal end of the extension tube to the proximal end of the extension tube, and a return conduit hydraulically coupled to the extension tube and configured to return to the vasculature of the subject fluid that has passed through the extension tube from distal to proximal.

In yet another embodiment of the present disclosure, a system for catheter aspiration includes a peristaltic pump, an aspiration catheter including an elongate shaft configured for placement within a blood vessel of a subject, the shaft having an aspiration lumen and an injection lumen, the aspiration lumen having an open distal end and a proximal end, the injection lumen extending within the aspiration lumen and having a distal end and a proximal end, the distal end of the injection lumen located within the aspiration lumen near the open distal end of the aspiration lumen, an orifice at the distal end of the injection lumen configured to create one or more jets when pressurized fluid is injected through the injection lumen, an extension tube having a distal end and a proximal end and a lumen extending therebetween, the distal end of the extension tube configured to be hydraulically coupled to the aspiration lumen of the aspiration catheter, the extension tube further having a compressible portion disposed between the distal end and the proximal end of the extension tube, the compressible portion configured for placement within the peristaltic pump, such that operation of the peristaltic pump causes fluid from the aspiration lumen of the aspiration catheter to transit through the extension tube from the distal end of the extension tube to the proximal end of the extension tube, and a filter located within a conduit that includes the aspiration lumen of the aspiration catheter and the lumen of the extension tube, the filter located between the orifice and the compressible portion of the extension tube.

In still another embodiment of the present disclosure a system for catheter aspiration includes an aspiration catheter including an elongate shaft configured for placement within a blood vessel of a subject, the shaft having an aspiration lumen and an injection lumen, the aspiration lumen having an open distal end and a proximal end, the injection lumen extending within the aspiration lumen and having a distal end and a proximal end, the distal end of the injection lumen located within the aspiration lumen near the open distal end of the aspiration lumen, an orifice at the distal end of the injection lumen configured to create one or more jets when pressurized fluid is injected through the injection lumen, an extension tube having a distal end and a proximal end and a lumen extending therebetween, the distal end of the extension tube configured to be hydraulically coupled to the aspiration lumen of the aspiration catheter, the extension tube further having a compressible portion disposed between the distal end and the proximal end of the extension tube, the compressible portion configured for placement within a peristaltic pump, such that operation of the peristaltic pump causes fluid from the aspiration lumen of the aspiration catheter to transit through the extension tube from the distal end of the extension tube to the proximal end of the extension tube, a controller configured to operate a piston pump configured to pressurize fluid through the injection lumen, and a sensor configured to sense the presence of air within pressurized fluid injected into or through the injection lumen, the sensor configured to output a signal to the controller.

In yet another embodiment of the present disclosure, a system for catheter aspiration includes an aspiration catheter including an elongate shaft configured for placement within a blood vessel of a subject, the shaft having an aspiration lumen having an open distal end and a proximal end, an extension tube having a distal end and a proximal end and a lumen extending therebetween, the distal end of the extension tube configured to be hydraulically coupled to the aspiration lumen of the aspiration catheter, the extension tube further having a compressible portion disposed between the distal end and the proximal end of the extension tube, the compressible portion configured for placement within a roller pump, such that operation of the roller pump causes fluid from the aspiration lumen of the aspiration catheter to transit through the extension tube from the distal end of the extension tube to the proximal end of the extension tube, a pressure sensor configured for placement in fluid communication with a conduit that includes the lumen of the extension tube and the aspiration lumen of the catheter, a measurement device coupled to the pressure sensor and configured for measuring deviations in fluid pressure, and a communication device coupled to the measurement device and configured to generate a signal related to the deviations in fluid pressure.

In still another embodiment of the present disclosure, a system for catheter aspiration includes an aspiration catheter including an elongate shaft configured for placement within a blood vessel of a subject, the shaft having an aspiration lumen having an open distal end and a proximal end, an extension tube having a distal end and a proximal end and a lumen extending therebetween, the distal end of the extension tube configured to be hydraulically coupled to the aspiration lumen of the aspiration catheter, the extension tube further having a compressible portion disposed between the distal end and the proximal end of the extension tube, the compressible portion configured for placement within a peristaltic pump, such that operation of the peristaltic pump causes fluid from the aspiration lumen of the aspiration catheter to transit through the extension tube from the distal end of the extension tube to the proximal end of the extension tube, a pressure sensor configured for placement in fluid communication with a conduit that includes the lumen of the extension tube and the aspiration lumen of the catheter, a measurement device coupled to the pressure sensor and configured for measuring deviations in fluid pressure, and a communication device coupled to the measurement device and configured to generate a signal related to the deviations in fluid pressure.

In yet another embodiment of the present disclosure, a method for performing a thrombectomy procedure includes providing an aspiration catheter including an elongate shaft configured for placement within a blood vessel of a subject, the shaft having an aspiration lumen having an open distal end and a proximal end, placing at least a distal portion of the elongate shaft into a blood vessel of the subject, placing an extension tube having a distal end and a proximal end and a lumen extending therebetween, the extension tube configured to be hydraulically coupled to the aspiration lumen of the aspiration catheter, within a roller pump such that a compressible portion of the extension tube disposed between the distal end and the proximal end of the extension tube is engageable by two or more rollers of a rotatable head of the roller pump, and operating the roller pump such that body fluid forced into the aspiration lumen of the aspiration catheter is caused to transit through the extension tube from the distal end of the extension tube to the proximal end of the extension tube.

In still another embodiment of the present disclosure, a system for catheter aspiration includes an aspiration catheter including an elongate shaft configured for placement within a blood vessel of a subject, the shaft having an aspiration lumen having an open distal end and a proximal end, an extension tube having a distal end and a proximal end and a lumen extending therebetween, the distal end of the extension tube configured to be hydraulically coupled to the aspiration lumen of the aspiration catheter, the extension tube further having a compressible portion disposed between the distal end and the proximal end of the extension tube, the compressible portion configured for placement within a peristaltic pump, such that operation of the peristaltic pump causes fluid from the aspiration lumen of the aspiration catheter to transit through the extension tube from the distal end of the extension tube to the proximal end of the extension tube, and a return conduit hydraulically coupled to the extension tube and configured to return to the vasculature of the subject fluid that has passed through the extension tube from distal to proximal.

In yet another embodiment of the present disclosure, a system for catheter aspiration includes a centrifugal pump, an aspiration catheter including an elongate shaft configured for placement within a blood vessel of a subject, the shaft having an aspiration lumen having an open distal end and a proximal end, and a controller configured to operate the centrifugal pump.

In still another embodiment of the present disclosure, a system for real time monitoring of catheter aspiration includes an ultrasound sensor configured for placement in fluid communication with a lumen which at least partially includes an aspiration lumen of a catheter, the aspiration lumen configured to couple to a negative pressure source, the ultrasound sensor configured to output a signal, a measurement device coupled to the ultrasound sensor and configured to count the number of times N during a predetermined time period P that the signal output by the ultrasound sensor surpasses a predetermined threshold amplitude A, the measurement device further configured to determine whether the number of times N is less than or less than or equal to a predetermined value V or whether the number of times N is greater than or greater than or equal to the predetermined value V, and a communication device coupled to the measurement device and configured to be in a first communication mode if the number of times N is less than or less than or equal to the predetermined value V and to be in a second communication mode if the number of times N is greater than or greater than or equal to the predetermined value V.

In yet another embodiment of the present disclosure, a system for catheter aspiration includes an aspiration catheter including an elongate shaft configured for placement within a blood vessel of a subject, the shaft including an aspiration lumen having an open distal end and a proximal end, an extension tube having a distal end and a proximal end and a lumen extending therebetween, the distal end of the extension tube configured to be hydraulically coupled to the proximal end of the aspiration lumen of the aspiration catheter, a receptacle having an interior volume, wherein the proximal end of the extension tube is configured to deliver material flowing from the lumen of the extension tube into the interior volume of the receptacle, a scale configured to weigh at least the material contained within the receptacle, and a communication element configured to demonstrate changes in the mass of the material contained within the receptacle over time to a user.

In still another embodiment of the present disclosure, a method for performing a thrombectomy procedure includes providing a system for aspiration including an aspiration catheter including an elongate shaft configured for placement within a blood vessel of a subject, the shaft having an aspiration lumen having an open distal end and a proximal end, an extension tube having a distal end and a proximal end and a lumen extending therebetween, the distal end of the extension tube configured to be hydraulically coupled to the proximal end of the aspiration lumen of the aspiration catheter, a receptacle having an interior volume, wherein the proximal end of the extension tube is configured to deliver material flowing from the lumen of the extension tube into the interior volume of the receptacle, and a scale configured to weigh at least the material contained within the receptacle, placing at least a distal portion of the elongate shaft into a blood vessel of the subject, causing at least some thrombus to be aspirated from the blood vessel of the subject through the aspiration lumen of the aspiration catheter and through the lumen of the extension tube, and into the interior volume of the receptacle, and monitoring a change in the mass of material within the receptacle over time.

In yet another embodiment of the present disclosure, a system for catheter aspiration includes an aspiration catheter including an elongate shaft configured for placement within a blood vessel of a subject, the shaft having an aspiration lumen, the aspiration lumen having an open distal end and a proximal end, an injection tube having an injection lumen extending therein, the injection tube configured to extend within the aspiration lumen and having a distal end and a proximal end, the distal end of the injection tube configured to be located within the aspiration lumen near the open distal end of the aspiration lumen, a microfabricated cap externally covering and providing a seal around an external perimeter of the distal end of the injection tube, and an orifice in at least one of the microfabricated cap or the injection tube proximal to the microfabricated cap, the orifice configured to create one or more jets into the aspiration lumen when pressurized fluid is injected through the injection lumen.

In still another embodiment of the present disclosure, a method for aspirating a thrombus includes providing an aspiration catheter having an elongate shaft having an aspiration lumen having a proximal end and an open distal end and an injection tube extending within the aspiration lumen and having an injection lumen having a proximal end, a closed distal end, and an orifice at or adjacent the close distal end, attaching a pressurizable fluid source to the proximal end of the injection lumen, coupling a pump to the proximal end of the aspiration lumen configured to aspirate fluid through the aspiration lumen in a distal to proximal direction, inserting a distal region of the shaft of the aspiration catheter into the vasculature of a patient such that the open distal end of the aspiration lumen is in or adjacent a thrombus, determining that the combination of the injection of the pressurized fluid through the injection lumen and the aspiration by the pump through the aspiration lumen is not sufficient to cause aspiration of the thrombus, advancing the aspiration catheter until the open distal end of the aspiration lumen is distal to the thrombus, injecting pressurized fluid through the injection lumen without operating the pump on the aspiration lumen, such that the pressurized fluid passes through the injection lumen, into the aspiration lumen and out of the open distal end of the aspiration lumen into a space distal to the thrombus, and aspirating at least some of the thrombus by injecting the pressurized fluid while also operating the pump on the aspiration lumen.

In yet another embodiment of the present disclosure, a system for catheter aspiration includes, an aspiration catheter comprising an elongate shaft configured for placement within a blood vessel of a subject, the shaft having an aspiration lumen, the aspiration lumen having an open distal end and a proximal end, an injection tube having an injection lumen extending therein, the injection tube extending within the aspiration lumen and longitudinally adjustable in relation to the elongate shaft, the injection lumen having an open distal end and a proximal end, the open distal end of the injection lumen configured to extend distally from the open distal end of the aspiration lumen, and an orifice through a wall of the injection tube proximal to the open distal end of the injection lumen, the orifice configured to create one or more jets into the aspiration lumen when pressurized fluid is injected through the injection lumen, and when the injection lumen of the injection tube is occluded distally of the orifice through the wall of the injection tube.

BRIEF DESCRIPTION OF THE DRAWINGS

FIG. 11 is a plan view of a system for aspiration according to another embodiment of the present disclosure.

FIG. 12 is a detailed view of an aspiration monitoring system of the system for aspiration of FIG. 11.

FIG. 13 is a plan view of a system for aspiration according to another embodiment of the present disclosure.

FIG. 14 is a detailed view of an aspiration monitoring system of the system for aspiration of FIG. 13.

FIG. 18 is a plan view of a portion of a multi-purpose system according to an embodiment of the present disclosure.

FIG. 19 is a perspective view of a proximal portion of the multi-purpose system of FIG. 18.

FIG. 25 is a plan view of an aspiration catheter according to an embodiment of the present disclosure.

FIG. 26 is a plan view of a tubing set according to an embodiment of the present disclosure.

FIG. 27 is a plan view of a stopcock according to an embodiment of the present disclosure.

FIG. 28 is a plan view of a stopcock according to an embodiment of the present disclosure.

FIG. 29 is a plan view of a vacuum source according to an embodiment of the present disclosure.

FIG. 40 is a perspective view of an ultrasonic sensor for use with an aspiration system, according to an embodiment of the present disclosure.

FIG. 41 is a plan view of an aspiration system comprising a y-connector having the ultrasonic sensor of FIG. 40 placed therein.

FIG. 42 is a perspective view of a console of the aspiration system of FIG. 41.

FIG. 53 is a plan view of a microcatheter being tracked over a guidewire, in a first step.

FIG. 54 is a plan view of the insertion of an insertable injection tube and cap being inserted into a microcatheter, in a second step according to an embodiment of the present disclosure.

FIGS. 66-69 illustrate a method for treating a patient using an aspiration catheter and system, according to an embodiment of the present disclosure.

DETAILED DESCRIPTION OF THE ILLUSTRATED EMBODIMENTS

Figure 1:
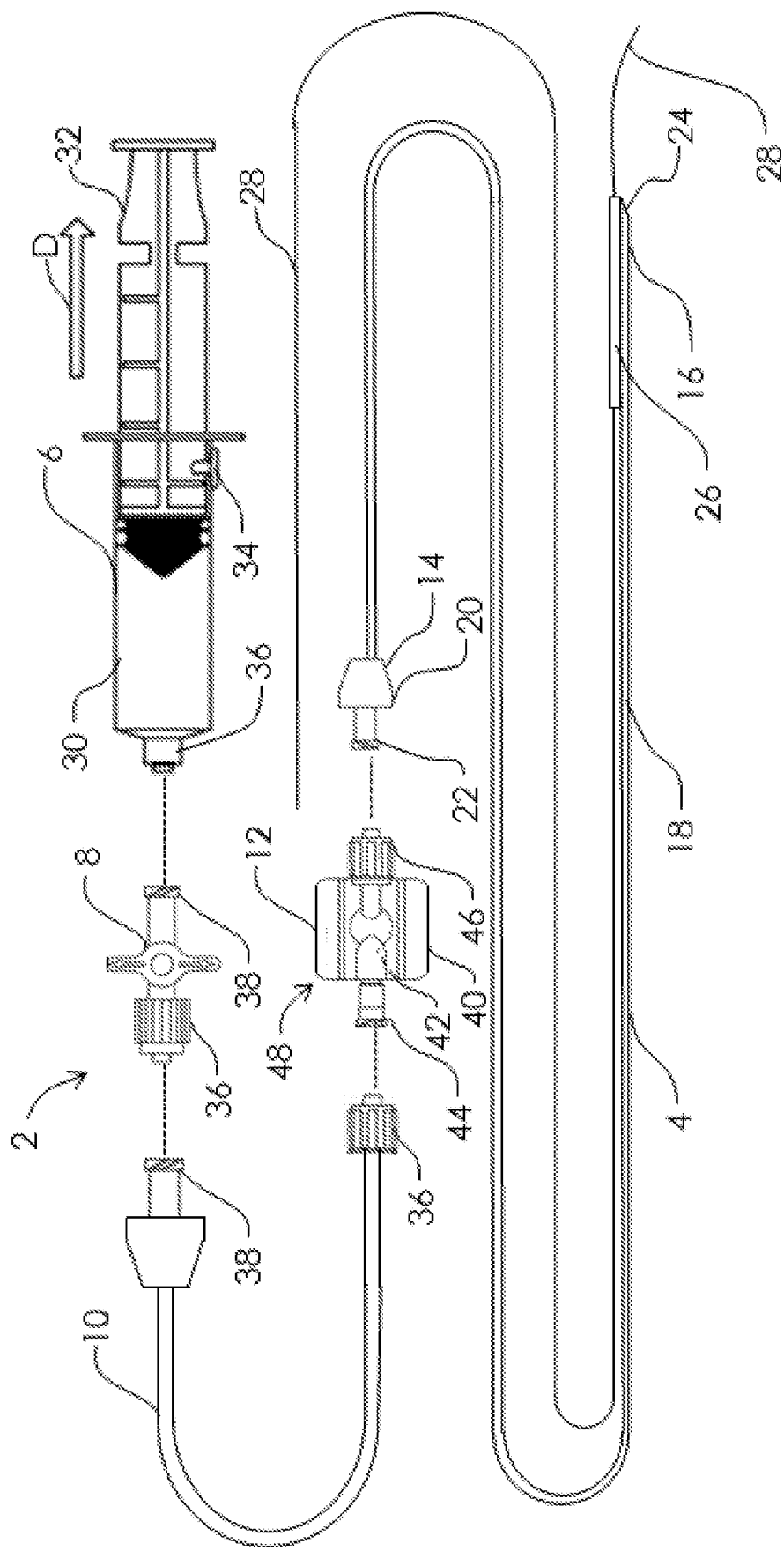
FIG. 1 is a plan view of a system for aspiration according to an embodiment of the present disclosure.

The present disclosure relates to aspiration catheter systems and monitoring, warning and communication systems for aspiration catheter systems, including aspiration systems for removing thrombus from the vasculature of patients. Such vasculature can include veins and arteries, including coronary arteries, carotid arteries, cerebral arteries, and other arteries of the head and neck. Clogging of aspiration catheters, for example by large pieces of thrombus, is a common concern for users. Techniques to avoid clogging/choking of material within the catheter often involve rapidly, aggressively advancing the aspiration catheter or gently plucking at edges of a thrombus to insure only small pieces or portions are introduced at a time, pieces which are small enough to not clog or occlude the aspiration lumen. When a device becomes clogged during use, the potential for inadvertent dislodgment of thrombus downstream increases; this is referred to as distal embolism. As aspiration procedures of this type are often used in highly technical emergent settings, early clog detection of the aspiration catheter for the user during aspiration can contribute to the success of the procedure and clinical outcome. Some sources have reported that up to 50% of aspiration catheters used get clogged during use.

The user may have difficulty determining whether there is a vacuum or negative pressure in the system or not. For example, the user may have difficulty determining whether the vacuum or negative pressure has been applied or not (e.g., the vacuum source has been turned on or off). Additionally, the user may have difficulty determining whether there has been a loss of vacuum in the system, for example because of the syringe (or other vacuum source) being full of fluid or because of a leak in the system. Blood is relatively opaque and can coat the wall of the syringe, thus making it difficult to determine when the syringe becomes full. This makes it difficult to determine whether sufficient vacuum or negative pressure is being applied to the aspiration catheter. The negative pressure gradient may change to an unacceptable level even before the syringe becomes full. Extension tubing or other tubing may also cause a loss in vacuum or negative pressure in the system. Certain tubing kinks may be difficult for a user to see or identify. It is also difficult to determine whether there is an air leak in the system, which can be another cause for a loss of vacuum or negative pressure even before the syringe becomes full of the aspirated fluid.

During the aspiration of thrombus with an aspiration catheter, it is difficult to identify when thrombus is actively being aspirated, or when only blood is being aspirated. Typically, it is desired to not aspirate sizable quantities of normal blood from blood vessels, because of the importance of maintaining normal blood volume and blood pressure. However, when tracking the tip of an aspiration catheter in proximity to a thrombus, it is difficult to know whether the aspiration catheter has actively engaged a thrombus, whether it has aspirated at least a portion of the thrombus, or whether it is not engaged with the thrombus, and is only aspirating blood. Though some aspiration catheters, such as those used in the peripheral blood vessels or in an arterio-venous fistula, may be around 50 cm or even less, the tip of an aspiration catheter may in same cases be more than 90 cm from the hands of the user, or as much as 135 cm from the hands of the user, or in some cases as much as 150 cm, and the particular status of aspiration capability at the tip of the catheter is often not known by the user. A user may thus be essentially plunging a catheter blindly without significant, usable sensory feedback. The catheter may have an outer diameter up to or even greater than 6 French, and may be as high as 10 French or greater. The increased catheter outer diameter can cause some concern of potential trauma inside a blood vessel. The use of aspiration catheters can therefore be inefficient, and cause more blood removal than desired, causing a user to minimize the length of the therapy and in severe cases necessitating blood transfusion. An increased volume of normal blood being aspirated also means that the vacuum source (e.g. syringe) will fill in a shorter amount of time, thus requiring more frequent replacement of the vacuum source. Distal embolism may occur if the negative pressure gradient is not sufficient, and yet the user is not aware.

In some cases, a syringe that is completely or mostly full or blood and/or thrombus may continue to be used, though in this state, there is not sufficient pressure to effectively aspirate thrombus or unwanted material, thus causing inefficient use of time, and lengthening the procedure. In some cases, the user may not realize the plunger of the syringe has mistakenly not been pulled back (to evacuate the syringe). In some cases, the syringe itself may be defective, and a sufficient negative pressure may not be achieved, without the user being aware. In some cases, kinked tubing, lines, or catheters may go unnoticed, because of bad visibility in a procedural laboratory, or simply from the extent of concurrent activities being performed. In many cases, the user's eyes are oriented or focused on a monitor, for example a fluoroscopic monitor or other imaging monitor, or a monitor with patient vital data. Though the user may be able to view flow through transparent or partially transparent lumens (such as extension tubing), in dim lighting with intermittent viewing, it is difficult for the user's mind to process flow of an opaque liquid (such as blood/thrombus). Even in good lighting with a focused eye, the movement of fluid through extension tubing may not present an accurate picture of the aspiration status, as the visual flow effect may be delayed in relation to the applied vacuum or negative pressure. More than one medical device personnel may be sharing sensory information with each other to attempt to build a current status in each other's minds of the aspiration procedure. When a user relies on another's interpretation, especially when either are multitasking, a false sense of the status may occur. A syringe attached to the aspiration catheter may cause kinking, for example, if placed on an uneven surface. The distal opening in an aspiration lumen of an aspiration catheter may be prone to aspirating directly against the wall of a blood vessel, thus being temporarily stuck against the vessel wall, and stopping flow throughout the aspiration lumen. In some cases, a negative pressure gradient that is too large may be accidentally or inappropriately applied to the aspiration lumen of the aspiration catheter, limiting effectiveness (for example, if it causes the walls surrounding the aspiration lumen to collapse and thus, cut off the significantly decrease the flow through the aspiration lumen). The syringes which are sometimes used as a vacuum source to connect to an aspiration lumen of an aspiration catheter may malfunction, and not be fully actuated/evacuated. But, even when the syringe is functioning correctly, it will tend to fill up at difficult to predict moments, and thus commonly have periods with no applied negative pressure gradient. In the cases wherein a portion of clot/thrombus is being aspirated through the aspiration lumen, a significant pressure drop may occur at the current position of the thrombus, and thus, a sufficient negative pressure may only exist from the proximal end of the aspiration lumen and distally up to the point of the thrombus. Thus, an insufficient negative pressure may exist, causing insufficient aspiration at the distal end of the aspiration lumen, e.g., at the distal end of the aspiration catheter. The same situation may occur if there is an actual clog at some intermediate point within the aspiration lumen. In either of these conditions, because of the insufficient aspiration at the distal end of the aspiration lumen, there may be a risk of thrombus or emboli being sent distally in the vasculature, which may cause occlusion, stroke, pulmonary embolism, or other disorders, depending upon the location of the intervention or procedure being performed. With current apparatus and techniques, these situations are very difficult to detect when they occur. It has been estimated that in as many as 50% of thrombus aspiration procedures, some sort of failure occurs.

An aspiration system 2 is illustrated in FIG. 1 and is configured to allow real time monitoring of catheter aspiration. The aspiration system 2 comprises an aspiration catheter 4, a vacuum source 6, a valve 8, extension tubing 10, and an aspiration monitoring system 48 including an in-line pressure transducer 12. The aspiration catheter 4 has a proximal end 14 and a distal end 16 and an aspiration lumen 18 extending from the proximal end 14 to the distal end 16. The aspiration lumen 18 may be sized for aspiration of thrombus, and in some embodiments may have an inner diameter of between about 0.38 millimeter (0.015 inches) and about 2.54 millimeters (0.100 inches). The aspiration catheter 4 includes a hub 20 at its proximal end which may include a female luer connector 22. The aspiration lumen 18 at the distal end 16 of the aspiration catheter 4 may include an angled orifice 24, which aids in the tracking through tortuous or occluded vasculature. In some embodiments, a guidewire lumen 26 is coupled to the distal end 16 of the aspiration catheter 4, and is configured to track over a guidewire 28. The vacuum source 6 may comprise a syringe, and may be sized between 5 ml and 100 ml, or between 20 ml and 60. The vacuum source 6 may comprise a VacLok® syringe, made by Merit Medical, South Jordan, Utah. The vacuum source 6 may include a barrel 30 and plunger 32, with a lock 34 which is configured to retain the plunger 32 in position in relation to the barrel 30, for example, when the plunger 32 is pulled back in direction D to create a negative pressure (vacuum) inside the barrel 30. In some embodiments, the vacuum source 6 may comprise any other type of evacuatable reservoir, or may comprise a vacuum pump. The vacuum source 6 is connected to the aspiration lumen 18 of the aspiration catheter 4 via the extension tubing 10 and the valve 8. In some embodiments, the vacuum source 6 may be connected directly to the aspiration lumen 18 of the aspiration catheter 4. Male luer connectors 36 and female luer connectors 38 are indicated in FIG. 1. The valve 8 may be a standard two-way stopcock, as illustrated.

Figure 2A:
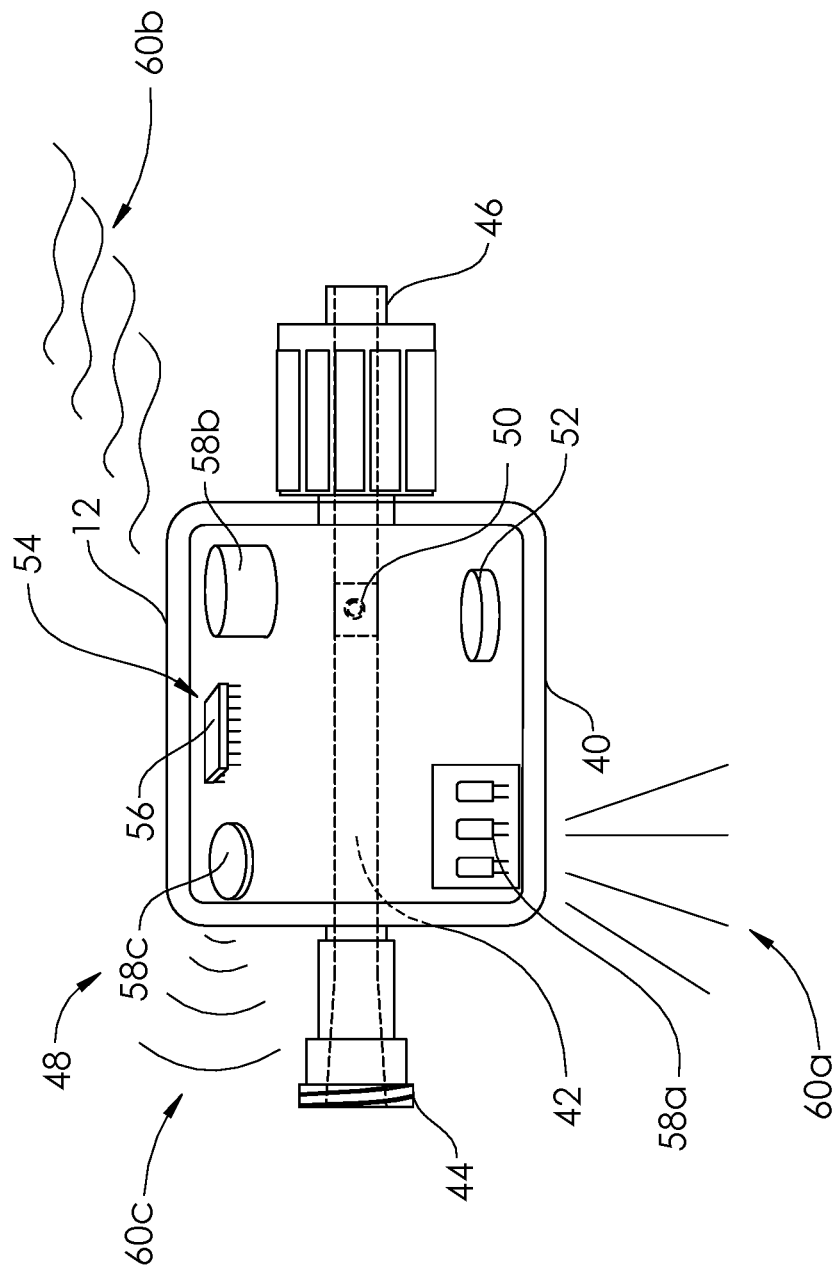
FIG. 2A is a view of an aspiration monitoring system according to a first embodiment of the present disclosure.

The pressure transducer 12 of the aspiration monitoring system 48 is configured to be fluidly coupled between the vacuum source 6 and the aspiration catheter 4. In FIG. 2A, the aspiration monitoring system 48 is illustrated as a self-contained device of a first embodiment. The pressure transducer 12 comprises a housing 40 having a cavity 42 extending between a first port 44 and a second port 46. In some embodiments, the first port 44 comprises a female luer and the second port 46 comprises a male luer. In some embodiments, the first port 44 comprises a female luer lock and the second port 46 comprises a male luer lock, each of which is attachable to and detachable from a corresponding luer lock of the opposite gender. The first port 44 is configured to be coupled to the vacuum source 6, either directly, or with the valve 8 and/or extension tubing 10 connected in between. The second port 46 is configured to be coupled to the aspiration lumen 18 of the aspiration catheter 4, for example, by coupling the second port 46 directly or indirectly to the hub 20 of the aspiration catheter 4. When the aspiration system 2 is used to aspirate body fluids and/or materials, for example blood and/or thrombus, the body fluids and/or materials are aspirated through the aspiration lumen 18 of the aspiration catheter from the angled orifice 24 at the distal end 16 to the female luer connector 22 at the proximal end 14, then pass through the second port 46 of the pressure transducer 12 first, through the cavity 42, and then through the first port 44. Depending on the amount of amount of vacuum or negative pressure applied by the vacuum source 6, and the amount of flow resistance and resulting pressure drop along the aspiration system 2, the pressure within the cavity 42 will vary. For example, a more viscous fluid like blood, or a fluid having solid, semi-solid, or gel-like particles or portions, will cause more flow resistance through the relatively small aspiration lumen 18 of the aspiration catheter 4 than would water or normal saline solution. Thus, the pressure within the cavity 42 of the pressure transducer 12 will decrease (the negative pressure gradient will increase) as the flow resistance in the aspiration lumen 18 increases.

For definition purposes, when speaking of the amount of "vacuum," a pressure of, for example, −15,000 pascal (−2.18 pounds per square inch, or psi) is a "larger vacuum" than −10,000 pascal (−1.45 psi). Actually, a true vacuum, where no molecules are present within the volume is extremely difficult. Additionally, −15,000 pascal is a "lower pressure" than −10,000 pascal. Furthermore, −15,000 pascal has a larger "absolute vacuum pressure" than does −10,000 pascal, because the absolute value of −15,000 is larger than the absolute value of −10,000. In FIG. 2A, a vacuum sensor 50 is disposed within the cavity 42 of the housing 40 and is in fluid communication with fluid that passes through the cavity 42. The vacuum sensor 50 may be a standard pressure sensor or transducer, including a pressure sensor designed primarily for measuring positive pressure. It may use any type of pressure sensing technology known in the art, including MEMS Technology. In some embodiments, the vacuum sensor 50 is configured for highest accuracy and/or precision within the range of pressures between about 0 pascal to about −101,325 pascal (−14.70 psi), or between about −45,000 pascal (−6.53 psi) and about −90,000 pascal (−13.05 psi), or between about −83,737 pascal (−12 psi) and about −96,527 pascal (−14 psi). In some embodiments, the power requirement for the vacuum sensor may range from 2.5 volts DC to 10 volts DC. In some embodiments, the vacuum sensor 50 may be an analog gauge with an output voltage. In the self-contained embodiment of the FIG. 2A, the vacuum sensor 50 is powered by one or more battery 52. Based on the power requirements of the vacuum sensor 50, and the power requirements of other components of the aspiration monitoring system 48 described herein, in some embodiments the one or more battery 52 may range between 1.5 volts and nine volts. Also contained within the housing is a measurement device 54, which in some embodiments may comprise a microprocessor. The measurement device 54 is coupled to the vacuum sensor 50 and receives signals from the vacuum sensor 50 indicative of real time measured pressure. In some embodiments, the measurement device 54 includes a memory module 56 in which information is stored that may be used by the measurement device 54, for example, in calculations. Information may include, for example, an array of one or more pressure values. In some embodiments, the array of one or more pressure values may be correlated with one or more different corresponding system models or catheter models. The vacuum sensor 50 may be used in some cases for detecting the presence or amount of vacuum or negative pressure alone, for the purpose of monitoring whether the vacuum source 6 (e.g., syringe) is significantly full, and thus needs to be changed. The vacuum sensor 50 may be used in some cases for detecting whether there is a vacuum or negative pressure in the system of not. For example, whether the vacuum or negative pressure has been applied or not (e.g., the vacuum source has been turned on or off).

One or more communication devices 58a, 58b, 58c are included within the aspiration monitoring system 48 and are coupled to the measurement device 54. Each of the one or more communication devices 58a-c are configured to generate a type of alert comprising an alert signal 60a-c, in response at least in part to activity and output of the measurement device 54. In some embodiments, the communication device 58a may include one or more LEDs (light emitting diodes) configured to generate a visible alert via a visible alert signal 60a, such as light that is continuously illuminated, or is illuminated in a blinking pattern. In some embodiments, the LEDs may be oriented on multiple sides of the communication device 58a, so that they may be easily seen from a variety of different locations. In some embodiments, lights other than LEDs may be used. Light pipes or other lighting conduits may also be incorporated in embodiments, to further place visual indicators at multiple locations and/or orientations. In some embodiments, the communication device 58b may include one or more vibration generators configured to generate a tactile alert via a tactile alert signal 60b, which may include, but is not limited to, vibration or heat. In some embodiments, the vibration device may be similar to a video game controller. In some embodiments, the vibration generator may comprise a piezoelectric device which is configured to vibrate when a voltage is applied. In some embodiments, the communication device 58c may include one or more sound generating devices configured to generate an audible alert via an audible alert signal 60c, such as a continuous noise, or a repeating noise. The communication device 58c in some embodiments may comprise a loudspeaker for generation of any variety of sounds, at any variety of frequencies (Hz) or sound pressures (dB) within the human audible range and/or human tolerance range. The communication device 58c may even be configured to generate sounds that are outside the human audible range in embodiments wherein the signal is intended to be felt as a vibration or other tactile sensation, instead of an audible sensation. In some embodiments, the sound generating device may comprise a buzzer which is configured to sound one or more audible pitches when a voltage is applied. In some embodiments a piezoelectric device, such as that described in relation to the communication device 58b may also serve as a sound generating device, included as communication device 58c. The alert signal 60a-c can at times serve as a "wake up" alarm for the user, in cases where the user has become too focused on other factors during the procedure.

A user of an aspiration system 2 may desire to be notified of several conditions which may occur during use of the aspiration system 2. These potential conditions include, but are not limited to clogging, a loss of vacuum or negative pressure due to filling of the vacuum source 6 and or a breach, break or puncture in the aspiration system 2, and the engagement or aspiration of non-fluid, solid or semi-solid material such as thrombus. The aspiration monitoring system 48 of FIG. 2A is configured to alert users of an aspiration system 2 about real time status of the aspiration system 2, including operational conditions, which include: whether vacuum or negative pressure is being applied or not; flow conditions, which include whether a thrombus is engaged, whether a thrombus is being actively aspirated, whether the system is leaking air, whether the system is clogged, whether the vacuum source 6 is full and/or needs to be changed; or other potential set up issues. The real time feedback provided frees a user or operator from the need of excessive personal monitoring of the vacuum source 6, extension tubing 10, or other portions of the aspiration system 2, for improper or undesired flow or operation conditions, and thus allows the user to focus more attention on the patient being treated. The user is kept aware of whether a clot is being aspirated or has been aspirated, or whether there is a clog. Additionally, the user is kept aware of whether there is too large an amount of blood being removed from the patient, or whether there are fault conditions like system leak or tubing kink. A tubing kink distal to the vacuum sensor 50 may be identified (for example by an increase in measured negative pressure) and a tubing kink proximal to the vacuum sensor 50 may be identified (for example, by a loss or degradation of the negative pressure gradient). In some cases, the user may attempt to operate the catheter with a vacuum source 6 that is already full (and thus has no significant negative pressure gradient). In some cases, a user may even forget to open the valve 8 to begin aspiration, but the aspiration monitoring system, 48 can also identify that the system is not yet functioning, and communicate a list of potential errors or specific errors (for the particular pressure waveform measured). By having the real-time awareness of the many factors related to the operating status, the procedure is made safer, the time of the procedure may be reduced, and blood loss may be reduced.

The pressure transducer 12 of the aspiration monitoring system 48 is configured to continuously measure and monitor the absolute pressure amplitude within the closed system of the aspiration system 2, and also is configured to measure and monitor the relative pressure over time to detect noteworthy flow changes within the flow circuit of the aspiration system 2. Some changes are discernible via absolute pressure measurement, while more subtle pressure deflections may be compared to a stored library in memory. Noteworthy conditions may be signaled to the user when appropriate. In some embodiments, the unfiltered signal may be amplified by an amplifier and filtered by a filter, for example, to increase the signal-to-noise ratio. Examples of the (background) noise 57 in an unfiltered signal can be seen in FIGS. 5A-5D (labeled in FIG. 5A). In some embodiments, one or more algorithms may be used, as described herein, to identify particular conditions of interest.

Figure 2B:
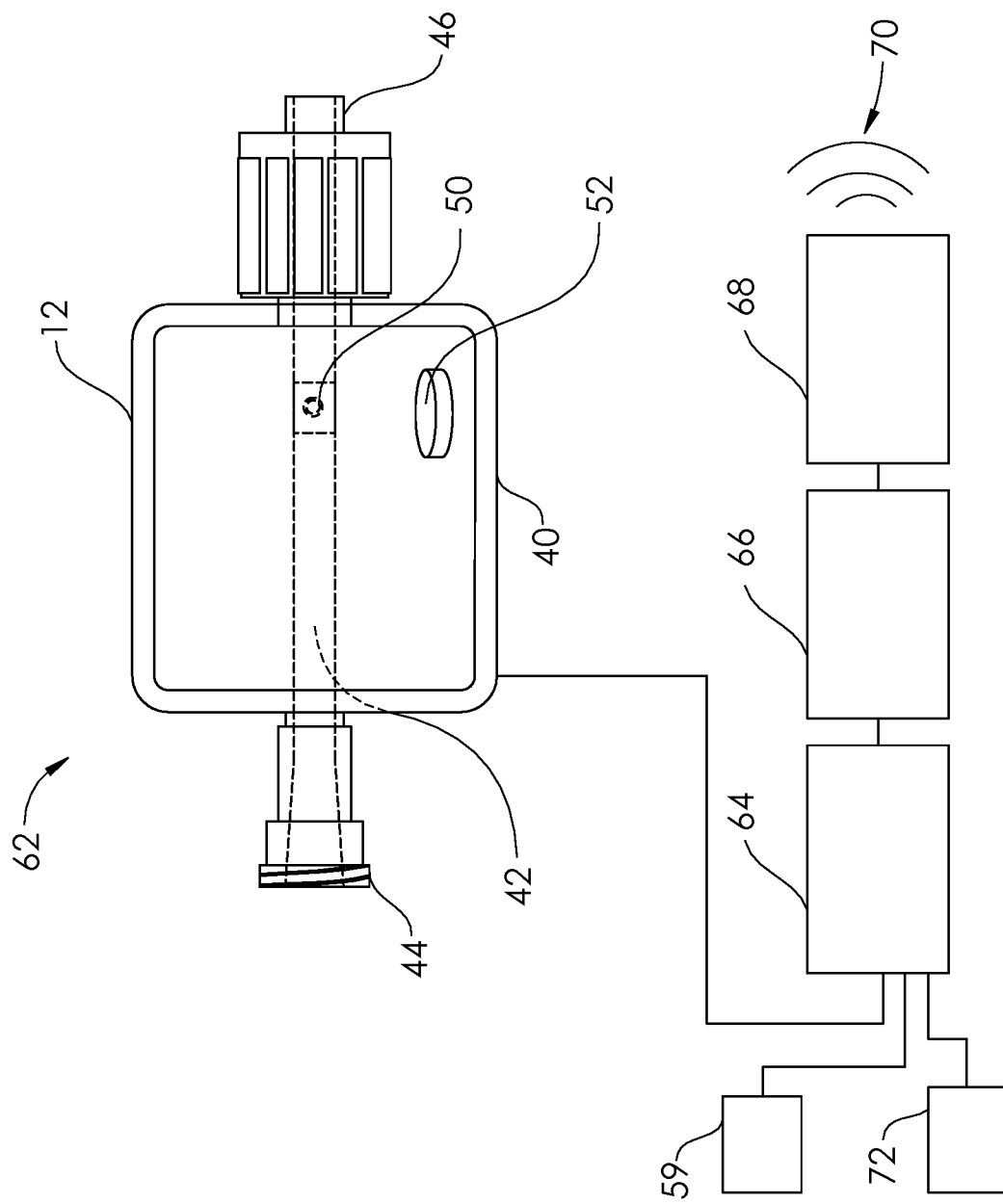
FIG. 2B is a view of an aspiration monitoring system according to a second embodiment of the present disclosure.

FIG. 2B illustrates a second embodiment of an aspiration monitoring system 62 having a pressure transducer 12 having a vacuum sensor 50 disposed within the cavity 42 of a housing 40. The vacuum sensor 50 may be powered by at least one battery 52. In some embodiments, the pressure transducer 12 may be reusable, and may be configured to allow charging of the battery 52, or of a capacitor (not shown) by direct charging methods, or by inductive power transfer methods and devices known in the art. Unlike the aspiration monitoring system 48 of FIG. 2A, the aspiration monitoring system 62 of FIG. 2B comprises a measurement device 64, memory module 66, and communication device 68 which are external to the pressure transducer 12. A power module 72, also external, may be used to power any of the measurement device 64, memory module 66, or communication device 68. The communication device 68 may be any of the communication device 58a, 58b, 58c described in relation to the aspiration monitoring system 48 of FIG. 2A, and are configured to product an alert via an alert signal 70. The communication device 68 may be portable so that it may be positioned close to the user.

Figure 3:
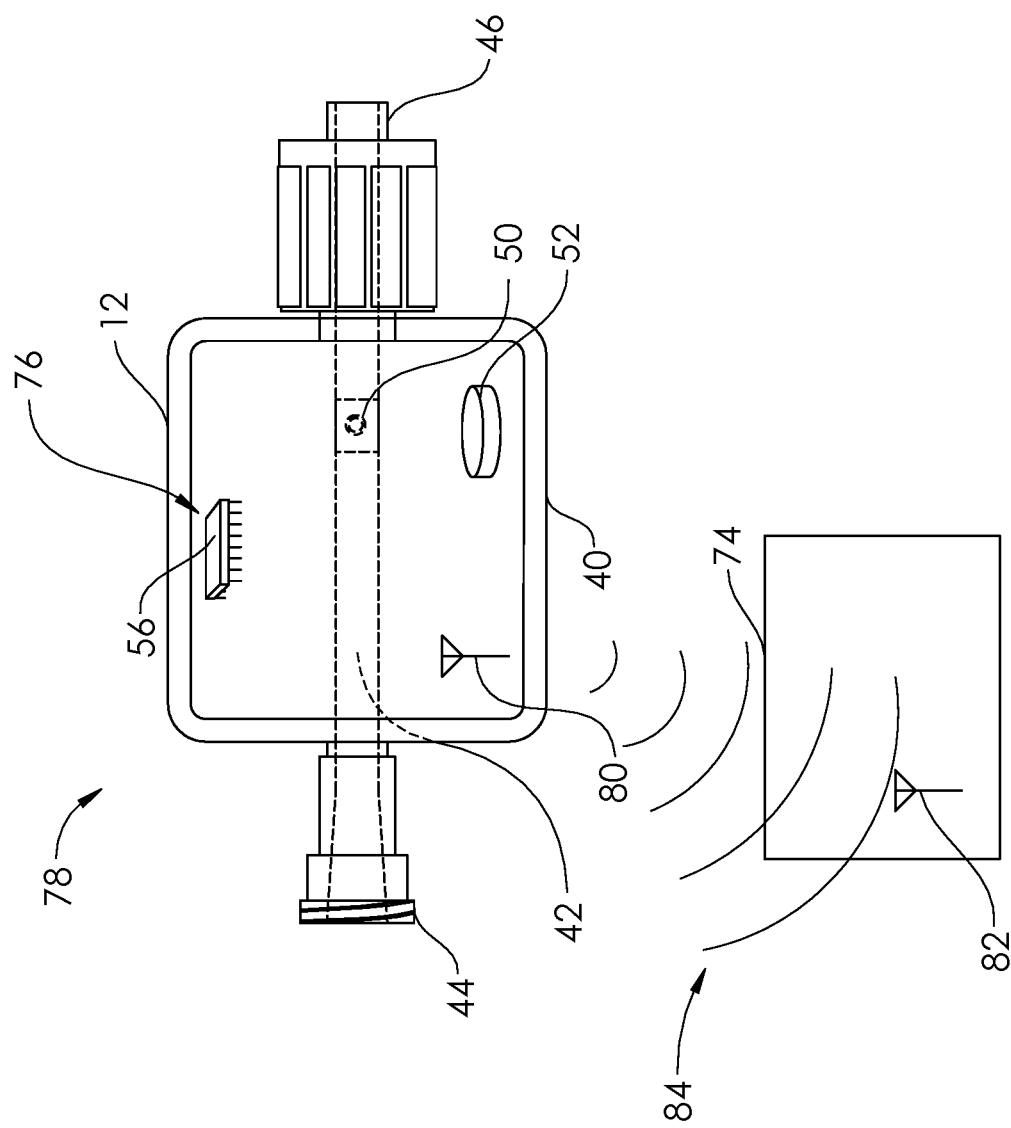
FIG. 3 is a view of an aspiration monitoring system according to a third embodiment of the present disclosure.

In some embodiments, the communication device 68 may be wearable by the user. FIG. 3 illustrates an aspiration monitoring system 78 which includes an antenna 80 coupled to a measurement device 76. The measurement device 76 is similar to the measurement device 54 of prior embodiments, except that it wirelessly sends a communication signal 84 via the antenna 80 to a corresponding antenna 82 of a communication device 74. In some embodiments, the communication device 74 comprises a wristband which the user wears, and which may include a vibration generator or heat generator. In some embodiments, the communication device 74 comprises an audio speaker which may be attached to equipment or even to the patient or user. In some embodiments, the communication device 74 comprises an audio speaker on an earpiece or earbud that the user may wear. In some embodiments, Bluetooth® communication technology may be used. The real time feedback supplied by the aspiration monitoring system 62 may decrease the time that the aspiration system 2 is actively aspirating without being engaged with a thrombus, thus minimizing the amount of non-thrombotic blood lost by aspiration. This may be particularly beneficial in larger bore catheters, for example in catheters having a diameter of 7 French or larger. The real time feedback may also minimize the amount of total time that catheters are tracked back-and-forth through the blood vessels, minimizing potential damage to the intima of the blood vessels, dissection of the blood vessels, or distal embolization. By lowering the risk of the aspiration catheter tip getting caught (via suction) against the blood vessel wall, the distal end of the aspiration lumen may be more aggressively designed for optimized aspiration characteristics. The technique of using the aspiration catheter may additionally be able to be performed in a more sophisticated manner, with continual or continuous knowledge of the aspiration status or negative pressure gradient sufficiency. For example, a piece of thrombus may be aspirated, followed by a "chaser" of blood aspiration, followed by another piece of thrombus, etc.

Figure 4A:
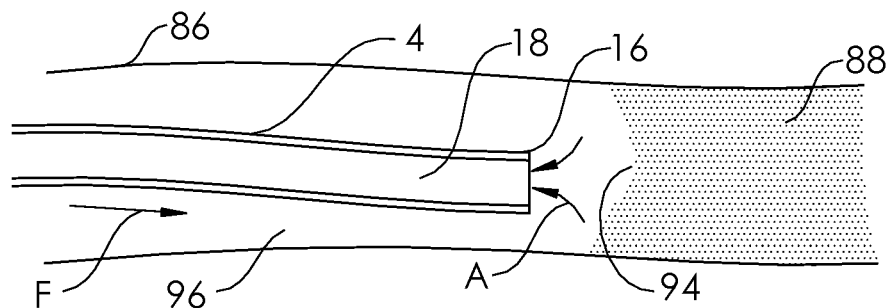
FIG. 4A is a sectional view of an aspiration catheter in a blood vessel prior to contact with a thrombus.
Figure 5A:
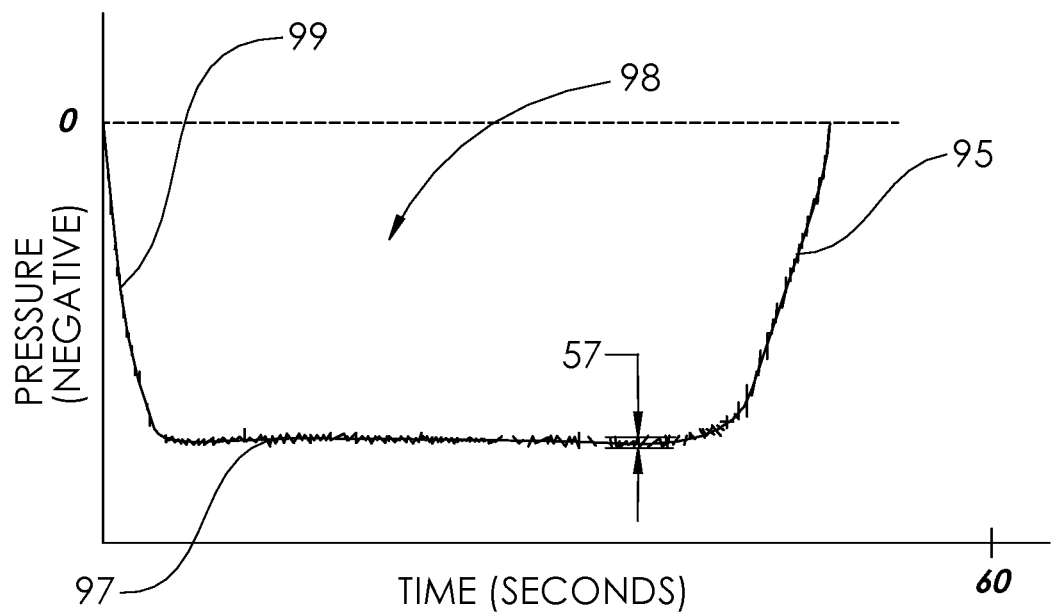
FIG. 5A is a graphic representation of pressure vs. time for the condition of FIG. 4A.

FIG. 4A illustrates the distal end 16 of an aspiration catheter 4 within a blood vessel 86 having at least one thrombus 88. The aspiration catheter 4 is being advanced in a forward direction F, but the distal end 16 of the aspiration catheter 4 has not yet reached the proximal extremity 94 of the thrombus 88. A vacuum source 6 (FIG. 1) has been coupled to the aspiration lumen 18 of the aspiration catheter 4 and activated (i.e. the valve 8 is open) causing blood 96 to be aspirated into the aspiration lumen 18 (arrows A). Turning to FIG. 5A, a corresponding curve 98 is represented for the normal fluid (e.g. blood) vacuum or negative pressure over time for the condition of FIG. 4A. The curve 98 represents vacuum or negative pressure over time sensed by the vacuum sensor 50 of any of the embodiments presented. No leaks are present and no thrombus is being evacuated, and therefore the curve 98 includes a downward slope 99 when the vacuum source 6 lowers the pressure within the cavity 42 of the pressure transducer 12 to a relatively steady state. The steady pressure curve 97 continues while blood 96 is being aspirated. As the vacuum source 6 is decoupled from the aspiration lumen 18, for example by closing the valve 8 or by detaching any two of the ports (e.g. luers), or if the vacuum source 6 fills completely with blood 96, then an upward slope 95 is measured.

The measurement device 54, 64 is configured to compare the curve 97 with information stored in the memory module 56, 66 to identify this condition. In some embodiments, the measurement device 54, 64 uses an algorithm to make the comparison. In some embodiments, the measurement device 54, 64 then sends a signal to the communication device 58a-c, 74, and the communication device 58a-c, 74 generates an appropriate alert. Communication device 58a, for example a particular color LED, may be illuminated, or an LED may flash in a particular pattern or number of flashes. Communication device 58b may create a characteristic sound, or may generate an audio message in a number of languages. For example, the audio message may state, "Thrombus encountered," or "No thrombus encountered." A different type of sound may be used for each of a plurality of "modes": "Thrombus encountered," "Actively flowing," and "No Vacuum." For example, a buzzing sound for "Thrombus encountered," a beep for "No vacuum," etc. The various characteristics of sound that may be varied include, but are not limited to timbre, or sound quality, spectrum, envelope, duration, phase, pitch (frequency), number of sounds (repetition). Communication device 58c may vibrate or heat in a characteristic pattern, for example, a certain number of repetitions or a certain frequency between repetitions. The user may determine that an additional fluoroscopic image (e.g. angiography) or other imaging modalities may be necessary to better identify the location of the thrombus 88.

Figure 4B:
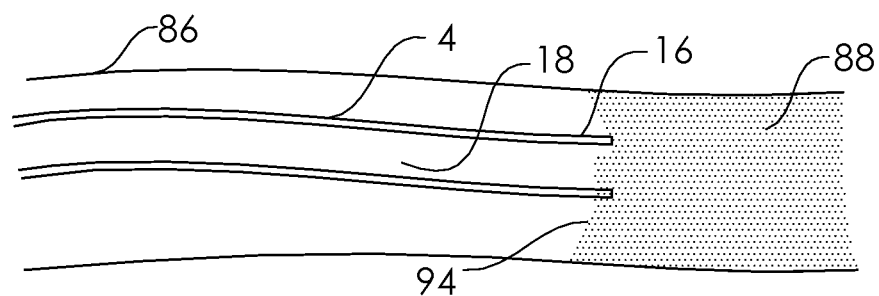
FIG. 4B is a sectional view of an aspiration catheter in a blood vessel upon contact with a thrombus.
Figure 5B:
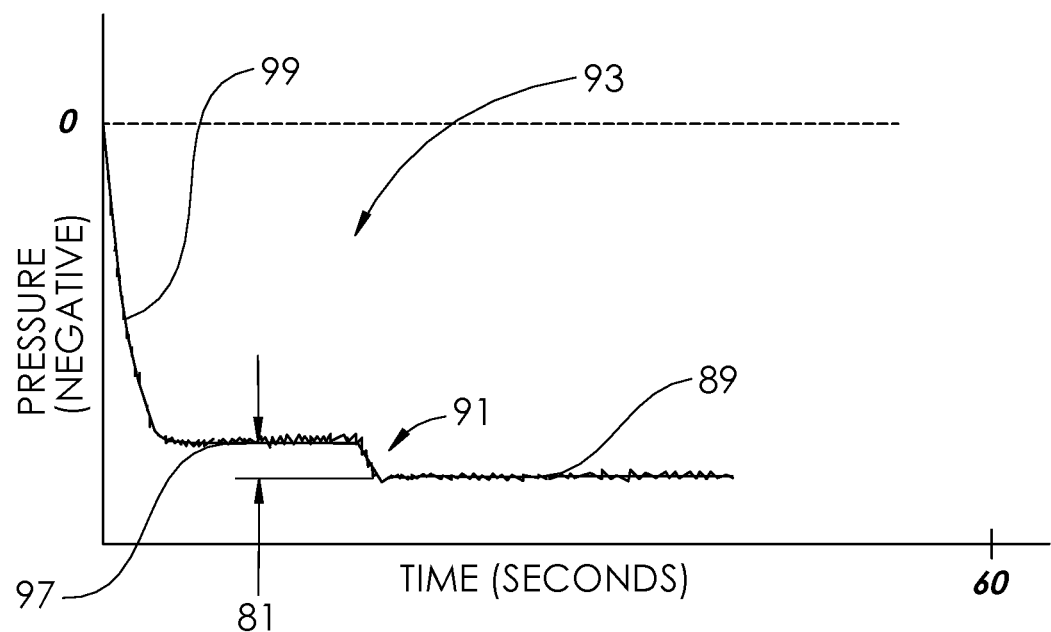
FIG. 5B is a graphic representation of pressure vs. time for the condition of FIG. 4B.
Figure 5C:
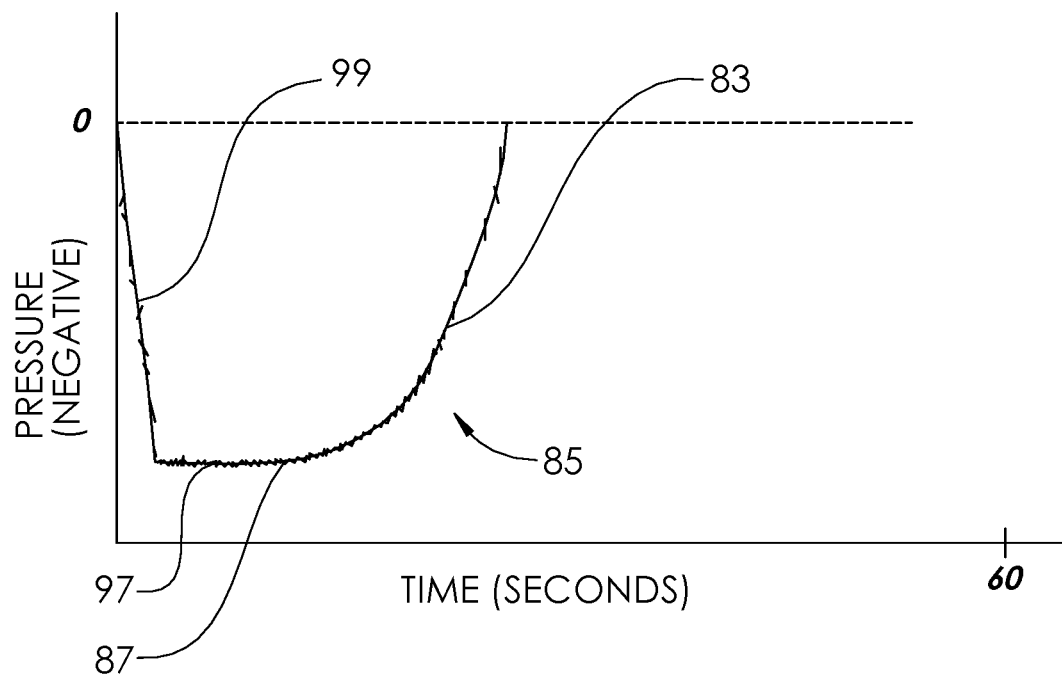
FIG. 5C is a graphic representation of pressure vs. time for the condition of FIG. 4C.

FIG. 4B illustrates the distal end 16 of an aspiration catheter 4 advanced to a position such that the distal end 16 of the aspiration catheter 4 contacts the proximal extremity 94 of the thrombus 88. The corresponding curve 93 in FIG. 5B represents vacuum or negative pressure over time sensed by the vacuum sensor 50 of any of the embodiments presented. The curve 93 initially has a downward slope 99 followed by a steady pressure curve 97, as in the condition of FIG. 4A, graphed in FIG. 5A, however, when the distal end 16 of the aspiration catheter 4 contacts the proximal extremity 94 of the thrombus 88, if the aspiration causes a portion of the thrombus 88 (for example a large or relatively hard portion) to enter and become trapped in the aspiration lumen 18, then a clog condition occurs. A similar condition occurs if the distal end 16 of the aspiration catheter 4 is caught on the thrombus 88 by a suction effect, with virtually nothing flowing through the aspiration lumen 18. In either condition, the curve 93 includes a deviation (or disturbance) in fluid pressure 91. If the clog (or stuck condition) continues, then a flat, depressed pressure 89 is measured.

The measurement device 54, 64 is configured to compare the curve 93 with information stored in the memory module 56, 66 to identify this condition. In some embodiments, the measurement device 54, 64 uses an algorithm to make the comparison. In some embodiments, a pre-set pressure differential $\Delta P_1$ may be stored in the memory module 56, 66 as a threshold, whereby the measurement of a pressure difference 81 less than this threshold does not result in the measurement device 54, 64 commanding the communication device 58a-c, 74 to send an alert signal 60a-c, 70. In some embodiments, when the pressure difference 81 is greater than (or greater than or equal to) the pre-set pressure differential $\Delta P_1$, the measurement device 54, 64 then sends a signal to the communication device 58a-c, 74, and the communication device 58a-c, 74 generates an appropriate alert. Communication device 58a, for example a particular color LED, may be illuminated, or an LED may flash in a particular pattern or number of flashes. Communication device 58b may create a characteristic sound, or may generate an audio message in a number of languages. For example, the audio message may state, "Clog Condition." Communication device 58c may vibrate or heat in a characteristic pattern, for example, a certain number of repetitions or a certain frequency between repetitions. When the user realizes that the clog condition is present, the user may pull on the aspiration catheter 4 and readvance it, in an attempt to contact a portion of the thrombus 88 that can be aspirated. If a portion of the thrombus is clogged in the aspiration lumen 18, and repositioning of the aspiration catheter 4 does not produce good results, the aspiration catheter 4 can be removed and the aspiration system 2 can be repurged, for example by a positive pressurization.

Figure 4C:
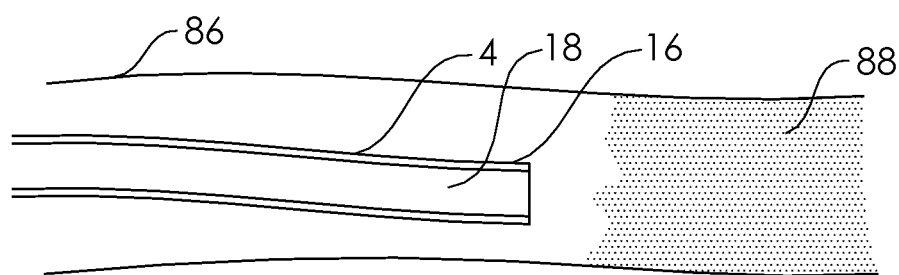
FIG. 4C is a sectional view of an aspiration catheter during a loss of aspiration.

FIG. 4C illustrates the distal end 16 of the aspiration catheter 4 in a general situation during which a breach in the aspiration system 2 has occurred. For example, a break, leak, puncture, pinhole, loosening, or disconnection may cause air to be pulled into the aspiration lumen 18 of the aspiration catheter 4, the cavity 42 of the pressure transducer 12, of the interior of the extension tubing 10, valve 8, or vacuum source 6. As graphed in the curve 85 of FIG. 5C, a downward slope 99 and a subsequent steady pressure curve 97 are measured, but at the point in time of the breach 87 an upward slope 83 begins.

The measurement device 54, 64 is configured to compare the curve 85 with information stored in the memory module 56, 66 to identify this condition. In some embodiments, the measurement device 54, 64 uses an algorithm to make the comparison. In some embodiments, the measurement device 54, 64 then sends a signal to the communication device 58a-c, 74, and the communication device 58a-c, 74 generates an appropriate alert. Communication device 58a, for example a particular color LED, may be illuminated, or an LED may flash in a particular pattern or number of flashes. Communication device 58b may create a characteristic sound, or may generate an audio message in a number of languages. For example, the audio message may state, "System Leak." Communication device 58c may vibrate or heat in a characteristic pattern, for example, a certain number of repetitions or a certain frequency between repetitions. Upon receiving the alert, the user will check the components of the aspiration system 2 and either fix the breach or replace one or more of the components of the aspiration system 2. For example, in some cases, the communication device 58a-c, 74 may alert the user when the measurement device 54, 64 confirms a loss of applied vacuum or negative pressure, allowing the user to change or recharge the vacuum source 6, which has become depleted (e.g. by filling with blood and/or thrombus).

Figure 4D:
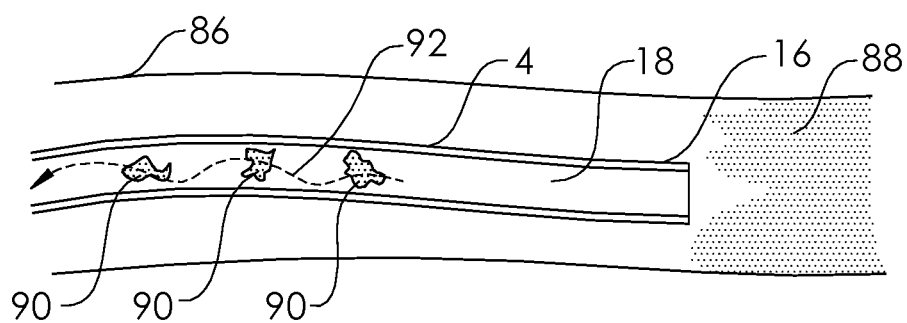
FIG. 4D is a sectional view of thrombi being aspirated through an aspiration catheter.

FIG. 4D illustrates the distal end 16 of the aspiration catheter 4 during the successful aspiration of pieces or portions 90 of the thrombus 88. In some cases, the pieces or portions 90 may follow a tortuous path 92, due to disturbances or collisions with the inner wall of the aspiration lumen 18 while being pulled through the aspiration lumen 18. In some cases, the pieces or portions 90 may catch and slip within the inner wall of the aspiration lumen 18, for example, do to variance of the inner diameter of the aspiration lumen 18 along the length. Either of these situations can cause a corresponding series of increases and decreases in the pressure being sensed by the pressure transducer 12, while the pieces or portions 90 are traveling through the aspiration lumen 18. As graphed in the curve 79 of FIG. 5D, a downward slope 99 and a subsequent steady pressure curve 97 are measured, but as the pieces or portions 90 of thrombus 88 travel down the aspiration lumen 18 of the aspiration catheter 4, a deviation 77 of fluid pressure comprising a one or more decreases and increases in pressure (increases and decreases in vacuum or negative pressure) is measured. As the pieces or portions 90 of thrombus 88 exit the proximal end of the aspiration lumen 18 of the aspiration catheter 4, a second steady pressure curve 75 is measured. The duration 67 of the deviation 77 is the amount of transit of the particular significant pieces or portions 90 of thrombus 88. The duration 67 can range quite a bit, but in some cases may be less than a second or up to about 30 seconds.

A single thrombus being aspirated may cause a single decrease in pressure (a blip) which is identified by the measurement device 54, 64. Subsequently, this occurrence may be communicated to the user by the communication device 58a-c, 74. When again additional pieces or portions 90 of thrombus 88 are aspirated into and travel down the aspiration lumen 18 of the aspiration catheter 4, another deviation 73 of fluid pressure comprising a one or more decreases and increases in pressure (increases and decreases in vacuum or negative pressure) is measured. At the end of the curve 79, the vacuum source 6 is shown filling completely with blood 96 and the pieces or portions 90 of thrombus 88, and so an upward slope 95 is measured.

The measurement device 54, 64 is configured to compare the curve 79 with information stored in the memory module 56, 66 to identify when the pieces or portions 90 of thrombus 88 are actively being aspirated, as in deviation 77 and deviation 73, and when the pieces or portions of thrombus 88 are not being actively, or substantially, aspirated, as in steady pressure curve 97, the steady pressure curve 75, and the steady pressure curve 71. In some embodiments, the measurement device 54, 64 uses an algorithm to make the comparison. In some embodiments, a pre-set pressure differential $\Delta P_2$ may be stored in the memory module 56, 66 as a threshold, whereby the measurement of a pressure difference 69 less than this threshold does not result in the measurement device 54, 64 commanding the communication device 58a-c, 74 to send a first type of alert via an alert signal 60a-c, 70. In some embodiments, when the pressure difference 69 is greater than (or greater than or equal to) the pre-set pressure differential $\Delta P_2$, the measurement device 54, 64 then sends a signal to the communication device 58a-c, 74, and the communication device 58a-c, 74 generates an appropriate alert. Communication device 58a, for example a particular color LED, may be illuminated, or an LED may flash in a particular pattern or number of flashes. In some embodiments, the communication device 58a may comprise a light whose intensity increases proportionally with the pressure. Communication device 58b may create a characteristic sound, or may generate an audio message in a number of languages. For example, the audio message may state, "Thrombus being aspirated." In some embodiments, communication device 58b may comprise one or more noises or beeps. In some embodiments, the communication device 58b may comprise a particular series of beeps corresponding to each different condition. For example, three short beeps may correspond to no thrombus being aspirated, while five long, loud beeps may correspond to a system leak. In some embodiments, a plurality of different tones (pitches) may be used to alert a user about different conditions. As an example, a low pitch sound may be used for a first condition (e.g. no thrombus being aspirated) and a second, higher pitch sound may be used for a second condition (e.g. a system leak). In some embodiments, a plurality of different tones may be used to alert a user about a first condition and a second plurality (e.g. in a different combination, or with additional tones) may be used to alert a user about a second condition. Communication device 58c may vibrate or heat in a characteristic pattern, for example, a certain number of repetitions or a certain frequency between repetitions. When the user realizes that the thrombus is being aspirated, the user may choose to advance (or retract) the aspiration catheter 4, for example with fluoroscopic visualization, along the length of the thrombus 88, in an attempt to continue the aspiration of the thrombus 88. In some cases, the user may choose to stop the advancement or retraction of the aspiration catheter 4 at a certain amount of time after the alert is generated, in order to allow the pieces or portions 90 of thrombus 88 to completely exit the aspiration lumen 18. When the measurement device 54, 64 identifies a subsequent steady pressure curve 75, 71 that follows a deviation 77, 73, the measurement device 54, 64 in some embodiments sends a signal that causes the communication device 58a-c, 74 to generate a second type of alert via an alert signal 60a-c, 70. For example, in some embodiments, communication device 58b may send an audio message that states, "Thrombus no longer being aspirated." When the user realizes that the thrombus is no longer being aspirated, the user may advance or retract the aspiration catheter, in an attempt to contact another portion of the thrombus 88 that can be aspirated. In some embodiments, the deviation 77 may be positively identified as a true deviation indicating thrombus being actively aspirated, pressure difference 69 is between about 700 pascal and about 1700 pascal. In some embodiments, the deviation 77 may be positively identified as a true deviation indicating thrombus being actively aspirated, pressure difference 69 is between about 1000 pascal and about 1300 pascal. In some embodiments, the deviation 77 may be positively identified as a true deviation indicating thrombus being actively aspirated, pressure difference 69 is about 1138 pascal. The pressure difference 69 may be measured by determining a baseline pressure 63 and a peak pressure 61 and determining the absolute value difference. For example:

Absolute value difference (AVD)=|(−89,631 pascal)−(−90,769 pascal)|=1138 pascal

Or for example:

Absolute value difference (AVD)=|(−43,710 pascal)−(−45,102 pascal)|=1281 pascal

The pressure difference 81 (FIG. 5B) may also represent a deviation that may be identified in a similar manner, after which the communication device 58a-c, 74 generates an appropriate alert, such as, "Clog condition."

Figure 5D:
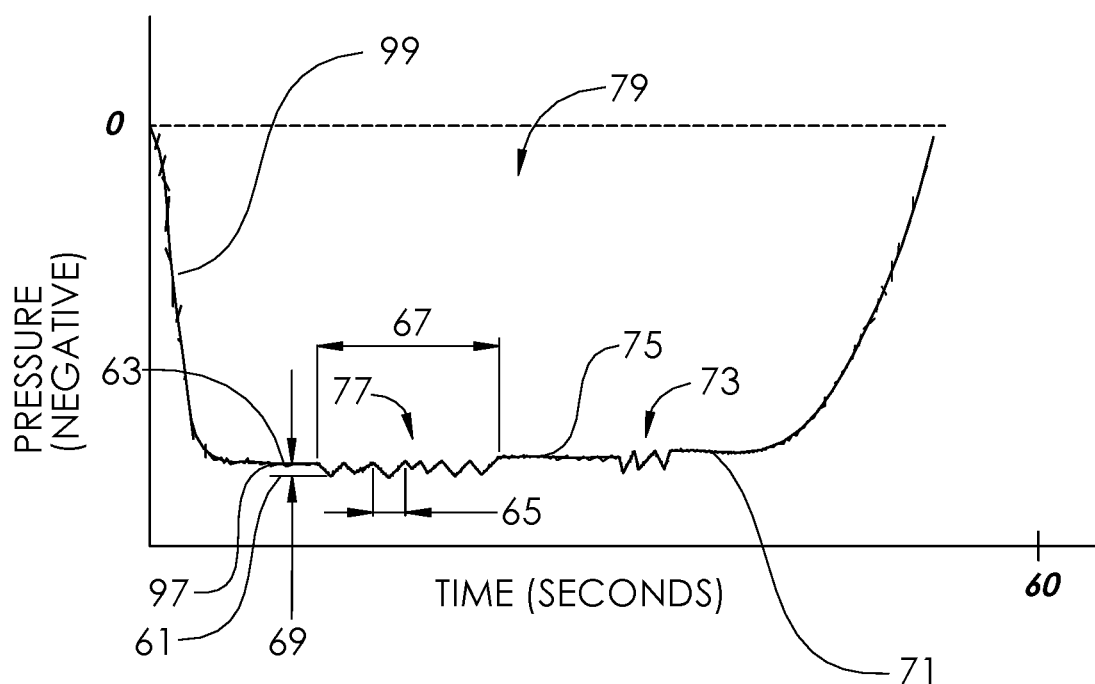
FIG. 5D is a graphic representation of pressure vs. time for the condition of FIG. 4D.

Because vacuum or negative pressure has a nominal value less than zero, the peak pressure 61, as shown in FIG. 5D, is actually a lower number than the baseline pressure 63. In some embodiments, the measurement device 54, 64 may also be configured to make a comparison, for example by using an algorithm, between a stored differential time ti and a duration 65 of a single one of the more or more decreases and increases in pressure in the deviation 77. For example, in some embodiments, the deviation may be positively identified as a true deviation indicating thrombus being actively aspirated, if the duration is between about 0.001 seconds and about 0.50 seconds. In some embodiments, the deviation may be positively identified as a true deviation indicating thrombus being actively aspirated, if the duration is between about 0.005 seconds and about 0.10 seconds. In some embodiments, the deviation may be positively identified as a true deviation indicating thrombus being actively aspirated if the duration is between about 0.05 seconds and about 0.20 seconds. In some embodiments, the measurement device 54, 64 is configured to recognize deviation 77 after two or more decreases and increases in pressure are measured. In some embodiments, the measurement device 54, 64 is configured to recognize deviation 77 after five or more decreases and increases in pressure are measured. In some embodiments, the measurement device 54, 64 is configured to recognize deviation 77 after ten or more decreases and increases in pressure are measured.

The baseline pressure 63 may in some embodiments be predetermined and may be stored in the memory module 56, 66. In some embodiments, the baseline pressure 63 may be stored in the memory module 56, 66 during the manufacture of the aspiration monitoring system 48, 62, 78, but the baseline pressure 63 may also be input by the user prior to or during a particular procedure. In some embodiments, the baseline pressure 63 may be determined or otherwise defined by the measurement device 54, 64, 76 based on averaging of a particular number of samples of measured pressure. The baseline pressure 63 may be constructed as a moving average, such as a running average or rolling average. Several types of moving average may be used, including a simple moving average, a cumulative moving average, a weighted moving average, or an exponential moving average. In any of these cases, a threshold may be determined by the measurement device 54, 64, 76 based on the determined baseline pressure 63 and a known pressure differential $\Delta P$. In some case, a pressure differential $\Delta P$ may even be calculated by the measurement device 54, 64, 76 based on the determined baseline pressure 63 and a known threshold.

Insertion of the pressure transducer 12 in line in either the embodiment of FIG. 2A or the embodiment of FIG. 2B does not measurably change performance characteristics of the aspiration system 2, because the cavity 42 is relatively short and has a relatively large inner diameter, and thus is not a significant source of fluid flow resistance. In some embodiments, the inner diameter may be between about 2.2 mm (0.086 inches) and about 3.2 mm (0.125 inches). In some embodiments, the measurement device 54, 64, 76 need not include a microprocessor, as pre-defined set points (e.g. for certain thresholds) may be included in firmware, microcontroller, or other locations. In some embodiments, including but not limited to the embodiment of FIG. 2B, the pressure transducer 12 may be an off-the-shelf blood pressure monitor system, which is modified or augmented with other components. In some embodiments an off-the-shelf blood pressure monitor system may be used as the output of the aspiration monitoring system 48, 62, 78. In some embodiments, an aspiration catheter 4 may have a pressure transducer in the distal end 16. This pressure transducer may be used as the pressure transducer 12 of the aspiration monitoring system 48, 62, 78. In some embodiments, a pressure sensor may be located within a Tuohy-Borst valve, and introducer sheath, a guiding catheter, or another component of the system through which is in fluid communication with the aspiration lumen 18. In some embodiments, the pressure sensor may be located anywhere within the aspiration lumen of the aspiration catheter.

In some embodiments, instead of an LED, the visual alert is provided by a communication device 58a comprising a display which displays visual messages of text in a particular language, for example, "Thrombus encountered," "No thrombus encountered," "Clog condition," "System leak," "Loss of vacuum," "Thrombus being aspirated," or "Thrombus no longer being aspirated." The visual messages may be combined with any of the other alert signals 60a-c, 70 described herein. The aspiration monitoring system 48, 62, 78 described herein give real time awareness to users performing aspiration procedures, such as the removal of thrombus via an aspiration system 2. One skilled in the art will recognize that by knowing the real time condition of the aspiration system 2, the user is able to immediately make changes to the procedure in order to optimize results, increase safety for the patient and/or medical personnel, reduce costs (e.g. number of vacuum sources 6 required), and reduce procedure time (also a cost benefit). Because the user is typically performing multiple tasks during an aspiration procedure, the sensory aid provided by the aspiration monitoring system 48, 62, 78 allows the user to focus on these tasks without having to continually attempt to monitor conditions which are often difficult to visually monitor. The user may also modify and control the aspiration monitoring system 48, 62, 78 via an input 59 (FIG. 2B), which may comprise a data entry module, keyboard, or a series of buttons with a display. The input 59 may in some embodiments comprise an auditory input which accepts voice commands. Alternatively, the user may input information and control the aspiration monitoring system, 48, 62, 78 remotely. Some of the alerts which the user may select or deselect in the aspiration monitoring system 48, 62, 78 include, but are not limited to: whether the aspiration system 2 is potentially blocked or clogged, or is flowing normally; whether thrombus has been contacted or not; whether a clog has occurred; whether the vacuum source 6 is adequate, or whether it has been depleted and requires replacement; whether there is a leak in the aspiration system 2; whether setup or connection of the components of the aspiration system 2 was done correctly or incorrectly; whether to advance the catheter distally; whether to retract the catheter; whether to continue moving the catheter at the same speed; whether to increase or decrease the speed of catheter advancement; whether thrombus is actively being aspirated; and whether thrombus stops being actively aspirated. As the user becomes familiar with the aspiration monitoring system 48, 62, 78, the user may even begin to make certain responses to the system subconsciously. For example, a user may automatically pull back the catheter upon hearing a clot warning signal (e.g., three beeps), and may automatically begin advancing the catheter and/or start fluoroscopic visualization upon hearing a free blood flow signal (e.g., two beeps). By being "at one" with the aspiration monitoring system 48, 62, 78 and the catheter, the user optimizes reactions and actions. This may be helpful improving the skill of having the catheter take a small "bite" of thrombus, and following the "bite" with a "chaser" of some fast flowing blood, the clean/open the lumen. This would also help minimize the chance of clogging, and would in turn reduce maintenance or corrections of the system (removing the catheter, flushing the lumen outside of the patient, replacing the catheter). The overall experience for the user is improved, as the user receives instant gratification for good results, and is instantly notified of errors or instances for concern.

In some embodiments, alternate power sources may be used, for example, standard AC power with or without an AC/DC convertor; direct connection to existing equipment (e.g. vacuum pumps, etc.); solar power. The aspiration monitoring system 48, 62, 78 may be packaged sterile or may be resterilizable by techniques known by those skilled in the art. In some embodiments, flow or volume gauges may be used in conjunction with or instead of the pressure gauge 12, in order to determine, for example, a clog, or a change in the amount of vacuum or negative pressure. In some embodiments, the input 59, power module 72, measurement device 64, memory module 66, and communication device 68 (e.g., of FIG. 2B) may all be incorporated into a single external device, which may in some cases be sold separately. In some embodiments, the external device may also have other functions, such as providing aspiration and/or injection (negative pressure and/or positive pressure) to a catheter. In other embodiments, the external device may comprise some, but not all of the input 59, power module 72, measurement device 64, memory module 66, and communication device 68. For example, in some embodiments, a communication device 58 (FIG. 2A) may replace the external communication device 68, and may be carried on the aspiration monitoring system 48, while the input 59, power module 72, measurement device 64, memory module 66 (FIG. 2B) are incorporated into a single external device. A number of combinations are possible, as described in more detail herein.

Though aspiration of thrombus has been described in detail, the aspiration monitoring system 48, 62, 78 has utility in any aspiration application wherein heterogeneous media is being aspirated. This may include the aspiration of emboli (including not thrombotic emboli) from ducts, vessels, or cavities of the body, or even from solid or semi-solid portions of the body, including, but not limited to, portions of fat, breasts, and cancerous tissue.

In some embodiments, the aspiration system 2 is be provided to the user as a kit with all or several of the components described, while in other embodiments, only the aspiration monitoring system 48 is provided. Though discussion herein includes embodiments for aspiration of thrombus and blood, the definition of the word "fluid" should be understood throughout to comprise liquids and gases.

In some embodiments, an additional or alternate sensor may be used to monitor flow conditions for the notification of the user, including, but not limited to: a Doppler sensor, an infrared sensor, or a laser flow detection device. In some embodiments, an externally-attached Doppler sensor may be employed. In some embodiments, an infrared sensor or a laser flow detection device may be employed around the extension tubing 10.

Additional embodiments allow real time communication of the particular value of fluid pressure (for example the level of vacuum or negative pressure) measured by the sensor 50. For example, as the negative pressure gradient increases, an audible sound may increase in sound intensity or in sound pressure level (dB) proportionally. Or, as the negative pressure gradient increases, the pitch (frequency) of an audible sound may made to rise, and as the negative pressure gradient decreases, the pitch may be made to fall (as does a siren). By controlling either the amplitude of a signal or the frequency of a signal by making them proportional to the fluid pressure, the system can give a user a real-time sense of whether the negative pressure gradient is increasing, decreasing, or staying the same, as well as whether the pressure is close to zero or quite different from zero. When an audible sound is used as the signal, the user's eyes can remain focused on the procedure, whether by viewing a monitor of fluoroscopic images, the patient, or a separate piece of equipment.

Figure 6:
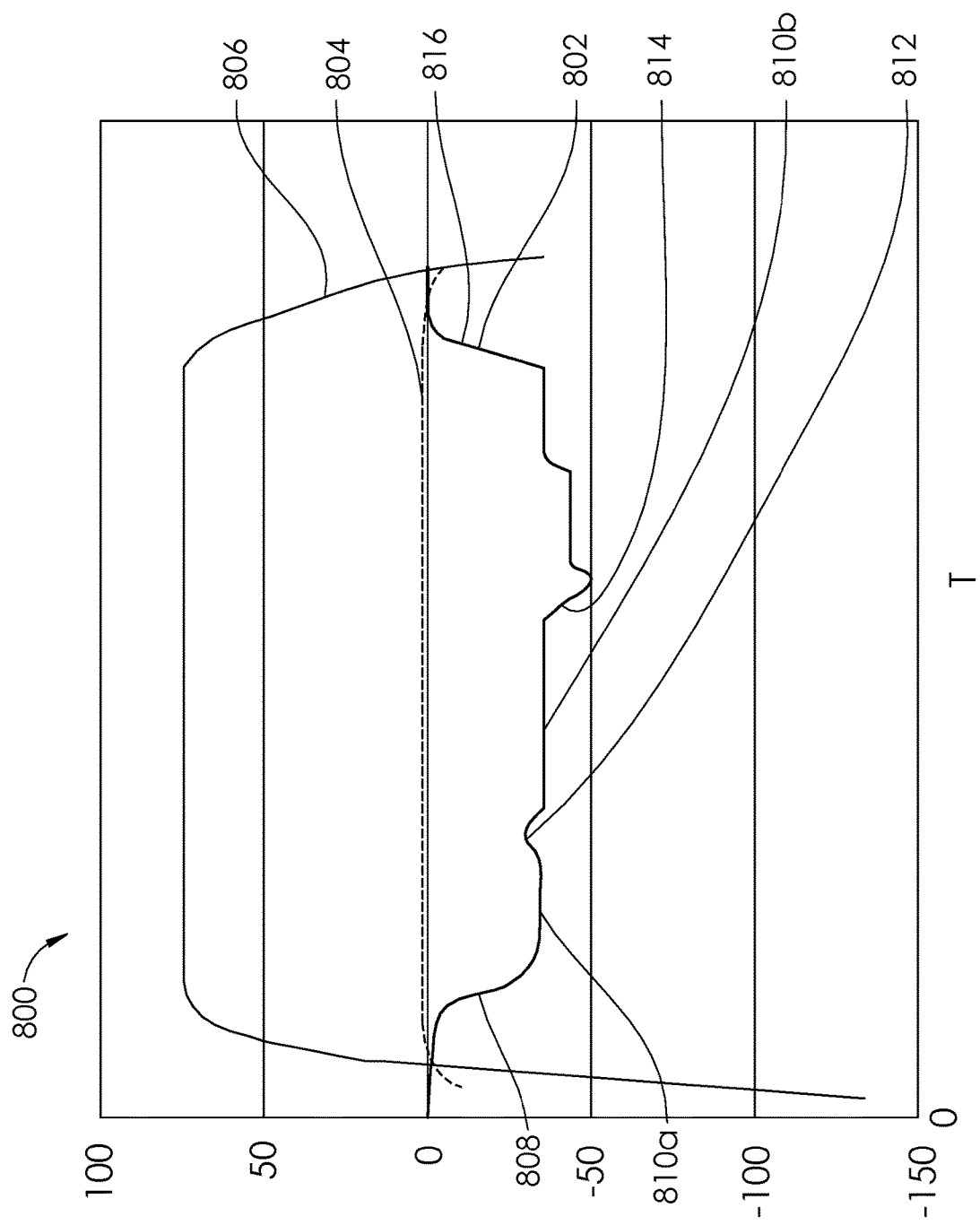
FIG. 6 is a graphic representation of pressure and an output sound amplitude vs. time for an embodiment of an aspiration monitoring system.

FIG. 6 illustrates a graph 800 of time (x-axis) and multiple variables (y-axis). A pressure curve 802 shows a vacuum or negative pressure being applied at a pressure drop 808, and a maintenance of vacuum or negative pressure 810a with a decrease in vacuum or negative pressure 812 and an increase in vacuum or negative pressure 814. A removal of vacuum or negative pressure 816 is shown at the end of the pressure curve 802. In some cases, the decrease in vacuum or negative pressure 812 may be caused by a temporary or permanent leak or detachment within the system or by filling of the vacuum source (e.g., syringe). In FIG. 6, the decrease in vacuum or negative pressure 812 is shown as temporary, as a subsequent maintenance of vacuum or negative pressure 810b is illustrated. The increase in vacuum or negative pressure 814 may in some cases be caused by thrombus being sucked through the system and may occur for a short or long amount of time, and may be steady or intermittent. Though the amount of vacuum or negative pressure applied in the pressure curve 802 varies, in some embodiments, it may only be desirable to show to a user only whether the vacuum or negative pressure is generally being applied or not being applied. The measurement device 54, 64, 76 may be configured to apply an algorithm to the signal from the vacuum sensor 50 (pressure sensor) that calculates an inverse value, represented by the dashed curve 804. The measurement device 54, 64, 76 further may apply an algorithm that increases, amplifies or otherwise augments the signal for ease of identification, for example within the human range of audible identification (hearing). For example, a modified signal curve 806 may be created that has the following general mathematical relationship with the signal from the vacuum sensor 50 represented by the pressure curve 802.

Sound Pressure Level (dB)=$A+B\times(1/\text{fluid pressure})$ where A is a first constant, and
B is a second constant In one particular example, a modified signal curve 806 may be created that has the following mathematical relationship with the signal from the vacuum sensor 50 represented by the pressure curve 802.

Sound Pressure Level (dB)=$70+20\times(1/\text{fluid pressure (kPa)})$ where dB is units in decibels, and
kPa is units of kiloPascal The modified signal curve 806 may be constructed of an algorithm such that the sound pressure level drops below the audible level of human hearing at relatively small amounts of vacuum or negative pressure, thus giving the user an "on/off" awareness of the vacuum or negative pressure being applied.

Figure 7:
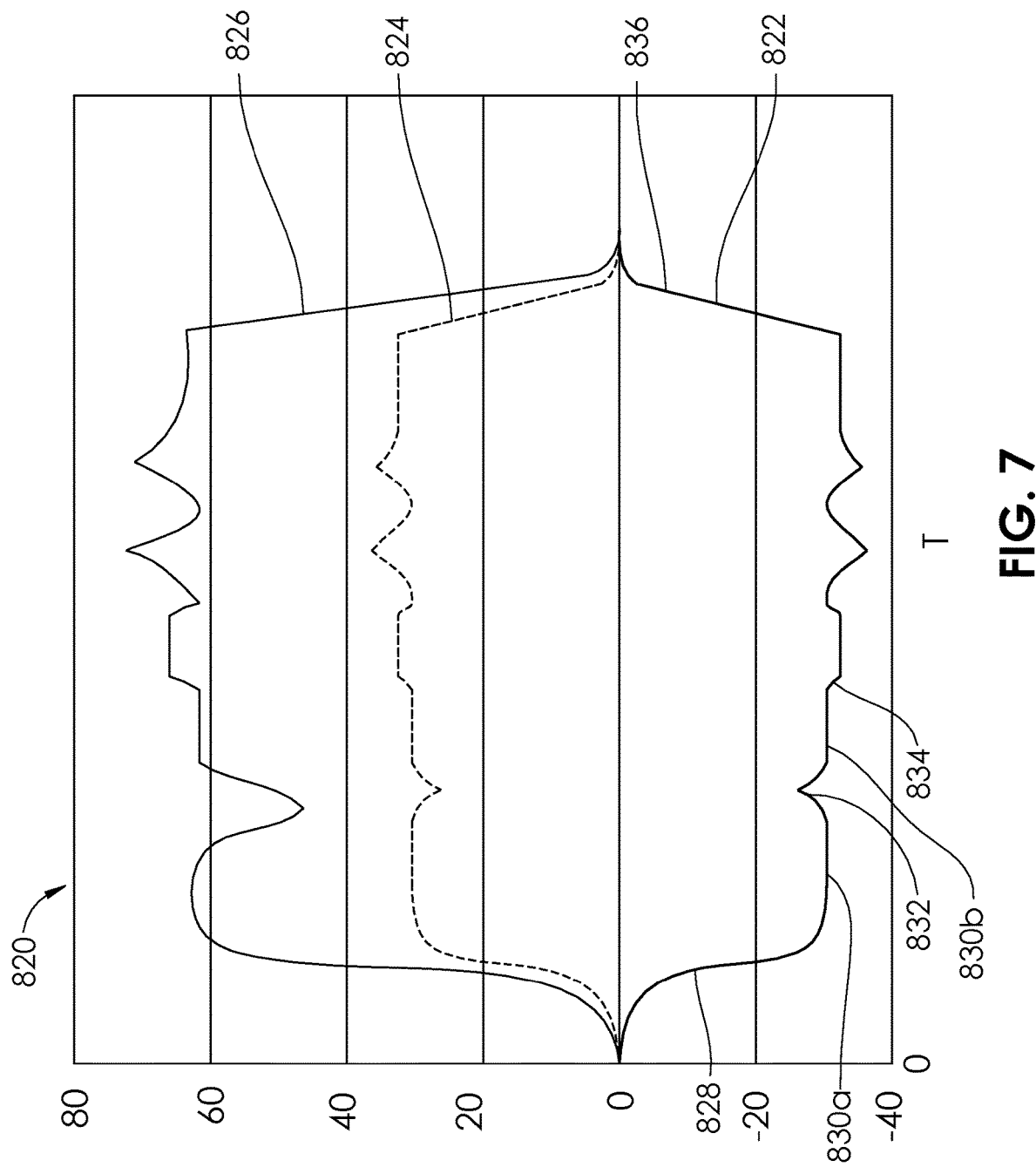
FIG. 7 is a graphic representation of pressure and an output sound amplitude vs. time for an embodiment of an aspiration monitoring system.

FIG. 7 illustrates a graph 820 of time (x-axis) and multiple variables (y-axis). A pressure curve 822 shows a vacuum or negative pressure being applied at a pressure drop 828, and a maintenance of vacuum or negative pressure 830a with a decrease in vacuum or negative pressure 832 and an increase in vacuum or negative pressure 834. A removal of vacuum or negative pressure 836 is shown at the end of the pressure curve 822. In some cases, the decrease in vacuum or negative pressure 832 may be caused by a temporary or permanent leak or detachment within the system or by filling of the vacuum source (e.g., syringe). In FIG. 7, the decrease in vacuum or negative pressure 832 is shown as temporary, as a subsequent maintenance of vacuum or negative pressure 830b is illustrated. The increase in vacuum or negative pressure 834 may in some cases be caused by thrombus being sucked through the system and may occur for a short or long amount of time, and may be steady or intermittent. In some cases or configurations, it may be desirable for the user to have a very specific real-time or close to real-time characterization of the amount or level of vacuum (negative pressure gradient in general) being applied. The measurement device 54, 64, 76 may be configured to apply an algorithm to the signal from the vacuum sensor 50 (pressure sensor) that calculates an absolute value, represented by the dashed curve 824. The measurement device 54, 64, 76 further may apply an algorithm that increases, amplifies or otherwise augments the signal for ease of identification, for example within the human range of audible identification (hearing). For example, a modified signal curve 826 may be created that has the following general mathematical relationship with the signal from the vacuum sensor 50 represented by the pressure curve 822.

Sound Pressure Level (dB)=$A+B\times|\text{(fluid pressure)}|$ where A is a first constant, and
B is a second constant In one particular example, a modified signal curve 826 may be created that has the following mathematical relationship with the signal from the vacuum sensor 50 represented by the pressure curve 822.

$$\text{Sound Pressure Level (dB)} = 2 \times |(\text{fluid pressure (kPa)})|$$

where dB is units in decibels and,
kPa is units of kiloPascal

The modified signal curve 826 may be constructed of an algorithm such that the sound pressure level seems to the user to follow the amount of vacuum or negative pressure being applied, thus becoming louder as the vacuum or negative pressure is increased.

Figure 8:
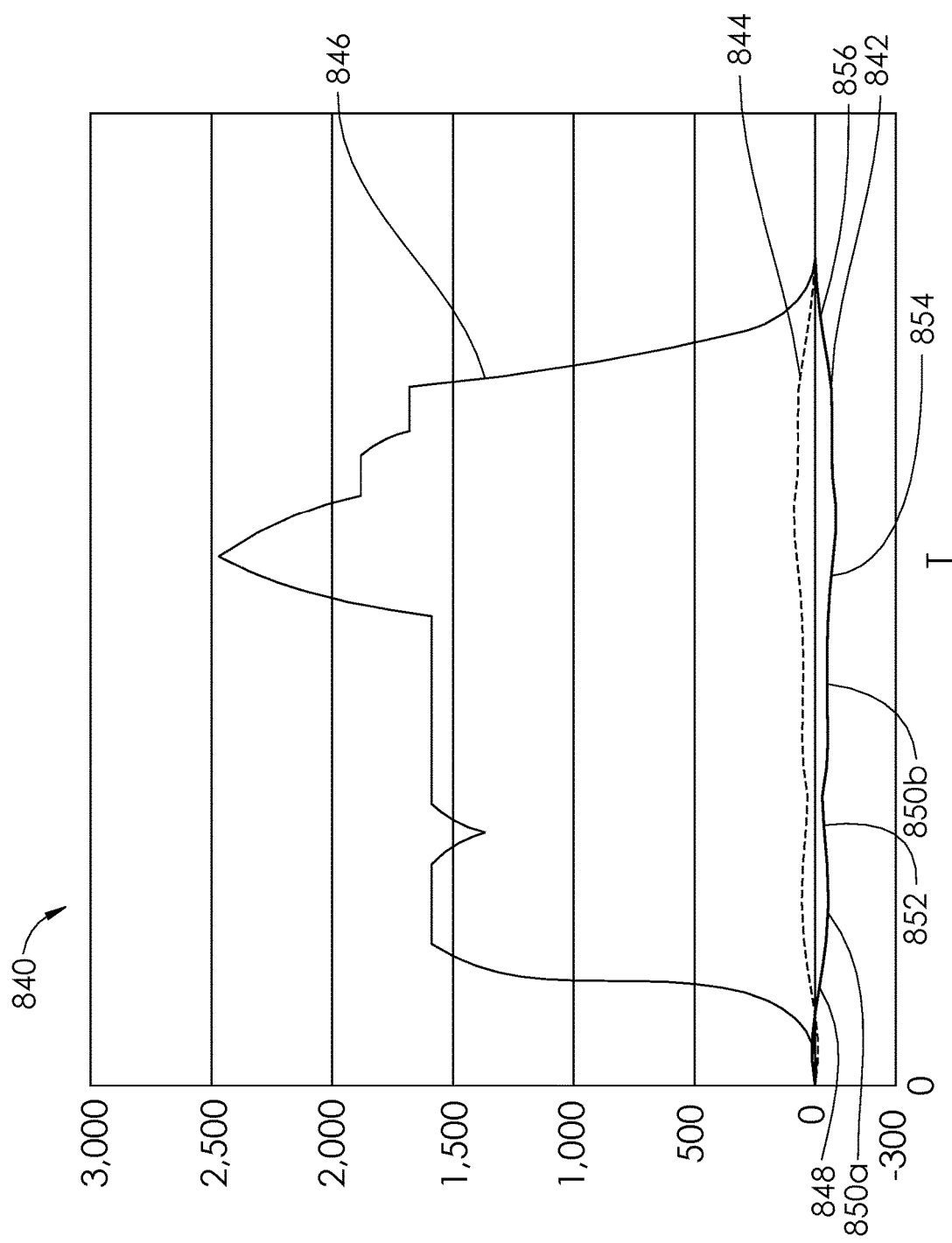
FIG. 8 is a graphic representation of pressure and an output sound frequency vs. time for an embodiment of an aspiration monitoring system.

FIG. 8 illustrates a graph 840 of time (x-axis) and multiple variables (y-axis). A pressure curve 842 shows a vacuum or negative pressure being applied at a pressure drop 848, and a maintenance of vacuum or negative pressure 850a with a decrease in vacuum or negative pressure 852 and an increase in vacuum or negative pressure 854. A removal of vacuum or negative pressure 856 is shown at the end of the pressure curve 842. In some cases, the decrease in vacuum or negative pressure 852 may be caused by a temporary or permanent leak or detachment within the system or by filling of the vacuum source (e.g., syringe). In FIG. 8, the decrease in vacuum or negative pressure 852 is shown as temporary, as a subsequent maintenance of vacuum or negative pressure 850b is illustrated. The increase in vacuum or negative pressure 854 may in some cases be caused by thrombus being sucked through the system and may occur for a short or long amount of time, and may be steady or intermittent. As mentioned, in some cases or configurations, it may be desirable for the user to have a very specific real-time or close to real-time characterization of the amount or level of vacuum (negative pressure gradient in general) being applied. The measurement device 54, 64, 76 may be configured to apply an algorithm to the signal from the vacuum sensor 50 (pressure sensor) that calculates an absolute value, represented by the dashed curve 844. The measurement device 54, 64, 76 further may apply an algorithm that determines a frequency of an audible sound (or pitch), for example within the human range of audible identification (hearing), that varies within the human range of audible frequencies. For example, a modified signal curve 846 may be created that has the following general mathematical relationship with the signal from the vacuum sensor 50 represented by the pressure curve 842.

$$\text{Sound Frequency (Hz)} = A + B \times |(\text{fluid pressure})|$$

where A is a first constant, and
B is a second constant

In one particular example, a modified signal curve 846 may be created that has the following mathematical relationship with the signal from the vacuum sensor 50 represented by the pressure curve 842.

$$\text{Sound Frequency (Hz)} = 50 \times |(\text{fluid pressure (kPa)})|$$

where Hz is Hertz (1/second), and
kPa is units of kiloPascal

The modified signal curve 846 may be constructed of an algorithm such that the sound frequency seems to the user to follow the amount of vacuum or negative pressure being applied. In this embodiment, the pitch of the sound becomes "higher" when vacuum is increased (fluid pressure decreases), and "lower" when the vacuum or negative pressure is decreased. Alternatively, the opposite may instead by chosen, wherein the pitch of the sound becomes lower when vacuum or negative pressure is increased.

Figure 9:
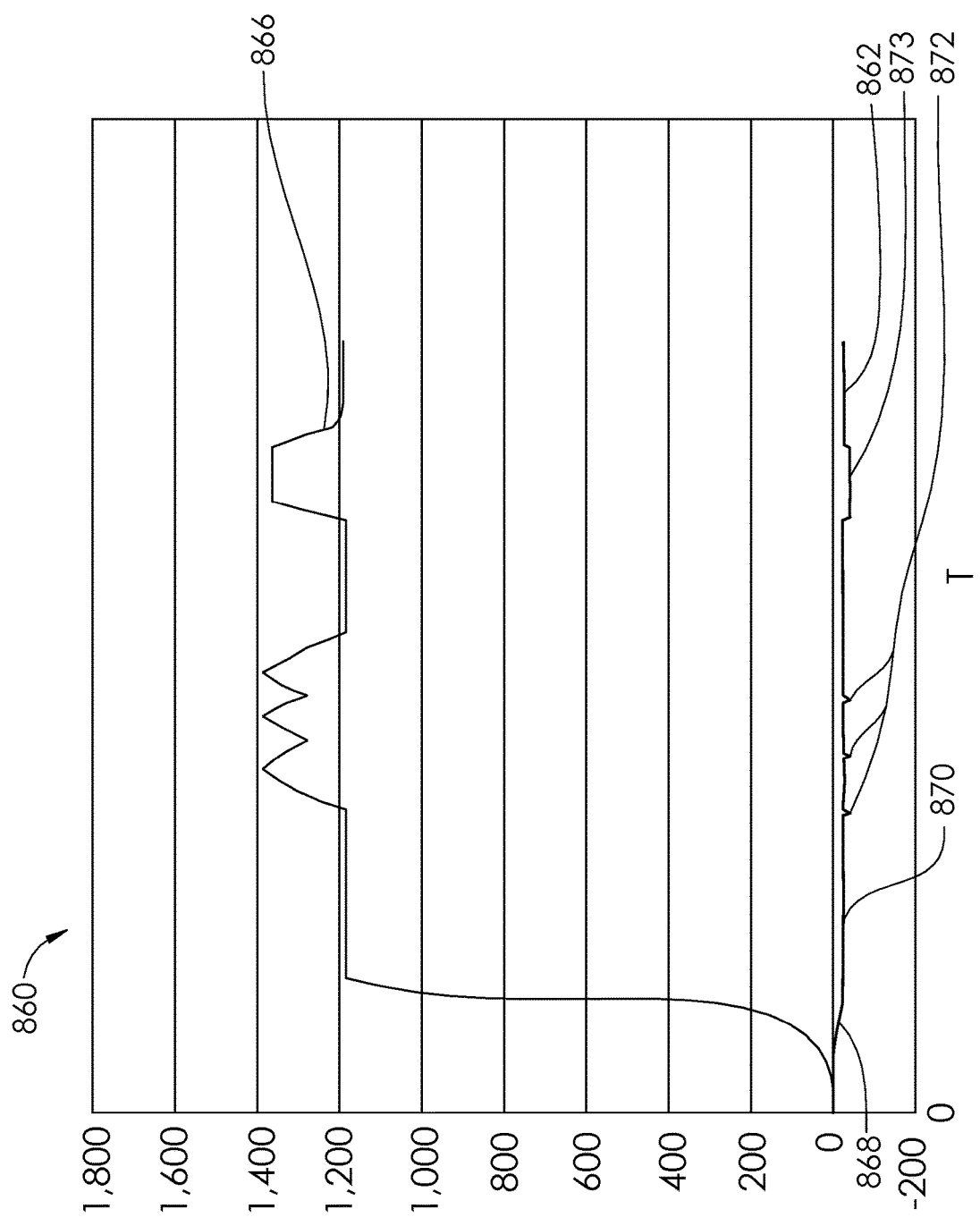
FIG. 9 is a graphic representation of pressure and an output of sound frequency vs. time for an embodiment of an aspiration monitoring system.

FIG. 9 illustrates a graph 860 of time (x-axis) and multiple variables (y-axis). A pressure curve 862 shows a vacuum or negative pressure being applied at a pressure drop 868, and a maintenance of vacuum or negative pressure 870 with a one or more decreases and increases in pressure 872. These one or more decreases and increases in pressure 872 (or increases and decreases in vacuum or negative pressure) may represent, in some instances, clot being sucked through aspiration lumen of an aspiration catheter. In some cases, a single decrease in pressure 873 (increase in vacuum or negative pressure) may occur. The single decrease in pressure 873 may in some cases be extended in duration, as shown in FIG. 9, as may any one of the one or more decreases and increases in pressure 872. In some cases or configurations, it may be desirable for the user to have a very specific real-time or close to real-time characterization of the instances when these small perturbations are occurring, as they may correspond to the catheter finding and aspirating a portion of thrombus. The measurement device 54, 64, 76 be configured to apply an algorithm that determines a frequency of an audible sound (or pitch), for example within the human range of audible identification (hearing), that varies within the human range of audible frequencies. For example, a modified signal curve 866 may be created that has the following general mathematical relationship with the signal from the vacuum sensor 50 represented by the pressure curve 862.

$$\text{Sound Frequency (Hz)} = A + B \times |(\text{fluid pressure})|$$

where A is a first constant, and
B is a second constant

In one particular example, a modified signal curve 866 may be created that has the following mathematical relationship with the signal from the vacuum sensor 50 represented by the pressure curve 862.

$$\text{Sound Frequency (Hz)} = 40 \times |(\text{fluid pressure (kPa)})|$$

where Hz is Hertz (1/second), and
kPa is units of kiloPascal

It should be noted that in this equation, no absolute value is used, but rather the actual value of fluid pressure. Or in some cases, an absolute (or negative) value may be used.

The modified signal curve 866 may be constructed of an algorithm such that the sound maintains a steady pitch until the clot is being sucked through the catheter, at which time the pitch changes slightly, but distinctly, away from a steady pitch. For example, in some embodiments, the pitch may change between about 20 Hz and about 2000 Hz to correspond to a pressure change of between about one kPa to about two kPa, or between about 40 Hz and about 80 Hz.

In any of the examples, the modification of signals may include any type of signal conditioning or signal modification that may be performed, including, but not limited to filtering, amplification, or isolation. The modified signal curve 806, 826, 846, 866 is used to determine the output signal to be generated by the communication device 58, 68, 74. As mentioned, if the output signal of the communication device 58, 68, 74 is configured to be an audible sound, the sound pressure level may be varied, or the sound frequency may be varied. In some embodiments, the output signal of the communication device 58, 68, 74 may have both its sound pressure level and sound frequency varied. In one embodiment, the sound frequency varies continuously in proportion to fluid pressure, but at one or more particular thresholds of fluid pressure, the sound pressure level may be caused to vary quite suddenly and strikingly. Thus there is a two-part communication occurring, a continuous real-time status indicator, with an intermittent, alert indicator (failure, danger, etc.). In some cases, the continuous real-time status indicator may represent a first continuous signal and the alert indicator may represent a second alert signal. In other cases, the continuous real-time status indicator and the alert indicator may be combined or integrated into the same signal. In some embodiments, other characteristics of psychoacoustics may be varied using variable sound generation devices. In some embodiments, the spectral envelope may be varied. In some embodiments, timbre may be changed to varies levels between light and dark, warm and harsh, or different noise "colors" (pink, white, blue, black, etc.).

Though an audible output from the communication device 58, 68, 74 has been described with the examples from FIGS. 6-9, other communication signals may be used, including visual or tactile signals. Tactile signals may also include vibration devices or heat generation devices, either of which could be varied (as described) in relation to the measured fluid pressure. Either the amplitude of the frequency could analogously be varied in communication signals that include signals other than the audible signals already described. For example, the intensity of a light can be varied, or the frequency (e.g., color) of a light can be varied. The amplitude of displacement of a vibration device can be varied (or other techniques that vary the vibration intensity) or the frequency of the vibration can be varied.

In some cases, a pseudo-continuous analog may be used in place of a truly variable output. For example, instead of a single light whose intensity is continuously varied, an array of multiple lights, for example and array comprising multiple LEDs, may be used, with an increased number of LEDs being lit when the level of vacuum or negative pressure is increased, and a decreased number of LEDs being lit when the level of vacuum or negative pressure is decreased. The same may be possible with an array comprising multiple vibrating elements, wherein more elements begin vibrating upon an increase or decrease, depending on the application, of fluid pressure.

In any of the embodiments described in relation to FIGS. 6-9, the equations for sound pressure level or for sound frequency which depend on fluid pressure as a variable, may depend on actual measured fluid pressure, or an absolute value of actual measured fluid pressure, but may also use measured fluid pressure in an alternative manner. For example, with a baseline pressure 63 either pre-set, pre-determined, or determined or calculated by any other method (averaging, etc.), the differential between the measured pressure and the baseline pressure 63 may be used as the variable on which to base the particular dependency (e.g., proportionality).

Thus, a base mathematical relationship used with the proportionality described with respect to the embodiment of FIG. 6 may be represented as:

$$\text{Sound Pressure Level (dB)} = A + B \times (1/\Delta P)$$

where A is a first constant,
B is a second constant, and
ΔP is a difference or differential between a baseline pressure and a measured fluid pressure.

Likewise, a base mathematical relationship used with the proportionality described with respect to the embodiment of FIG. 7 may be represented as:

$$\text{Sound Pressure Level (dB)} = A + B \times |(\Delta P)|$$

where A is a first constant,
B is a second constant, and
ΔP is a difference or differential between a baseline pressure and a measured fluid pressure.

Likewise, a base mathematical relationship used with the proportionality described with respect to the embodiment of FIG. 8 may be represented as:

$$\text{Sound Frequency (Hz)} = A + B \times |(\Delta P)|$$

where A is a first constant,
B is a second constant, and
ΔP is a difference or differential between a baseline pressure and a measured fluid pressure.

Likewise, a base mathematical relationship used with the proportionality described with respect to the embodiment of FIG. 9 may be represented as:

$$\text{Sound Frequency (Hz)} = A + B \times (\Delta P)$$

where A is a first constant,
B is a second constant, and
ΔP is a difference or differential between a baseline pressure and a measured fluid pressure.

Figure 10:
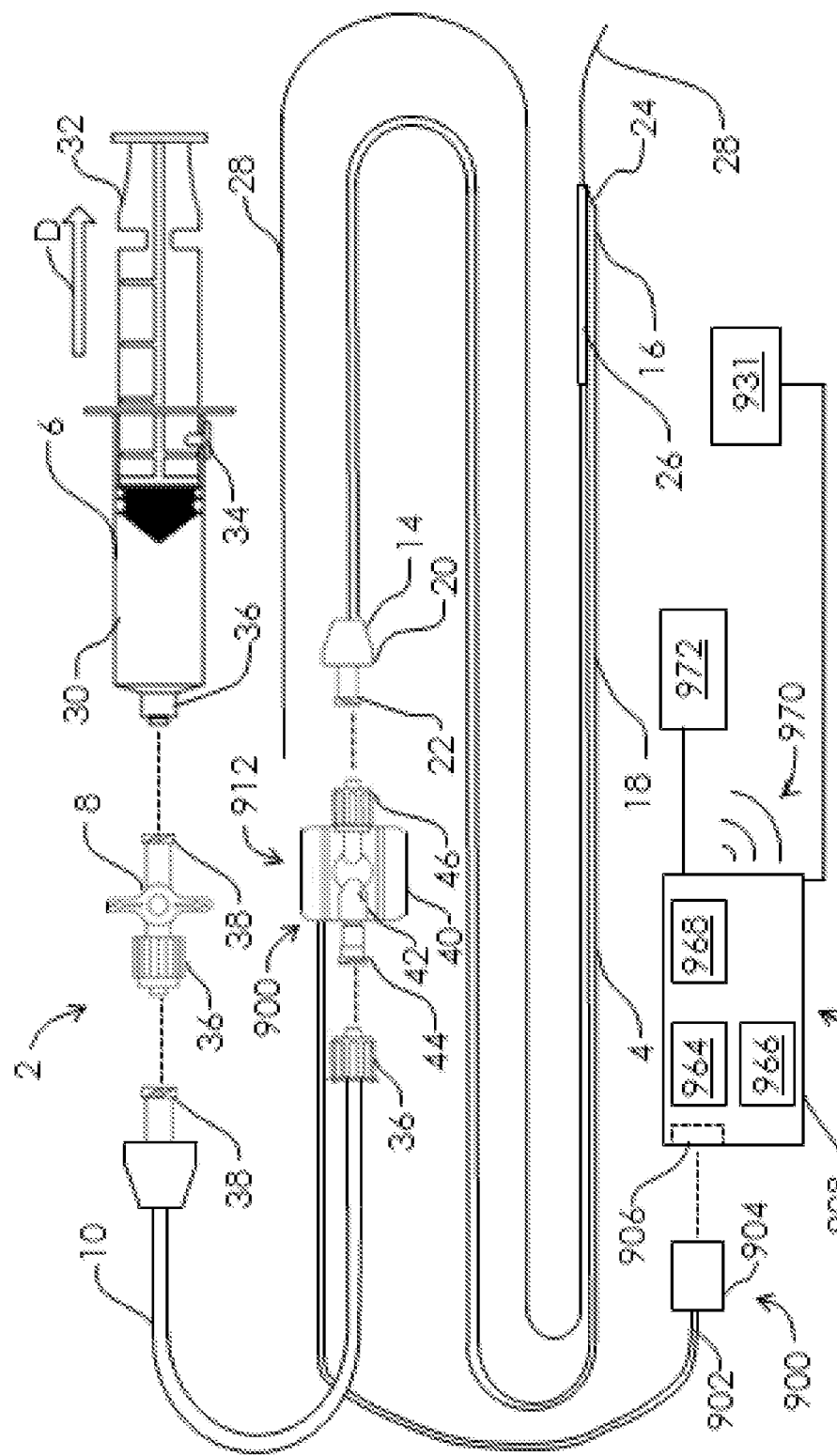
FIG. 10 is a plan view of a system for aspiration according to another embodiment of the present disclosure.

A pressure transducer 912 of an aspiration monitoring system 900 is illustrated in FIG. 10, for coupling to an aspiration system including an aspiration catheter 4. The pressure transducer 912 includes a housing 40, a first port 44, a second port 46 and a cable 902 for carrying a signal. The cable 902 includes an interface 904, or plug, which is configured to connect to a port 906 of a console 908 of the aspiration monitoring system 900. The housing 40 of the pressure transducer 912 includes a cavity 42 extending between the first port 44 and the second port 46. The console 908 is powered by a power module 972, which is connected to the console 908, and may comprise a source of AC or DC power. The console 908 may include a measurement device 964, a memory module 966 and a communication device 968, which may be coupled to each other as described in the prior embodiments and configured such that the communication device 968 is capable of creating a signal 970, which may be an alert signal, a continuous signal, a combined signal, or other type of signal. The console 908 may also include wired or wireless connections to other interfaces or displays which may be found in health care sites, such as a monitor 931. In some embodiments, the monitor 931 may be a monitor which also displays fluoroscopy or angiogram images, or a monitor which also displays electrocardiography or blood pressure graphics or other information. The monitor 931 may have a portion that maintains the status of the aspiration. For example, it may read "Thrombus being aspirated" or "No thrombus detected." The pressure transducer 912 (housing 40, ports 44, 46, cable 902, interface 904) may be sold sterile, and may be configured to output a signal that is received by the console 908, for example the measurement device 964 of the console 908. The pressure transducer 912 may have its own internal source of power (e.g., the battery 52 in FIG. 2A), or may be powered by its connection to the console 908, or alternatively, by its connection to the aspiration catheter 4, or even the extension tubing 10. In some embodiments, the console 908 may be configured to identify and/or recognize the pressure transducer 912, for example, to recognize the particular model of the pressure transducer 912. In some embodiments, the console 908 may be configured to measure a resistance between two electrical contacts in the pressure transducer 912 in order to identify the type (e.g., model) of pressure transducer. In some embodiments, the console 908 may be configured to read an RFID chip on the pressure transducer 912. The console 908 may also be configured to connect to two or more different models of pressure transducer. The port 906, may comprise at least one port, which may comprise two or more ports, each port configured to allow connection of a different model of pressure transducer.

An aspiration system 1000 in FIG. 11 includes an aspiration console 1001 having a connector 1002, or hub, (e.g., male luer) for connecting to an aspiration catheter 4, for example, to a connector 22 (e.g., female luer) of the aspiration catheter 4. The aspiration console 1001 is powered by a power module 972, which is connected to the aspiration console 1001, and may comprise a source of AC or DC power. The aspiration console 1001 may include a canister 1006 for collecting the aspirated materials, and may include a vacuum pump 1004 for creating a vacuum or negative pressure with which to create the aspiration. Tubing 1008 may be connected between the canister 1006 and the connector 1002. In some embodiments, the canister 1006 is removable or replaceable. An aspiration monitoring system 900 includes a pressure sensor 1010 (e.g., a vacuum sensor) in fluid communication with the tubing 1008. The tubing 1008 may instead comprise a lumen formed inside fabricated parts. The aspiration monitoring system 900 is shown in more detail in FIG. 12, and may include some or all of the features described in relation to FIG. 10. The aspiration console 1001 may also include wired or wireless connections to other interfaces or displays which may be found in health care sites, such as a monitor 931. In some embodiments, the monitor 931 may be a monitor which also displays fluoroscopy or angiogram images, or a monitor which also displays electrocardiography or blood pressure graphics or other information. By combining all communication related to the procedure on or at a single monitor or single monitor location, uninterrupted focus can be achieved by the user, who may be freely dedicated to the safe advancement and placement of the aspiration catheter in proximity to the thrombus.

A system for forced (or assisted) aspiration 1100 in FIG. 13 includes an aspiration/injection console 1101 having a first connector 1016, or hub, (e.g., male luer) for connecting to an injection lumen 1020 of a forced aspiration catheter 1013, and a second connector 1012, or hub (e.g., male luer) for connecting to an aspiration lumen 1018 of the forced aspiration catheter 1013. The first connector 1016 is configured to connect to connector 1024 (e.g., female luer) of a y-connector 1022 and the second connector 1012 is configured to connect to connector 1026 of the y-connector 1022 at a proximal end 14 of the forced aspiration catheter 1013. The aspiration/injection console 1101 is powered by a power module 972, which is connected to the aspiration console 1101, and may comprise a source of AC or DC power. The aspiration console 1101 may include a canister 1106 for collecting the aspirated materials, and may include a vacuum pump 1104 for creating a vacuum or negative pressure with which to create the aspiration. Tubing 1108 may be connected between the canister 1106 and the connector 1012. A positive pressure pump 1014 is coupled to a fluid source 1032 (e.g., a saline bag) and is configured to inject infusate out the connector 1016 at a high pressure. An aspiration monitoring system 900 includes a pressure sensor 1110 (e.g., a vacuum sensor) in fluid communication with the tubing 1108. The tubing 1108 may instead comprise a lumen formed inside fabricated parts. The aspiration monitoring system 900 is shown in more detail in FIG. 14, and may include some or all of the features described in relation to FIG. 10. At a distal end 16 of the forced aspiration catheter 1013, the injection lumen 1020 terminates in an orifice 1028, which is configured to create a jet 1030 formed from the high pressure infusate exiting the orifice 1028. The jet 1030 enters the aspiration lumen 1018, thus creating suction at the distal end 16 of the forced aspiration catheter 1013, which forces materials (e.g., thrombus) into the aspiration lumen 1018, and into the canister 1106. The aspiration/injection console 1101 may also include wired or wireless connections to other interfaces or displays which may be found in health care sites, such as a monitor 931. In some embodiments, the monitor 931 may be a monitor which also displays fluoroscopy or angiogram images, or a monitor which also displays electrocardiography or blood pressure graphics or other information.

In an alternative embodiment, the forced aspiration catheter 1013 of the aspiration catheter 4 may have an additional lumen or guide channel for placement of an additional device or tool. In some embodiments, the guidewire lumen 26 may be used as this additional lumen, and may extend the entire length or most of the length of the catheter, so that the lumen is accessible from the proximal end 14. The additional device or tool may comprise a laser fiber, a mechanical screw, a vibrating wire or a variety of other modalities for disrupting thrombus or other material.

In any of the embodiments presented, the system may be configured so that most or all of the components are supplied together. For example, a catheter and an aspiration monitoring system that are permanently attached to each other. In some embodiments, the aspiration catheter and/or the aspiration monitoring system may include configurations that purposely make it difficult to reprocess (e.g., clean or resterilize) them, thus protecting from potential uses that are not recommended or warranted, and which may risk patient infection and/or device malfunction. For example, the sensor or the portion adjacent the sensor may be purposely difficult to access or clean. Alternatively, one or more batteries may be impossible to access or change.

In some embodiments, it may be desired to have other descriptive warnings that can be tied to pressure measurement or pressure measurement combined with another measured attribute. For example, if a sensor (accelerometer or temperature sensor) within the aspiration catheter is used to detect catheter movement, a change in this sensor may be tied to the pressure sensor. In this manner, a catheter that is engaged with a thrombus at its tip and is moved (e.g., begins to be pulled out of the patient) may then cause a warning: "Warning, do not move catheter; risk of thromboembolus."

Figure 15:
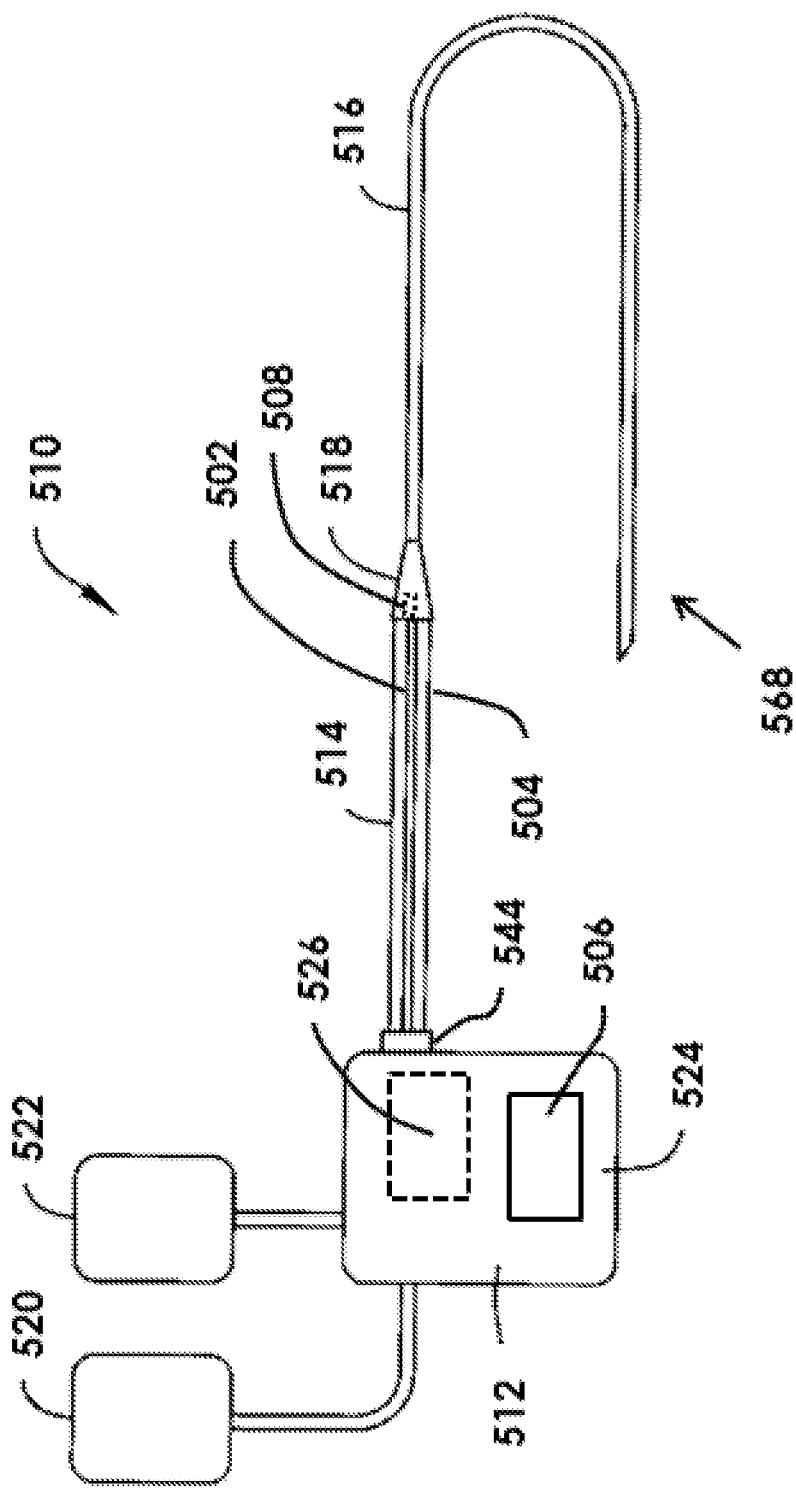
FIG. 15 is a diagrammatic view of a system for aspirating thrombus according to an embodiment of the present disclosure.

FIG. 15 is a diagrammatic figure depicting an assisted aspiration system 510. The aspiration system 510 includes a remote hand piece 512 that contains a fluid pump 526 and an operator control interface 506. In one contemplated embodiment, the system 510 is a single use disposable unit. The aspiration system 510 may also include extension tubing 514, which contains a fluid irrigation lumen 502 and an aspiration lumen 504, and which allows independent manipulation of a catheter 516 without requiring repositioning of the hand piece 512 during a procedure performed with the aspiration system 510. Extension tubing 514 may also act as a pressure accumulator. High pressure fluid flow from the pump 526, which may comprise a displacement pump, pulses with each stroke of the pump 526 creating a sinusoidal pressure map with distinct variations between the peaks and valleys of each sine wave. Extension tubing 514 may be matched to the pump 526 to expand and contract in unison with each pump pulse to reduce the variation in pressure caused by the pump pulses to produce a smooth or smoother fluid flow at tip of catheter 516. Any tubing having suitable compliance characteristics may be used. The extension tubing 514 may be permanently attached to the pump 526 or it may be attached to the pump 526 by a connector 544. The connector 544 is configured to ensure that the extension tubing 514 cannot be attached to the pump 526 incorrectly.

Figure 17:
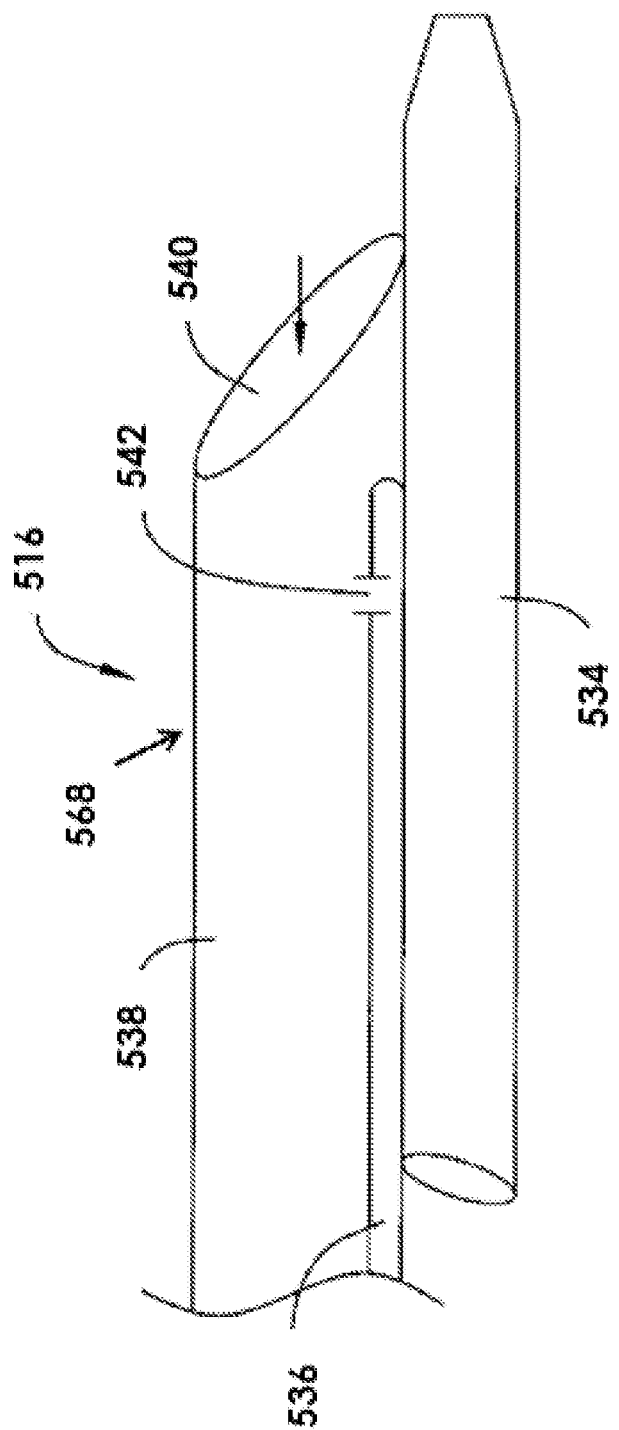
FIG. 17 is a diagrammatic view of the distal end portion of the system for aspirating thrombus of FIG. 15.

An interface connector 518 joins the extension tubing 514 and the catheter 516 together. In one contemplated embodiment, the interface connector 518 may contain a filter assembly 508 between high pressure fluid injection lumen 502 of the extension tubing 514 and a high pressure injection lumen 536 of the catheter 516 (FIG. 17). The catheter 516 and the extension tubing 514 may be permanently joined by the interface connector 518. Alternatively, the interface connector 518 may contain a standardized connection so that a selected catheter 516 may be attached to the extension tubing 514. In some embodiments, the filter assembly 508 may be removably coupled to the extension tubing 514 by a quick disconnect connection. A pressure transducer of an embodiment of the aspiration monitoring system presented herein may be located at a point along the aspiration lumen 504 or any extension of the aspiration lumen 504.

Attached to the hand piece 512 are a fluid source 520 and a vacuum source 522. A standard hospital saline bag may be used as fluid source 520; such bags are readily available to the physician and provide the necessary volume to perform the procedure. Vacuum bottles may provide the vacuum source 522 or the vacuum source 522 may be provided by a syringe, a vacuum pump or other suitable vacuum source. The filter assembly 508 serves to filter particulate from the fluid source 520 to avoid clogging of the high pressure injection lumen 536 and an orifice 542 (FIG. 17). As described herein, distal sections of the high pressure injection lumen 536 may be configured with small inner diameters, and to the filter assembly 508 serves to protect their continuing function. By incorporating one of a variety of catheters 516 into the assisted aspiration system 510, for example with varying lumen configurations (inner diameter, length, etc.), a variety of aspiration qualities (aspiration rate, jet velocity, jet pressure) may be applied in one or more patients. These aspiration qualities can be further achieved by adjustment of the pump 526, to modify pump characteristics (flow rate, pump pressure). In some embodiments, the catheter 516 may be used manually, for example, without the pump 526, and controlled by hand injection. The manual use of the catheter 516 may be appropriate for certain patient conditions, and may serve to reduce the cost of the procedure.

In one contemplated embodiment, the catheter 516 has a variable stiffness ranging from stiffer at the proximal end to more flexible at the distal end. The variation in the stiffness of the catheter 516 may be achieved with a single tube with no radial bonds between two adjacent tubing pieces. For example, the shaft of the catheter 516 may be made from a single length of metal tube that has a spiral cut down the length of the tube to provide shaft flexibility. Variable stiffness may be created by varying the pitch of the spiral cut through different lengths of the metal tube. For example, the pitch of the spiral cut may be lower (where the turns of the spiral cut are closer together) at the distal end of the device to provide greater flexibility. Conversely, the pitch of the spiral cut at the proximal end may be greater (where the turns of the spiral cut are further apart) to provide increased stiffness. A single jacket covers the length of the metal tube to provide for a vacuum tight (air tight, outside to inside) catheter shaft. Other features of catheter 516 are described with reference to FIG. 17, below.

Figure 16:
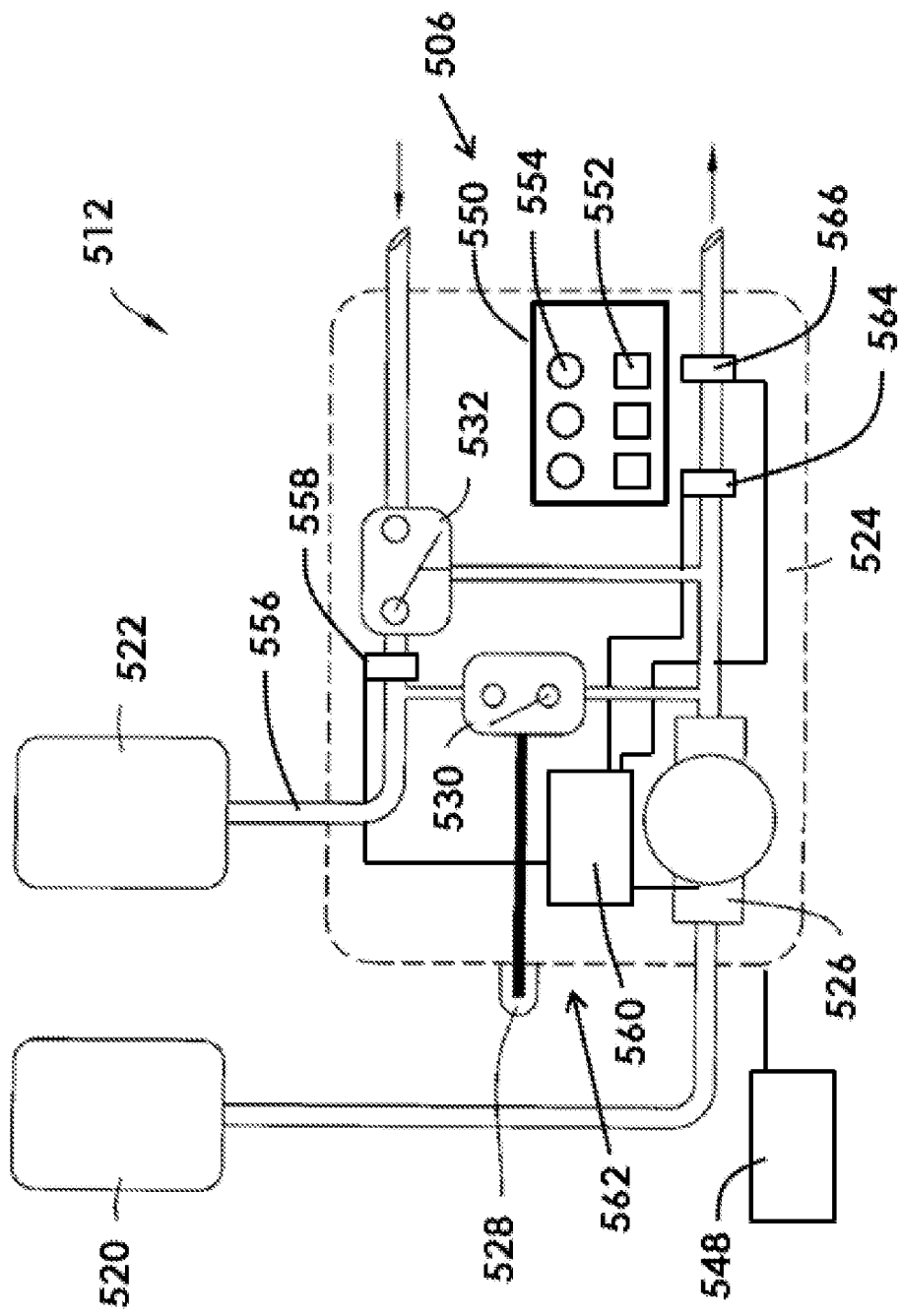
FIG. 16 is a diagrammatic view showing more detail of the proximal portion of the system for aspirating thrombus of FIG. 15.

FIG. 16 is a diagrammatic view showing more detail of the hand piece 512 and the proximal portion of assisted catheter aspiration system 510. The hand piece 512 includes a control box 524 where the power and control systems are disposed. The pump 526 may be a motor driven displacement pump that has a constant output. This pump displacement to catheter volume, along with the location of the orifice 542 (exit) of the catheter high pressure lumen 536 within the aspiration lumen 538 (FIG. 17), ensures that no energy is transferred to the patient from the saline pump as all pressurized fluid is evacuated by the aspiration lumen. A prime button 528 is mechanically connected to a prime valve 530. When preparing the device for use, it is advantageous to evacuate all air from the pressurized fluid system to reduce the possibility of air embolization. By depressing the prime button 528, the user connects the fluid source 520 to the vacuum source 522 via the pump 526. This forcefully pulls fluid (for example 0.9% NaCl solution, or "saline", no "normal saline", or heparinized saline) through the entire pump system, removing all air and positively priming the system for safe operation. A pressure/vacuum valve 532 is used to turn the vacuum or negative pressure on and off synchronously with the fluid pressure system. One contemplated valve 532 is a ported one-way valve. Such a valve is advantageous with respect to manual or electronic valve systems because it acts as a tamper proof safety feature by mechanically and automatically combining the operations of the two primary systems. By having pressure/vacuum valve 532, the possibility of turning the vacuum or negative pressure on without activating the fluid system is eliminated.

The operator control interface 506 is powered by a power system 548 (such as a battery or an electrical line), and may comprise an electronic control board 550, which may be operated by a user by use of one or more switches 552 and one or more indicator lamps 554. The control board 550 also monitors and controls several device safety functions, which include over pressure and air bubble detection and vacuum or negative pressure charge. A pressure sensor 564 monitors pressure, and senses the presence of air bubbles. Alternatively, an optical device 566 may be used to sense air bubbles. In one contemplated embodiment, the pump pressure is proportional to the electric current needed to produce that pressure. Consequently, if the electric current required by pump 526 exceeds a preset limit, the control board will disable the pump by cutting power to it. Air bubble detection may also be monitored by monitoring the electrical current required to drive the pump at any particular moment. In order for a displacement pump 526 to reach high fluid pressures, there should be little or no air (which is highly compressible) present in the pump 526 or connecting system (including the catheter 516 and the extension tubing 514). The fluid volume is small enough that any air in the system will result in no pressure being generated at the pump head. The control board monitors the pump current for any abrupt downward change that may indicate that air has entered the system. If the rate of drop is faster than a preset limit, the control board will disable the pump by cutting power to it until the problem is corrected. Likewise, a block in the high pressure lumen 536, which may be due to the entry of organized or fibrous thrombus, or a solid embolus, may be detected by monitoring the electrical current running the pump 526. In normal use, the current fluxuations of the pump 526 are relatively high. For example, the pump may be configured so that there is a variation of 200 milliAmps or greater in the current during normal operation, so that when current fluxuations drop below 200 milliAmps, air is identified, and the system shuts down. Alternatively, current fluxuations in the range of, for example, 50 milliAmps to 75 milliAmps may be used to identify that air is in the system.

Additionally, an increase in the current or current fluxuations may indicate the presence of clot or thrombus within the high pressure lumen 536. For example, a current of greater than 600 milliAmps may indicate that thrombus it partially or completely blocking the high pressure lumen 536, or even the aspiration lumen 538.

A vacuum line 556, connected to the vacuum source 522, may be connected to a negative pressure sensor 558. If the vacuum or negative pressure of the or negative pressure source 522 is low or if a leak is detected in the vacuum line 556, the control board 550 disables the pump 526 until the problem is corrected. The negative pressure sensor 558 may also be part of a safety circuit 560 that will not allow the pump 526 to run if a vacuum is not present. Thereby a comprehensive safety system 562, including the safety circuit 560, the pressure sensor 564 and/or the optical device 566, and the negative pressure sensor 558, requires both pump pressure and vacuum or negative pressure for the system to run. If a problem exists (for example, if there is either a unacceptably low pump pressure or an absence of significant vacuum or negative pressure), the control board 550 will not allow the user to operate the aspiration system 510 until all problems are corrected. This will keep air from being injected into a patient, and will assure that the aspiration system 510 is not operated at incorrect parameters.

FIG. 17 is a diagrammatic view of the distal end portion 568 of the assisted catheter aspiration system 510, showing more details of the catheter 516. The catheter 516 is a single-operator exchange catheter and includes a short guidewire lumen 534 attached to the distal end of the device. The guidewire lumen 534 can be between about 1 and about 30 cm in length, or between about 5 and about 25 cm in length, or between about 5 and about 20 cm in length, or approximately 13.5 cm in length. An aspiration lumen 538 includes a distal opening 540 which allows a vacuum or negative pressure (for example, from vacuum source 522) to draw thrombotic material into the aspiration lumen 538 (straight, horizontal arrow, FIG. 17). A high pressure lumen 536 includes a distal orifice 542 that is set proximally of distal opening 540 by a set amount. For example, distal orifice 42 can be set proximally of distal opening 540 by about 0.0508 cm (0.020 inches), or by 0.0508 cm±0.00762 cm (0.020 inches±0.003 inches) or by another desired amount. The orifice 542 is configured to spray across the aspiration lumen to macerate and/or dilute the thrombotic material for transport to vacuum source 522, for example, by lowering the effective viscosity of the thrombotic material. The axial placement of the fluid orifice 542 is such that the spray pattern interaction with the opposing lumen wall produces a spray mist and not a swirl pattern that could force embolic material out from the distal opening 540. The system may be configured so that the irrigation fluid leaves the pump at a pressure of between about 3,447,378 pascal (500 psi) and about 10,342,135 pascal (1500 psi). In some embodiments, after a pressure head loss along the high pressure lumen 536, the irrigation fluid leaves orifice 542 at between about 4,136,854 pascal (600 psi) and about 8,273,708 pascal (1200 psi), or between about 4,481,592 pascal (650 psi) and about 5,860,543 pascal (850 psi). In some cases, it may be possible (and even desired) to use the assisted catheter aspiration system 510 without operating the pump 526, and thus use the catheter 516 while providing, for example, a hand saline injection via a syringe. Or, in some cases, the assisted catheter aspiration system 510 may be used without the pump 526 attached, with the saline injections done by hand using a syringe through the high pressure lumen 536. If a clog occurs, the syringe may be removed and the pump 526 attached and initiated, for example, for the purpose of unclogging the high pressure lumen 536.

When normal blood flow is achieved after unblocking occlusions or blockages from atherosclerotic lesions and/or thrombosis, there is sometimes a risk of reperfusion injury. This may be particularly significant following thrombectomy of vessels feeding the brain for treatment of thromboembolic stroke, or following thrombectomy of coronary vessels feeding the myocardium. In the case of the revascularization of myocardium following a coronary intervention (e.g. thrombectomy). Reperfusion injury and microvascular dysfunction may be mechanisms that limit significant or full recovery of revascularized myocardium. The sudden reperfusion of a section of myocardium that had previously been underperfused may trigger a range of physiological processes that stun or damage the myocardium. Distal coronary emboli, such as small portions of thrombus, platelets and atheroma, may also play a part. Controlled preconditioning of the myocardium at risk has been proposed to limit the effect of reperfusion injury and microvascular dysfunction. The embodiments of the thrombectomy systems 100, 300 presented herein may be combined with additional features aimed at allowing flow control, in order to limit the potential dangers due to reperfusion following thrombectomy.

FIG. 18 illustrates a multi-purpose system 1200 comprising a multi-purpose catheter 1202 having an infusion/injection port 1204 and an aspiration port 1206. The infusion/injection port 1204 and the aspiration port 1206 may each comprise luer connectors, such as female luer lock connectors. A tubing set 1208 and a pressure sensor 1210 are connected in line with a vacuum source 1212. A cable 1214 carries signals from the pressure sensor 1210 to an aspiration monitoring system 1216 (FIG. 19), and connects to the aspiration monitoring system 1216 via an interface 1218, or plug, which is configured to connect to a port 1220 of a console 1222 of the aspiration monitoring system 1216. Apparatus and methods described herein may be used to monitor aspiration using the aspiration monitoring system 1216. In one manner of use, a syringe 1224 (FIG. 18) may be used to manually inject through the injection port 1204 and injection lumen 1225 (e.g., high pressure lumen) of the multi-purpose catheter 1202. The syringe 1224 may have an injectable volume of about 5 ml or less, or in some embodiments about 1 ml or less. The injection lumen 1225 in some embodiments may be configured for injection of saline at a relatively high pressure, or at either high or low pressures. If the valve 1226 (e.g., stopcock) is closed, blocking the vacuum source 1212 from applying a vacuum or negative pressure to the aspiration lumen 1227 via the aspiration port 1206, then injection through the injection lumen 1225 causes injectate to be delivered to a site in the blood vessel near the distal exit of the injection lumen 1225 (at the distal end of the multi-purpose catheter 1202). Or, if the vacuum source 1212 is removed from, or simply not coupled to, the aspiration lumen 1227, then injection through the injection lumen 1225 may also cause injectate to be delivered to a site in the blood vessel near the distal exit of the injection lumen 1225. Either of these techniques may be utilized to apply a medicant to a blood vessel wall, or to an atherosclerotic plaque, or to a thrombus. In some cases, a clot busting drug (tissue plasminogen activator-tPA, thrombokinase, urokinase, thrombin, plasmin) is infused into a clot or thrombus, allowing it to act over a period of time. One purpose may be to soften the thrombus over time. Lytics, glycoprotein inhibitors (GPIs), vasodilators, and other drugs may be used to dilate the blood vessel, or treat disease in the area. The controlled, precision, local delivery allows an efficient use of the drug, with the desired amount delivered to the tissue to be treated with minimal runoff or waste. As many of these drugs are quite expensive, this efficiency reduces procedural costs. Because of the precision diameter of the injection lumen 1225, and its known length, the injection lumen 1225 contains a known volume, or dead space. This additionally allows a known, controlled, precision injection of medicant. A representative injection lumen 1225 may have a length of 150 cm and have an inner diameter of 0.038 cm (0.015 inches), and thus a total volume of only 0.17 ml. The injection lumen 1225 volume may be varied, by controlling the diameter of the inner diameter of the injection lumen 1225 and/or the length of the injection lumen 1225. For example, the injection lumen 1225 volume may be between about 0.08 ml and about 0.26 ml, or between about 0.14 ml and about 0.20 ml. By injecting through the injection lumen 1225 with a small bore syringe (e.g., 1 ml) or with a precision pump, an accurate measurement of the medicant delivered can be made. If, however, the valve 1226, or stopcock, is opened, connecting the vacuum source 1212 to the aspiration port 1206 and applying a vacuum or negative pressure on the aspiration lumen 1227, a forced aspiration is commenced, as described herein. As described, the injection lumen 1225 may serve either a closed system (aspiration) or an open system (injection of infusate). At the beginning of a procedure, it is not always known what different actions will be required, thus the use of the multi-purpose catheter 1202 and multi-purpose system 1200 may eliminate the need to use multiple catheters (e.g., both a microcatheter and a single function aspiration catheter).

Figure 20:
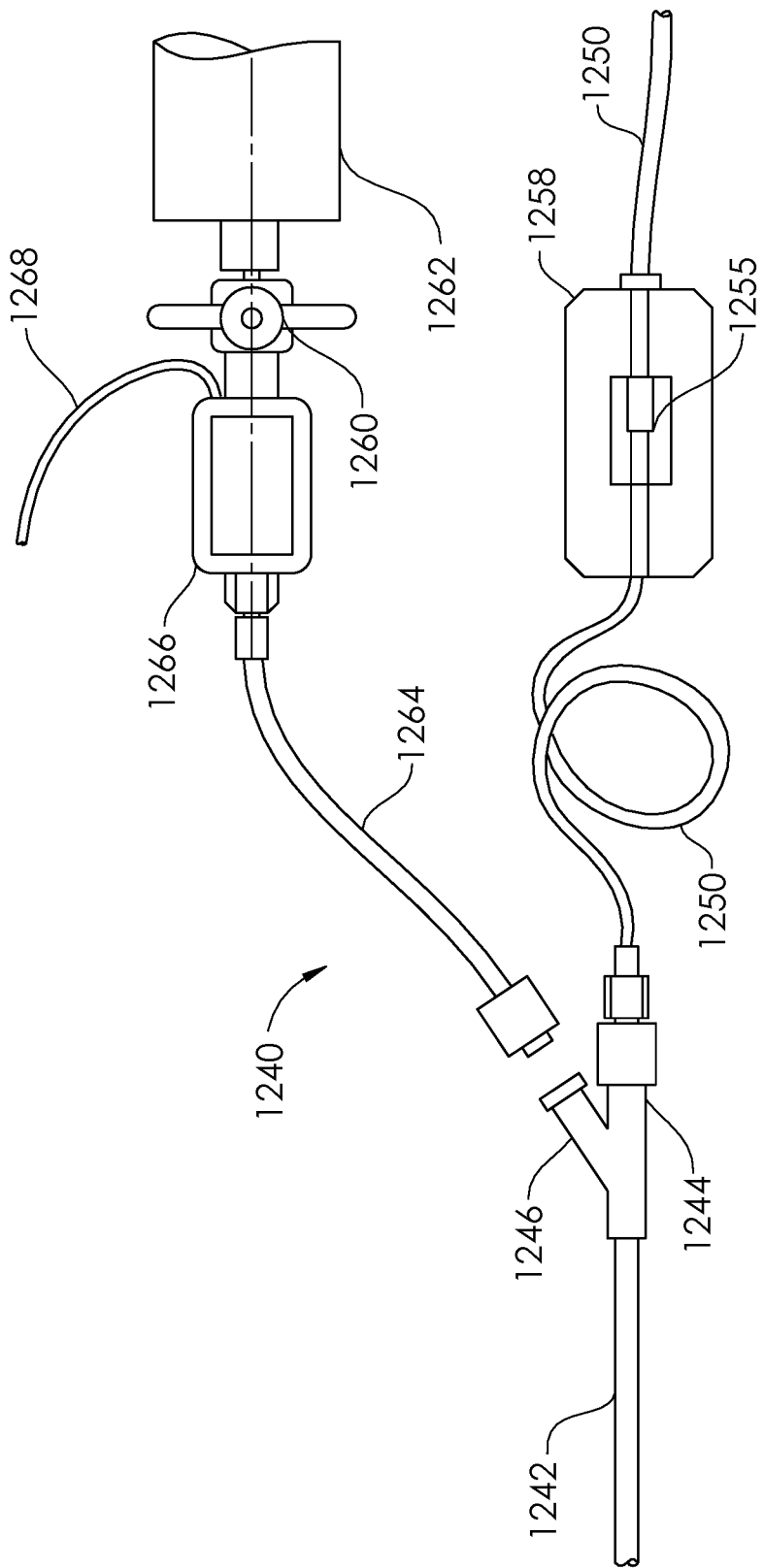
FIG. 20 is a plan view of a portion of a multi-purpose system according to an embodiment of the present disclosure.
Figure 21:
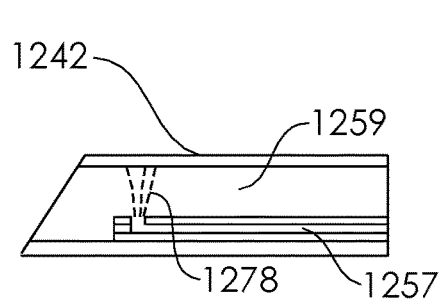
FIG. 21 is a detail view of the distal end of a multi-purpose catheter of the multi-purpose system of FIG. 20.
Figure 22:
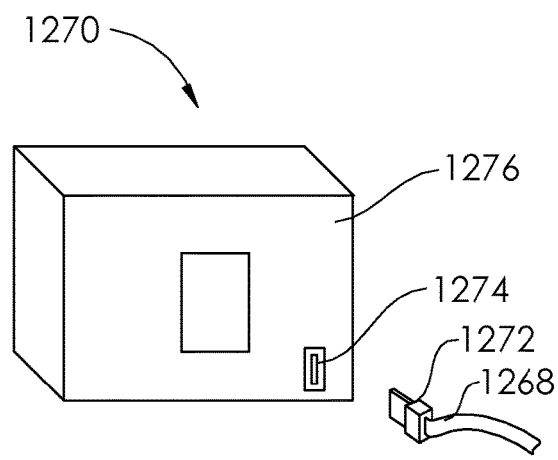
FIG. 22 is a perspective view of a proximal portion of the multi-purpose system of FIG. 20.
Figure 23:
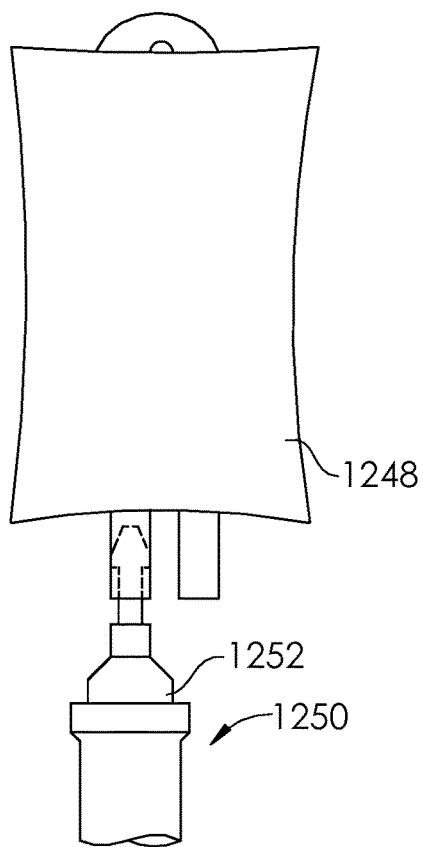
FIG. 23 is a plan view of a proximal portion of the multi-purpose system of FIG. 20.
Figure 24:
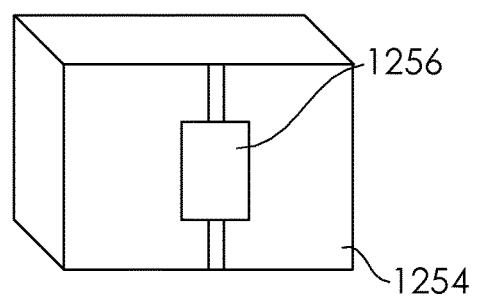
FIG. 24 is a perspective view of a portion of the multi-purpose system of FIG. 20.

FIGS. 20-24 illustrate a multi-purpose system 1240 comprising a multi-purpose catheter 1242 having an infusion/injection port 1244 and an aspiration port 1246. Cooled saline may be injected from a saline bag 1248 (FIG. 23) through a tubing set 1250, attached to the saline bag 1248 via a spike 1252. A pump 1254 (FIG. 24), which may include a displacement pump, such as a piston pump, includes an interface 1256 for attaching a cassette 1258 (FIG. 20). In some embodiments, the pump 1254 has moving portions that connect to a moving piston 1255 in the cassette 1258 to inject controlled amounts of fluid. As described in relation to the multi-purpose system 1200 of FIG. 18, the injection may serve either a closed system (aspiration) or an open system (injection of infusate), depending on whether a valve 1260 which couples a vacuum source 1262 to the aspiration port 1246 via extension tubing 1264 is open or closed, or simply whether the vacuum source 1262 is attached or not attached. A pressure sensor 1266 communicates with the interior of the extension tubing 1264, but may communicate with the interior of other parts of the flow path. A cable 1268 carries signals from the pressure sensor 1266 to an aspiration monitoring system 1270 (FIG. 22), and connects to the aspiration monitoring system 1270 via an interface 1272, or plug, which is configured to connect to a port 1274 of a console 1276 of the aspiration monitoring system 1270. The utility of the multi-purpose systems 1200, 1240 in multiple modes is facilitated by the sterile fluid path combined with precision volume control (either by small syringe 1224, or by the precision pump 1254). In addition, the aspiration monitoring system 1216, 1270 allows real-time feedback to the user, further facilitating controlled delivery and/or aspiration.

The multipurpose system 1200, 1240 optimizes interventional procedures, such as percutaneous coronary interventions (PCIs), for simplicity, case flow, and cost. Infusing drugs intracoronary prepares clot for aspiration by placing highly concentrated pharmaco agents directly at the lesion site, at a location which can be more distal (e.g., more superselective) than that which is typically accessible by the tip of a guiding catheter. This can minimize the volume of drug/medicant/agent used. By limiting the amount of certain medicants, systemic complications (bleeding, etc.) can be minimized or eliminated. The direct application of the medicant, for example at the thrombus itself, allows it to soften or disaggregate the thrombus. The maceration of the thrombus, for example by a saline jet 1278 (FIG. 21) injected through the injection lumen 1257 of the multi-purpose catheter 1242, keeps the catheter aspiration lumen 1259 patient at all times without interruption, and allows standardized catheter advancement technique, for example, moving the catheter slowly from a proximal location to a distal location in the vessel (in relation to the thrombus). The maceration also dilutes the proximally flowing aspirate for optimal aspiration efficiency. In certain situation, aspiration may be performed until the normal blood flow is restored (at least to a significant level), and then the vacuum source 1262 may be closed off via the valve 1260 and cooled injectate may be infused into the blood vessel. The resultant selective cooling of this area serves to reduce reperfusion injury by potentially slowing ischemic cell metabolism. The injection of cooled infusate may be used any time post-aspiration, pre-stenting, without having to remove an aspiration device, advance a new injection device. Because the multi-purpose catheter 1202, 1242 is already in place, this critical operation may be started immediately. By having these functionalities all on one catheter, there is also a cost saving to the user.

In aspiration mode, the aspiration monitoring system 1216, 1270 is able to monitor proper function of the aspiration circuit at all times. The user knows when warnings are communicated or when the system (e.g., motor) shuts down, that a key event has occurred, an event that needs attending. This knowledge helps the user avoid plunging the catheter distally, potentially causing distal embolism. In infusion/infusate cooling mode, the pump 1254 pumps at a predetermined constant volume or speed to deliver constant temperature cooling infusate. Core temperature feedback (e.g., via rectal, esophageal, ear or other temperature probes) may be used to indicate to the system that further cooling must stop. For example, a core body temperature below 35° C. or below 34° C. The feedback of a temperature below the threshold may be used to shut down the pump and/or to send a warning. The infusate path, which is precision and direct to the catheter tip and/or ischemic area, results in concentrated cooling, causing the least systemic hypothermic potential. By bypassing the aspiration lumen (e.g., with the valve 1260 closed), unintentional embolic debris is less likely to be infused back into the blood vessel, and less likely to thus be sent downstream to critical areas. This eliminates the need to exchange devices after flow has been restored.

In some cases, in infusion mode, infusate is injected into the fluid injection lumen 1225, 1257 with a relatively low pressure. In some cases, maceration is performed at a relatively high pressure. In some cases, the multi-purpose system 1240 may be used without the pump 1254 attached, with the saline injections done by hand using a syringe attached to the infusion/injection port 1244. If a clog occurs, the syringe may be removed and the pump 1254 attached and initiated, for example, for the purpose of unclogging the injection lumen 1257. In an exemplary procedure, a user places a catheter similar to the multi-purpose catheter 1202 of FIG. 18 or multi-purpose catheter 1242 of FIGS. 20-21 in the vasculature. Initially, the user may choose to have neither a pump 1254, nor a syringe 1224 (FIG. 18) attached to the multi-purpose catheter 1202, 1242. The user may then commence aspiration through the aspiration lumen 1227, 1259 via a vacuum source 1212, 1262, thus utilizing the multi-purpose catheter 1202, 1242 as a simple (vacuum or negative pressure only) aspiration catheter. If at any time, the user determines that additional positive pressure injection of saline and/or medicant is needed, for example, to overcome clogging, overcome slow aspiration, or to increase maceration or dilution of the thrombus, the user can attach the pump 1254 or the syringe 1224 to the infusion/injection port 1204, 1244 and begin injecting the saline and/or medicant.

In one embodiment, an aspiration system includes an elongate catheter having a proximal end and a distal end, the catheter including an aspiration lumen having a proximal end and a distal end and a high pressure injection lumen having a proximal end and a distal end and extending from a proximal end of the catheter to a location adjacent a distal end of the aspiration lumen, and at least one orifice at or near the distal end of the high pressure injection lumen and configured to allow high pressure liquid injected through the high pressure injection lumen to be released into the aspiration lumen, wherein the proximal end of the high pressure injection lumen is configured to be repeatably coupled to and uncoupled from one or more injection modules. In some embodiments, the one or more injection modules include a first injection module and a second injection module. In some embodiments, the first injection module comprises a pump and the second injection module comprises a syringe. In some embodiments, the second injection module comprises a syringe having a volume of about 5 ml or less. In some embodiments, the second injection module comprises a syringe having a volume of about 1 ml or less. In some embodiments, the second injection module comprises a syringe containing a drug.

FIGS. 25 through 33 illustrate several different embodiments of devices having a pressure sensor 1300, which is configured to function as a component in an aspiration monitoring system sharing some or all of the functionality of any one of the aspiration monitoring systems 48, 62, 78, 900, 1216, 1270 presented herein. FIG. 25 illustrates an aspiration catheter 1302 having a distal end 1304 and a proximal end 1306, the proximal end 1306 comprising a female luer connector 1308. The pressure sensor 1300 is in fluid communication with (e.g., fluidly coupled to) a lumen of the aspiration catheter 1302. FIG. 26 illustrates a tubing set 1310 having a male luer 1312 and a female luer 1314, extension tubing 1316, and a stopcock 1318. The pressure sensor 1300 is in fluid communication with a lumen of the extension tubing 1316. FIG. 27 illustrates a stopcock 1320 having a male luer 1322, a female luer 1324, and a valve 1326, the valve 1326 located proximally of the pressure sensor 1300. The pressure sensor 1300 is in fluid communication with an internal cavity of the stopcock 1320. FIG. 28 illustrates a stopcock 1328 having a male luer 1330, a female luer 1332, and a valve 1334, the valve 1334 located distally of the pressure sensor 1300. The pressure sensor 1300 is in fluid communication with an internal cavity of the stopcock 1328. FIG. 29 illustrates a syringe 1336 having a male luer 1342, a barrel 1338, and a plunger 1340. The syringe 1336 may include a locking feature 1344, which allows the plunger 1340 to be locked in relation to the barrel 1338, such as a VacLok® syringe. The pressure sensor 1300 is located distally of the barrel 1338 and is in fluid communication with an internal cavity of the barrel 1338.

Figure 30:
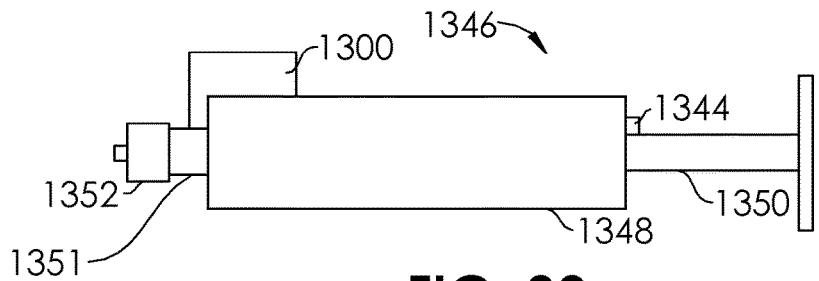
FIG. 30 is a plan view of an aspiration system according to an embodiment of the present disclosure.
Figure 31:
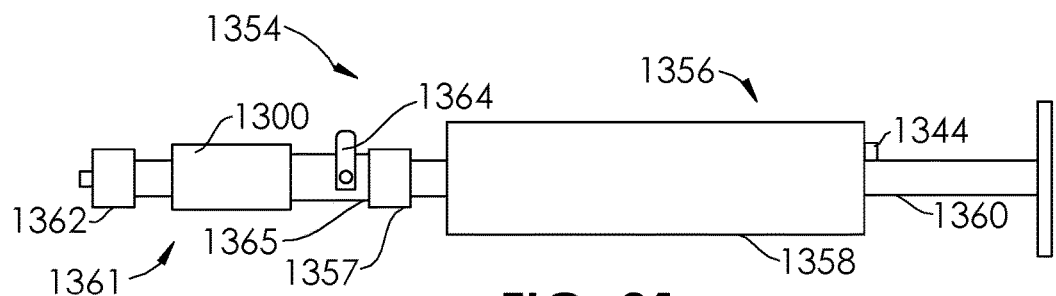
FIG. 31 is a plan view of an aspiration system according to an embodiment of the present disclosure.
Figure 32:
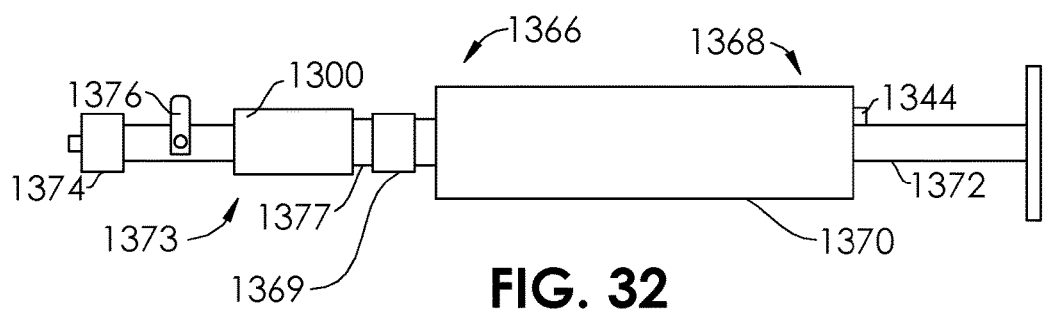
FIG. 32 is a plan view of an aspiration system according to an embodiment of the present disclosure.
Figure 33:
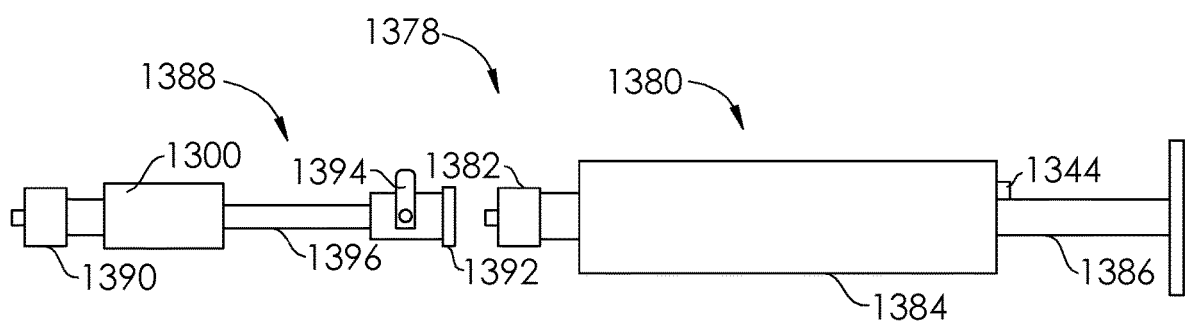
FIG. 33 is a plan view of an aspiration system according to an embodiment of the present disclosure.

FIG. 30 illustrates a syringe 1346 having a male luer 1352 (i.e., luer connector, luer lock), a barrel 1348, and a plunger 1350. The syringe 1346 may include a locking feature 1344. The pressure sensor 1300 is in fluid communication with an internal cavity of the barrel 1348, and may be directly connected to either the barrel 1348 or the male luer 1352, or a hollow transition 1351 between them. FIG. 31 illustrates an aspiration system 1354 comprising a syringe 1356 having a male luer 1357, a barrel 1358 and a plunger 1360. The syringe 1356 may include a locking feature 1344. The aspiration system 1354 also comprises a connector assembly 1361 comprising a male luer 1362, a valve 1364, and a female luer 1365 (connected under the male luer 1357 in FIG. 31). The pressure sensor 1300 is in fluid communication with an internal lumen or cavity between the barrel 1358 of the syringe 1356 and the male luer 1362 of the connector assembly 1361. FIG. 32 illustrates an aspiration system 1366 comprising a syringe 1368 having a male luer 1369, a barrel 1370 and a plunger 1372. The syringe 1368 may include a locking feature 1344. The aspiration system 1366 also comprises a connector assembly 1373 comprising a male luer 1374, a valve 1376, and a female luer 1377 (connected under the male luer 1369 in FIG. 32). The pressure sensor 1300 is in fluid communication with an internal lumen or cavity between the barrel 1370 of the syringe 1368 and the male luer 1374 of the connector assembly 1373. FIG. 33 illustrates an aspiration system 1378 comprising a syringe 1380 having a male luer 1382, a barrel 1384 and a plunger 1386. The syringe 1380 may include a locking feature 1344. The aspiration system 1378 further comprises a tubing set 1388 having a male luer 1390 and a female luer 1392. A valve 1394 is located either proximal or distal to the pressure sensor 1300. Extension tubing 1396 may be utilized to connect one or more of the components of the tubing set 1388, but in some cases, the components may be connected directly. The pressure sensor 1300 is in fluid communication with an internal lumen of the tubing set 1388. The stopcock or valve in any of these embodiments may be a one-way stopcock or a three-way stopcock or a one-way valve or a three-way valve. Other embodiments may exist which combine one or more elements of each of the embodiments presented herein. These embodiments are also included within the scope of this disclosure. In any of the embodiments in which a male luer is used, it may be replaced with a female luer or another liquid-tight connector. In any of the embodiments in which a female luer is used, it may be replaced with a male luer or another liquid-tight connector. As such, either of the connector assemblies 1361, 1373 may be connected in reverse manner to the syringes 1356, 1368, i.e., wherein the distal end becomes the proximal end and is thus connected to the syringe 1356, 1368, and wherein the proximal end becomes the distal end.

Figure 34:
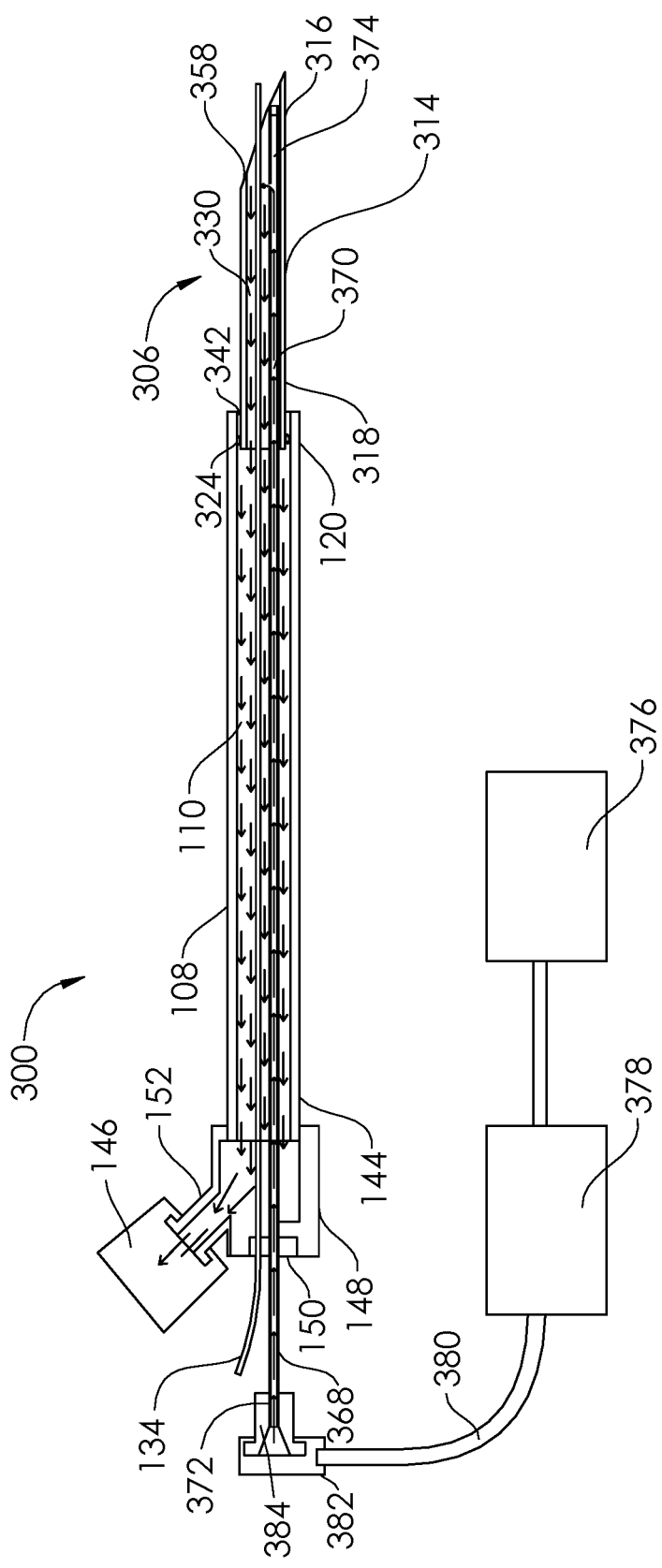
FIG. 34 is a partial sectional view of an embodiment of a saline injection aspiration (thrombectomy) catheter according to an embodiment of the present disclosure, with a guidewire in place.
Figure 35:
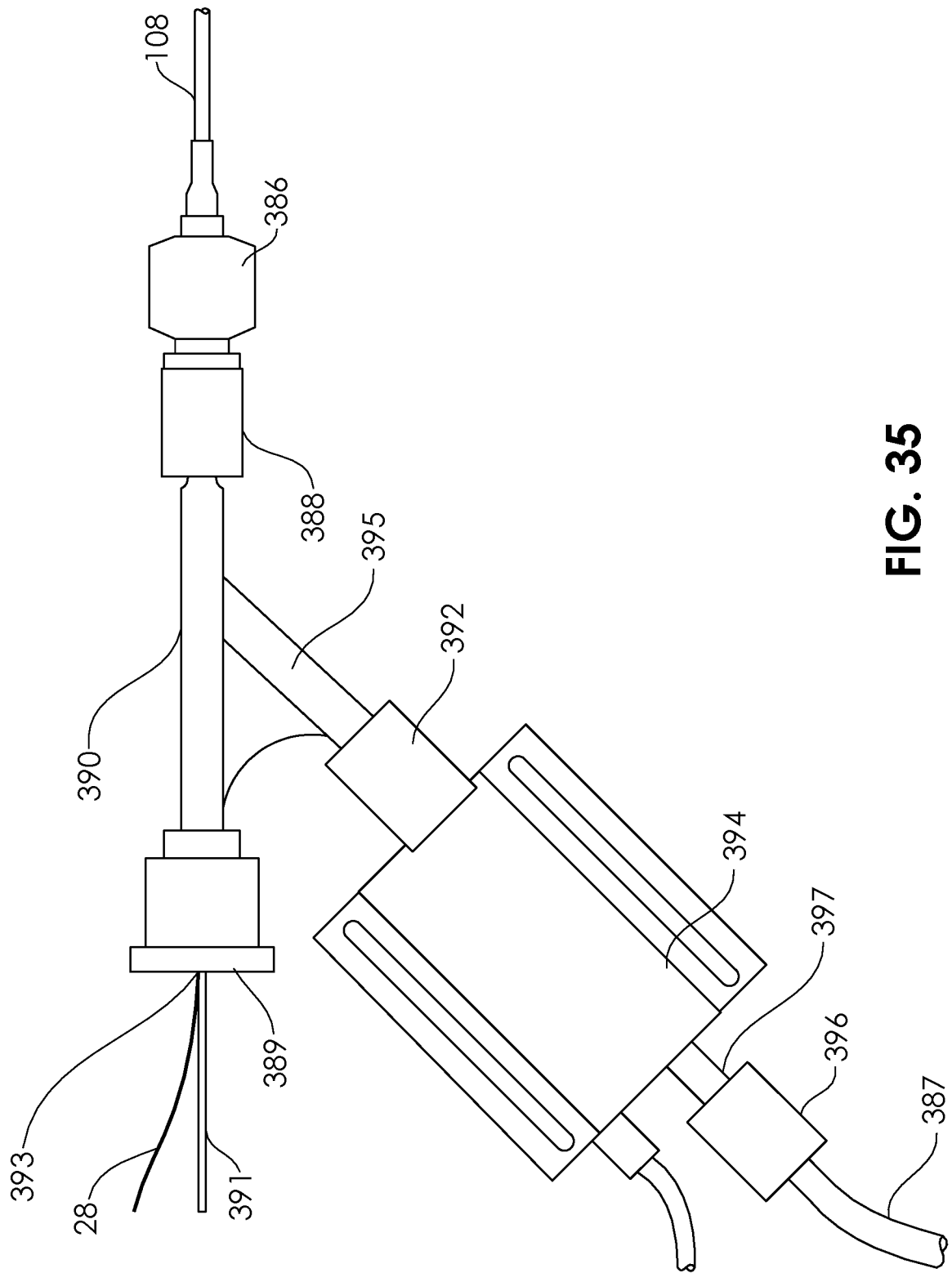
FIG. 35 is a plan view of the proximal end of a guiding catheter with an aspiration catheter placed therein.

FIG. 34 illustrates a thrombectomy system 300 which incorporates the high pressure injection of a liquid, for example sterile saline solution, in order to macerate and aspirate thrombus 104. A guiding catheter 108 has an inner lumen 110 extending between a proximal end 144 and a distal end 120. A y-connector 148, coupled to the proximal end 144 of the guiding catheter 108, includes a proximal seal 150 and a sideport 152 and is configured to couple the inner lumen 110 of the guiding catheter 108 to a vacuum source 146, as described in relation to the prior embodiments. A thrombectomy catheter 306 comprises a distal tube 314 having a distal end 316 and a proximal end 318, the proximal end 318 incorporating one or more sealing members 324 for sealing off an annulus 342 between the guiding catheter 108 and the distal tube 314, as described in relation to the prior embodiments. The distal tube 314 has an aspiration lumen 330. A support/supply tube 368, having a lumen 370, is coupled to the distal tube 314. The support/supply tube 368 serves as a support member for pushing and pulling the thrombectomy catheter 306, but is also a conduit (via the lumen 370) for high pressure saline, which is injected from the proximal end 372 to the distal end 374. The saline is supplied from a saline source 376 (e.g. saline bag, bottle) and pressurized by a pump 378, through a supply tube 380 and through a luer connector 382 which is connected to a luer hub 384 coupled to the support/supply tube 368. In some embodiments, the support/supply tube 368 comprises a hypo tube. In some embodiments, the support/supply tube 368 comprises stainless steel or nitinol. The distal end 316 of the distal tube 314 may include a skive 358, which aids in the trackability of the distal tube 314 through vasculature of a patient. In some embodiments, the inner diameter of the aspiration lumen 330 of the distal tube 314 may be approximately one French size smaller than the inner diameter of the inner lumen 110 of the guiding catheter 108. In some embodiments, the thrombectomy catheter 306 may include a support tube or support shaft to replace the support/supply tube, and not comprise a lumen 370. Thus, aspiration is only controlled by evacuation of the inner lumen 110 of the guiding catheter 108 in combination of the aspiration lumen 330 of the distal tube 314, and injection of a high pressure liquid is not necessary. Other embodiments of the thrombectomy catheter 306 are described in U.S. Pat. No. 9,433,427, issued Sep. 6, 2016, and entitled "Systems and Methods for Management of Thrombosis," which is hereby incorporated by reference in its entirety for all purposes FIG. 35 illustrates the proximal end of a guiding catheter 108 used with aspiration catheters, such as the thrombectomy catheter 306 of FIG. 34. A hemostasis valve 389 of y-connector 390 seals over both the support/supply tube 391 and the guidewire 28. The hemostasis valve 389 (e.g., Touhy-Borst, longitudinally spring-loaded seal, etc.) must be adjusted to allow catheter and/or guidewire 28 movement (translation, rotation), but must keep air from being pulled into the lumens during aspiration. Because of the continual adjustment often required to the hemostasis valve 389, for example, to aid movement of the catheter and/or guidewire, the hemostasis valve 389 may create significant variability in the amount of air that may leak. A leak (e.g., at location 393) may be fast, and may be unknown to the user. A pressure sensor 394 used in conjunction with any of the aspiration monitoring systems described herein allows the user to know immediately if the seal of the hemostasis valve 389 of the y-connector 390 is not correctly sealed. Additionally, any leaks between the distal luer 388 of the y-connector 390 and the luer hub 386 of the guiding catheter 108 can be detected by the aspiration monitoring system. Furthermore, any leaks between a luer 392 of the pressure sensor 394 and a sideport 395 of the y-connector 390 or between a luer connector 396 of the extension tube 387 and a luer fitting 397 of the pressure sensor 394 can be detected by the aspiration monitoring system. The aspiration monitoring system may be configured to be integral or attachable to any component of the aspiration circuit (e.g., aspiration catheter, syringe/vacuum source), or may be connected in series (at any point) between these components. In some embodiment, the aspiration monitoring system may comprise a flow or pressure sensor or detector that is in series or in parallel with the components, or is configured to be placed in series or in parallel with the components. In any of these configurations, a number of different leak locations may be assessed by the aspiration monitoring system of the embodiments disclosed herein. The aspiration monitoring system may be configured to detect: changes, relative changes, absolute changes, thresholds, absolute values, the presence of or the lack of pressure and/or flow. The aspiration monitoring system may be configured to determine the operation status of a system including a catheter having an aspiration lumen. In some cases, the aspiration monitoring system may be configured to provide information about the operation of the system that is not discernable from typical clues such as angiography, sound, feel, or other visual, auditory, tactile or other feedback from the system itself.

Figure 36:
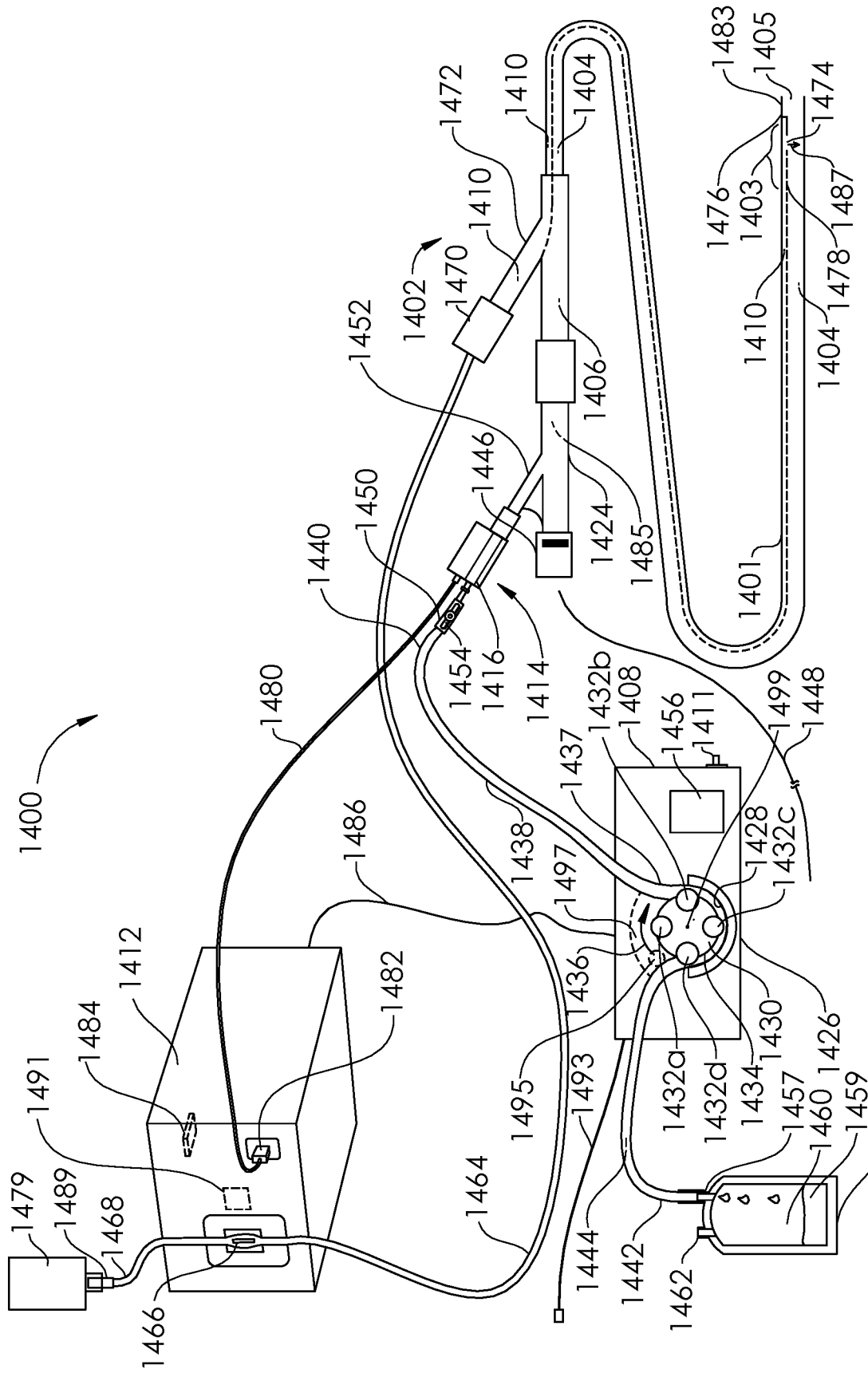
FIG. 36 is a perspective view of an aspiration system according to an embodiment of the present disclosure.

FIG. 36 illustrates an aspiration system 1400 comprising an aspiration catheter 1402 comprising an elongate shaft 1401 including an aspiration lumen 1404 having an open distal end 1405 and a proximal end 1406 configured to couple to a peristaltic pump 1408. The peristaltic pump 1408 may be a roller pump having a base 1426, a pressure shoe 1428 carried by the base 1426, and a rotatable head 1430, rotatably coupled to the base 1426, and carrying two or more rollers 1432a-d. The rollers 1432a-d are arrayed around a perimeter 1434 of the rotatable head 1430. The rotatable head 1430 is configured to be rotatable in at least a first rotational direction 1436 with respect to a rotational axis 1499. The rotatable head 1430 may be rotated by a motor 1497, either directly, or with a gear train 1495. The peristaltic pump 1408 may be battery powered, and the battery (ies) may be rechargeable by wired or wireless means. The peristaltic pump 1408 may alternatively, or additionally be powered by a power cord 1493 configured to connect to a power supply. An extension tube 1438 having a distal end 1440 and a proximal end 1442, and having a lumen 1444 extending therethrough, is hydraulically coupled to the proximal end 1406 of the aspiration lumen 1404 via a connector 1424. The extension tube 1438 may be supplied (e.g., sterile) with the aspiration catheter 1402, or may be packaged and supplied separately. A Touhy-Borst seal 1446 carried on the connector 1424 is configured to be loosened/opened to allow the insertion of a guidewire 1448 through the connector 1424 and the aspiration lumen 1404. The aspiration lumen 1404 may thus be used to track the aspiration catheter 1402 over the guidewire 1448 through a subject's vasculature. The Touhy-Borst 1446 can be tightened to seal over the guidewire 1448, to maintain hemostasis. Other types of seals may be incorporated in place of the Touhy-Borst 1446, including a spring-loaded, longitudinally compressible and actuatable seal. The extension tube 1438 includes a male luer 1450 at its distal end 1440, for connecting to a female luer 1452 of the connector 1424. The male luer 1450 may include a stopcock 1454, which is configured to be turned to select between an open position (shown) or a closed position. The extension tube 1438 and its components may be supplied sterile as a single unit. Alternatively, the extension tube 1438 may be integral with the aspiration lumen 1404, or may be permanently attached to the connector 1424. In use, a compressible portion 1437 of the extension tube 1438 is placed within the pressure shoe 1428 of the peristaltic pump 1408 such that rotation of the rotatable head 1430 in the rotational direction 1436 causes fluid to be forced through the lumen 1444 of the extension tube 1438 from the distal end 1440 to the proximal end 1442, via compression of the compressible portion 1437 by the rollers 1432, one at a time. The single insertion step to couple the compressible portion 1437 to the peristaltic pump 1408 is simple, quick, reliable, and does not involve any connection that has to seal (e.g., luer, etc.). It is also easier to visualize whether a peristaltic pump is successfully operating, vs. a vacuum pump or evacuated syringe. This may be because, under relatively high vacuum or negative pressure conditions, blood tends to cavitate, thus filling the space of a container (e.g., canister or syringe) at an accelerated rate due to the excess gaseous volume. The gaseous bubbles may also make it more difficult to see inside and visually inspect the condition. Optionally, an interface 1456 on the peristaltic pump 1408 is configured to allow a user to input information or commands to the peristaltic pump 1408 or other components of the system 1400. Otherwise, hardware or firmware may be pre-programmed with specific run parameters (motor speed, rotation speed, etc.). In some embodiments, there are only two rollers 1432. In other embodiments, there are three rollers 1432. In still other embodiments, as shown, there are four rollers 1432. In an alternative embodiment, instead of rollers, smooth, radiused bumps of a rigid material slide over the compressible portion 1437, compressing it. In this alternative embodiment, the compressible portion 1437 and/or the bumps may be treated with a lubricious material or may be constructed from significantly lubricious materials to lover the sliding friction between the compressible portion 1437 and the bumps. Returning to the embodiment of FIG. 36, the compressible portion 1437 may comprise silicone tubing, polyurethane tubing, polyvinyl chloride tubing, or other compressible tubing. The compressible section 1437 may be a relatively short section that is attachable to and detachable from the peripheral ends of the extension tube 1438, or in other embodiments, may comprise the entirety of the extension tube 1438 between the distal end 1440 and the proximal end 1442. The proximal end 1442 of the extension tube 1438 may be coupled to a hub 1457 of a canister 1458 having an interior 1460, to allow fluid 1459 passing through the extension tube 1438 to pass into the interior 1460. An additional hub 1462 in the canister 1458 may be left open (as shown) to allow the unfilled interior 1460 to match atmospheric pressure. Alternatively, the canister 1458 may be replaced by another type of receptacle, such as a bag, or more specifically an empty infusion bag, configured for collecting aspirate therein.

The aspiration catheter 1402 additionally has a high pressure injection lumen 1410 for injecting saline from a fluid source 1479, for example, via a high pressure pump 1412. A tubing set 1464 may include a pump cartridge 1466 having a piston, or bellows, or other movable element that the pump 1412 may manipulate using an internal motor 1491, thus pressurizing saline (or other fluid) from the fluid source 1479 with a significantly high pressure such that the saline is forced through the injection lumen 1410 of the aspiration catheter 1402. The tubing set 1464 includes proximal end 1468 having a spike 1489, or other connecting element, for hydraulically coupling the tubing set 1464 to the fluid source 1479. The tubing set 1464 further has a distal end 1470, which may comprise a male luer, and which is configured to hydraulically couple the tubing set 1464 to the injection lumen 1410 via a female luer 1472. The tubing set 1464 may be supplied sterile as a single unit, or alternatively may be permanently attached to the aspiration catheter 1402. In use, injected saline is forced through the injection lumen 1410 by the pump 1412 and exits an orifice 1474 at a distal end 1476 of the injection lumen 1410. The injection lumen 1410 may extend within a separate tube 1478 (injection tube) that is substantially or entirely within the shaft 1401. In some embodiments, the tube 1478 is attached to the internal wall of the shaft 1401 only at a distal end portion 1403. Thus, the free-floating nature of the remainder of the tube 1478 within the aspiration lumen 1404 increases the flexibility and trackability of the shaft 1401. There also a reduced chance of the tube 1478 being kinked because of flexing of the shaft 1401, because the bending of the shaft 1401 is not directly applied to the tube 1478. The high pressure saline is forced through the injection tube 1478 and out the orifice 1474, causing a jet 1487. The jet 1487 is within the aspiration lumen 1404, just proximal the open distal end 1405 which can create a Venturi effect that forces blood or thrombus that is external and adjacent the open distal end 1405 into the aspiration lumen 1404. The operation of the peristaltic pump 1408 with the rotatable head 1430 rotating in the first rotational direction 1436 moves fluid and thrombus from the open distal end 1405 of the aspiration lumen 1404 to the proximal end 1442 of the extension tube 1438 by continually and forceably moving the fluid column within the lumen 1444 of the extension tube 1438, which pulls the fluid column within the aspiration lumen 1404 along with it. The combination of the operation of the peristaltic pump 1408 and the jet 1487 created by the high pressure saline cause the maceration of thrombus, and the movement/flow of material (saline/blood/macerated thrombus/small pieces of thrombus) through the aspiration lumen 1404 from the open distal end 1405 to the proximal end 1406, through the interior 1485 of the connector 1424, and through the lumen 1444 of the extension tube 1438 from its distal end 1440 to its proximal end 1442, and finally into the interior 1460 of the canister 1458. Thus, thrombus within a blood vessel of a subject may be macerated and removed by use of the system 1400. Blood vessels may include peripheral blood vessels, coronary blood vessels, or blood vessels within the head or neck of the subject, including carotid arteries or cerebral arteries.

An aspiration monitoring system 1414 comprising a pressure transducer 1416 may be coupled, for example, between the distal end 1440 of the extension tube 1438 and the connector 1424 and/or the proximal end 1406 of the aspiration lumen 1404 of the aspiration catheter 1402. The aspiration monitoring system 1414 can include any of the features described in relation to the other aspiration monitoring systems 48, 62, 78, 900, 1216, 1270 disclosed herein. Signals from the pressure transducer 1416 are carried on an electric cable 1480 to an input 1482 of the pump 1412. A controller 1484 within the pump 1412 is configured to control the operation of the pump 1412, including motor 1491, but the controller 1484 may also be configured to control the operation of the peristaltic pump 1408, with via a cable 1486, or wirelessly. The controller 1484 may comprise a microcontroller. The controller 1484 may alternatively be located within the peristaltic pump 1408, or may be located at another location. Control using signals of measured pressure from the pressure transducer 1416 adds an additional safety element to the system 1400. Furthermore, a non-functional system 1400 or particular component of the system 1400 can be quickly identified. For example, a leak, incomplete connection, incomplete priming of one of the lumens, rupture, or breakage can cause changes in the signal from the pressure transducer 1416, thus allowing their identification. Unallowably high pressures can also be quickly identified, and the controller 1484 is configured to automatically shut down the pump 1412, thus protecting the motor 1491 of the pump 1412 from burnout or overheating, and the failure or danger associated therewith. The peristaltic pump 1408 may also be shut down by the controller 1484. In some embodiments, the peristaltic pump 1408 is configured to be shut down by the controller 1484 after the pump 1412 is shut down (e.g., after a finite delay). The delay may be between about 0.01 second and about 1.00 second, or between about 0.10 second and about 0.25 second. The integrity of the tube 1478 is also protected, e.g., avoiding unnaturally high pressures that could lead to burst. In some embodiments, the peristaltic pump 1408 may be battery powered, and the controller 1484 may be located within the peristaltic pump 1408, thus providing a self-contained peristaltic pump 1408 which may be easily moved from one location to another. In some embodiments, the peristaltic pump 1408 may even be easily cleanable and sterilizable, such that it may be placed within a sterile field, such as a sterile field in the vicinity of a patient. In some embodiments, the pump 1412 is configured to remain in a non-sterile area, while the peristaltic pump 1408 is configured for sterile use. A push button 1411 may be carried on the peristaltic pump 1408, and may be configured for activation by a user, for example, a user who is scrubbed for contact of sterile articles only. The push button 1411 may be configured to start or stop the operation of the peristaltic pump 1408. Additionally, the push button may be configured to start or stop the operation of the pump 1412 (e.g., via the cable 1486). In some embodiments, the peristaltic pump 1408 and the pump 1412 are combined into a single console. This allows for a smaller size that may be mounted on a standard IV pole.

In some embodiments, activation of the push button 1411 by a finger of a user starts the operation of the peristaltic pump 1408, and then starts the operation of the pump 1412, with a slight delay after the peristaltic pump 1408 is started. The delay is useful to assure that some aspiration, or a significant amount of aspiration, is being applied to the aspiration lumen 1404 prior to the injection of pressurized fluid (e.g., saline) through the injection lumen 1410. Thus, blood vessels or other vasculature in the vicinity of the open distal end 1405 are spared any injection of fluid from a high pressure jet, as it is instead aspirated through the aspiration lumen 1404, along with any aspirated thrombus or blood. In addition, in some embodiments, activation of the push button 1411 by a finger of a user during the operation of the pump 1412 and the peristaltic pump 1408 stops the operation of the pump 1412 and the operation of the peristaltic pump 1408 at the same time. In other embodiments, a delay may be applied, for example, such that the pump 1412 is stopped, and then the peristaltic pump 1408 is stopped slightly afterwards. The length of the delays described may be between about 0.01 second and about 1.00 second, or between about 0.10 second and about 0.25 second. In some embodiments, the controller 1484 is configured to change the rotational speed of the rotatable head 1430 of the peristaltic pump 1408, for example, increase the speed or decrease the speed. In some embodiments, the controller 1484 is configured to change the flow rate (injection rate) of the pump 1412, for example, increase the injection rate or decrease the injection rate. In some embodiments, the controller 1484 is configured to change the speed/rate of both pumps 1408, 1412 at the same time. In some embodiments, the controller 1484 is configured to change the speed/rate of one of the pumps 1408, 1412 and then change the speed/rate of the other of the pumps 1408, 1412 after a particular delay. Any of these commands from the controller 1484 may be in response to changes in the signal received from the pressure transducer 1416. The peristaltic pump 1408 in its peak pulse (e.g., sinusoidal peak amplitude) provides a significant negative pressure gradient such that the difference between a clog state pressure transducer 1416 reading and a free flow state pressure transducer 1416 reading is amplified. Thus, a larger number of potential thromboembolic events are avoided, such as thrombus being release from the open distal end 1405 of the aspiration lumen 1404 of the aspiration catheter 1402. The pressure variations on the pressure transducer 1416 tend to be significantly greater when using a peristaltic pump 1408 than when using a vacuum pump, or other vacuum source (e.g., evacuated syringe). One significant advantage is that the user can be made clearly aware when clot/thrombus is not being aspirated, and thus, when aspiration is free flow, causing loss of blood without removal of thrombus 1402. It is much easier to be aware of the status at the open distal end 1405 of the aspiration catheter. Current vacuum pumps do not have a similar clear-cut manner of demonstrating active vs. resting states. The user is thus notified, and the pumps 1408, 1412 are stopped to minimize blood loss, and to allow repositioning onto thrombus. Peristaltic pumps 1408 also tend to be less noisy than vacuum pumps, and less likely to disturb communication of medial personnel during a procedure, or increase stress.

Stopping the peristaltic pump 1408 leaves at least one roller 1432 in a position compressing the compressible portion 1437 of the extension tube 1438. Thus, an open/close valve or pinch valve, or stopcock, or other valve is not needed. The fact that the rotatable head 1430 is already moving means that roller 1432 moves to the occluding position rapidly, without a large inertial requirement, when the peristaltic pump 1408 is stopped. This can thus be faster than the activation of standard electrically-activated pinch valves, which are initially motionless and need to be placed into motion prior to pinching. The motor 1497 may comprise a stepper motor that is directed (e.g., by the controller 1484) such that the rotatable head directs one of the rollers 1432 to occlude the lumen 1444 of the extension tube 1438 at the compressible portion 1437. In FIG. 36, the roller 1432c is in position (if the motor 1497 were stopped) to occlude the lumen 1444. Thus, the peristaltic pump 1408 itself can inherently minimize the potential of distal embolization, as stoppage of pump immediately or almost immediately creates stasis. Alternatively, a non-stepper motor, such as a brushless DC motor, may be utilized along with an encoder (e.g., optical encoder), or another type of position sensor, in place of a stepper motor. Additionally, unmacerated clot can thus be stopped from entering the aspiration lumen 1404. As discussed, in other embodiments, the rollers 1432 may be replaced by non-rotating bumps or protrusions, that slide over the compressible portion 1437 of the extension tube 1438, instead of rolling over. In some embodiments, the bumps/protrusions and/or the external surface of the compressible portion 1437 may be coated with a silicone, hydrophilic, or other lubricious material to lower the friction.

The controller 1484 can be configured to control the operation of the pump 1412 to cause the pump 1412 to inject pressurized fluid in a pulsatile manner. The high pressure jet is applied in a pulsatile fashion to optimize the cutting ability of the jet on a piece of thrombus. For example, a portion of thrombus that is aspirated into the open distal end 1405 of the aspiration lumen 1404 of the aspiration catheter 1402 can be more readily severed by a pulsating jet, much in the manner that a reciprocating saw. The controller 1484 is configured to operate the pump 1412 to pressurize fluid through the injection lumen such that the one or more jets are pulsatile. The controller 1484 is also configured to operate the peristaltic pump 1408 to further aid that that pressurized fluid injected through the injection lumen causes the one or more jets to be pulsatile. For example, the controller 1484 may send a signal to cause a sinusoidal variation in the speed of the motor 1491. The degree of pulsatility (pulse rate, peak pulse, pulse wave shape, rise time, on time, off time) can be tailored and controllably applied by the controller 1484 on the pump 1412 and/or the peristaltic pump 1408.

The use of a peristaltic pump 1408 assures that the interior of the aspiration lumen 1404 and lumen 1444 of the extension tube 1438, and its contents, are not contacted, thus further assuring maintenance of sterility. The use of a peristaltic pump 1408 also causes minimal or virtually no cavitation to blood being removed. If there were any cavitation during aspiration, proximal to the peristaltic pump 1408, after the blood and aspirate passes through the rollers 1432, the blood is exposed to atmospheric pressure, and the cavitation disappears. Thus, it is easier to judge the amount of blood that has been collected or is being collected into the canister 1458 for it is not obscured by bubbles or foam, such that an indicative volume of collected blood is clearly visible and reliable to measure. Additionally, it is easier to reuse the blood quickly, if, for example, it is to be reinjected into the subject. It is also safer and more reliable to infuse blood that does not have significant air bubbles. The use of a vacuum source such as a vacuum bottle or evacuated syringe can tend to create a larger amount of cavitation. Thus, the peristaltic pump 1408 can be used in order to provide an efficient procedure, and also to maximize the volume of blood that may be reinjected/reinfused. The tubing set 1464 separates the extension of the injection lumen 1410 from the aspiration lumen 1404 at the male luer 1410 of the connector 1424, thus only the compressible portion 1437 of the extension tube 1438 need be compressed by the rollers 1432. Other portions of the aspiration catheter 1402 are thus not compressed by the rollers 1432, and therefore are not in danger of being crushed or otherwise damaged. The distal end 1483 of the aspiration catheter 1402 may in some embodiments resemble that of the catheter 516 of FIG. 17. The aspiration catheter 1402 may in some embodiments be replaced by the thrombectomy system 300 of FIG. 34, or the other embodiments of the thrombectomy catheter 306 described in U.S. Pat. No. 9,433,427, issued Sep. 6, 2016, and entitled "Systems and Methods for Management of Thrombosis," which is hereby incorporated by reference in its entirety for all purposes. The use of the peristaltic pump 1408 has additional advantages in comparison to a vacuum pump. The peristaltic pump 1408 can be configured to be controlled by the controller 1484 such that it runs only when the pump 1412 is injecting. Thus, the noise is reduced in comparison to a system using a vacuum pump, as the vacuum pump is on (operating) the entire time.

Figure 37:
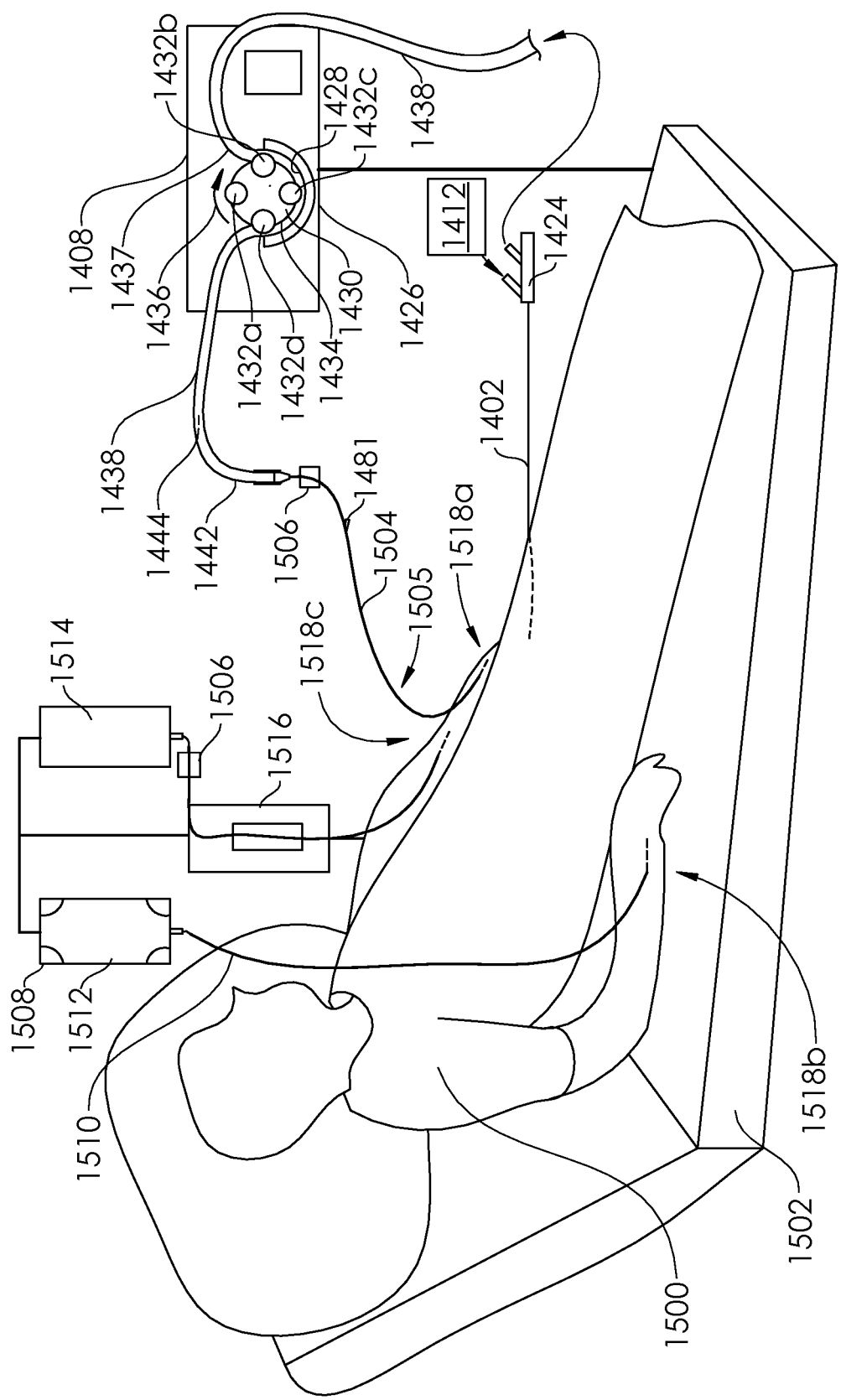
FIG. 37 is a perspective view of a subject being reinjected with blood, according to an embodiment of the present disclosure.

FIG. 37 illustrates a subject 1500 in a hospital bed 1502 or table being injected with blood in three different modalities. During thrombectomy procedures, thrombus/clot is removed from the blood vessels of the subject 1500. In some instances, the blood volume of the patient becomes abnormally low, and fluids or blood need to be reinjected into the patient. In a first modality, the peristaltic pump 1408 of the system 1400 of FIG. 36 is shown. The aspiration catheter 1402 is inserted in the subject 1500 and the aspiration (thrombectomy) procedure is being performed. Instead of the canister 1458, the extension tube 1438 at its distal end 1442 is connected to a return conduit 1505 comprising an intravascular (IV) line 1504 which is inserted into a vein of the subject 1500. The blood is driven by the rollers 1432 of the peristaltic pump 1408 so that it passes through a blood filter 1506, which removes any residual thrombus or particulate prior to the blood being infused into the veins of the subject. Heparin, or other additives may also be added to the blood as it is being injected into the subject 1500 at port 1481, which communicates with the intravascular (IV) line 1504. As the blood only flows through a single sterile composite conduit, an efficient, cleanly reinfusion method is provided. The blood may be purified, for example, to remove red blood cells or portions of red blood cells that have undergone hemolysis. One such reinfusion device is the Haemonetics Cell Saver® Elite+ Autotransfusion System. It is believed that peristaltic pumps 1408 cause less damage to blood cells, and thus less cleaning may be needed, if any. Thus, a higher yield of blood after using the Cell Saver is possible because of the advantages of the peristaltic pump 1408. Also, the blood can be easily transferred to the Cell Saver in a non-contact manner, directly from the extension tube 1438, that is not possible in the transfer from a collection container used with a vacuum source. The blood may even be kept sterile upon being sent directly into the Cell Saver. In some embodiments, the extension tube 1438 may be significantly translucent, so that the thrombus can be assessed during aspiration. A video camera or magnifying element (low power microscope, etc.) may be focused on the extension tube 1438 to better identify the state of the thrombus being aspirated (quantity, amount of maceration). There can be an almost real-time feedback of the condition of the thrombus being removed from within the vasculature of the patient.

In a second modality, blood is collected in a prior procedure in the canister 1458 (FIG. 36). The blood may then be filtered, or even spun in a centrifuge to obtain particular components. Heparin, or other additives may also be added to the blood. The blood is then placed in a blood bag 1508 (or blood bottle) and infused into the vein of the subject 1500 using a passive drip through an IV line 1510 (e.g., via gravity alone). In other cases, a pressurizable bag 1512 may be used around the blood bag 1508 to increase the compression on the blood bag 1508, thus increasing the flow rate into the vein. In some cases, the blood may even by injected directly into the arterial system, for example, through an arterial line (a-line). The blood may additionally be purified as described above.

In a third modality, blood is collected in a prior procedure in the canister 1458 (FIG. 36). The blood may then be filtered, or even spun in a centrifuge to obtain particular components. Heparin, or other additives may also be added to the blood. The blood is then placed into a blood bag 1514, and pumped into a vein of the subject 1500 using an infusion pump 1516. Insertion points 1518a, 1518b, 1518c are shown for the first, second, and third modalities, respectively. The blood may additionally be purified as described above.

Figure 38:
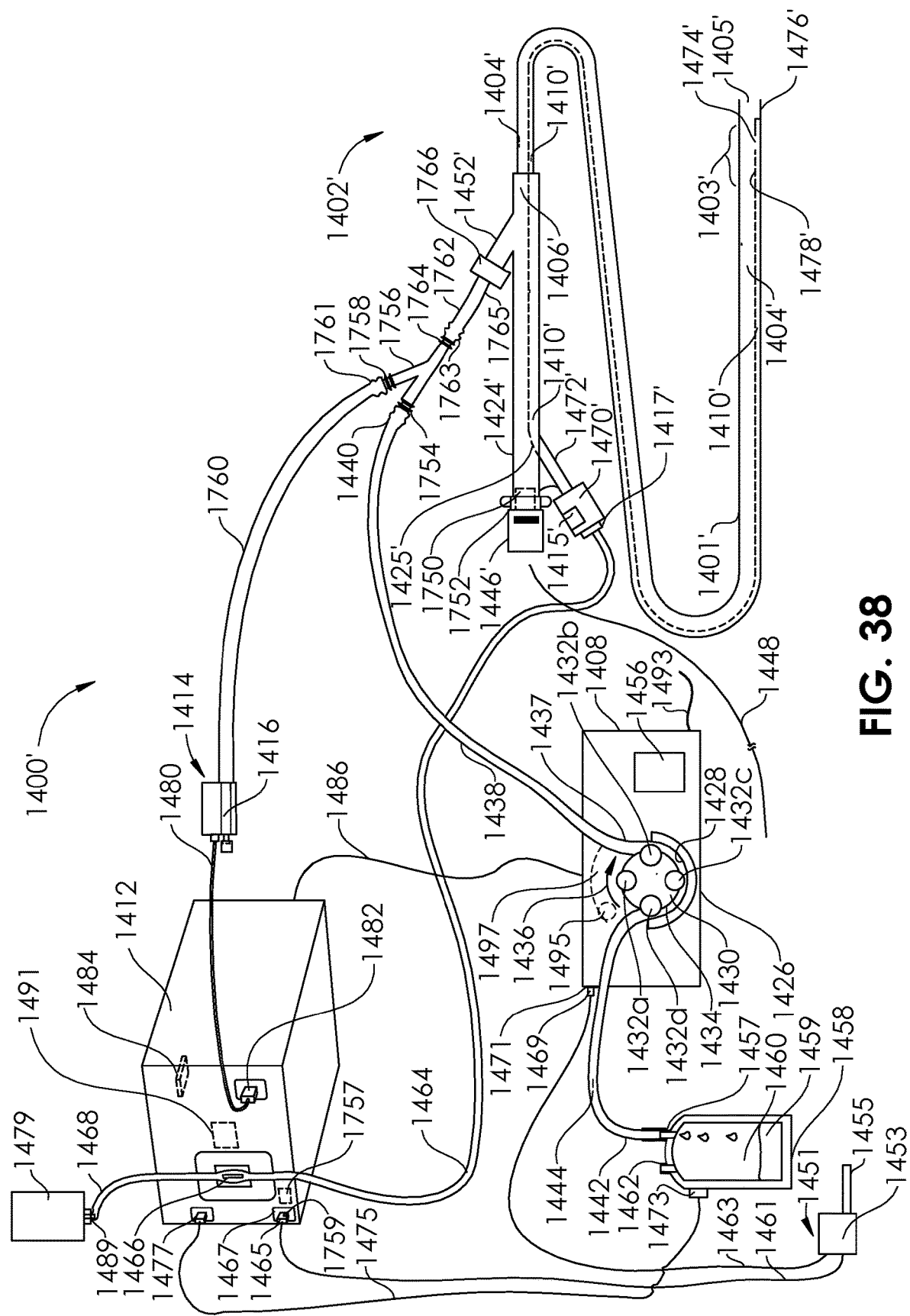
FIG. 38 is a perspective view of an aspiration system according to an embodiment of the present disclosure.

FIG. 38 illustrates an alternative aspiration system 1400' comprising an aspiration catheter 1402' comprising an elongate shaft 1401' including an aspiration lumen 1404' having an open distal end 1405' and a proximal end 1406' configured to couple to the peristaltic pump 1408. The peristaltic pump 1408 may be a roller pump having a base 1426, a pressure shoe 1428 carried by the base 1426, and a rotatable head 1430, rotatably coupled to the base 1426, and carrying two or more rollers 1432a-d. The rollers 1432a-d are arrayed around a perimeter 1434 of the rotatable head 1430. The rotatable head 1430 is configured to be rotatable in at least a first rotational direction 1436 with respect to a rotational axis 1499. The rotatable head 1430 may be rotated by a motor 1497, either directly, or with a gear train 1495. The peristaltic pump 1408 may be battery powered, and the battery(ies) may be rechargeable by wired or wireless means. The peristaltic pump 1408 may alternatively, or additionally be powered by a power cord 1493 configured to connect to a power supply. An extension tube 1438 having a distal end 1440 and a proximal end 1442, and having a lumen 1444 extending therethrough, is hydraulically coupled to the proximal end 1406' of the aspiration lumen 1404' via a connector 1424'. The extension tube 1438 may be supplied (e.g., sterile) with the aspiration catheter 1402', or may be packaged and supplied separately. A Touhy-Borst seal 1446' is coupleable and decouplable to the connector 1424' (e.g., via luer connections 1750, 1752) and is configured to be loosened/opened to allow the insertion of a guidewire 1448 through the connector 1424' and the aspiration lumen 1404'. The aspiration lumen 1404' may thus be used to track the aspiration catheter 1402' over the guidewire 1448 through a subject's vasculature. The Touhy-Borst 1446' can be tightened to seal over the guidewire 1448, to maintain hemostasis. Other types of seals may be incorporated in place of the Touhy Borst 1446', including a spring-loaded, longitudinally compressible and actuatable seal. The distal end 1440 of the extension tube 1438 is slipped over a first barb fitting 1754 of a y-connector 1756. A second extension tube 1760 has a distal end 1761 that is slipped over a second barb fitting 1758 of the y-connector 1756. A third extension tube 1762 has a proximal end 1763 that is slipped over a third barb fitting 1764 of the y-connector 1756. The second extension tube 1760 and third extension tube 1762 are configured to operate under negative pressure without collapsing, and may comprise standard suction tubing. A distal end 1765 of the third extension tube 1762 is coupled to a female luer 1452' sideport of the connector 1424', either permanently by molding, or an adhesive bond or weld, or by an attachable and detachable connection, such as a luer 1766. The lengths of each of the second extension tube 1760 and third extension tube 1762 may be varied. In some embodiments, the third extension tube 1762 is relatively short, and the y-connector 1756 is configured to be located in a sterile area near the patient. In other embodiments, the third extension tube 1762 is configured to be relatively long, and the y-connector 1756 is configured to be located in a non-sterile area, away from the patient. The second extension tube 1760 is optional, as the third extension tube 1762 may have a much longer length and the pressure transducer 1416/aspiration monitoring system 1414 may be attached directly to the y-connector 1756 at the location of the barb fitting 1758. This connection may be direct, and so the barb fitting 1758 is also optional. With the longer third extension tube 1762, the y-connector 1756 and the aspiration monitoring system 1414 can both be close to the pump 1412, and can both reside in a non-sterile area.

In use, a compressible portion 1437 of the extension tube 1438 is placed within the pressure shoe 1428 of the peristaltic pump 1408 such that rotation of the rotatable head 1430 in the rotational direction 1436 causes fluid to be forced through the lumen 1444 of the extension tube 1438 from the distal end 1440 to the proximal end 1442, via compression of the compressible portion 1437 by the rollers 1432, one at a time. Optionally, an interface 1456 on the peristaltic pump 1408 is configured to allow a user to input information or commands to the peristaltic pump 1408 or other components of the system 1400'. Otherwise, hardware or firmware may be pre-programmed with specific run parameters (motor speed, rotation speed, etc.). In some embodiments, there are only two rollers 1432. In other embodiments, there are three rollers 1432. In still other embodiments, as shown, there are four rollers 1432. As described, the rollers 1432 may be replaced by bumps or protrusions. The compressible portion 1437 may comprise silicone tubing, polyurethane tubing, polyvinyl chloride tubing, or other compressible tubing. The compressible section 1437 may be a relatively short section that is attachable to and detachable from the peripheral ends of the extension tube 1438, or in other embodiments, may comprise the entirety of the extension tube 1438 between the distal end 1440 and the proximal end 1442. The proximal end 1442 of the extension tube 1438 may be coupled to a hub 1457 of a canister 1458 having an interior 1460, to allow fluid 1459 passing through the extension tube 1438 to pass into the interior 1460. An additional hub 1462 in the canister 1458 may be left open (as shown) to allow the unfilled interior 1460 to match atmospheric pressure. Alternatively, the canister 1458 may be replaced by a bag, such as an empty infusion bag, configured for collecting aspirate therein.

The aspiration catheter 1402' additionally has a high pressure injection lumen 1410' for injecting saline from a fluid source 1479, for example, via a high pressure pump 1412. A tubing set 1464 may include a pump cartridge 1466 having a piston or bellows or other movable element that the pump 1412 may manipulate using an internal motor 1491, thus pressurizing saline (or other fluid) from the fluid source 1479 with a significantly high pressure such that the saline is forced through the injection lumen 1410' of the aspiration catheter 1402'. The tubing set 1464 includes proximal end 1468 having a spike 1489, or other connecting element for hydraulically coupling the tubing set 1464 to the fluid source 1479. The tubing set 1464 further has a distal end 1470 (which may include a male luer) which is configured to hydraulically couple to the injection lumen 1410' via a female luer 1472'. In use, injected saline is forced through the injection lumen 1410' by the pump 1412 and exits an orifice 1474' at a distal end 1476' of the injection lumen 1410'. The injection lumen 1410' may extend within a separate tube 1478' (injection tube) that is substantially entirely within the shaft 1401'. In some embodiments, the tube 1478' is attached to the internal wall of the shaft 1401' only at a distal end portion 1403'. Thus, the free-floating nature of the remainder of the tube 1478' within the aspiration lumen 1404' increases the flexibility and trackability of the shaft 1401'. The high pressure saline is forced through the injection tube 1478' and out the orifice 1474', causing a jet (similar to jet 1487 of FIG. 36). The jet is aimed within the aspiration lumen 1404', just proximal the open distal end 1405' which may create a Venturi effect that forces blood or thrombus that is external and adjacent the open distal end 1405' into the aspiration lumen 1404'. The combination of the operation of the peristaltic pump 1408 and the jet created by the high pressure saline cause the maceration of thrombus, and the movement/flow of material (saline/blood/macerated thrombus/small pieces of thrombus) through the aspiration lumen 1404' from the open distal end 1405' to the proximal end 1406', through the female luer 1452' of the connector 1424', and through the lumen 1444 of the extension tube 1438 from its distal end 1440 to its proximal end 1442, and finally into the interior 1460 of the canister 1458. Thus, thrombus within a blood vessel of a subject may be macerated and removed by use of the system 1400'. Blood vessels may include peripheral blood vessels, coronary blood vessels, or blood vessels within the head or neck of the subject, including carotid arteries or cerebral arteries.

An aspiration monitoring system 1414 comprising a pressure transducer 1416 may be coupled, for example, proximal to the connector 1424' and/or proximal to the proximal end 1406' of the aspiration lumen 1404' of the aspiration catheter 1402', such that the pressure transducer 1416 is hydraulically coupled to the aspiration lumen 1404'. In the aspiration system 1400' of FIG. 38, the aspiration monitoring system 1414 is spaced a distance from the y-connector 1756 by a relatively long second extension tube 1760 (or alternatively by a relatively long third extension tube 1762, as in the aspiration system 2100 of FIG. 74) such that the aspiration monitoring system 1414 resides in a non-sterile area. Thus, the aspiration monitoring system 1414 may be set up, prepped, calibrated, and operated by a technologist, sales representative, nurse, or other medical personnel that has not "scrubbed" and thus does not need to maintain sterility. For example, the aspiration monitoring system 1414 may be located near the pump 1412, or on the same table as the pump 1412. The aspiration monitoring system 1414 can include any of the features described in relation to the other aspiration monitoring systems 48, 62, 78, 900, 1216, 1270 disclosed herein. Signals from the pressure transducer 1416 are carried on an electric cable 1480 to an input 1482 of the pump 1412. A controller 1484 within the pump 1412 is configured to control the operation of the pump 1412, including motor 1491, but the controller 1484 may also be configured to control the operation of the peristaltic pump 1408, with via a cable 1486, or wirelessly. The controller 1484 may comprise a microcontroller. The controller 1484 may alternatively be located within the peristaltic pump 1408, or may be located at another location. Control using signals of measured pressure from the pressure transducer 1416 adds an additional safety element to the system 1400'. Additionally, a non-functional device (because of a leak, incomplete connection, incomplete priming, rupture, blockage) can be quickly identified. Unallowably high pressures can also be quickly identified, protecting the motor 1491 of the pump 1412 from burnout or overheating danger. The integrity of the tube 1478' is also protected, e.g., avoiding unnaturally high pressures that could lead to burst.

The aspiration catheter 1402' is similar to the aspiration catheter 1402 of FIG. 36, except that the female luer 1452' is located distally on the connector 1424' from the female luer 1472'. Thus, aspirated blood/thrombus/saline enters the female luer 1452' without ever having to contact interior irregularities 1425' (in geometry, shape) within the connector 1424', that may otherwise cause flow resistance, or cause thrombus to catch (e.g., between the tube 1478' and the interior of the connector 1424'.

A foot pedal 1451 has a base 1453 and a pedal 1455 that is coupled to the base 1453 and movable or activatable by application of the foot of a user. The pedal 1455 may be spring-loaded and depressible by application of a moment or a compressive force, or may instead comprise a membrane switch. The pedal 1455, when activated, may in some embodiments toggle on and off, and in other embodiments may be activatable when a force, a pressure, or a moment is applied, and inactivated when the force, pressure, or moment is not applied. A first cable 1461 carries signals from the foot pedal 1451 to pump 1412 via a plug 1465 that is connected to an input jack 1467. In some embodiments, activation of the pedal 1455 by the foot of a user starts the operation of the pump 1412 and starts the operation of the peristaltic pump 1408 at the same time, as a signal through the first cable 1461 is received by the controller 1484, which commands the pump 1412 to start and, via the cable 1486, commands the peristaltic pump 1408 to start. In some embodiments, activation of the pedal 1455 by the foot of a user starts the operation of the peristaltic pump 1408, and then starts the operation of the pump 1412, with a slight delay after the peristaltic pump 1408 is started. The delay is useful to assure that some aspiration, or a significant amount of aspiration, is being applied to the aspiration lumen 1404' prior to the injection of pressurized fluid (e.g., saline) through the injection lumen 1410'. Thus, blood vessels or other vasculature in the vicinity of the open distal end 1405' are spared any injection of fluid from a high pressure jet, as it is instead aspirated through the aspiration lumen 1404', along with thrombus or blood. In some embodiments, the plug 1465 of the foot pedal 1451 may include a resistor 1759, and the pump 1412 may include an identification circuit 1757 configured to read the resistance value of the resistor 1759. For example, the resistor 1759 may complete a partial Wheatstone bridge carried on the identification circuit 1757, such that the pump 1412 can recognize the foot pedal 1451, and operate accordingly. Alternatively, the resistor 1759 may reside in the foot pedal 1451 itself, instead of the plug 1465. The cable 1461 may provide the electrical connection to the resistor 1759 in that particular case. Alternatively, the resistor 1759 may be replaced by an RFID chip that is configured to be powered and read by the identification circuit 1757.

In addition, in some embodiments, activation of the pedal 1455 by the foot of a user during the operation of the pump 1412 and the peristaltic pump 1408 stops the operation of the pump 1412 and the operation of the peristaltic pump 1408 at the same time. In other embodiments, a delay may be applied, for example, such that the pump 1412 is stopped, and then the peristaltic pump 1408 is stopped slightly afterwards. The length of the delays described may be between about 0.01 second and about 1.00 second, or between about 0.10 second and about 0.25 second. The operation (on/off) of the pump 1412 and/or peristaltic pump 1408 via the foot pedal 1451 allows hands-free activation, enabling a single user the manipulate the aspiration catheter 1402' and guidewire 1448 with both hands. The location of the foot pedal 1451 can be tactilely found with the foot of the user, while the user maintains visual contact with the patient and/or any monitors, or even other medical personnel. Alternatively, a second cable 1463 carries signals from the foot pedal 1451 directly to the peristaltic pump 1408 via a plug 1469 that is connected to an input jack 1471. Thus, the operation of the foot pedal 1451 may be configured to control the operation of the peristaltic pump 1408 in embodiments, for example, in which there is no cable 1486. However, in the embodiment of FIG. 38, which includes the cable 1486, the cable 1463 is not required.

In other embodiments, the foot pedal 1451 may be replaced by another type of switch, including, but not limited to a toggle on/off push button or hand switch, an audio-activated switch (voice activated, clap activated, click activated), an optical switch (beam/light sensor for hand or foot interruption), or any other kind of switch that can be activated by medical personnel. The switch may be remote (e.g., in a control room) or may be located near the procedural area. The switch may also be a sterile switch or sterilizable for location on a sterile area.

In some cases, the activation and deactivation (turning on and off) of the aspiration flow applied by the peristaltic pump 1408 on the aspiration lumen 1404' may be done by leaving the peristaltic pump 1408 in a running condition, while the user opens and closes the stopcock 1454. In some embodiments, the controller 1484 controls the initiation of both the peristaltic pump 1408 and the pump 1412 at substantially the same time. In some embodiments, the controller 1484 controls the initiation the peristaltic pump 1408 and, following a particular delay, the initiation of the pump 1412. The delay may be within the ranges previously described.

The controller 1484 also monitors and controls several device safety functions, which include over pressure detection, air bubble detection, and vacuum or negative pressure charge. An additional pressure transducer 1415' carried on the connector 1424' monitors pressure (i.e. injection pressure), and senses the presence of air bubbles. Alternatively, or in conjunction, an optical device 1417' may be used to sense air bubbles. In one contemplated embodiment, the pump pressure is proportional to the electric current needed by the pump 1412 to produce that particular pressure. Consequently, if the electric current required by pump 1412 exceeds a preset limit, the controller 1484 will disable the pump 1412 by cutting power to it. Air bubble detection may also be monitored by monitoring the electrical current required to drive the pump 1412 at any particular moment. In order for a pump 1412 to reach high fluid pressures, there should be little or no air (which is highly compressible) present in the pump 1412 or connecting system (including the aspiration lumen 1404' of the aspiration catheter 1402' and the tubing set 1464). The fluid volume is small enough that any air in the system will result in no pressure being generated at the pump head. A sufficient volume of liquid is needed proximally to flush any finite amount of air through. The controller 1484 monitors the pump 1412 current for any abrupt downward change that may indicate that air has entered the system. If the rate of drop is faster than a preset limit, the controller 1484 will disable the pump 1412 by cutting power to it until the problem is corrected.

In some embodiments, a fluid level sensor 1473 is carried on the side of the canister 1458 and is configured to sense when the canister 1458 has approached or reached its full level. The fluid level sensor 1473 is configured to output a signal through a cable 1475 that is attached to via an input 1477 (plug/jack) at the pump 4112. The signal from the fluid level sensor 1473 may be received by the controller 1484 which can be configured to immediately stop the pump 1412 and, via cable 1486, the peristaltic pump 1408 at the same time, or with a delay therebetween, as previously described. The fluid level sensor 1473 may comprise an optical sensor, and the canister 1458 may have a clear wall, to allow the optical sensor to measure the reflection variations when fluid is not adjacently present or when fluid is adjacently present. Alternatively, the fluid level sensor 1473 may comprise a piezoresistive pressure sensor that is within the volume 1460 of the canister 1458 at the desired height that represents a "full" canister 1458. Other types of fluid sensors are also contemplated, including floats, strain gauges, laser sensors, ultrasonic sensors, or capacitive sensors. In each of these embodiments, a signal is sent wirelessly or through cable 1475 so that the peristaltic pump 1408 and/or pump 1412 may be shut down when a "full" level is reached.

Figure 74:
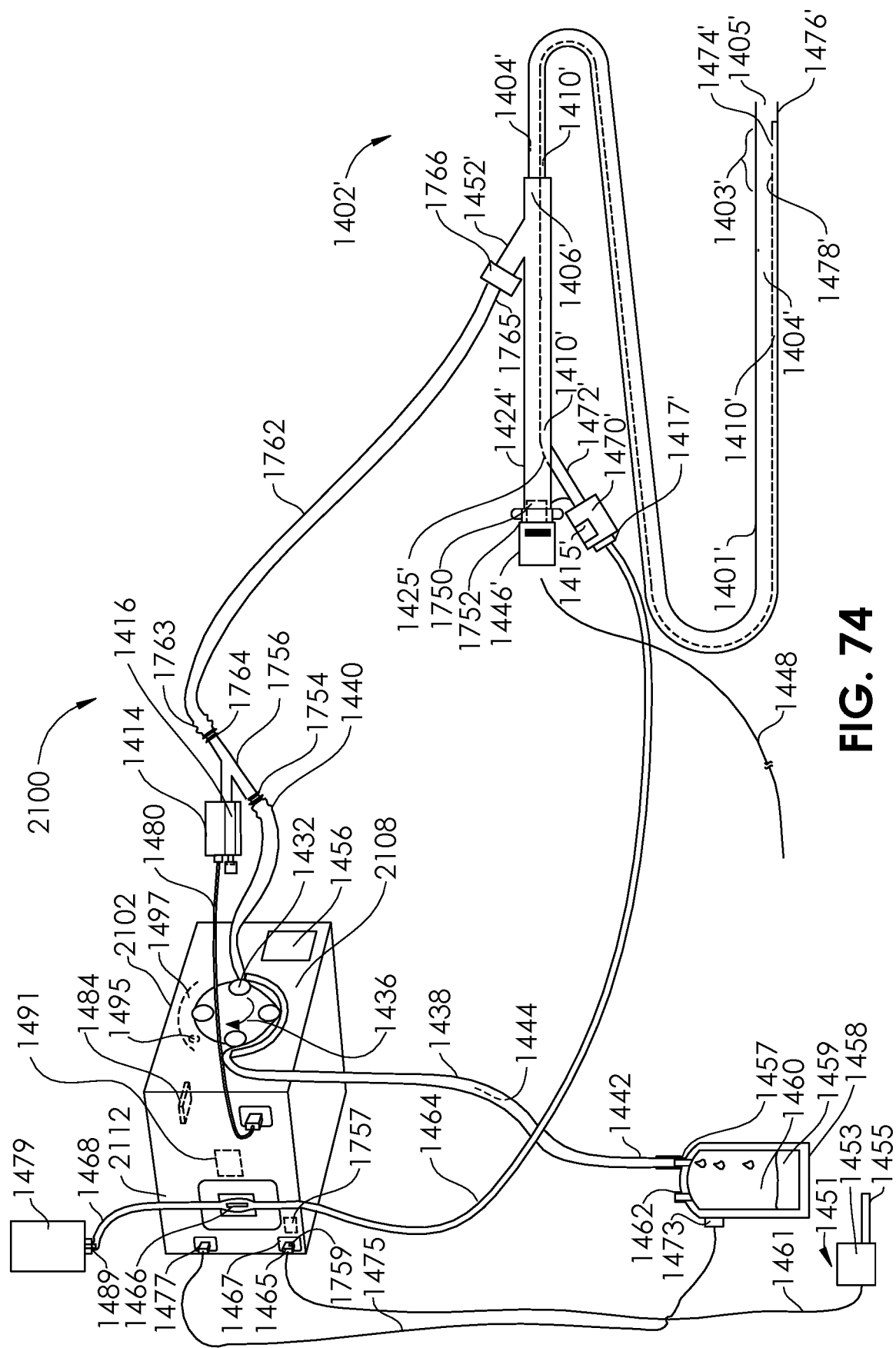
FIG. 74 is a perspective view of an aspiration system according to an embodiment of the present disclosure.

In some embodiments, the peristaltic pump 1408 and the pump 1412 are combined into a single console. This allows for a smaller size that may be mounted on a standard IV pole. FIG. 74 illustrates an aspiration system 2100 that has all the features of the aspiration system, 1400' of FIG. 38, but the peristaltic pump features 2108 and the injection pump features 2112 are both included on a single console 2102. The third extension tube 1762 is elongated and the aspiration monitoring system 1414 is directly coupled or couplable to the y-connector 1756. The aspiration monitoring system 1414 may reside in a non-sterile area. Thus, the aspiration monitoring system 1414 may be set up, prepped, calibrated, and operated by a technologist, sales representative, nurse, or other medical personnel that has not "scrubbed" and thus does not need to maintain sterility. For example, the aspiration monitoring system 1414 may be located on the same table as the console 2102. The cable 1486 of the system 1400' of FIG. 38 is not necessary, as similar connectivity is located inside the console 2100. The cable 1463 of the system 1400' of FIG. 38 is also not necessary, as the cable 1461 is capable of transferring all of the signals to and from the foot pedal 1451. The luer 1766 may be attachable and detachable, or in other embodiments may be permanently bonded to the female luer 1452' of the connector 1424'.

Figure 39:
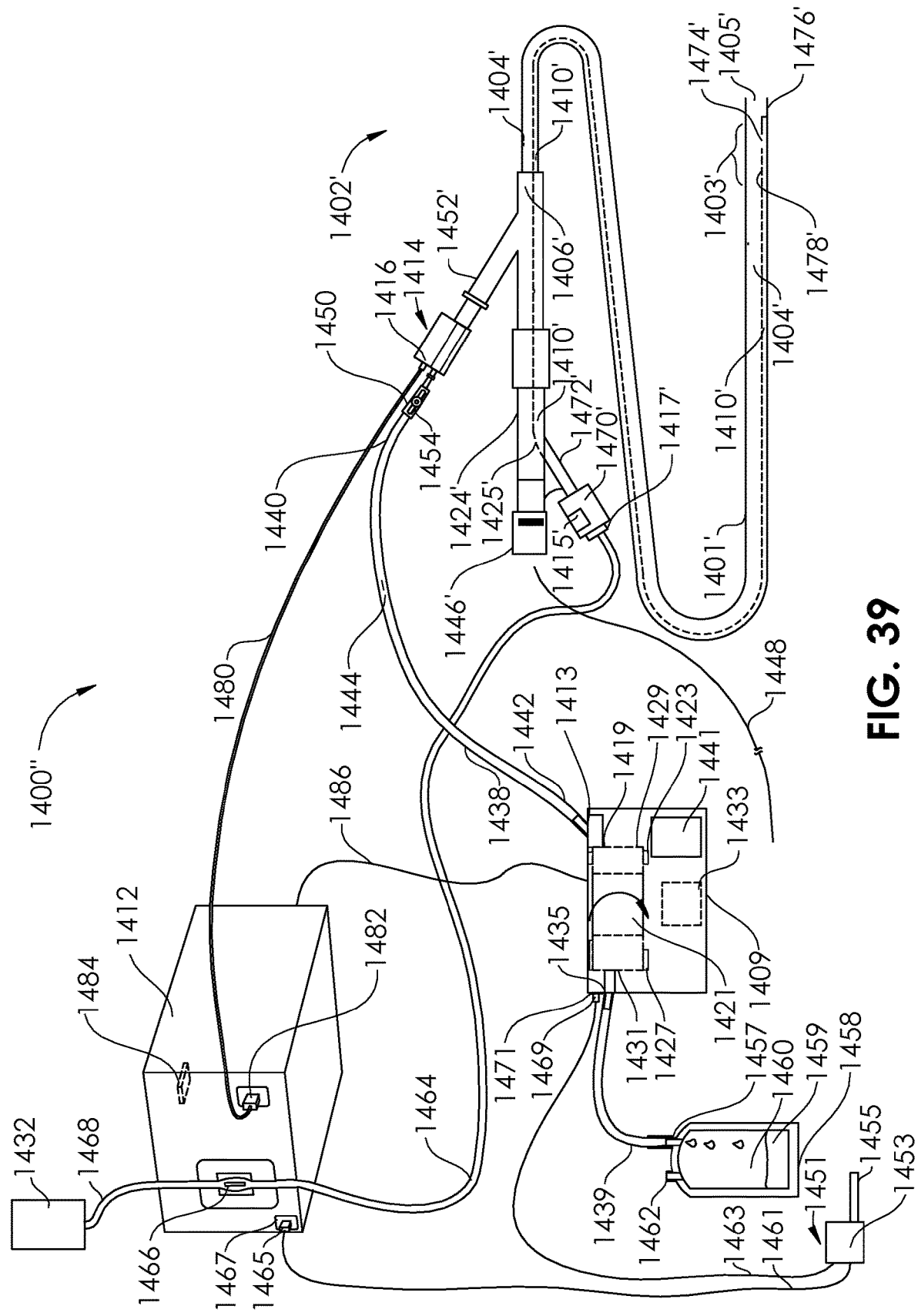
FIG. 39 is a perspective view of an aspiration system according to an embodiment of the present disclosure.

FIG. 39 illustrates an alternative aspiration system 1400" comprising the aspiration catheter 1402' of FIG. 38. However, a centrifugal pump 1409 is substituted in place of the peristaltic pump 1408. The proximal end 1442 of the extension tube 1438 coupled to an inlet 1413 which allows the aspirate to enter a chamber 1419. An impeller 1421 is rotatably held within the chamber 1419 by a first bearing 1423 and a second bearing 1427. A first seal 1429 and second seal 1431 allow the impeller 1421 to rotate (curved arrow) without the aspirate leaking. A motor 1433 is configured to rotate the impeller 1421. The aspirate is forced out an outlet 1435 into an exit tube 1439 which is coupled to the hub 1457 of the canister 1458. A user interface 1441 may be manipulated by a user to operate the centrifugal pump 1409. In some embodiments, an Angiodynamics AngioVac centrifugal pump may be used as the centrifugal pump 1409.

The aspiration catheters 1402, 1402' of FIGS. 36, 38, and 39 are illustrated as having pressurized fluid injection through injection lumens 1410, 1410'. However, other embodiments of the aspiration systems 1400, 1400' in which the aspiration catheters 1402, 1402' are replaced by a standard aspiration catheter, not having an injection lumen, such as the aspiration catheter 4 of FIG. 1.

As an alternative to collecting the aspirated material in a blood bag, blood bottle, or the canister 1458, aspirated components (blood, thrombus, saline, slurry, etc.) can be placed into a reinfusion device, such as a Stryker ConstaVac (CBCII) Blood Conservation System, or a Haemonetics OrthoPAT Orthopedic Perioperative Autotransfusion System. The blood may be purified by the reinfusion device, for example, to remove red blood cells or portions of red blood cells that have undergone hemolysis. One such reinfusion device is the Haemonetics Cell Saver® Elite+ Autotransfusion System.

In some embodiments, the blood may be cooled prior to being injected. In some embodiments, the blood may be heated prior to being injected. In some embodiments, other drugs may be added to the blood prior to it being inserted. In some cases, the blood may be diluted with saline, to decrease its viscosity, or decrease its hematocrit. This may allow for decrease hemolysis to occur. In some cases, blood collected in the canister 1458, or blood coming from the extension tube 1438, may even be used as donor blood, to infuse into a different patient.

In some embodiments, an additional or alternate sensor may be used to monitor flow conditions for the notification of the user, including, but not limited to: a Doppler sensor, an infrared sensor, or a laser flow detection device. In some embodiments, an externally-attached (non-contact) Doppler sensor may be employed. In some embodiments, an infrared sensor or a laser flow detection device may be employed around the extension tubing 1438. The alternate sensor (e.g., flow sensor, etc.) may be located at a number of different locations along the aspiration path, including on or in the extension tube 1438, distal to the impeller 1421 of the centrifugal pump 1409, or on or in the exit tube 1439 proximal to the impeller 1421 of the centrifugal pump 1409. Or in embodiments using a peristaltic pump 1408, the alternate sensor may be located on or in the extension tube 1438, distal or proximal to the rotatable head 1430 of the peristaltic pump 1408.

An aspiration system 1600 utilizing an ultrasound sensor 1602 is shown in FIGS. 40-42. The aspiration system 1600 is similar to the aspiration system 1400' of FIG. 38, with the addition of the ultrasound sensor 1602 and other related components. Alternative embodiments may utilize the teachings of other aspiration system embodiments disclosed herein. The ultrasound sensor may be configured for an analog output (e.g., with varying voltage output), for example, with a range of 0 Volts DC to 1 Volt DC, or 0 Volts DC to 5 Volts DC, or 0 Volts DC to 10 Volts DC. Turning to FIG. 41, the ultrasound sensor 1602 is inserted within a sideport 1606 of a y-connector 1604. The y-connector 1604 has a distal connector 1608 attached to a proximal end 1603 of tubing 1610. The tubing 1610 is slide over barbs 1605 which comprise the distal connector 1608. A distal end 1607 of the tubing 1610 is coupled to the proximal end 1406' of the aspiration lumen 1404' of the aspiration catheter 1402', via a connector 1609 and the aspiration monitoring system 1414, attached to the female luer 1452' of the connector 1424'. A proximal connector 1612 of the y-connector 1604 is connected to a friction fitting 1616 of an extension tube 1614. The proximal connector 1612 also comprises barbs. The extension tube 1614 is connectable to the peristaltic pump 1608, but may alternatively be coupled to the centrifugal pump 1409, or one of the vacuum sources described herein. The ultrasound sensor 1602 is positioned so that its distal end 1618 is adjacent aspiration flow (straight arrow, FIG. 41). A fitting 1620 at the proximal end of the ultrasound sensor 1602 is configured to secure the ultrasound sensor 1602 to the sideport 1606 in its desired position. This may be a friction fit, a screw attachment, a snap, and adhesive bond, a thermal bond, or other securement means. The output of the ultrasound sensor (e.g., voltage) is communicated through a cable 1622. A strain relief 1601 coupled to the cable 1622 and the fitting 1620 serves to protect the first end 1611 of the cable 1622 from damage due to bending, tension, or compression.

In one embodiment, the ultrasound sensor 1602 has an analog channel that outputs a signal referenced to ground that varies between 0 to 5 Volts DC. For very small flow rates, the signal is often sinusoidal, but in the higher flow rates commonly occurring during the aspiration of clot/thrombus/blood the flow is substantial enough that it saturates the channel and appears as a variable digital pulse stream, roughly proportional to flow. The pulse frequency is relatively high on this channel. In other words, a pseudo-digital on/off occurs when flow rates exceed a particular value. This particular value may be adjusted by connecting appropriate electronics. Along with the pseudo-digital properties of the channel, a dedicated digital I/O pin is utilized that feeds a high-priority interrupt handler. This allows the counting of rising signal transitions in this pulse stream very efficiently over a fixed interval of time. The pulse count above/below one or more pre-determined thresholds is ultimately what determines whether the overall system is in a free-flow or clot removal state and to what degree.

FIG. 42 illustrates a console 1624 having an input jack 1626 into which a plug 1628 at the second end 1613 of the cable 1622 attaches. The console 1624 includes an internal measurement device 1630 which is configured to count the number of times N during a predetermined time period P that a signal being output by the ultrasound sensor 1602 surpasses a predetermined threshold amplitude A. The measurement device 1630 is further configured to determine whether the number of times N is (a) greater than (or greater than or equal to) or (b) less than (or less than or equal to) a predetermined value V. For example, in one embodiment, a predetermined time period P is entered into the measurement device 1630 (e.g., via a user interface 1632) as 0.33 seconds. An algorithm within the measurement device 1630 counts the number threshold crossings that are output by the ultrasound sensor 1602 during this predetermined time period P. The measurement device 1630 then applies a particular logic scheme. In some embodiments, this logic scheme may simply be "flow" or "no flow." For example, if there are between 0 counts and 150 counts within the time period P, then a "no flow" condition is identified and if there are 151 or greater counts within the time period P, then a "flow" condition is identified. The measurement device 1630 may comprise a microprocessor. A communication device 1634 carried on the console 1624 may be controlled by the measurement device 1630, or by a separate controller, to identify a first communication mode for the "no flow" condition and a second communication mode for the "flow" condition. In some embodiments, the first communication mode may comprise the non-existence of a signal (e.g., no light lit, no sound produced, no vibration or heat produced) from the communication device 1634, and the second communication mode may comprise a light lit, or a message shown (e.g., the word "flow"), or an audio message played (a voice stating "aspiration occurring"), or an audio warning (e.g., "beep"), or a mechanical warning (e.g., vibration). The amplitude of the communication (e.g., dB of sound, intensity of light, etc.) may be increase by pressing increase button 1615 or decreased by pressing decrease button 1617. The current level of the amplitude is displayed on display 1619. The display may comprise a series of LEDs 1621 that are configured to be lit up such that a higher amplitude corresponds to a larger number of the LEDs being lit.

In other embodiments, the first communication mode and the second communication mode may each include some perceptible signal (audible, visual, tactile), each one different from the other. In other embodiments, a more complex logic scheme may be used. For example, for a predetermined time period P of 0.33 seconds, if there are between 0 counts and 150 counts within the time period P, then a "no flow" condition is identified; if there are between 151 and 225 counts within the time period P, then a "low flow" condition is identified; if there are between 226 and 350 counts within the time period P, then a "medium flow" condition is identified; and, if there are 351 counts or greater, then a "high flow" condition is identified. The "no flow" condition can correspond to a first communication mode, the "low flow" condition to a second communication mode, the "medium flow" condition to a third communication mode, and the "high flow" condition to a fourth communication mode. The first communication mode may be treated by the communication device 1634 remaining silent and/or non-visual/non-vibrational/non heating, etc. The second communication mode may be treated by the communication device beeping (via audio speaker) or flashing (via led or other light) at a frequency of 2 Hz. The third communication mode may be treated by the communication device beeping (via audio speaker) or flashing (via led or other light) at a frequency of 4 Hz. The fourth communication mode may be treated by the communication device beeping (via audio speaker) or flashing (via led or other light) at a frequency of 10 Hz. In another embodiment, the second communication mode may be treated by the communication device beeping (via audio speaker) or flashing (via led or other light) at a frequency of 0.5 Hz. The third communication mode may be treated by the communication device beeping (via audio speaker) or flashing (via led or other light) at a frequency of 1 Hz. The fourth communication mode may be treated by the communication device beeping (via audio speaker) or flashing (via led or other light) at a frequency of 2 Hz. Additionally, or alternatively, the intensity of the signal may increase from the second to the fourth communication modes. For example, by 10 dB from second to third and by 10 more dB from third to fourth. Or, by 5 dB, each time.

In an alternative embodiment, the ultrasound sensor 1602 may have an analog-to-digital module, and may output digital signals only, particular to 1 (flow at or above a particular threshold flow rate) or 0 (flow below a particular threshold flow rate).

The predetermined time period P, may be between about 0.01 seconds and about 1.00 seconds, or between about 0.10 seconds and about 0.50 seconds, or between about 0.20 seconds and about 0.40 seconds. The predetermined time period P may be adjustable by a user, for example, via the user interface 1632.

In certain aspiration procedures, when thrombus is not being sufficiently aspirated but aspiration continues, an unacceptably large volume of blood may be aspirated from the patient. This may cause dehydration, decreased blood pressure, or even exsanguination of the patient, all potentially serious events which can risk the success of the procedure and endanger the patient. The ability to be aware at all times whether the blood is being aspirated at an unacceptable rate is an important factor for achieving a high degree of safety and efficiency.

Systems for catheter aspiration are disclosed herein which are configured to communicate flow status and/or flow rate information to a user as determined by weighing the fluid, blood, thrombus, or other materials being aspirated from the patient over a period of time.

Figure 43:
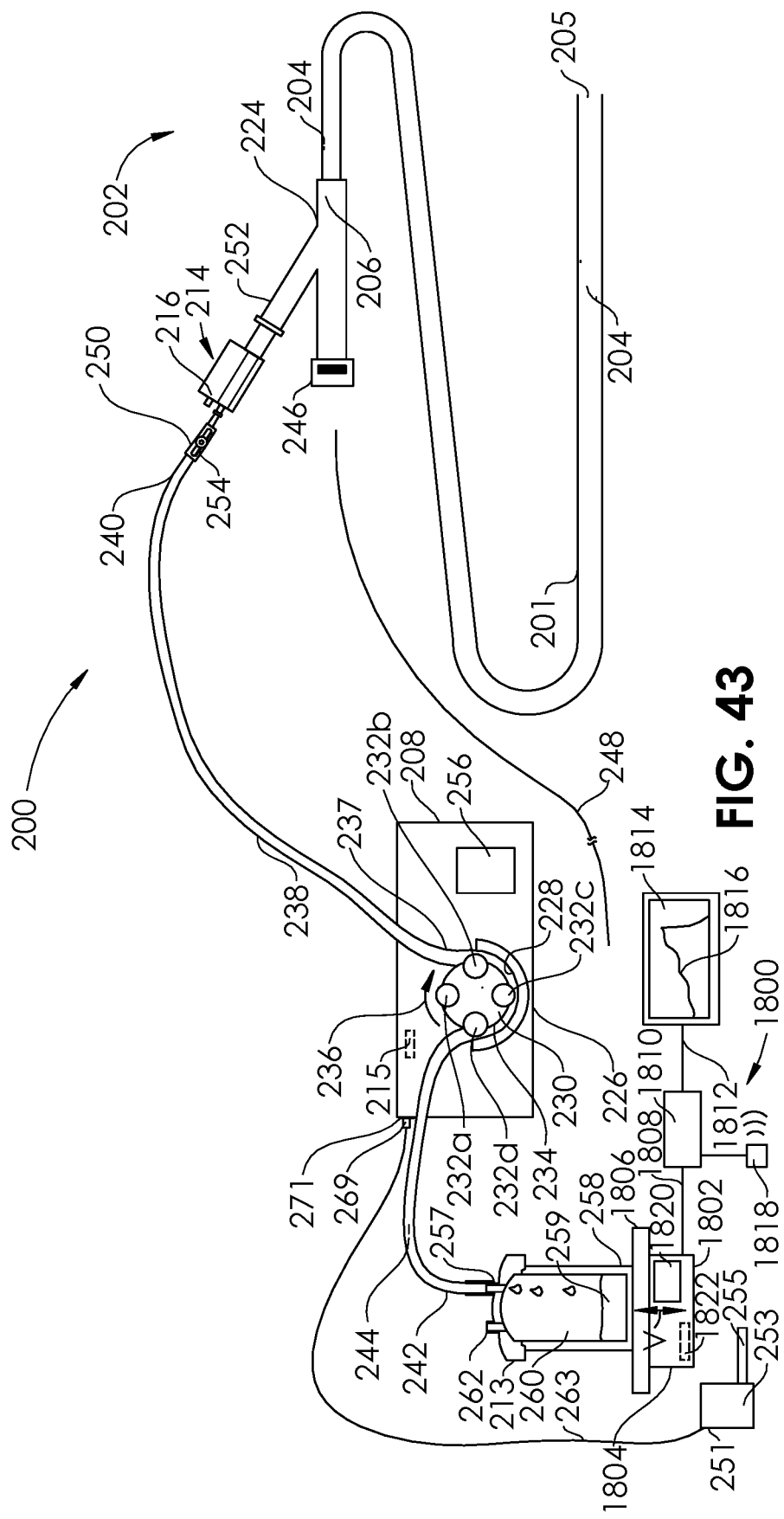
FIG. 43 is a plan view of an aspiration system according to an embodiment of the present disclosure.

FIG. 43 illustrates an aspiration system 200 comprising an aspiration catheter 202 comprising an elongate shaft 201 including an aspiration lumen 204 having an open distal end 205 and a proximal end 206 configured to couple to a peristaltic pump 208. The peristaltic pump 208 may be a roller pump having a base 226, a pressure shoe 228 carried by the base 226, and a rotatable head 230, rotatably coupled to the base 226, and carrying two or more rollers 232*a-d*. The rollers 232*a-d* are arrayed around a perimeter 234 of the rotatable head 230. The rotatable head 230 is configured to be rotatable in at least a first rotational direction 236 (e.g., by a motor, directly, or with a gear train, as shown in FIG. 36). The peristaltic pump 208 may be battery powered, and the battery(ies) may be rechargeable by wired or wireless means. The peristaltic pump 208 may alternatively, or additionally be powered by a power cord configured to connect to a power supply. An extension tube 238 having a distal end 240 and a proximal end 242, and having a lumen 244 extending therethrough, is hydraulically coupled to the proximal end 206 of the aspiration lumen 204 of the aspiration catheter 202 via a connector 224. The extension tube 238 may be supplied (e.g., sterile) with the aspiration catheter 202, or may be packaged and supplied separately. A Touhy-Borst seal 246 carried on the connector 224 is configured to be loosened/opened to allow the insertion of a guidewire 248 through the connector 224 and the aspiration lumen 204, which may be used to track the aspiration catheter 202 through a subject's vasculature. The Touhy-Borst 246 can be tightened to seal over the guidewire 248, to maintain hemostasis. Other types of seals may be incorporated in place of the Touhy-Borst 246, including a spring-loaded, longitudinally compressible and actuatable seal. The extension tube 238 includes a male luer 250 at its distal end 240, for connecting to a female luer 252 of the connector 224. Or, as shown, an aspiration monitoring system 214 may be attached therebetween. The male luer 250 may include a stopcock 254, which is configured to be turned to select between an open position (shown) or a closed position. Alternatively, the extension tube 238 may be integral with the aspiration lumen 204, or may be permanently attached to the connector 224. In use, a compressible portion 237 of the extension tube 238 is placed within the pressure shoe 228 of the peristaltic pump 208 such that rotation of the rotatable head 230 (e.g., via input to an interface 256 by a user) in the rotational direction 236 causes fluid to be forced through the lumen 244 of the extension tube 238 from the distal end 240 to the proximal end 242, via compression of the compressible portion 237 by the rollers 232, one at a time. In some embodiments, there are only two rollers 232. In other embodiments, there are three rollers 232. In still other embodiments, as shown, there are four rollers 232. As described, the rollers 232 may be replaced by bumps or protrusions. The compressible portion 237 may comprise silicone tubing, polyurethane tubing, polyvinyl chloride tubing, or other compressible tubing. The compressible portion 237 may be a relatively short section that is attachable to and detachable from the peripheral ends of the extension tube 238, or in other embodiments, may comprise the entirety of the extension tube 238 between the distal end 240 and the proximal end 242. The proximal end 242 of the extension tube 238 may be coupled to a hub 257 formed on a cap 213 of a canister 258, the canister 258 having an interior 260, to allow fluid 259 passing through the extension tube 238 to pass into the interior 260. An additional hub 262 in the canister 258 may be provided, and can be left open (as shown) to allow the unfilled interior 260 to match atmospheric pressure.

In use, a distal section of the aspiration catheter 202 is inserted into the vasculature of a subject such that the open distal end 205 is adjacent or within a thrombus. Then, fluid, including thrombus, is aspirated into the aspiration lumen 204 by action of the peristaltic pump 208 and removed by use of the aspiration system 200. Blood vessels treated may include peripheral blood vessels, pulmonary blood vessels, such as pulmonary arteries, coronary blood vessels, or blood vessels within the head or neck of the subject, including carotid arteries or cerebral arteries.

The aspiration system 200 further comprises an aspiration monitoring system 1800 which is configured to provide information to a user concerning the status of aspiration. The aspiration monitoring system 1800 functions by measuring the fluid 259 which has accumulated at the bottom of the interior 260 of the canister 258 at a plurality of points in time, thus estimating a (volumetric) flow rate of the fluid 259 issuing out the lumen 244 of the extension tube 238. The aspiration monitoring system 1800 comprises a scale 1802 (or balance) having a base 1804. A weighing platform 1806 is coupled to and movable with respect to the base 1804 (e.g., along a vertical axis V), such that the weight of the fluid 259 accumulated at the bottom of the canister 258 causes a signal 1808 indicative of the weight to be output. The scale may be configured to output a signal 1808 indicative of weight, or, in some embodiments, the particular elevation (above sea level) at which the scale 1802 resides may be input into the scale 1802 such that a value of mass can be output. A standard setting may assume that the procedure occurs at sea level, and may calculate mass accordingly. In some embodiments, the scale 1802 may even include an altimeter or other sensor to automatically determine elevation, such that mass can be output. Regardless, even when a weight is output, changes to the weight of the fluid 259 over time are proportional to changes to mass of the fluid 259 over time, at any particular elevation. Thus, the signal 1808 may be indicative of mass or indicative of weight, while remaining within the scope of allowing changes in the mass of the fluid 259 over time to be demonstrated. Thus, the system 200 can predict the loss of blood from the patient by its assessment of total cumulative weight/mass of blood captured in the canister 258. Weight/mass of blood measured can be converted by the system 200 into volume of blood (ml) lost.

The signal 1808 is sent to a processor 1810. See also, FIG. 44. The processor 1810, which may comprise a microprocessor, includes a clock that allows the combination of time data with weight or mass values from the signal. In some embodiments, the scale 1802 may include a tare button or control, such that the tare weight of the canister 258 can be subtracted out from the amount being weighed by the scale 1802. Thus, the scale 1802 is "zeroed" and only the weight or mass of the fluid 259 in the canister 258 is weighed at each time point. The sample rate at which values in the signal 1808 are obtained along with the time stamp may range between about 0.01 Hz and about 10 kHz, or between about 0.02 Hz and about 1 kHz, or between about 1 Hz and about 100 Hz. A processed signal 1812 is output to a graphic display 1814 for viewing by a user. In some embodiments, the graphic display 1814 may display an x-y graph 1816, wherein the x-axis represents time and the y-axis represents weight or mass of the fluid 259 within the canister 258. In other embodiments, the graphic display 1814 may display an x-y graph 1816, wherein the x-axis represents time and the y-axis represents flow rate. The flow rate (FR) may be calculated from the formula:

$$FR = (W_c - W_p)/(T_c - T_p), \text{ wherein}$$

$W_C$ is the current value for weight of the fluid 259
$W_p$ is the previous value of weight of the fluid 259
$T_c$ is the current time stamp value
$T_p$ is the previous time stamp value In other embodiments, the flow rate (FR) may be calculated from the formula:

$$FR = (W_c - W_{pn})/(T_c - T_{pn}), \text{ wherein}$$

$W_c$ is the current value for weight of the fluid 259
$W_p n$ is the $n^{th}$ prior value of weight of the fluid 259
$T_c$ is the current time stamp value
$T_{pn}$ is the $n^{th}$ prior time stamp value In other embodiments, the flow rate may be constructed as a moving average, such as a running average or rolling average. Several types of moving average may be used, including a simple moving average, a cumulative moving average, a weighted moving average, or an exponential moving average.

Instead of an x-y graph, a visual display comprising one or more LED lights may be used. For example, a higher flow rate may be indicated by a range of shades of green, while a lower flow rate may be indicated by a range of shades of red. Alternatively, the intensity of a light may be changed in response to changes in the flow rate, or changes in weight or mass. For example, the intensity of the light may be proportional to the measured/calculated flow rate. A loudspeaker may present the changes in weight/mass over time or changes in flow rate over time as a continuous or continual sound having a pitch that changes proportionally with changes in value. For example, a higher pitch with a larger flow rate. The sound intensity may alternatively be varied (higher flow rate=higher dB).

Changes in the flow rate can be indicative of a number of operation occurrences in the aspiration system 200. For example, a flow rate that suddenly decreases a significant amount may be indicative of thrombus becoming clogged within the aspiration lumen 204 or the lumen 244 of the extension tube 238. In some cases, a reduction in the flow rate of 90% or more may be indicative of clogging. When a clog occurs, the volume of fluid being aspirated and dispensed into the canister 258 can be severely limited. A loudspeaker 1818 is also configured to produce an audible alarm, when a threshold value of flow rate is crossed. A threshold flow rate may be input into a memory 1822 of the scale 1802 using a user interface 1820. When the flow rate decreases to a value below the threshold flow rate, the loudspeaker 1818 is made to sound an alarm. In some embodiments, a controller 215 in the peristaltic pump 208 may be coupled to the processor 1810 (wired or wireless) and may be configured to activate the alarm of the loudspeaker 1818. When the flow rate increases above the threshold flow rate, the loudspeaker 1818 may be deactivated such that the alarm is no longer sounded. Alternatively, the loudspeaker 1818 may be replaced by, or augmented with a visual alarm and/or a tactile alarm. The visual alarm may include one or more light, including one or more LEDs. The tactile alarm may include a vibration device, such as a piezoelectric, or a weight-offset rotational device.

Changes in the flow rate may also be indicative of other changes in status, such as a rupture in a wall of one of the tubular members or a disconnection of one of the connections. In one of these leak conditions, the flow rate may be significantly reduced, and thus identified by the flow rate changes measured by the aspiration monitoring system 1800. The system 200 may be configured to activate the alarm (e.g., via the loudspeaker 1818) when a free flow of blood is detected. In other words, when the system is apparently aspirating only blood, and not aspirating thrombus. Thus, the measured flow rate crossing above a particular threshold stored in memory 1822 indicative of free flowing blood would cause the controller 215 to activate the alarm.

A secondary aspiration monitoring system 214 comprising a pressure transducer 216 may be coupled, for example, between the distal end 240 of the extension tube 238 and the connector 224 and/or proximal end 206 of the aspiration lumen 204 of the aspiration catheter 202. Signals from the pressure transducer 216 may be carried wirelessly or by a cable (not shown) to the controller 215. The controller 215 may comprise a microcontroller. The controller 215 may be located within the peristaltic pump 208, or may alternatively be located at another component or location. Control using measured pressure adds an additional safety element to the system 200. Additionally, a non-functional device (because of a leak, incomplete connection, incomplete priming, rupture, blockage) can be quickly identified. Unallowably high pressures or low pressures can also be quickly identified, protecting the motor of the peristaltic pump 208 from burnout or overheating danger. Data from the pressure transducer 216 and the scale 1802 can be used together to optimize or create a more correct signal indicative of aspiration flow, or indicative of the presence of clot/thrombus, or the presence of a clog, or the presence of a burst or disconnection in the fluid circuit.

A foot pedal 251 is illustrated having a base 253 and a pedal 255 that is coupled to the base 253 and movable or activatable by application of the foot of a user. The pedal 255 may be spring-loaded and depressible by application of a moment or a compressive force, or may instead comprise a membrane switch. The pedal 255, when activated, may in some embodiments toggle on and off, and in other embodiments may be activatable when a force, a pressure, or a moment is applied, and inactivated when the force, pressure, or moment is not applied. A cable 263 carries signals from the foot pedal 251 to the peristaltic pump 208 via a plug 269 that is connected to an input jack 271. The pedal 255 can be activated by the foot of a user to start or stop the operation of the peristaltic pump 208.

In other embodiments, the foot pedal 251 may be replaced by another type of switch, including, but not limited to a toggle on/off push button or hand switch, an audio-activated switch (voice activated, clap activated, click activated), an optical switch (beam/light sensor for hand or foot interruption), or any other kind of switch that can be activated by medical personnel. The switch may be remote (e.g., in a control room) or may be located near the procedural area. The switch may also be a sterile switch or sterilizable for location on a sterile area.

In some cases, the activation and deactivation (turning on and off) of the aspiration flow applied by the peristaltic pump 208 on the aspiration lumen 204 may be done by leaving the peristaltic pump 208 in a running condition, while the user opens and closes the stopcock 254. Alternatively, a pinch valve (not shown) coupled to the extension tube 238 may be used for opening and closing the lumen 244, and thus starting and stopping aspiration. The pinch valve may be operated by a foot pedal (similar to the foot pedal 251), or may be operated by another control (e.g., on the interface 256 of the peristaltic pump 208).

After collecting the aspirated material in a blood bag, blood bottle, or the canister 258, aspirated components (blood, thrombus, saline, slurry, etc.) can be placed into a reinfusion device, such as a Stryker ConstaVac (CBCII) Blood Conservation System, or a Haemonetics OrthoPAT Orthopedic Perioperative Autotransfusion System.

In some embodiments, the blood may be cooled prior to being injected. In some embodiments, the blood may be heated prior to being injected. In some embodiments, other drugs may be added to the blood prior to it being inserted. In some cases, the blood may be diluted with saline, to decrease its viscosity, or decrease its hematocrit. This may allow for decrease hemolysis to occur. In some cases, blood collected in the canister 258, or blood coming from the extension tube 238, may even be used as donor blood, to infuse into a different patient.

In some embodiments, an additional or alternate sensor may be used to monitor flow conditions for the notification of the user, including, but not limited to: a Doppler sensor, an infrared sensor, or a laser flow detection device. In some embodiments, an externally-attached (non-contact) Doppler sensor may be employed. In some embodiments, an infrared sensor or a laser flow detection device may be employed around the extension tubing 238. The alternate sensor (e.g., flow sensor, etc.) may be located at a number of different locations along the aspiration path, including on or in the extension tube 238, either proximal to or distal to the rotatable head 230 of the peristaltic pump 208.

Figure 45:
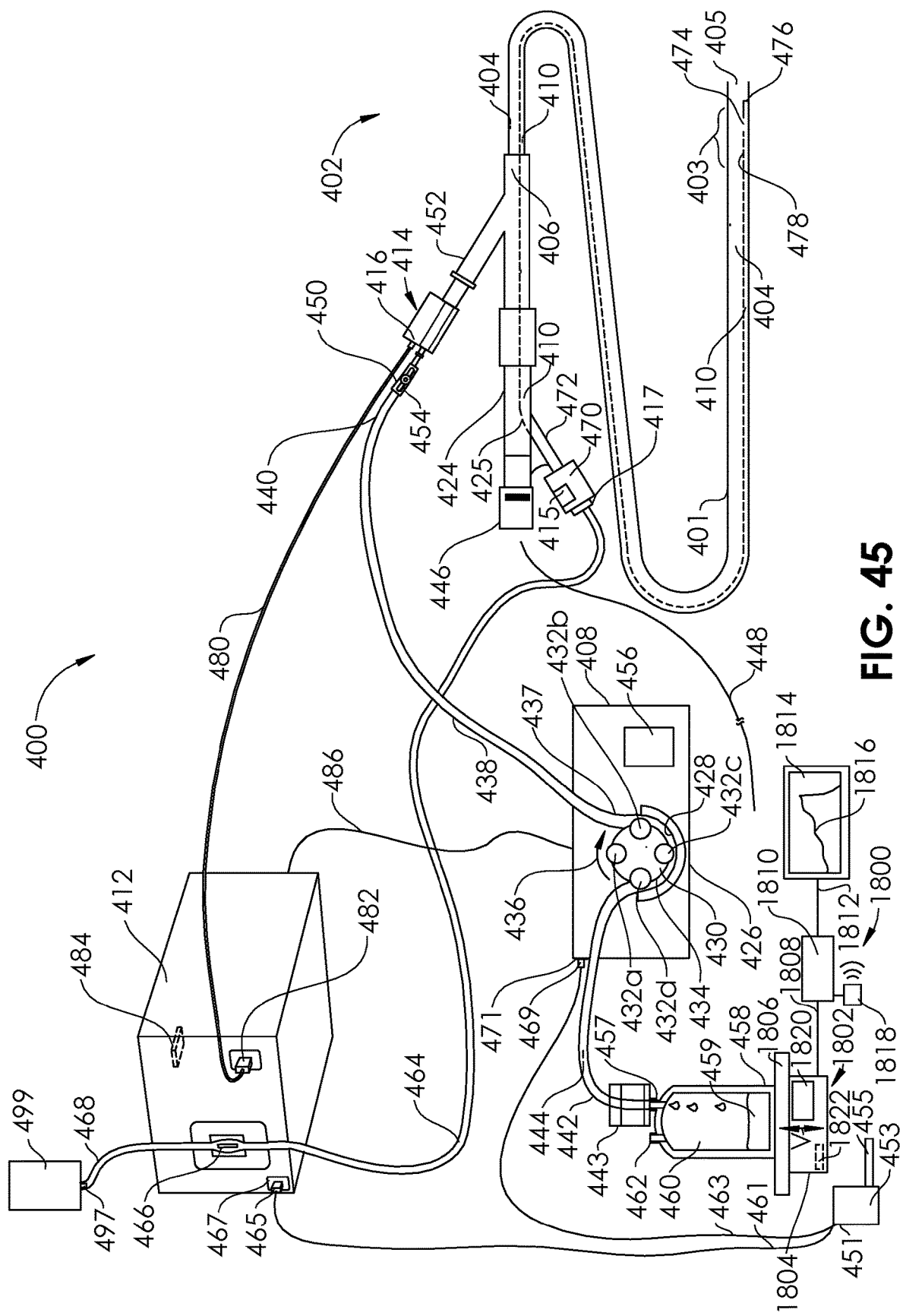
FIG. 45 is a perspective view of an aspiration system according to an embodiment of the present disclosure.

FIG. 45 illustrates a forced aspiration system 400 comprising an aspiration catheter 402 comprising an elongate shaft 401 including an aspiration lumen 404 having an open distal end 405 and a proximal end 406 configured to couple to a peristaltic pump 408. The peristaltic pump 408 may be a roller pump having a base 426, a pressure shoe 428 carried by the base 426, and a rotatable head 430, rotatably coupled to the base 426, and carrying two or more rollers 432*a-d*. The rollers 432*a-d* are arrayed around a perimeter 434 of the rotatable head 430. The rotatable head 430 is configured to be rotatable in at least a first rotational direction 436 (e.g., by a motor, directly, or with a gear train, as shown in FIG. 36). The peristaltic pump 408 may be battery powered, and the battery(ies) may be rechargeable by wired or wireless means. The peristaltic pump 408 may alternatively, or additionally be powered by a power cord configured to connect to a power supply. An extension tube 438 having a distal end 440 and a proximal end 442, and having a lumen 444 extending therethrough, is hydraulically coupled to the proximal end 406 of the aspiration lumen 404 of the aspiration catheter 402 via a connector 424. The extension tube 438 may be supplied (e.g., sterile) with the aspiration catheter 202, or may be packaged and supplied separately. A Touhy-Borst seal 446 carried on the connector 424 is configured to be loosened/opened to allow the insertion of a guidewire 448 through the connector 424 and aspiration lumen 404, which may be used to track the aspiration catheter 402 through a subject's vasculature. The Touhy-Borst 446 may be tightened to seal over the guidewire 448, to maintain hemostasis. Other types of seals may be incorporated in place of the Touhy-Borst 246, including a spring-loaded, longitudinally compressible and actuatable seal. The extension tube 438 includes a male luer 450 at its distal end 440, for connecting to a female luer 452 of the connector 424. Or, as shown, an aspiration monitoring system 414 may be attached therebetween. The male luer 450 may include a stopcock 454, which is configured to be turned to select between an open position (shown) or a closed position. Alternatively, the extension tube 438 may be integral with the aspiration lumen 404, or may be permanently attached to the connector 424. In use, a compressible portion 437 of the extension tube 438 is placed within the pressure shoe 428 of the peristaltic pump 408 such that rotation of the rotatable head 430 (e.g., via input to an interface 456 by a user) in the rotational direction 436 causes fluid to be forced through the lumen 444 of the extension tube 438 from the distal end 440 to the proximal end 442, via compression of the compressible portion 437 by the rollers 432, one at a time. In some embodiments, there are only two rollers 432. In other embodiments, there are three rollers 432. In still other embodiments, as shown, there are four rollers 432. As described, the rollers 432 may be replaced by bumps or protrusions. The compressible portion 437 may comprise silicone tubing, polyurethane tubing, polyvinyl chloride tubing, or other compressible tubing. The compressible portion 437 may be a relatively short section that is attachable to and detachable from the peripheral ends of the extension tube 438, or in other embodiments, may comprise the entirety of the extension tube 438 between the distal end 440 and the proximal end 442. The proximal end 442 of the extension tube 438 may be coupled to a hub 457 of a canister 458 having an interior 460, to allow fluid 459 passing through the extension tube 438 to pass into the interior 460. An additional hub 462 in the canister 458 may be left open (as shown) to allow the unfilled interior 460 to match atmospheric pressure. A filter 443 (optional) is placed in line between the extension tube 438 and canister 458 to catch thrombus that is aspirated from the patient. The filter 443 may have clear side walls so that the physician or other medical staff can visually assess the thrombus, such as the size of each piece, the number or pieces, the total amount of thrombus (e.g., volumetrically) or the condition of the thrombus or residual thrombus (organized/fibrous, or soft). The buildup of the thrombus within the filter 443, or lack thereof, may be utilized as a cue for moving the open distal end 405 of the aspiration catheter 402 to a different location, or temporarily or permanently stopping the procedure, or even increasing or decreasing the speed of the pump(s).

The aspiration catheter 402 additionally has a high pressure injection lumen 410 for injecting saline from a fluid source 499, for example, via a high pressure pump 412. A tubing set 464 may include a pump cartridge 466 having a piston or bellows or other movable element that the pump 412 may manipulate using an internal motor (not shown), this applying a high pressure to saline from the fluid source 499 such that the saline is forced through the injection lumen 410 of the aspiration catheter 402. The tubing set 464 includes proximal end 468 having a spike 497 or other element for hydraulically coupling it to the fluid source 499. The tubing set 464 further has a distal end 470 (which may include a male luer) which is configured to hydraulically couple to the injection lumen 410 via a female luer 472. Injected saline is forced through the injection lumen 410 by the pump 412 and exits an orifice 474 at a distal end 476 of the injection lumen 410. The injection lumen 410 may be within a tube 478 that is substantially or entirely within the shaft 401. In some embodiments, the tube 478 is attached to the internal wall of the shaft 401 only at a distal end portion 403. Thus, the free-floating nature of the remainder of the tube 478 within the aspiration lumen 404 increases the flexibility and trackability of the shaft 401. The high pressure saline is forced through the orifice 474, causing a jet. The jet is aimed within the aspiration lumen 404, just proximal the open distal end 405 which may create a Venturi effect that forces blood or thrombus external and adjacent the open distal end 405 into the aspiration lumen 404. The combination of the operation of the peristaltic pump 408 and the jet caused by the high pressure saline cause the maceration of thrombus, and the movement/flow of material (saline/blood/macerated thrombus/small pieces of thrombus) through the aspiration lumen 404 from the open distal end 405 to the proximal end 406, through the connector 424, and through the lumen 444 of the extension tube 438 from its distal end 440 to its proximal end 442, and finally into the interior 460 of the canister 458. Thus, thrombus within a blood vessel of a subject may be macerated and removed by use of the system 400. Blood vessels treated may include peripheral blood vessels, pulmonary blood vessels, such as pulmonary arteries, coronary blood vessels, or blood vessels within the head or neck of the subject, including carotid arteries or cerebral arteries.

The forced aspiration system 400 further comprises an aspiration monitoring system 1800 which is configured to provide information to a user concerning the status of aspiration. The aspiration monitoring system 1800 functions by measuring the fluid 459 which has accumulated at the bottom of the interior 460 of the canister 458 at a plurality of points in time, thus estimating a flow rate of the fluid 459 issuing out the lumen 444 of the extension tube 438. The aspiration monitoring system 1800 comprises a scale 1802 (or balance) having a base 1804. A weighing platform 1806 is coupled to and movable with respect to the base 1804 (e.g., along a vertical axis V), such that the weight of the fluid 459 accumulated at the bottom of the canister 458 causes a signal 1808 indicative of the weight to be output. The scale may be configured to output a signal 1808 indicative of weight, or, in some embodiments, the particular elevation (above sea level) at which the scale 1802 resides may be input into the scale 1802 such that a value of mass can be output. In some embodiment, the scale 1802 may even include an altimeter or other sensor to automatically determine elevation, such that mass can be output. Regardless, even when a weight is output, changes to the weight of the fluid 459 over time are proportional to changes to mass of the fluid 459 over time, at any particular elevation. Thus, the signal 1808 may be indicative of mass or indicative of weight, while remaining within the scope of allowing changes in the mass of the fluid 459 over time to be demonstrated. Thus, the system 400 can predict the loss of blood from the patient by its assessment of total cumulative weight/mass of blood captured in the canister 458. Weight/mass of blood measured can be converted by the system 400 into volume of blood (ml) lost.

The signal 1808 is sent to a processor 1810. See also, FIG. 44. The processor 1810, which may comprise a microprocessor, includes a clock that allows the combination of time data with weight or mass values from the signal. In some embodiments, the scale 1802 may include a tare button or control, such that the tare weight of the canister 458 can be subtracted out from the amount being weighed by the scale 1802. Thus, the scale 1802 is "zeroed" and only the weight or mass of the fluid 459 in the canister 458 is weighed at each time point. The sample rate at which values in the signal 1808 are obtained along with the time stamp may range between about 0.01 Hz and about 10 kHz, or between about 0.02 Hz and about 1 kHz, or between about 1 Hz and about 100 Hz. A processed signal 1812 is output to a graphic display 1814 for viewing by a user. In some embodiments, the graphic display 1814 may display an x-y graph 1816, wherein the x-axis represents time and the y-axis represents weight or mass of the fluid 459 within the canister 458. In other embodiments, the graphic display 1814 may display an x-y graph 1816, wherein the x-axis represents time and the y-axis represents flow rate. The flow rate (FR) may be calculated from the formula:

$$FR=(W_c-W_p)/(T_c-T_p), \text{ wherein}$$

$W_c$ is the current value for weight of the fluid 459
$W_p$ is the previous value of weight of the fluid 459
$T_c$ is the current time stamp value
$T_p$ is the previous time stamp value In other embodiments, the flow rate (FR) may be calculated from the formula:

$$FR=(W_c-W_{pn})/(T_c-T_{pn}), \text{ wherein}$$

$W_c$ is the current value for weight of the fluid 459
$W_p p$ is the $n^{th}$ prior value of weight of the fluid 459
$T_c$ is the current time stamp value
$T_{pn}$ is the $n^{th}$ prior time stamp value In other embodiments, the flow rate may be constructed as a moving average, such as a running average or rolling average. Several types of moving average may be used, including a simple moving average, a cumulative moving average, a weighted moving average, or an exponential moving average.

Instead of an x-y graph, a visual display comprising one or more LED lights may be used. For example, a higher flow rate may be indicated by a range of shades of green, while a lower flow rate may be indicated by a range of shades of red. Alternatively, the intensity of a light may be changed in response to changes in the flow rate or changes in weight or mass. For example, the intensity of the light may be proportional to the measured/calculated flow rate. A loudspeaker may present the changes in weight/mass over time or changes in flow rate over time as a continuous or continual sound having a pitch that changes proportionally with changes in value. For example, a higher pitch with a larger flow rate. The sound intensity may alternatively be varied (higher flow rate=higher dB).

Changes in the flow rate can be indicative of a number of operation occurrences in the forced aspiration system 400. For example, a flow rate that suddenly decreases a significant amount may be indicative of thrombus becoming clogged within the aspiration lumen 404 or the lumen 444 of the extension tube 438. In some cases, a reduction in the flow rate of 90% or more may be indicative of clogging.

When a clog occurs, the volume of fluid being aspirated and dispensed into the canister 458 can be severely limited. A loudspeaker 1818 is also configured to produce an audible alarm, when a threshold value of flow rate is crossed. A threshold flow rate may be input into memory 1822 of the scale 1802 using a user interface 1820. When the flow rate decreases to a value below the threshold flow rate, the loudspeaker 1818 is made to sound an alarm. In some embodiments, the controller 484 on the pump 412, or a different controller in one of the other components may be coupled to the processor 1810 (wired or wireless) and may be configured to activate the alarm of the loudspeaker 1818. When the flow rate increases above the threshold flow rate, the loudspeaker 1818 may be deactivated such that the alarm is no longer sounded. Alternatively, the loudspeaker 1818 may be replaced by, or augmented with a visual alarm and/or a tactile alarm. The visual alarm may include one or more light, including one or more LEDs. The tactile alarm may include a vibration device, such as a piezoelectric, or a weight-offset rotational device.

Changes in the flow rate may also be indicative of other changes in status, such as a rupture in a wall of one of the tubular members or a disconnection of one of the connections. In one of these leak conditions, the flow rate may be significantly reduced, and thus identified by the flow rate changes measured by the aspiration monitoring system 1800. The system 400 may be configured to activate the alarm (e.g., via the loudspeaker 1818) when a free flow of blood is detected. In other words, when the system is apparently aspirating only blood, and not aspirating thrombus. Thus, the measured flow rate crossing above a particular threshold stored in memory 1822 indicative of free flowing blood would cause the controller 484 to activate the alarm.

A secondary aspiration monitoring system 414 comprising a pressure transducer 416 may be coupled, for example, between the distal end 440 of the extension tube 438 and the connector 424 and/or proximal end 406 of the aspiration lumen 404 of the aspiration catheter 402. Signals from the pressure transducer 416 are carried on an electric cable 480 to an input 482 of the pump 412. The controller 484 within the pump 412 is configured to control the operation of the pump 412, but also may be configured to control the operation of the peristaltic pump 408, with via a cable 486, or wirelessly. The controller 484 may comprise a microcontroller. The controller 484 may alternatively be located within the peristaltic pump 408, or may be located at another component or location. Control using measured pressure adds an additional safety element to the system 400. Additionally, a non-functional device (because of a leak, incomplete connection, incomplete priming, rupture, blockage) can be quickly identified. Unallowably high pressures can also be quickly identified, protecting the motor of the pump 412 from burnout or overheating danger. The integrity of the tube 478 is also protected, e.g., avoiding unnaturally high pressures that could lead to a burst of the tube 478. Data from the pressure transducer 416 and the scale 1802 can be used together to optimize or create a more correct signal indicative of aspiration flow, or indicative of the presence of clot/thrombus, or the presence of a clog, or the presence of a burst or disconnection in the fluid circuit.

The female luer 452 is located distally on the connector 424 from the female luer 472. Thus, aspirated blood/thrombus/saline enters the female luer 452 without ever having to contact interior irregularities 425 (in geometry, shape) within the connector 424, that may otherwise cause flow resistance, or cause thrombus to catch (e.g., between the tube 478 and the interior of the connector 424.

A foot pedal 451 is illustrated having a base 453 and a pedal 455 that is coupled to the base 453 and movable or activatable by application of the foot of a user. The pedal 455 may be spring-loaded and depressible by application of a moment or a compressive force, or may instead comprise a membrane switch. The pedal 455, when activated, may in some embodiments toggle on and off, and in other embodiments may be activatable when a force, a pressure, or a moment is applied, and inactivated when the force, pressure, or moment is not applied. A first cable 461 carries signals from the foot pedal 451 to the pump 412 via a plug 465 that is connected to an input jack 467. A second cable 463 carries signals from the foot pedal 451 to the peristaltic pump 408 via a plug 469 that is connected to an input jack 471. In some embodiments, activation of the pedal 455 by the foot of a user starts the operation of the pump 412 and starts the operation of the peristaltic pump 408 at the same time. In some embodiments, activation of the pedal 455 by the foot of a user starts the operation of the peristaltic pump 408, and then starts the operation of the pump 412, with a slight delay after the peristaltic pump 408 is started. The controller 484 is programmed or programmable to impart the delay, or the lack of delay. The delay is useful to assure that some aspiration, or a significant amount of aspiration, is being applied to the aspiration lumen 404 prior to the injection of pressurized fluid (e.g., saline) through the injection lumen 410. All may be controlled by the controller 484 of the pump 412, in response to a signal through the cable 463 from the foot pedal 451. Thus, blood vessels or other vasculature in the vicinity of the open distal end 405 are spared any injection of fluid from a high pressure jet, as it is instead aspirated through the aspiration lumen 404.

In addition, in some embodiments, activation of the pedal 455 by the foot of a user during the operation of the pump 412 and the peristaltic pump 408 stops the operation of the pump 412 and the operation of the peristaltic pump 408 at the same time. In other embodiments, a delay may be applied (e.g., by the controller 484), such that the pump 412 is stopped, and then the peristaltic pump 408 is stopped slightly afterwards. The length of the delays described may be between about 0.01 second and about 1.00 second, or between about 0.10 second and about 0.25 second. The operation (on/off) of the pump 412 and/or peristaltic pump 408 via the foot pedal 451 allows hands-free activation, enabling a single user the manipulate the aspiration catheter 402 and guidewire 448 with both hands.

In other embodiments, the foot pedal 451 may be replaced by another type of switch, including, but not limited to a toggle on/off push button or hand switch, an audio-activated switch (voice activated, clap activated, click activated), an optical switch (beam/light sensor for hand or foot interruption), or any other kind of switch that can be activated by medical personnel. The switch may be remote (e.g., in a control room) or may be located near the procedural area. The switch may also be a sterile switch or sterilizable for location on a sterile area.

In some cases, the activation and deactivation (turning on and off) of the aspiration flow applied by the peristaltic pump 408 on the aspiration lumen 404 may be done by leaving the peristaltic pump 408 in a running condition, while the user opens and closes the stopcock 454. Alternatively, a pinch valve (not shown) coupled to the extension tube 438 may be used for opening and closing the lumen 444, and thus starting and stopping aspiration. The pinch valve may be operated by a foot pedal (similar to the foot pedal 451), or may be operated by another control (e.g., on the interface 456 of the peristaltic pump 408 or even an interface on the pump 412).

The controller 484 also monitors and controls several device safety functions, which include over pressure detection, air bubble detection, and vacuum or negative pressure charge. An additional pressure transducer 415 monitors pressure (i.e. injection pressure), and senses the presence of air bubbles. Alternatively, or in conjunction, an optical device 417 may be used to sense air bubbles. In one contemplated embodiment, the pump pressure is proportional to the electric current needed to produce that pressure. Consequently, if the electric current required by pump 412 exceeds a preset limit, the controller 484 will disable the pump 412 by cutting power to it. Air bubble detection may also be monitored by monitoring the electrical current required to drive the pump 412 at any particular moment. In order for a pump 412 to reach high fluid pressures, there should be little or no air (which is highly compressible) present in the pump 412 or connecting system (including the aspiration lumen 404 of the aspiration catheter 402 and the tubing set 464). The fluid volume is small enough that any air in the system will result in no pressure being generated at the pump head. A sufficient volume of liquid is needed proximally to flush any finite amount of air through. The controller 484 monitors the pump 412 current for any abrupt downward change that may indicate that air has entered the system. If the rate of drop is faster than a preset limit, the controller 484 will disable the pump 412 by cutting power to it until the problem is corrected.

After collecting the aspirated material in a blood bag, blood bottle, or the canister 458, aspirated components (blood, thrombus, saline, slurry, etc.) can be placed into a reinfusion device, such as a Stryker ConstaVac (CBCII) Blood Conservation System, or a Haemonetics OrthoPAT Orthopedic Perioperative Autotransfusion System.

In some embodiments, the blood may be cooled prior to being injected. In some embodiments, the blood may be heated prior to being injected. In some embodiments, other drugs may be added to the blood prior to it being inserted. In some cases, the blood may be diluted with saline, to decrease its viscosity, or decrease its hematocrit. This may allow for decrease hemolysis to occur. In some cases, blood collected in the canister 458, or blood coming from the extension tube 438, may even be used as donor blood, to infuse into a different patient.

In some embodiments, an additional or alternate sensor may be used to monitor flow conditions for the notification of the user, including, but not limited to: a Doppler sensor, an infrared sensor, or a laser flow detection device. In some embodiments, an externally-attached (non-contact) Doppler sensor may be employed. In some embodiments, an infrared sensor or a laser flow detection device may be employed around the extension tubing 438. The alternate sensor (e.g., flow sensor, etc.) may be located at a number of different locations along the aspiration path, including on or in the extension tube 438, either proximal to or distal to the rotatable head 430 of the peristaltic pump 408.

Figure 44:
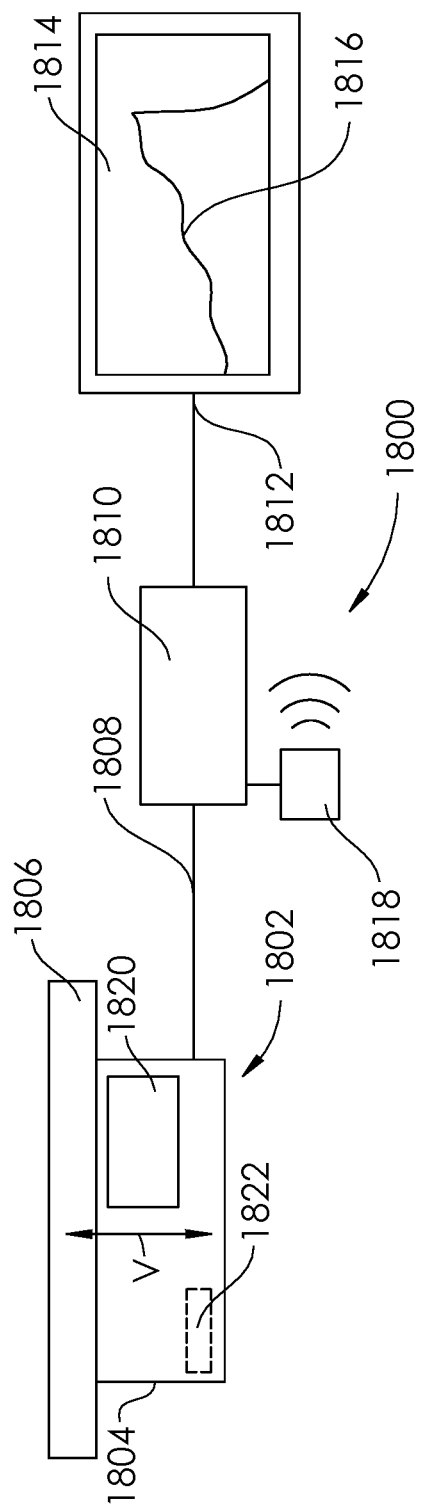
FIG. 44 is a detail view of the weight-based aspiration monitoring system of the system of FIG. 43.
Figure 46:
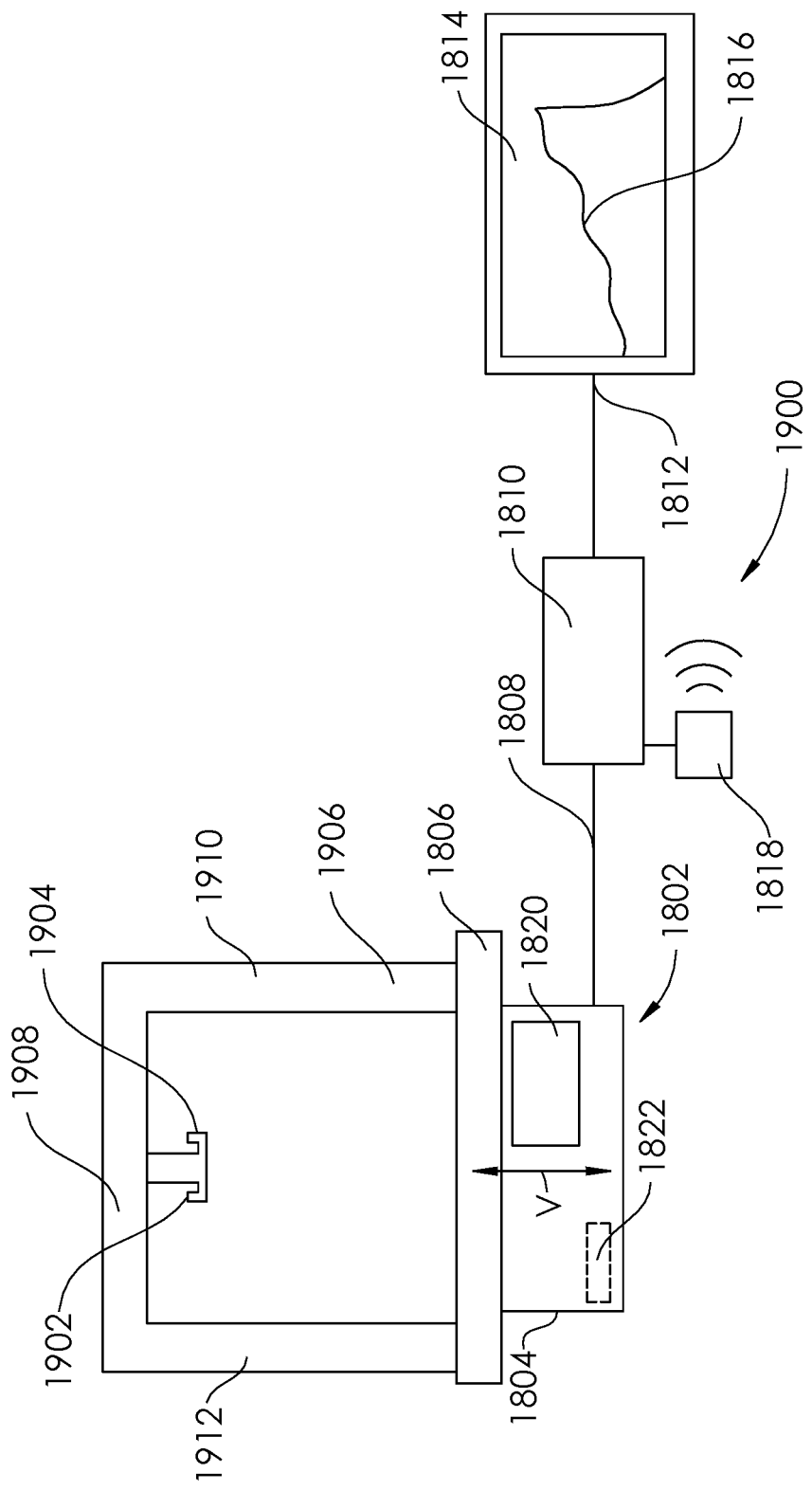
FIG. 46 is a detail view of an alternative weight-based aspiration monitoring system of the system.

FIG. 46 illustrates an alternative aspiration monitoring system 1900 that shares features with the aspiration monitoring system 1800 of FIG. 44, but is configured to weigh the fluid 259, 459 contained in the canister 258, 458 by suspending the canister 258, 458 from hooks 1902, 1904 that extend from a frame 1906 that is supported on the weighing platform 1806. The frame 1906 comprises two vertical legs 1910, 1912 and a crossbar 1908 coupled to each of the vertical legs 1910, 1912. The crossbar 1908 is configured to support the hooks 1902, 1904 and the canister 258, 458 (when hung). The canister 258, 458 may include hooks, indentations, or loops that are configured to engagingly interface with one or both of the hooks 1902, 1904.

Figure 47:
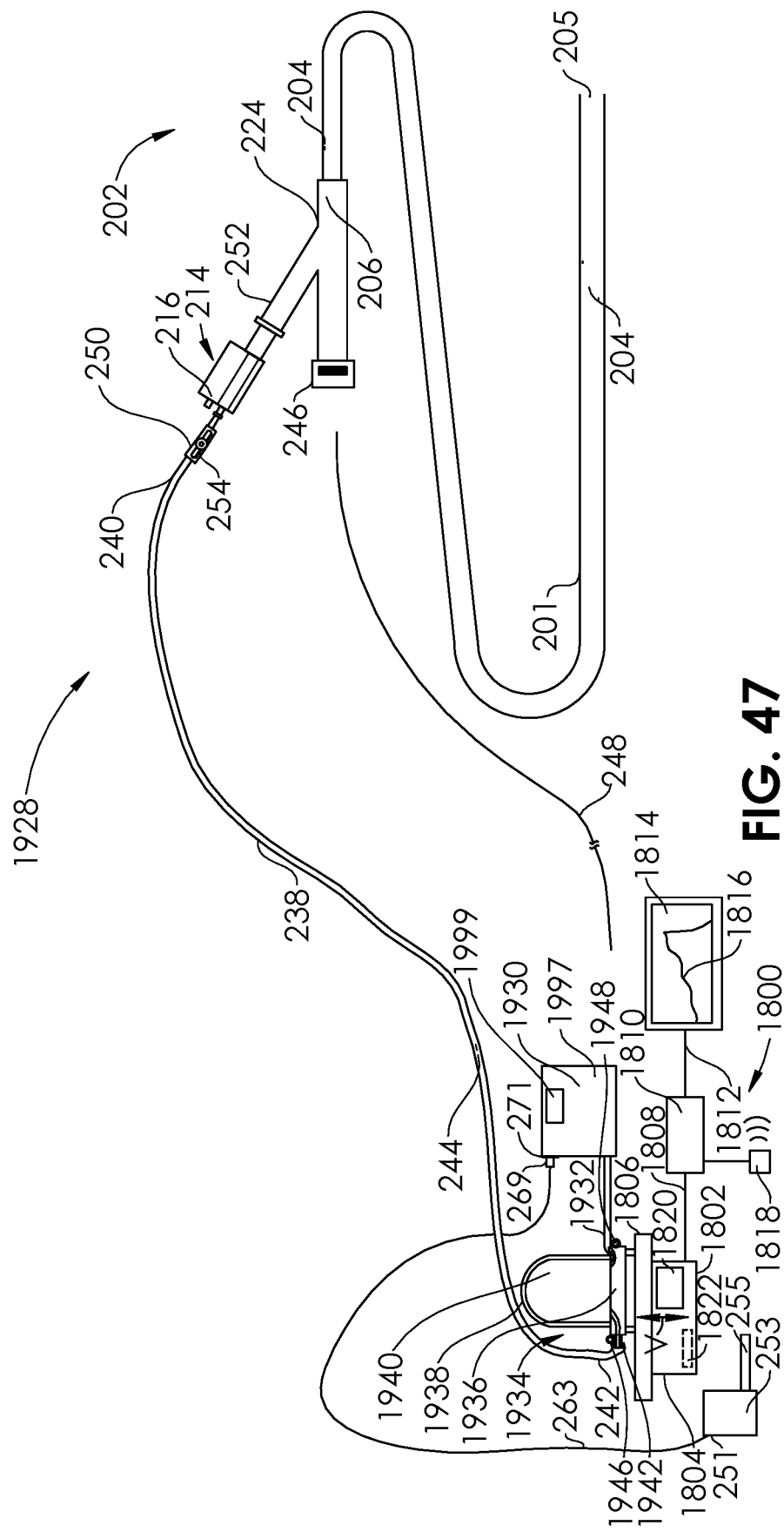
FIG. 47 is a plan view of an aspiration system according to an embodiment of the present disclosure.

While the foregoing is directed to embodiments of the present disclosure, other and further embodiments may be devised without departing from the basic scope thereof. Alternatively, instead of using the extension tube 238, 438 that is configured to be used with a peristaltic pump 208, 408, an extension tube 238, 438 may comprise a luer connector (or other sealing connector) at its proximal end, and may be configured to attached to an evacuatable syringe (e.g., 20 ml or 30 ml). The syringe may be hung from the hooks 1902, 1904 (or the equivalent) and the weight of the syringe and extension tube 238, 438 may be tared from the scale 1802. Thus, as the syringe fills, the increase of weight/mass of the aspirate collecting in the syringe is measured over time, in the same manner that the contents of the canister 258, 458 is weighed. The evacuatable syringe may even be replaced by a bell jar connected to a vacuum pump, again, with the bell jar and any connecting tubing tared from the measured weight/mass. FIG. 47 illustrates an aspiration system 1928 similar to the aspiration system 200 of FIG. 43, except that the peristaltic pump 208 and canister 258 are replaced by a vacuum pump 1930 and a vacuum chamber 1934 or bell jar having a base 1936 and a lid 1938 sealably placed thereon. The vacuum pump 1930 may be operated by controls 1999 carried on its outer surface 1997, or may be controllable (on/off) by the foot pedal 251. A vacuum tubing 1932 connects the vacuum pump 1930 to an interior 1940 of the vacuum chamber 1934. A control valve 1948 is adjustable for controlling the aperture between the vacuum tubing 1932 and the interior 1940 of the vacuum chamber 1934. The interior 1940 communicates with the lumen 244 of the extension tube 238 via the proximal end 242, which is coupled to a port 1942 of the vacuum chamber 1934. An adjustable valve 1946 controls an aperture between the interior 1940 of the vacuum chamber 1934 and the lumen 244 of the extension tube 238. The vacuum pump 1930 is supported separately on a table, cart, or other support. The weight of the vacuum tubing 1932 and extension tube 238 can be tared from the readout of the scale 1802, so that only the weight of fluid/clot, etc. pulled into the interior 1940 of the vacuum chamber 1934 is measured over time.

Thrombosis (thrombus, clot) within vasculature, including blood vessels such as arteries or veins, is a significant risk factor that can be debilitating or even cause death. Aspiration systems including aspiration catheter include aspiration-only devices as well as forced aspiration devices, which are configured to inject pressurized fluid, such as heparinized saline, into the distal portion of an aspiration lumen, to create a larger aspiration pressure gradient, and thus more significant thrombus maceration and removal. Though many of these aspiration systems are used in peripheral or coronary arteries, thromboembolic stroke involving arteries of the neck and head is also of concern. Many of the arteries of the neck and head, including cerebral arteries, the basilar artery, and other communicating arteries in proximity, are located quite a distance from traditional insertion/puncture locations, such as the femoral artery or radial artery. The pathway to these arteries can also be quite tortuous, and the vessels are often of a small caliber, such that long, small diameter catheters with a great deal of flexibility at their distal ends are utilized. Many of these design criteria confound other physical requirements of an aspiration catheter, such as a large diameter aspiration lumen for increased aspiration flow, or the multiple lumens of a force aspiration catheter, which must now fit into a small overall catheter shaft diameter.

Clogging of aspiration catheters, for example by large pieces of thrombus, is a common concern for users. Techniques to avoid clogging/choking of material within the catheter often involve rapidly, aggressively advancing the aspiration catheter or gently plucking at edges of a thrombus to insure only small pieces or portions are introduced at a time, pieces which are small enough to not clog or occlude the aspiration lumen. When a device becomes clogged during use, the potential for inadvertent dislodgment of thrombus downstream increases; this is referred to as distal embolism. As aspiration procedures of this type are often used in highly technical emergent settings, early clog detection of the aspiration catheter for the user during aspiration can contribute to the success of the procedure and clinical outcome. Some sources have reported that up to 50% of aspiration catheters used get clogged during use.

The user may have difficulty determining whether there is a vacuum or a negative pressure gradient in the system or not. For example, the user may have difficulty determining whether the vacuum or negative pressure has been applied or not (e.g., the vacuum source or negative pressure supplying pump has been turned on or off). Additionally, the user may have difficulty determining whether there has been a loss of vacuum or negative pressure in the system, for example because of the syringe (or other vacuum source or negative pressure supplying pump) being full of fluid or because of a leak in the system. Blood is relatively opaque and can coat the wall of the syringe, thus making it difficult to determine when the syringe becomes full. This makes it difficult to determine whether sufficient vacuum or negative pressure is being applied to the aspiration catheter. The vacuum or negative pressure level may change to an unacceptable level even before the syringe becomes full. Extension tubing or other tubing may also cause a loss in vacuum or negative pressure gradient in the system. Certain tubing kinks may be difficult for a user to see or identify. It is also difficult to determine whether there is an air leak in the system, which can be another cause for a loss of vacuum or negative pressure even before the syringe becomes full of the aspirated fluid.

Figure 48:
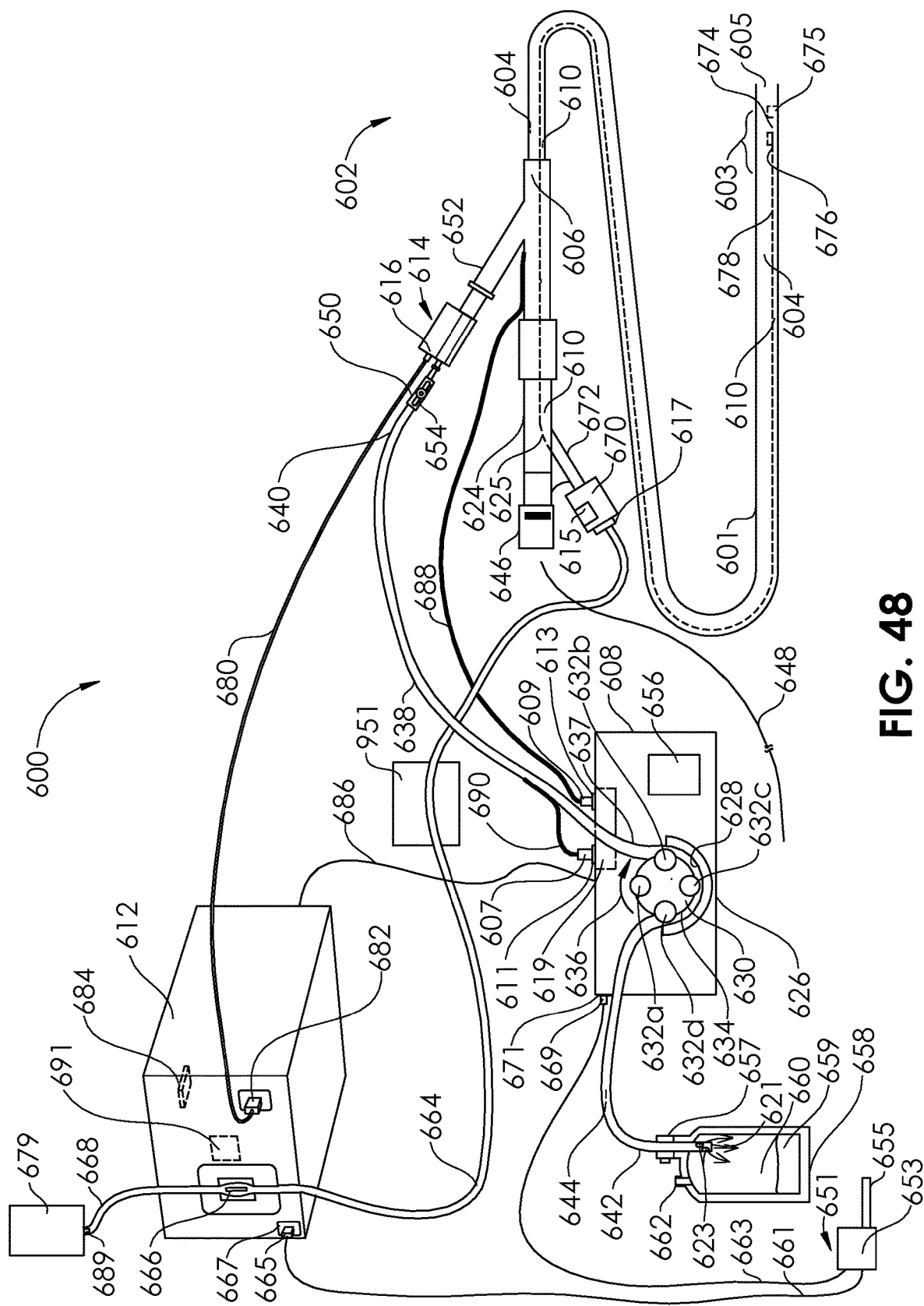
FIG. 48 is a perspective view of an aspiration system, according to an embodiment of the present disclosure.

FIG. 48 illustrates an aspiration system 600 comprising an aspiration catheter 602 comprising an elongate shaft 601 including an aspiration lumen 604 having an open distal end 605 and a proximal end 606 configured to couple to a peristaltic pump 608. The peristaltic pump 608 may be a roller pump having a base 626, a pressure shoe 628 carried by the base 626, and a rotatable head 630, rotatably coupled to the base 626, and carrying two or more rollers 632a-d. The rollers 632a-d are arrayed around a perimeter 634 of the rotatable head 630. The rotatable head 630 is configured to be rotatable in at least a first rotational direction 636 (e.g., by a motor, directly, or with a gear train, not shown). The peristaltic pump 608 may be battery powered, and the battery(ies) may be rechargeable by wired or wireless means. The peristaltic pump 608 may alternatively, or additionally be powered by a power cord (not shown) configured to connect to a power supply. An extension tube 638 having a distal end 640 and a proximal end 642, and having a lumen 644 extending therethrough, is hydraulically coupled to the proximal end 606 of the aspiration lumen 604 via a connector 624. A Touhy-Borst seal 646 allows the insertion of a guidewire 648 through the connector 624 and aspiration lumen 604, as described herein, and the guidewire 648 may be used to track the aspiration catheter 602 through a subject's vasculature. The Touhy-Borst 646 may be tightened to seal over the guidewire 648, to maintain hemostasis. The extension tube 638 may include a male luer 650 at its distal end 640, for connecting to a female luer 652 of the connector 624. The male luer 650 may include a stopcock 654, which is configured to be turned between an open position (shown) or a closed position. Alternatively, the extension tube 638 may be integral with the aspiration lumen 604, or may be permanently attached to the connector 624. In use, a compressible portion 637 of the extension tube 638 is placed within the pressure shoe 628 of the peristaltic pump 608 such that rotation of the rotatable head 630 (e.g., via input to an interface 656 by a user) in the rotational direction 636 causes fluid to be forced through the lumen 644 of the extension tube 638 from the distal end 640 to the proximal end 642, via compression of the compressible portion 637 by the rollers 632, one at a time. In some embodiments, there are only two rollers 632. In other embodiments, there are three rollers 632. In still other embodiments, as shown, there are four rollers 632. As described, the rollers 632 may be replaced by bumps or protrusions. The compressible portion 637 or any of the compressible portions described herein may comprise silicone tubing, polyurethane tubing, polyvinyl chloride tubing, thermoplastic elastomer (TPE), such as Bioprene®, a registered trademark of Watson-Marlow or Wilmington, Mass., USA, or other compressible tubing. The compressible section 637 may be a relatively short section that is attachable to and detachable from the peripheral ends of the extension tube 638, or in other embodiments, may comprise the entirety of the extension tube 638 between the distal end 640 and the proximal end 642. The proximal end 642 of the extension tube 638 may be coupled to a canister 658 having an interior 660, to allow fluid 659 passing through the extension tube 638 to pass into the interior 660. The proximal end 642 of the extension tube 638 is coupled to the canister 658 by a tubing clamp 657 which holds the extension tube 638 longitudinally without compromising the patency of the lumen 644. To minimize fluid resistance at the proximal end 642 of the extension tube, besides an endhole 621, there is also a plurality of sideholes 623, similar to sump tubing. In other embodiments, the endhole 621 may be blocked off, with the outflow emanating only from the plurality of sideholes 623. The sideholes 623 assure that the minimum area of flow resistance in the extension tube 638 is not at the proximal end 642. The sideholes 623 help prevent against jetting into the canister 658. Jetting of the blood would be a negative factor, adding shear stress to the blood, and causing hemolysis or platelet activation, and thus damaging or otherwise altering blood that might have been desired for reinfusion into the patient. An additional hub 662 in the canister 658 may be left open (as shown) to allow the unfilled interior 660 to match atmospheric pressure.

Because the aspiration catheter 602 is configured to be inserted into arteries that may feed to critical organs (heart, brain, etc.), strict control of flows through the catheter allow for a higher level of security. A recognition system is provided to assure that the aspiration catheter 602 is only used with the peristaltic pump 608 and the injection pump 612, and not with alternative devices that do not have the same levels of control regarding aspiration and injection. An identification circuit 619 within the peristaltic pump 608 is coupled to the controller 684 (e.g., via cable 686) and also electrically connects to a first port 611 and a second port 613. The extension tube 638 may be provided with a first tether 690 having a first identification module 607 configured to plug into or otherwise be secured in close proximity to the first port 611. Additionally, or alternatively, the aspiration catheter 602 may be provided with a second tether 688 having a second identification module 609 configured to plug into or otherwise be secured in close proximity to the second port 613. The controller 684 is configured to only allow the operation of the injection pump 612 and/or the peristaltic pump 608 to occur if one of both of the identification modules 607, 609 are identified by the identification circuit 619 as being correct components (e.g., correct models, correct sizes, correct clinical applications, etc.). Thus, the pumps 612, 608 are enabled or un-enabled by the controller 684, depending upon the information provided by the identification modules 607, 609. In some embodiments one or both of the identification modules 607, 609 make comprise an RFID (radiofrequency identification) chip, and the identification circuit 619 configured to power the RFID chips to receive and read data. In some embodiments, the identification circuit 619 may additionally be configured to write to the RFID chips. In other embodiments one or both of the identification modules 607, 609 make comprise a resistor, and the identification circuit 619 configured to read the resistance value of the resistor. For example, the resistor may complete a partial Wheatstone bridge carried on the identification circuit 619.

The aspiration catheter 602 additionally has a high pressure injection lumen 610 for injecting saline from a fluid source 679, for example, via a high pressure pump 612. A tubing set 664 may include a pump cartridge 666 having a piston or bellows or other movable element that the pump 612 may manipulate using an internal motor 691, thus pressurizing saline or other fluid from the fluid source 679 with a significantly high pressure such that the saline is forced through the injection lumen 610 of the aspiration catheter 602. The tubing set 664 includes proximal end 668 having a spike 689 or other element for hydraulically coupling it to the fluid source 679. The tubing set 1464 further has a distal end 670 (which may include a male luer) which is configured to hydraulically couple to the injection lumen 610 via a female luer 672. Injected saline is forced through the injection lumen 610 by the pump 612 and exits an orifice 674 in a hollow end piece 675 coupled to a distal end 676 of an injection tube 678, containing the injection lumen 610. The tube 678 may be substantially or entirely within the shaft 601. In some embodiments, the tube 678 is attached to the internal wall of the shaft 601 only at a distal end portion 603. Thus, the free-floating nature of the remainder of the tube 678 within the aspiration lumen 604 increases the flexibility and trackability of the shaft 601. The high pressure saline is forced through the orifice 674, causing a jet, or one or more jets. The jet is aimed within the aspiration lumen 604, just proximal the open distal end 605 which may create a Venturi effect that forces blood or thrombus that is external and adjacent the open distal end 605 into the aspiration lumen 640. The combination of the operation of the peristaltic pump 608 and the jet created by the high pressure saline cause the maceration of thrombus, and the movement/flow of material (saline/blood/macerated thrombus/small pieces of thrombus) through the aspiration lumen 604 from the open distal end 605 to the proximal end 606, through the connector 624, and through the lumen 644 of the extension tube 638 from its distal end 640 to its proximal end 642, and finally into the interior 660 of the canister 658. Thus, thrombus within a blood vessel of a subject may be macerated and removed by use of the system 600. Blood vessels may include peripheral blood vessels, coronary blood vessels, or blood vessels within the head or neck of the subject, including carotid arteries, cerebral arteries, and basilar and communicating arteries. An aspiration monitoring system 614 comprising a pressure transducer 616 may be coupled, for example, between the distal end 640 of the extension tube 638 and the connector 624 and/or proximal end 606 of the aspiration lumen 604 of the aspiration catheter 602. The aspiration monitoring system 614 or any other described herein can include any of the features described in relation to aspiration monitoring systems described in U.S. Pat. App. Pub. No. 2017/0056032 to Look et al., filed Aug. 23, 2016 and published Mar. 2, 2017, which is hereby incorporated by reference in its entirety for all purposes. Signals from the pressure transducer 616 are carried on an electric cable 680 to an input 682 of the pump 612. A controller 684 within the pump 612 is configured to control the operation of the pump 612, including motor 691, but the controller 684 may also be configured to control the operation of the peristaltic pump 608, with via a cable 686, or wirelessly. The controller 684 may comprise a microcontroller. The controller 684 may alternatively be located within the peristaltic pump 608, or may be located at another location. Control using signals of measured pressure from the pressure transducer 616 adds an additional safety element to the system 600. Additionally, a non-functional device (because of a leak, incomplete connection, incomplete priming, rupture, blockage) can be quickly identified. Unallowably high pressures can also be quickly identified, protecting the motor 691 of the pump 612 from burnout or overheating danger. The integrity of the tube 678 is also protected, e.g., avoiding unnaturally high pressures that could lead to burst.

The female luer 652 of the aspiration catheter 602 is located distally on the connector 624 from the female luer 672. Thus, aspirated blood/thrombus/saline enters the female luer 652 without ever having to contact interior irregularities 625 (in geometry, shape) within the connector 624, that may otherwise cause flow resistance, or cause thrombus to catch (e.g., between the tube 678 and the interior of the connector 624.

A foot pedal 651 has a base 653 and a pedal 655 that is coupled to the base 653 and movable or activatable by application of the foot of a user. The pedal 655 may be spring-loaded and depressible by application of a moment or a compressive force, or may instead comprise a membrane switch. The pedal 655, when activated, may in some embodiments toggle on and off, and in other embodiments may be activatable when a force, a pressure, or a moment is applied, and inactivated when the force, pressure, or moment is not applied. A first cable 661 carries signals from the foot pedal 651 to the pump 612 via a plug 665 that is connected to an input jack 667. A second cable 663 carries signals from the foot pedal 651 to the peristaltic pump 608 via a plug 669 that is connected to an input jack 671. In some embodiments, activation of the pedal 655 by the foot of a user starts the operation of the pump 612 and starts the operation of the peristaltic pump 608 at the same time. In some embodiments, activation of the pedal 655 by the foot of a user starts the operation of the peristaltic pump 608, and then starts the operation of the pump 612, with a slight delay after the peristaltic pump 608 is started. The delay is useful to assure that some aspiration, or a significant amount of aspiration, is being applied to the aspiration lumen 604 prior to the injection of pressurized fluid (e.g., saline) through the injection lumen 610. Thus, blood vessels or other vasculature in the vicinity of the open distal end 605 are spared any injection of fluid from a high pressure jet, as it is instead aspirated through the aspiration lumen 604.

In addition, in some embodiments, activation of the pedal 655 by the foot of a user during the operation of the pump 612 and the peristaltic pump 608 stops the operation of the pump 612 and the operation of the peristaltic pump 608 at the same time. In other embodiments, a delay may be applied, for example, such that the pump 612 is stopped, and then the peristaltic pump 608 is stopped slightly afterwards. The length of the delays described may be between about 0.01 second and about 1.00 second, or between about 0.10 second and about 0.25 second. The operation (on/off) of the pump 612 and/or peristaltic pump 608 via the foot pedal 651 allows hands-free activation, enabling a single user the manipulate the aspiration catheter 602 and guidewire 648 with both hands. The location of the foot pedal 651 can be tactily found with the foot of the user, while the user maintains visual contact with the patient, and/or any monitors, or even other medical personnel.

In other embodiments, the foot pedal 651 may be replaced by another type of switch, including, but not limited to a toggle on/off push button or hand switch, an audio-activated switch (voice activated, clap activated, click activated), an optical switch (beam/light sensor for hand or foot interruption), or any other kind of switch that can be activated by medical personnel. The switch may be remote (e.g., in a control room) or may be located near the procedural area. The switch may also be a sterile switch or sterilizable for location on a sterile area.

In some cases, the activation and deactivation (turning on and off) of the aspiration flow applied by the peristaltic pump 608 on the aspiration lumen 604 may be done by leaving the peristaltic pump 608 in a running condition, while the user opens and closes the stopcock 654. In other embodiments, the stopcock may be replaced by a pinch valve (not shown) to open or compress the extension tubing 638. The pinch valve may be operable by a foot switch or by a push button (on/off).

The controller 684 also monitors and controls several device safety functions, which include over pressure detection, air bubble detection, and vacuum or negative pressure charge. An additional pressure transducer 615 carried on the connector 624 monitors pressure (i.e. injection pressure), and senses the presence of air bubbles. Alternatively, or in conjunction, an optical device 617 may be used to sense air bubbles. In one contemplated embodiment, the pump pressure is proportional to the electric current needed by the pump 612 to produce that particular pressure. Consequently, if the electric current required by pump 612 exceeds a preset limit, the controller 684 will disable the pump 612 by cutting power to it. Air bubble detection may also be monitored by monitoring the electrical current required to drive the pump 612 at any particular moment. In order for a pump 612 to reach high fluid pressures, there should be little or no air (which is highly compressible) present in the pump 612 or connecting system (including the aspiration lumen 604 of the aspiration catheter 604 and the tubing set 664). The fluid volume is small enough that any air in the system will result in no pressure being generated at the pump head. A sufficient volume of liquid is needed proximally to flush any finite amount of air through. The controller 684 monitors the pump 612 current for any abrupt downward change that may indicate that air has entered the system. If the rate of drop is faster than a preset limit, the controller 684 will disable the pump 612 by cutting power to it until the problem is corrected.

The aspiration catheter 602 of FIG. 48 is illustrated as having pressurized fluid injection through injection lumen 610. However, other embodiments of the aspiration system 600 exist in which the aspiration catheter 602 is replaced by a standard aspiration catheter, not having an injection lumen.

As an alternative to collecting the aspirated material in a blood bag, blood bottle, or the canister 658, aspirated components (blood, thrombus, saline, slurry, etc.) can be placed into a reinfusion device, such as a Stryker ConstaVac (CBCII) Blood Conservation System, or a Haemonetics OrthoPAT Orthopedic Perioperative Autotransfusion System. In some embodiments, the canister 658, itself, may comprise the reinfusion device. Returning at least some of the aspirated blood to the patient via reinfusion helps to diminish what is one of the inherent drawbacks to aspiration, blood loss.

In some embodiments, the blood may be cooled prior to being injected. In some embodiments, the blood may be heated prior to being injected. In some embodiments, other drugs may be added to the blood prior to it being inserted. In some cases, the blood may be diluted with saline, to decrease its viscosity, or decrease its hematocrit. This may allow for decrease hemolysis to occur. In some cases, blood collected in the canister 658, or blood coming from the extension tube 638, may even be used as donor blood, to infuse into a different patient.

In some embodiments, an additional or alternate sensor may be used to monitor flow conditions for the notification of the user, including, but not limited to: a Doppler sensor, an infrared sensor, or a laser flow detection device. In some embodiments, an externally-attached (non-contact) Doppler sensor may be employed. In some embodiments, an infrared sensor or a laser flow detection device may be employed around the extension tubing 638. The alternate sensor (e.g., flow sensor, etc.) may be located at a number of different locations along the aspiration path, including on or in the extension tube 638, either proximal to or distal to the rotatable head 630 of the peristaltic pump 608.

Figure 49:
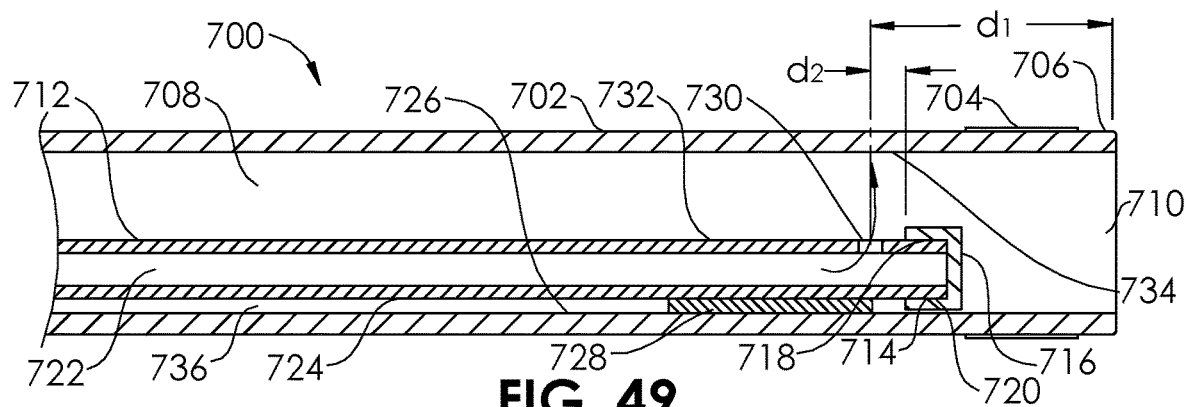
FIG. 49 is a sectional view of the distal end of an aspiration catheter, according to an embodiment of the present disclosure.

FIG. 49 illustrates an aspiration catheter 700 having an elongate shaft 702, and with a radiopaque marker band 704 attached to the distal end 706 of the shaft 702. The shaft 702 defines an aspiration lumen 708 having an open distal end 710. An injection tube 712 having a distal end 714 is capped off with a microfabricated cap 716. The microfabricated cap 716 has an inner cylindrical cavity 718 configured for placing over the distal end 714 of the injection tube 712. An outer cylindrical surface 720 at the distal end 714 of the injection tube 712 is sealingly coupled to the microfabricated cap 716 at the inner cylindrical cavity 718, so that the injection lumen 722 of the injection tube 712 is closed and sealed at the distal end 714 to resist a high pressure. The outer cylindrical surface 720 may be bonded to the microfabricated cap 716 at the inner cylindrical cavity 718 by at least one of an adhesive, an epoxy, a weld (e.g., ultrasonic weld, or other fusing of materials), or a solvent. Alternatively, a circumferential seal (thin elastomeric ring) may be interposed between the outer cylindrical surface 720 and the microfabricated cap 716 at the inner cylindrical cavity 718 to create a seal, and a friction fit. The microfabricated cap 716 may comprise a number of different materials, including polymers or metals. The microfabricated cap 716 may be constructed by a number of different processes, including: micromachining, micro injection molding, three-dimensional printing, photolithography, shadow masking, etching, or microforming. These processes include additive processes and subtractive processes. An orifice 730 is formed in a wall 732 of the injection tube 712 and has a similar function to the orifice 674 of FIG. 48. High pressure fluid is forced out of the orifice 730 and into the aspiration lumen 708 (arrow) because the distal end 714 of the injection tube 712 is sealed.

An outer surface 724 of the injection tube 712 is bonded to an inner surface 726 of the aspiration lumen 708 with an adhesive 728 (or epoxy, or other joining means). The injection tube 712 is bonded at a particular rotational orientation with respect to the aspiration lumen 708 such that the orifice 730 is oriented toward an opposing surface 734 in the aspiration lumen 708. An unbonded section 736 extends a significant portion of the length of the aspiration catheter 700 in the proximal direction, thus allowing for enhanced flexibility and trackability. The center of the orifice 730 may be located a distance $d_2$ from the proximal end of the microfabricated cap 716, such as between about 0.05 mm and about 10.00 mm so that a jet emanating from the orifice 730 clears the microfabricated cap 716. The center of the orifice 730 is located a distance $d_1$ from the open distal end 710 of the aspiration lumen 708 such that the distal end of the microfabricated cap 716 does not extend from the aspiration lumen 708. However, in some embodiments, the microfabricated cap may be configured to extend from the aspiration lumen 708, as long it does not have any sharp leading features.

Figure 50:
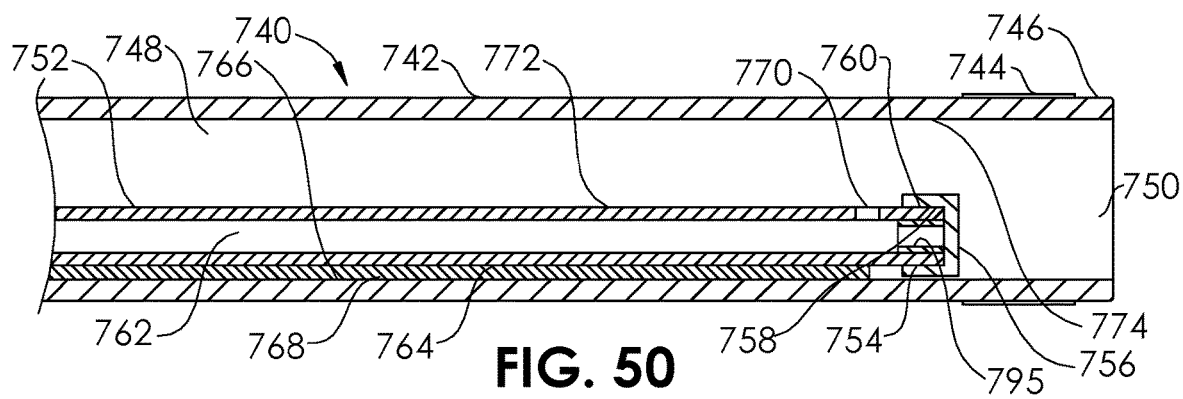
FIG. 50 is a sectional view of the distal end of an aspiration catheter, according to an embodiment of the present disclosure.

FIG. 50 illustrates an aspiration catheter 740 having an elongate shaft 742, and with a radiopaque marker band 744 attached to the distal end 746 of the shaft 742. The shaft 742 defines an aspiration lumen 748 having an open distal end 750. An injection tube 752 having a distal end 754 is capped off with a microfabricated cap 756. The microfabricated cap 756 has an inner cylindrical cavity 758 configured for placing over the distal end 754 of the injection tube 752. An outer cylindrical surface 760 at the distal end 754 of the injection tube 752 is sealingly coupled to the microfabricated cap 756 at the inner cylindrical cavity 758, so that the injection lumen 762 of the injection tube 752 is closed and sealed at the distal end 754 to resist a high pressure. A reinforcement ring 795 is fit into the injection lumen 762 of the injection tube 752 at the distal end 754 to reinforce the distal end 754 and allow for higher strength seal. The reinforcement ring 795 may also be configured to allow a friction fit seal. The reinforcement ring may comprise a high strength metallic material such as stainless steel, or a rigid polymer. The outer cylindrical surface 760 may be bonded and/or sealed to the microfabricated cap 756 at the inner cylindrical cavity 758 by any of the methods or materials described in relation to the aspiration catheter 700 of FIG. 49. The microfabricated cap 756 may comprise any of the materials and be formed by any of the processes described in relation to the microfabricated cap 716 in FIG. 49. An orifice 770 is formed in a wall 772 of the injection tube 752 and has a similar function to the orifice 674 of FIG. 48. High pressure fluid is forced out of the orifice 770 and into the aspiration lumen 748 because the distal end 754 of the injection tube 752 is sealed.

An outer surface 764 of the injection tube 752 is bonded to an inner surface 766 of the aspiration lumen 748 with an adhesive 768 (or epoxy, or other joining means). The injection tube 752 is bonded at a particular rotational orientation with respect to the aspiration lumen 748 such that the orifice 770 is oriented toward an opposing surface 774 in the aspiration lumen 748. The adhesive 768 bond extends a significant portion of the length of the aspiration catheter 740 in the proximal direction.

Figure 51:
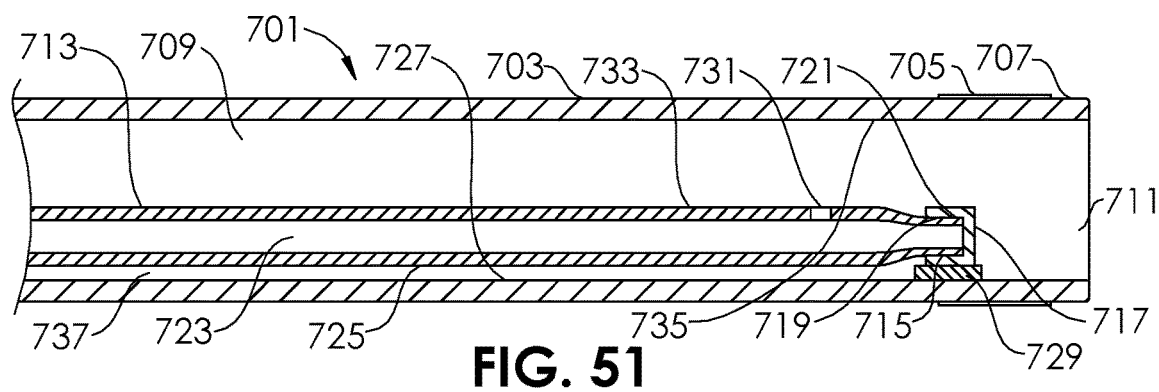
FIG. 51 is a sectional view of the distal end of an aspiration catheter, according to an embodiment of the present disclosure.

FIG. 51 illustrates an aspiration catheter 701 having an elongate shaft 703, and with a radiopaque marker band 705 attached to the distal end 707 of the shaft 703. The shaft 703 defines an aspiration lumen 709 having an open distal end 711. An injection tube 713 having a distal end 715 is capped off with a microfabricated cap 717. The distal end 715 is necked down from the rest of the injection tube 713 by a heating and/or tensile stretching process to create a smaller outer diameter of the distal end 715. The microfabricated cap 717 has an inner cylindrical cavity 719 configured for placing over the reduced diameter distal end 715 of the injection tube 713. An outer cylindrical surface 721 at the distal end 715 of the injection tube 713 is sealingly coupled to the microfabricated cap 717 at the inner cylindrical cavity 719, so that the injection lumen 723 of the injection tube 713 is closed and sealed at the distal end 715 to resist a high pressure. The smaller diameter of the distal end 715 and the inner cylindrical cavity 719, allow for a relatively higher strength bond, because of the thereby increased hoop strength of the distal end 715. The outer cylindrical surface 721 may be bonded and/or sealed to the microfabricated cap 717 at the inner cylindrical cavity 719 by any of the methods or materials described in relation to the aspiration catheter 700 of FIG. 49. The microfabricated cap 717 may comprise any of the materials and be formed by any of the processes described in relation to the microfabricated cap 716 in FIG. 49. An orifice 731 is formed in a wall 733 of the injection tube 713 and has a similar function to the orifice 674 of FIG. 48. High pressure fluid is forced out of the orifice 731 and into the aspiration lumen 709 because the distal end 715 of the injection tube 713 is sealed.

An outer surface 725 of the injection tube 713 is not bonded to an inner surface 727 of the aspiration lumen 709. Instead, the microfabricated cap 717 is bonded to the inner surface 727 with an adhesive 729 (or epoxy, or other joining means). An unbonded section 737 of the injection tube 713 extends a significant portion of the length of the aspiration catheter 701 in the proximal direction, thus allowing for enhanced flexibility and trackability. The microfabricated cap 717 is bonded such that the injection tube 713 is held at a particular rotational orientation with respect to the aspiration lumen 709 such that the orifice 731 is oriented toward an opposing surface 735 in the aspiration lumen 709.

Figure 52:
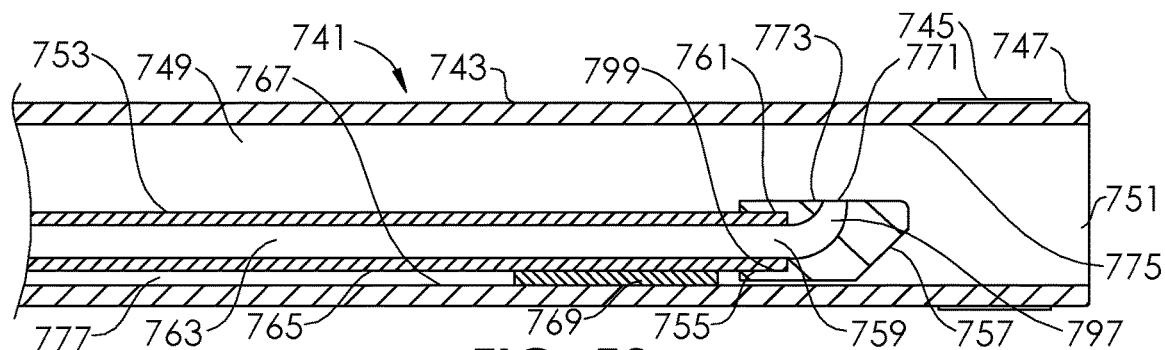
FIG. 52 is a sectional view of the distal end of an aspiration catheter, according to an embodiment of the present disclosure.

FIG. 52 illustrates an aspiration catheter 741 having an elongate shaft 743, and with a radiopaque marker band 745 attached to the distal end 747 of the shaft 743. The shaft 743 defines an aspiration lumen 749 having an open distal end 751. An injection tube 753 having a distal end 755 is capped off with a microfabricated cap 757. The microfabricated cap 757 has an inner cylindrical cavity 759 which includes a proximal portion 799 configured for placing over the distal end 755 of the injection tube 753. An outer cylindrical surface 761 at the distal end 755 of the injection tube 753 is sealingly coupled to the microfabricated cap 757 at the inner proximal portion 799 of the cylindrical cavity 759, so that the injection lumen 763 of the injection tube 753 is sealed to resist a high pressure. The outer cylindrical surface 761 may be bonded and/or sealed to the microfabricated cap 757 at the proximal portion 799 of the inner cylindrical cavity 759 by any of the methods or materials described in relation to the aspiration catheter 700 of FIG. 49. The microfabricated cap 757 may comprise any of the materials and be formed by any of the processes described in relation to the microfabricated cap 716 in FIG. 49. An orifice 771 is an exit of a distal portion 797 of the inner cylindrical cavity 759 that communicates with the proximal portion 799. The inner cylindrical cavity 759 in FIG. 52 has a curved shape, but may alternatively form an L-shape, or make take a 45° angle with respect to the longitudinal axis of the aspiration catheter 741. The angle may vary between 45° and 135°. The orifice 771 is formed in a wall 773 of the microfabricated cap 757 and has a similar function to the orifice 674 in FIG. 48. High pressure fluid is forced through the inner cylindrical cavity 759, out of the orifice 771, and into the aspiration lumen 749 because the distal end 755 of the injection tube 753 is sealed.

An outer surface 765 of the injection tube 753 is bonded to an inner surface 767 of the aspiration lumen 708 with an adhesive 769 (or epoxy, or other joining means). The injection tube 753 is bonded at a particular rotational orientation with respect to the aspiration lumen 749 such that the orifice 771 is oriented toward an opposing surface 775 in the aspiration lumen 749. An unbonded section 777 extends a significant portion of the length of the aspiration catheter 741 in the proximal direction, thus allowing for enhanced flexibility and trackability. One of more of the individual features of the aspiration catheters 700, 740, 701, 741 of FIGS. 49-52 may be rearranged to create other new embodiments. The individual features each allow the production of a small diameter aspiration catheter capable of tracking into distal vasculature, such as the vasculature of the head and neck, and also provide for aspiration including high pressure forced injection.

FIGS. 53-56 illustrate an insertable injection tube 920, and a method for using it in a patient. The patient is not shown, for simplicity, and the devices are shown in a straight configuration, but in use, it is common for the devices to be tracked through tortuosities of a patient's vasculature. In FIG. 53, a microcatheter 924 is configured for tracking into the neurovasculature of a patient, including the Circle of Willis and the cerebral arteries. The microcatheter 924 may be incorporated as a component of an aspiration system 922 (FIGS. 54-56), or may be a standard microcatheter purchased separately by a user. The microcatheter 924 comprises a shaft 926 having a proximal end 928 and a distal end 930, with a lumen 932 extending through the shaft 926. A luer hub 934 (e.g., female luer connector) is sealingly attached to the proximal end 928 of the shaft 926. The microcatheter 924 may have a distal radiopaque marker (not shown), which is allied in a similar manner to the radiopaque marker bands 704, 744, 705, 745 in the aspiration catheters 700, 740, 701, 741 of FIGS. 49-52. A connector 936 includes a male luer 938 for connecting to the luer hub 934, and can include a valve 940, which may comprise a Touhy-Borst or the equivalent. The sideport 942 of the connector 936 may include a female luer for connecting to the male luer 650 of the extension tube 638 of the system 600 described in detail in relation to FIG. 48. In FIG. 53 a user tracks the microcatheter 924 over a guidewire 944 into the blood vessels that are the region of interest. In some cases, the region of interest may be one of the cerebral arteries or other arteries in the vicinity, where a thrombus 946 (FIG. 54) is causing a thromboembolic stroke in the patient.

Figure 55:
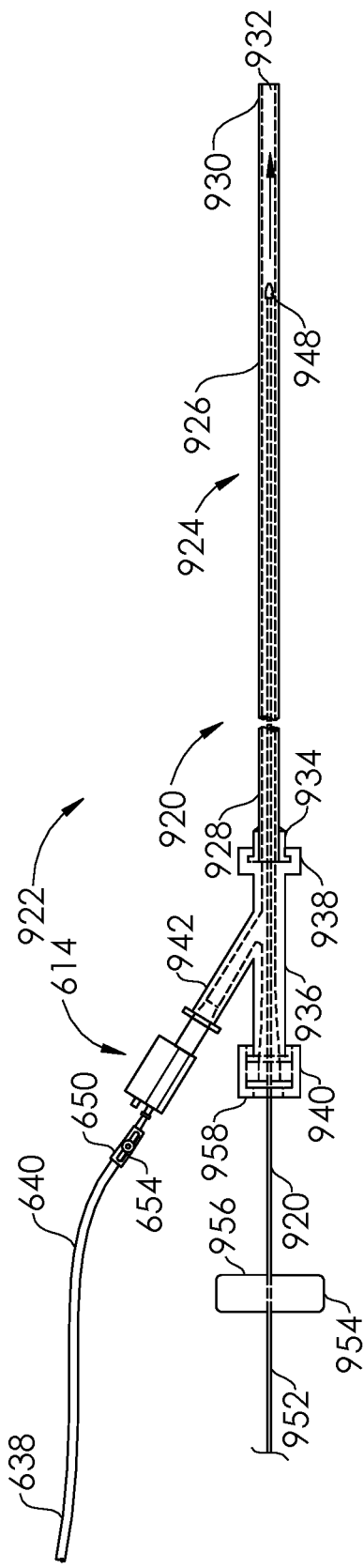
FIG. 55 is a plan view of the insertable injection tube and cap being advanced through a lumen of the microcatheter, in a third step.
Figure 56:
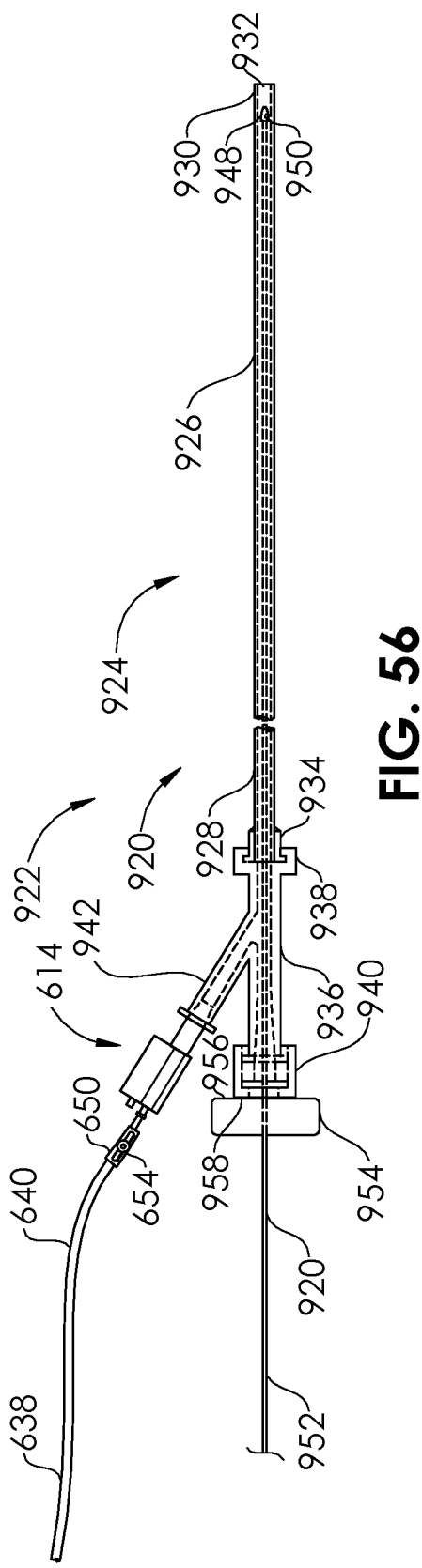
FIG. 56 is a plan view of the insertable injection tube and cap in a fully inserted position within the microcatheter, in a fourth step.

In FIG. 54, the user removes the guidewire 944 and inserts the insertable injection tube 920 through the Touhy-Borst 940 and into the connector 936 and the lumen 932 of the microcatheter 924. The insertable injection tube 920 may include a microfabricated cap 948, as described in any of the embodiments of FIGS. 49-52, or may comprise an alternative configuration. However, the insertable injection tube 920 at the minimum comprises a high strength hollow tube 952 which may comprise stainless steel, nickel-titanium alloy, polyimide, or other high strength materials having sufficient column strength to be inserted through the lumen 932 of the microcatheter 924. The microfabricated cap 924 includes an orifice 950 configured to provide a jet of pressurized fluid, similar to the orifice 771 of the microfabricated cap 757 in FIG. 52. In FIG. 55, the user advances the insertable injection tube 920 further through the lumen 932 of the microcatheter 924, toward the distal end 930. A stop 954 is bonded to the outside of the high strength hollow tube 952 and has a front face 956 configured to butt up against a proximal face 958 of the connector 936 when the center of the orifice 950 is located at the preferred distance (e.g., $d_1$, as in FIG. 49) from the distal end of the microcatheter 924. The insertable injection tube 920 may be provided with different models, each having a different length between the front face 956 and the center of the orifice 950, and each configured to be used with a particular length of microcatheter 924, or a particular model of microcatheter 924, or a particular microcatheter 924 model/connector 936 model combination. In some embodiments, the connector 936 may be a component of the insertable injection tube 920, and instead of the Touhy-Borst 940, may instead be permanently sealed and coupled to the high strength hollow tube 952 at a proximal region. Thus, the coupling of the male luer 938 to the luer hub 934 provides the longitudinal stop that controls the $d_1$ distance.

It may not always be possible to track an aspiration catheter 602 having high pressure injection forced aspiration capabilities (FIG. 48) into the neurovasculature, because of the smaller diameters and tortuosities of the vessels. Thus, the insertable injection tube 920 allows a microcatheter 924 to be converted into a forced aspiration catheter. Thus, forced aspiration can occur in very distal locations, and locations that are distal to significant tortuosity, where normally microcatheters are the preferred access means. The small diameter insertable injection tube 920 is capable of being inserted through the lumen 932 of a microcatheter 924 after the microcatheter 924 is inserted into the region of interest. In alternative procedures and alternative embodiments of a system, a microcatheter 924 being inserted over a guidewire 944 may be replaced by a flow-directed catheter having a lumen configured for placement of the insertable injection tube 920 being inserted to the region of interest without a guidewire.

Figure 57:
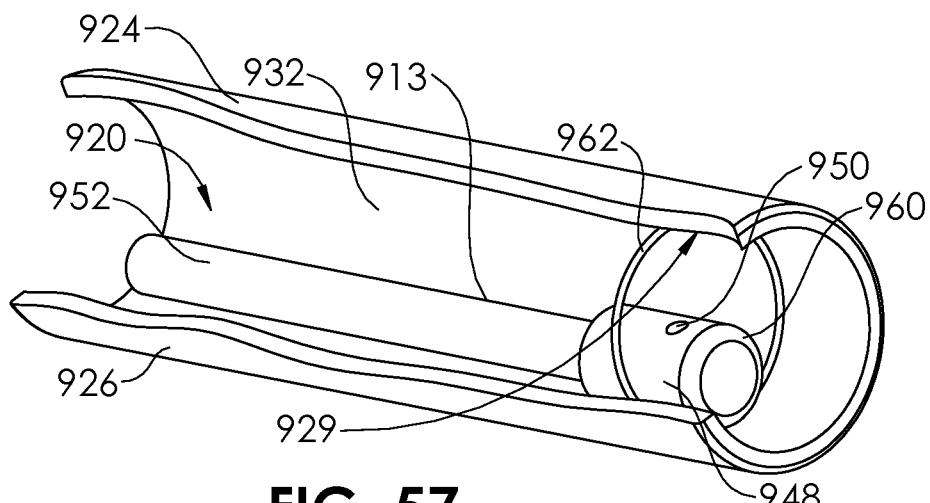
FIG. 57 is a perspective cut-away view of a distal end of an insertable injection tube and cap with a spline inserted within a microcatheter, according to an embodiment of the present disclosure.
Figure 58:
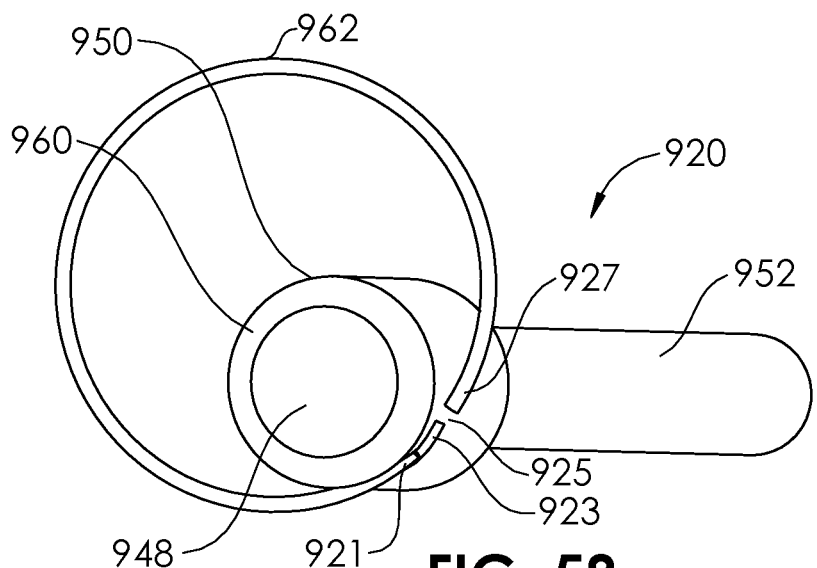
FIG. 58 is a perspective view of the insertable injection tube and cap with spline of FIG. 57.

FIG. 57 illustrates a particular distal configuration of a distal end 913 of the insertable injection tube 920. This configuration allows the microfabricated cap 948 and orifice 950 to be controllably and repeatably inserted through the lumen 932 of the microcatheter 924 such that the orifice is automatically oriented and the one or more jets emanating from the orifice 950 (or one or more orifices 950) are directed against an opposite wall 929 in the lumen 932 of the microcatheter 924. The microfabricated cap 948 has a distal taper 960, that may comprise a fillet or a bevel, or other type of lead-in shape. The purpose of the distal taper 960 is to facilitate the insertion into the connector 936, the luer hub 934, or the lumen 932 (FIG. 54), and to ease the advancement of the microfabricated cap 948 through the lumen 932, especially when the shaft 926 is in a tortuous condition. A spline loop 962 is coupled to the microfabricated cap 948 and may be formed from a wire, such as stainless steel or cobalt-chromium-nickel-molybdenum, or may comprise a superelastic material, such as a nickel-titanium alloy. The spline loop 962 is configured to have a diameter that is slightly less than, equal to, or slightly greater than the diameter of the lumen 932 of the microcatheter 924. Turning to FIG. 58, a first end 921 of the spline loop 962 is bonded into a circumferential groove 923 in the microfabricated cap 948. There is a gap 925 between the first end 921 and a second end 927 of the spline loop 962, which allows space for the two ends 921, 927 to approach each other, and thus the diameter of the spline loop 962 to be forced smaller, for example, by stress placed on the spline loop 962 from the wall around the lumen 932 of the microcatheter 924. Because the rotational orientation between the spline loop 962 and the microfabricated cap 948 are fixed in relation to each other (by the bonding of the first end 921 into the groove 923), the orifice 950 remains oriented toward an opposite wall 929 in the lumen 932. The spline loop 962 is located at a different longitudinal position on the microfabricated cap 948 than the orifice 950, and thus, the spline loop 962 does not block or deflect the jet emanating from the orifice 950. In this embodiment, the spline loop 962 is slightly distal to the orifice 950, though in other embodiments, it may instead be located proximally. In other alternative embodiments, the spline loop 962 (or any analogous structure) may actually be used to at least somewhat deflect the jet emanating from the orifice 950, with the purpose of changing the shape or direction of the jet, for instance, deflecting it at least partially in a proximal longitudinal direction. In these alternative embodiments, therefore, it may actually be desired to have the spline loop 962 located at substantially the same longitudinal location as the orifice 950.

Figure 59:
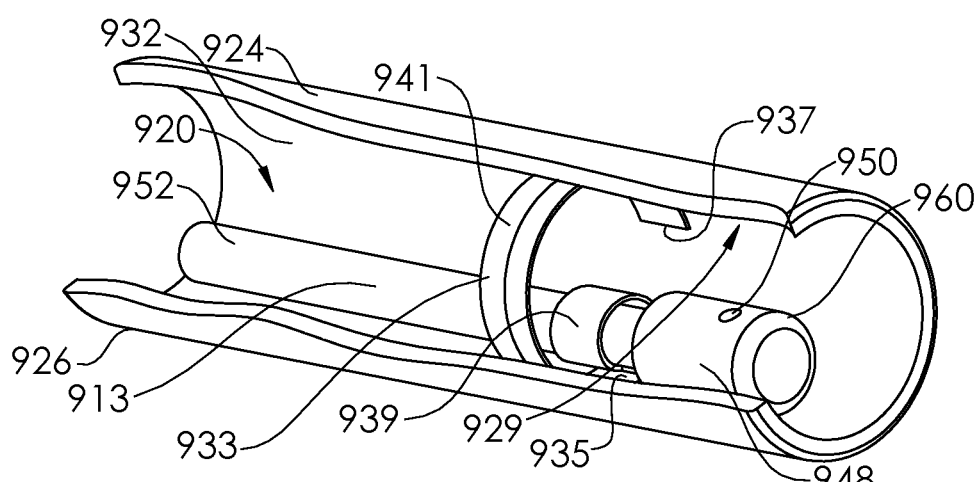
FIG. 59 is a perspective cut-away view of a distal end of an insertable injection tube and cap with a spline inserted within a microcatheter, according to an embodiment of the present disclosure.

FIG. 59, the spline loop 962 is replaced by a spline ring 933, which is attached to the high strength hollow tube 952 instead of to the microfabricated cap 948. The spline ring 933 is formed from a flat wire (stainless steel or nickel-titanium alloy, or other) or from a stiff polymeric strip (polyimide or other stiff polymer), and has a shape somewhat like the number "6," extending between a first end 935 and a second end 937. A first loop portion 939 is configured to extend around the high strength hollow tube 952 for bonding thereon, and a second loop portion 941 serves the same purpose as the spline loop 962 of FIGS. 57-58, to guide the microfabricated cap 948 and to rotationally orient the orifice 950 within the lumen 932. Other spline shapes may alternatively be used which also serve to maintain the microfabricated cap 948 against the wall on one side of the lumen 932, and/or serve to resist rotation between the shaft 926 of the microcatheter 924 and either the high strength hollow tube 952 or the microfabricated tip 948 (whichever of the two includes the orifice 950). The spline loop 962 or the spline ring 933 may each be made from a radiopaque material, or may include a radiopaque material as a base, or plating or coating. Thus, during a procedure, it will be easier to visualize on x-ray or fluoroscopy the movement of the orifice 950 down the lumen 932 of the microcatheter 924. The microfabricated cap 948 may also or may alternatively comprise a radiopaque material or radiopaque coating or plating. The insertable injection tube 920 in the embodiments presented, is configured to be removable from the lumen 932 of the microcatheter 924, so that the microcatheter 924 may be subsequently used for one of its other functions (delivering embolic coils or embolic materials, drugs, replacing the guidewire 944 or even aspirating through the empty lumen 932). In alternative embodiments, the orifice 950 of the microfabricated cap 948 may be used to inject drugs or other materials into the vasculature, for example, by stopping or avoiding any vacuum or negative pressure placed on the proximal end of the lumen 932.

Figure 60:
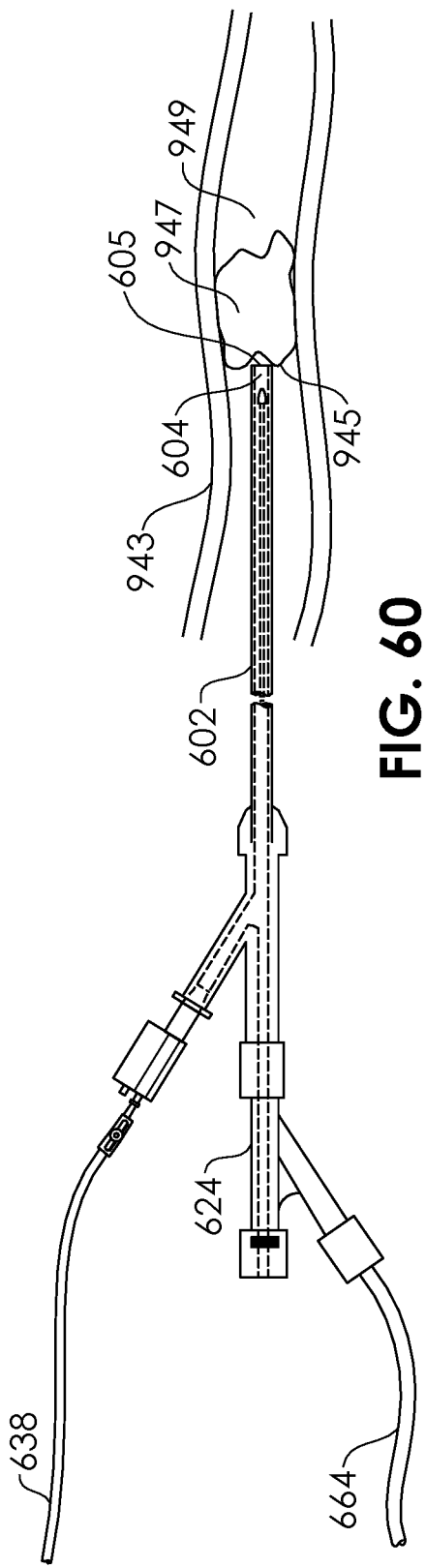
FIGS. 60-63 illustrate a method for treating a patient using an aspiration catheter and system, according to an embodiment of the present disclosure.

FIGS. 60-63 illustrate a method for treating a patient using the aspiration system 600 of FIG. 48, using aspiration catheter 602, or any of the alternative aspiration catheters 700, 740, 701, 741. Alternatively, the method may be accomplished using the aspiration system 922, or using the insertable injection tube 920 with a standard single lumen catheter, such as a microcatheter 924, a guiding catheter, or a guide sheath (long sheath). In all of these systems, the pump 612 and the peristaltic pump 608 as described in FIG. 48 can be utilized. In FIG. 60, an aspiration catheter 602 has been tracked into a blood vessel 943 (e.g., using a guidewire 648) and is advanced so that the open distal end 605 is adjacent the proximal end 945 of a thrombus 947. In some cases, aspiration utilizing the high pressure injection from the pump 612 through the tubing set 664 combined with distal-to-proximal flow impulse imparted on the extension tube 638 by the peristaltic pump 608 are not enough to cause the thrombus 947 to be sufficiently aspirated into the open distal end 605 and into the aspiration lumen 604 so that it may be macerated and aspirated. At times, the cause for this is that a space 949 distal to the thrombus 947 acts as a relative vacuum and pulls on the thrombus with a force (e.g., distally, away from the aspiration catheter 602), thus making it difficult to aspirate the thrombus. Though the blood vessel 943 is shown in a relatively normal state, at time the blood vessel may have become collapsed because of lack of blood pressure from occlusion by the thrombus 947. Other times, some of the thrombus 947 may have significantly solid or semi-solid portions that impede the ability to flow from a distal to proximal direction.

Figure 61:
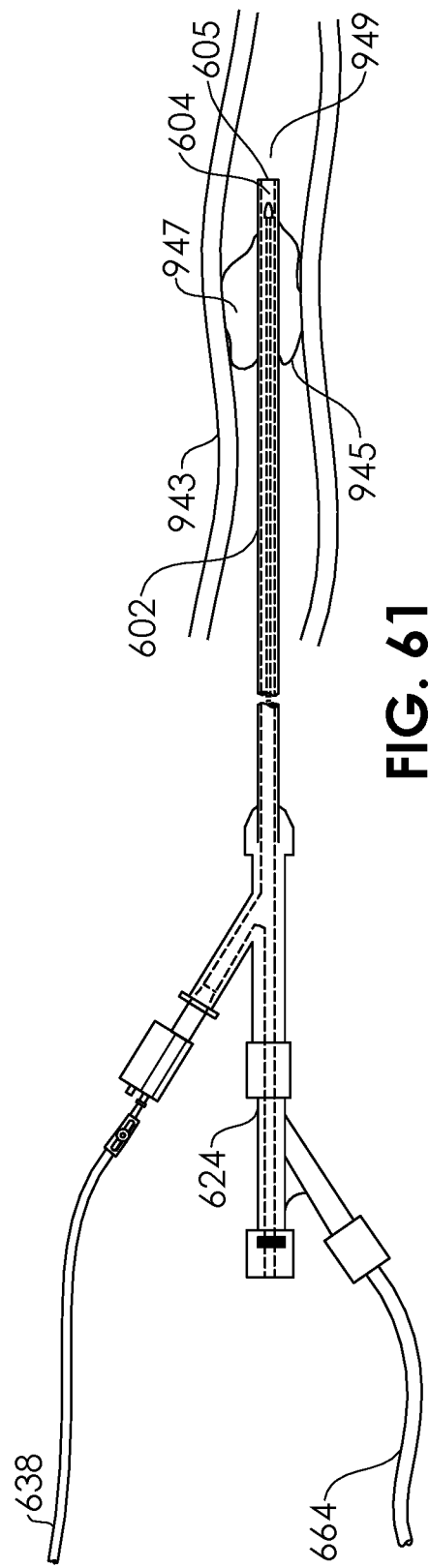

A user has encountered this condition while attempting to aspirate through operation of the pump 612 and peristaltic pump 608, and the aspiration catheter 602 is inserted and advanced into the blood vessel 943 as shown in FIG. 60. The user then may use a technique with the aspiration system 600 to alleviate the substantially no flow condition. In FIG. 61, the user advances the aspiration catheter 602 so that the open distal end 605 of the aspiration lumen 604 is distal to the thrombus 947. The advancement of the open distal end 605 of the aspiration catheter 602 through or past the thrombus 947 may be done without using a guidewire 648, but in certain instances, the guidewire 648 will need to be used to cannulate and pass through or past the thrombus 947 and then to track the aspiration catheter 602.

Figure 62:
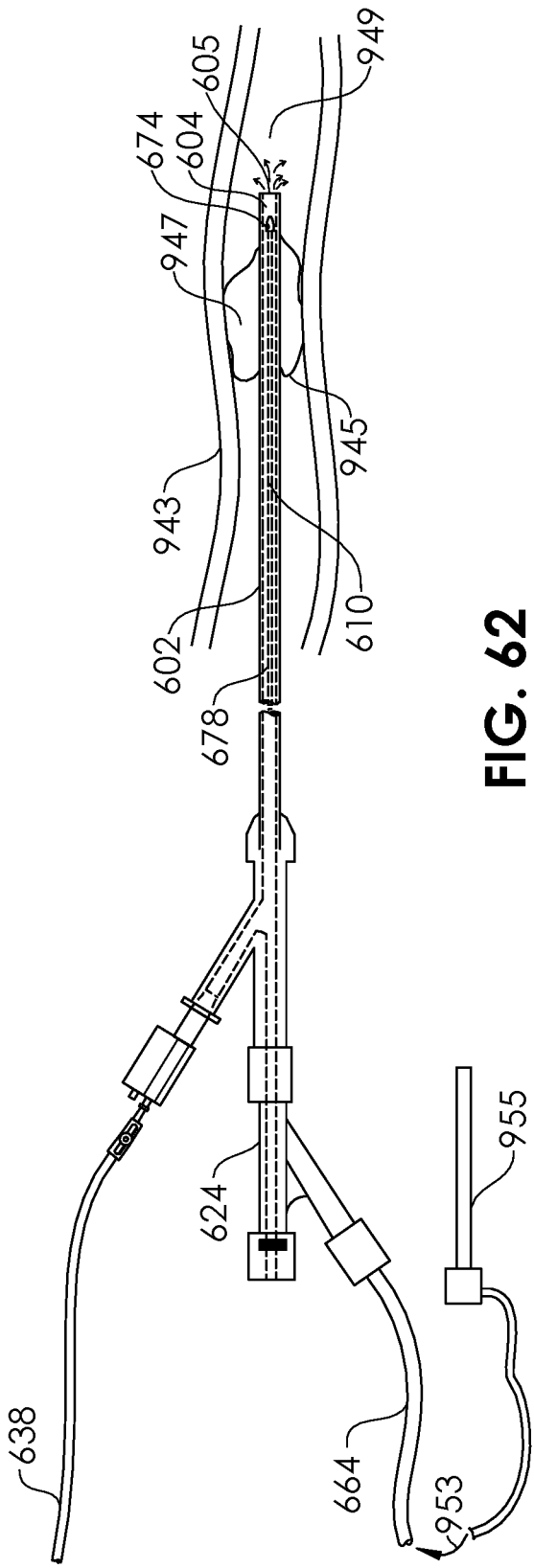
Figure 63:
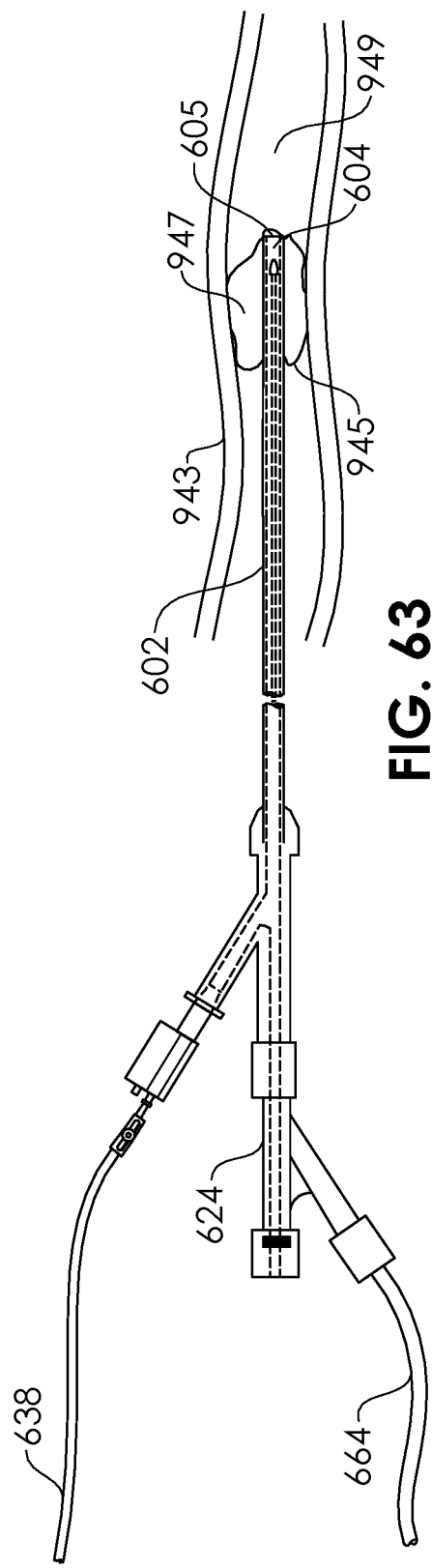

In FIG. 62, the user operates the pump 612 to inject fluid, while the peristaltic pump 608 is not being operated. Thus, pressurized fluid (e.g., heparinized saline, or saline mixed with a thrombolytic drug) is injected through the injection lumen 610 of the tube 678, through the orifice 674, into the aspiration lumen 604, and then out the open distal end 605 (arrows) and into the space 949 in the blood vessel 943. This occurs because there is no aspiration through the aspiration lumen 604, and the stopped peristaltic pump 608 acts as a closed valve, with one of the rollers 632 compressing the compressible portion 637 of the extension tube 638. The injection of the fluid increases the fluid volume of the space 949, and by doing so, is able to also increase its internal pressure, thus neutralizing the prior relative vacuum effect caused by the space 949. There is now flowable material in the space 949, such that aspiration using the peristaltic pump 608 with the pump 612 can allow maceration and aspiration of the thrombus 947 to begin (by now turning on the peristaltic pump 608). The aspiration catheter 602 can also be retracted as shown in FIG. 63, to better contact the thrombus 947 and to increase the percentage of thrombus 947 being aspirated. This can be continued until all or at least a clinically significant portion of the thrombus 947 is aspirated.

Returning to FIG. 62, in certain cases, such as thromboembolic stroke, the downstream tissue may not be receiving sufficient flow because of the occlusion caused by the thrombus 947. The user may run the fluid from the fluid source 679 through a cooling system, such as a heat exchanger or thermoelectric cooler 951 (FIG. 48) through which the tubing set 664 may run, and by which the fluid may be cooled. Additionally, an extracorporeal circuit 953 (FIG. 62) may be attached to the tubing set 664, so that blood removed from the patient (e.g., via a femoral artery, femoral vein, or jugular vein sheath 955) is added to the fluid from the fluid source 679, so that there is some oxygenated blood being injected into the space 949, some which may potentially feed downstream tissue with oxygen or nutrients. The cooled fluid (saline, blood, or saline plus blood) can additionally reduce the metabolic demands of the downstream tissue by actively cooling it. The inventors have demonstrated that using a pump 612 that utilizes a removable cartridge having a piston, hemolysis can be maintained at an acceptably low value during this sort of injection and mixing of blood with the injected saline, from a mixture that includes about 10% blood, to a mixture that includes about 80% blood.

Figure 64:
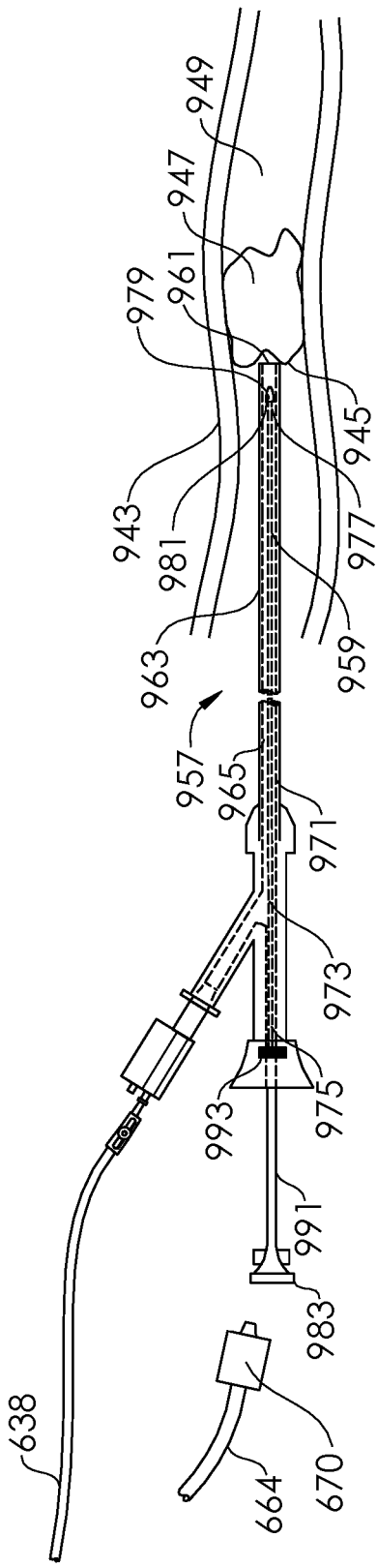
FIGS. 64-65 illustrate a method for treating a patient using an aspiration catheter and system, according to an embodiment of the present disclosure.
Figure 65:
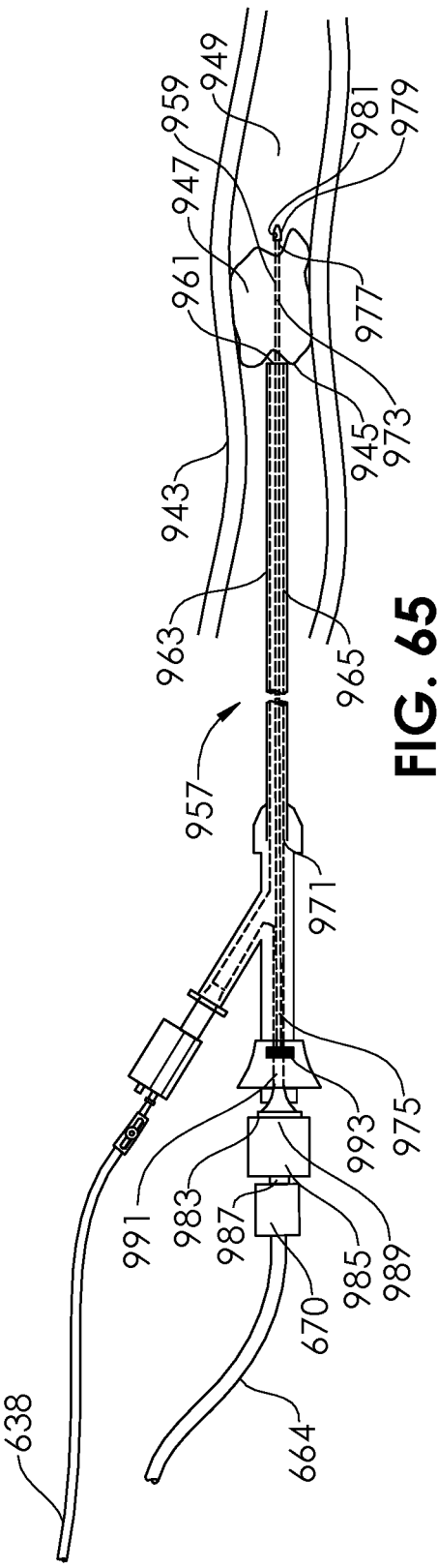

FIGS. 64-65 illustrate a method for treating a patient using the aspiration system 600 of FIG. 48, but incorporating an aspiration catheter 957 having a translatable injection tube 959. The aspiration catheter 957 has an elongate shaft 963 having an aspiration lumen 965 with a proximal end 971 and an open distal end 961. The translatable injection tube 959 has an injection lumen 973 having a proximal end 975 and a distal end 977. The distal end 977 is coupled to a microfabricated cap 979 having an orifice 981, such that pressurized fluid injected through the injection lumen 973 exits from the orifice 981, as in the orifice 771 in FIG. 52. At a high enough injection pressure, the fluid may emanate from the orifice 981 in a jet. Alternatively, the distal end 977 of the injection lumen 973 may be plugged or capped, and there may be an orifice formed in the wall of the injection tube 959, as in FIGS. 49-51. The pump 612 and the peristaltic pump 608 as described in FIG. 48 can be utilized. In FIG. 64, the aspiration catheter 957 has been tracked into a blood vessel 943 (e.g., using a guidewire 648) and is advanced so that the open distal end 961 is adjacent the proximal end 945 of a thrombus 947. A proximal female luer connector 983 is coupled to the injection lumen, 973, and configured to couple to the male luer/distal end 670 of the tubing set 664. A filter 985 may be interposed between the female luer connector 983 and the male luer 670, to filter out particulate (FIG. 65). The filter has a proximal female luer 987 and a distal male luer 989. The filter 985 may be used with any of the embodiments described herein, in which fluid may be injected (intentionally or not) into the bloodstream of a patient.

As described, in some cases, aspiration utilizing the high pressure injection from the pump 612 through the tubing set 664 combined with distal-to-proximal flow impulse imparted on the extension tube 638 by the peristaltic pump 608 are not enough to cause the thrombus 947 to be sufficiently aspirated into the open distal end 961 and into the aspiration lumen 965 so that it may be macerated and aspirated. A stiff tube 991 is bonded coaxially over the injection tube 959 at a proximal length, or the injection tube 959, itself, may be made stiff proximally. The stiff tube 991 and/or the female luer connector 983 and/or the attached filter 985 can be gripped by the user, such that the user is able to advance the stiff tube 991 and the injection tube 959, in turn, distally, such that the microfabricated cap 979 and the orifice 981 are translated distally, through the thrombus 947 and into the space 949 distal to the thrombus 947. In some cases, being translated distally into a distal portion of the thrombus 947 may be sufficient. A dynamic seal 993 (o-ring, quad ring, etc.) can be sealed over the stiff tube 991 at all longitudinal positions of the stiff tube 991. Once the orifice 981 is located within the space 949, the pump 612 is operated without the operation of the peristaltic pump 608 (or with a significantly low setting of the peristaltic pump), such that fluid is injected through the injection lumen 973 and out the orifice 981, into the space 949.

The injection of the fluid increases the fluid volume of the space 949, and by doing so, is able to also increase its pressure, thus neutralizing the prior relative vacuum effect from the space 949. There is now flowable material within the space 949 such that aspiration using the peristaltic pump 608 with the pump 612 can allow maceration and aspiration of the thrombus 947 to begin (by now turning on the peristaltic pump 608). The shaft 963 of the catheter 957 can also be advanced and retracted during aspiration, to increase the percentage of thrombus 947 being aspirated. In addition, the injection tube 959 can be advanced or retracted, in relation to the catheter. The orifice 981 may be adjusted to an appropriate position inside the aspiration lumen 965, or even slightly outside the aspiration lumen 965. This can be continued until all or at least a clinically significant portion of the thrombus 947 is aspirated. As described, in relation to certain ischemic conditions caused by the thrombus 947, including stroke, the user may run the fluid from the fluid source 679 through a cooling system, such as a heat exchanger or thermoelectric cooler 951 (FIG. 48) through which the tubing set 664 may run, and by which the fluid may be cooled. Additionally, an extracorporeal circuit 953 (as in FIG. 62) may be attached to the tubing set 664, so that blood removed from the patient (e.g., via a femoral artery, femoral vein, or jugular vein sheath 955) is added to the fluid form the fluid source 679, so that there is some oxygenated blood being injected into the space 949, some which may potentially feed downstream tissue. The cooled fluid (saline, blood, or saline plus blood) can additionally reduce the metabolic demands of the downstream tissue.

Figure 70:
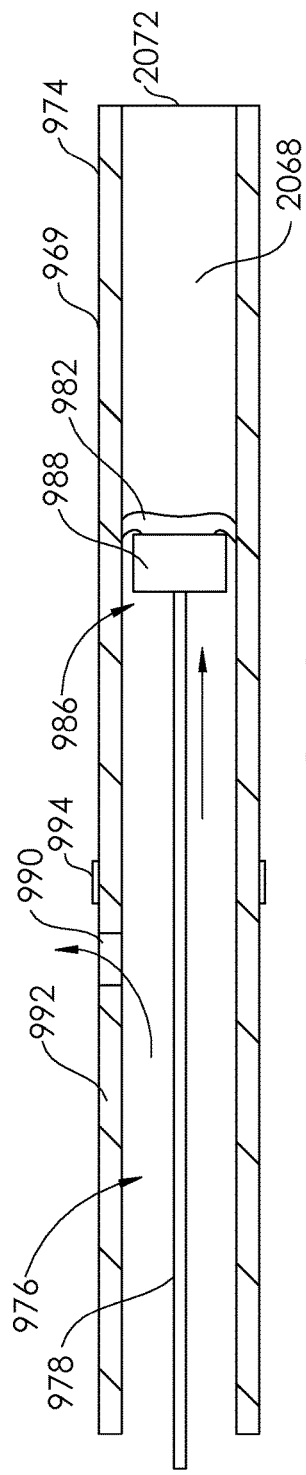
FIG. 70 is a sectional view of a translatable occluder of the aspiration system of FIGS. 66-69 in a first position, according to an embodiment of the present disclosure.
Figure 71:
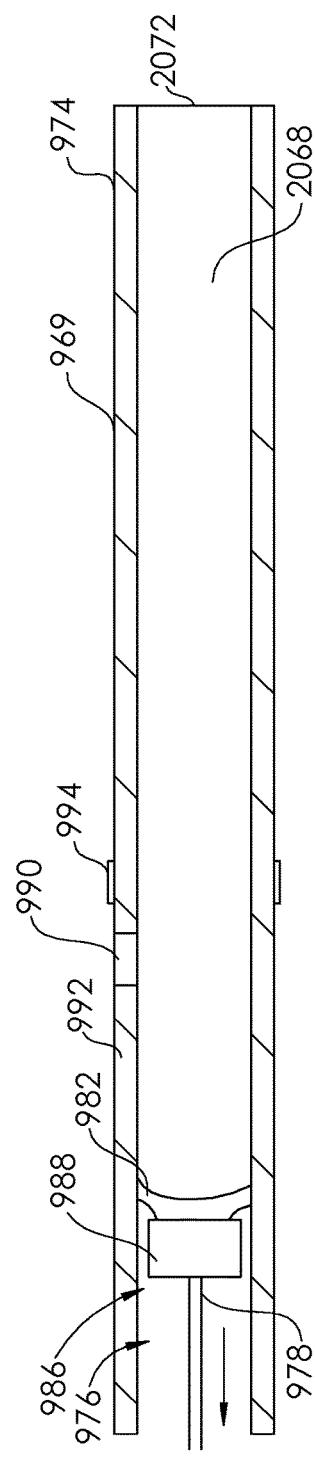
FIG. 71 is a sectional view of the translatable occluder of the aspiration system of FIGS. 66-69 in a second position.

FIGS. 66-69 illustrate a method for treating a patient using the aspiration system 600 of FIG. 48, but incorporating an aspiration catheter 967 having a translatable injection tube 969. The aspiration catheter 967 has an elongate shaft 995 having an aspiration lumen 997 with a proximal end 999 and an open distal end 2066. The translatable injection tube 969 has an injection lumen 2068 having a proximal end 2070 and a distal end 974. The distal end 974 has a distal orifice 2072, such that pressurized fluid injected through the injection lumen 2068 exits from the orifice 2072, as in FIG. 69. At a high enough injection pressure, the fluid may emanate in a jet. The pump 612 and the peristaltic pump 608 as described in FIG. 48 can be utilized. Turning to FIG. 68 and FIG. 70, an occluder 976 comprising an elongate shaft 978, and a handle 980 at its proximal end 984, has an elastomeric occlusion element 982 coupled to its distal end 986 by a connection member 988. The occlusion element 982 may comprise a circular ring or a spheroid or ovoid, and be formed of any elastomeric material, such as silicone, or thermoplastic elastomers. The occlusion element 982 has a diameter that is slightly larger than the diameter of the injection lumen 2068, and is configured to significantly occlude flow distally to its particular longitudinal position within the injection lumen 2068. The position shown in FIG. 70 shows the occlusion element 982 occluding the injection lumen 2068 at a longitudinal position that is distal to a side orifice 990 in the wall 992 in the injection tube 969. Thus, when the occluder 976 is in the position shown in FIGS. 68 and 70, the orifice 2072 is blocked by the occlusion element 982, and pressurized fluid flows through the side orifice 990 (curved arrow, FIG. 70). The connection member 988 may comprise a radiopaque material. A radiopaque marker 994 attached to the injection tube 969 may be viewed on x-ray or fluoroscopy along with the radiopaque connection member 988 to assess the particular relative longitudinal position of the occlusion element 982 with respect to the side orifice 990. If desired, the radiopaque marker 994 may be located just proximal to the side orifice 990, though it is shown just distal to the side orifice 990 in FIG. 70. If the occlusion element 982 is retracted as shown in FIG. 71, and the occluder 976 removed, as shown in FIG. 69, injection of fluid through the injection lumen 2068 may exit the orifice 2072. The size of the side orifice 990 may be made small enough such that, when the occluder 976 is removed, most of the fluid injected exits the orifice 2072, due to the fact that there is more resistance through the side orifice 990 than through the orifice 2072. Thus, with the injection tube 969 in a particular longitudinal position in relation the shaft 995, either injection through the orifice 2072 and into the space 949, or injection through the side orifice 990 and into the aspiration lumen 997 of the aspiration catheter 967 may be selected, using the occluder 976.

Figure 72:
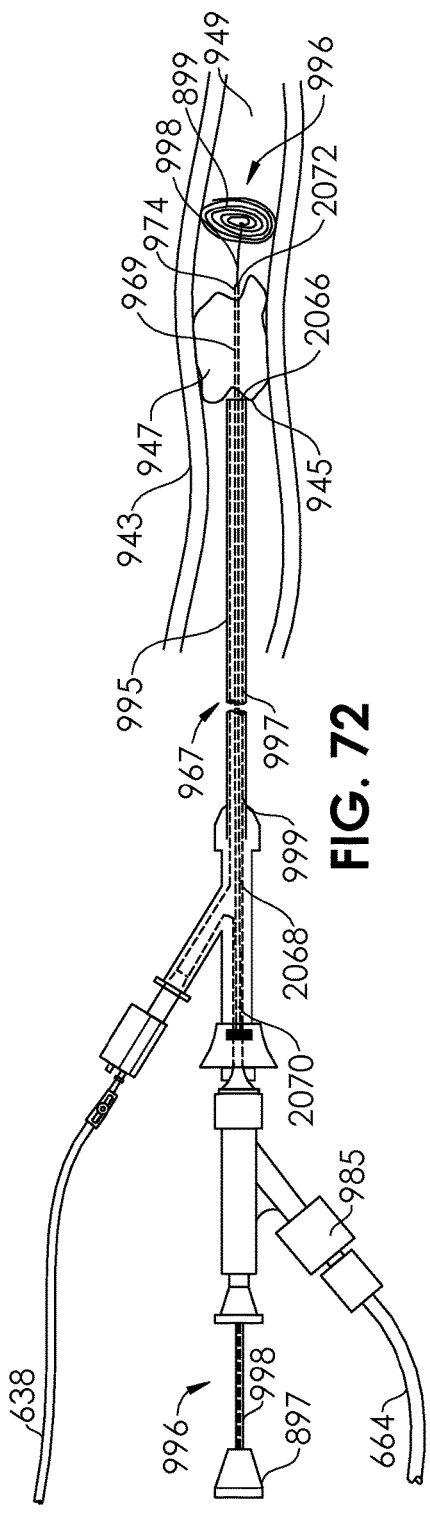
FIG. 72 illustrates an optional blocking step in the method of FIGS. 66-69, according to an embodiment of the present disclosure.

FIG. 72 illustrates an additional or alternative embodiment and step, that may be used in conjunction with the systems and steps of FIGS. 66-69. A blocking member 996 includes an elongate shaft 998, which may be a larger diameter proximally and a smaller diameter distally. The blocking member 996 also includes a spiral blocking element (or feature) 899 at its distal end and a handle 897 at its proximal end. The blocking member 996 may be constructed of any of the or may include embodiments or features described in relation to blocking members described in the co-owned PCT Pub. No. PCT/US2018/029196 to Incuvate, LLC, filed Apr. 24, 2018 and published Nov. 1, 2018 as WO 2018/200566 A1, which is hereby incorporated by reference in its entirety for all purposes. The blocking element 899 is configured to be placed down the injection lumen 2068 and delivered out of the orifice 2072 and into the space 949, as shown in FIG. 72, to catch potential distal emboli, and protect downstream tissue (brain tissue, heart tissue, etc.). In some embodiments, the blocking element 899 may be attached to the distal end of the occluder 976, so that they are combined into a single component. Thus, the occluding described in relation to FIGS. 68-71 may occur along with the distal protection/blocking described in relation to FIG. 72.

Figure 73:
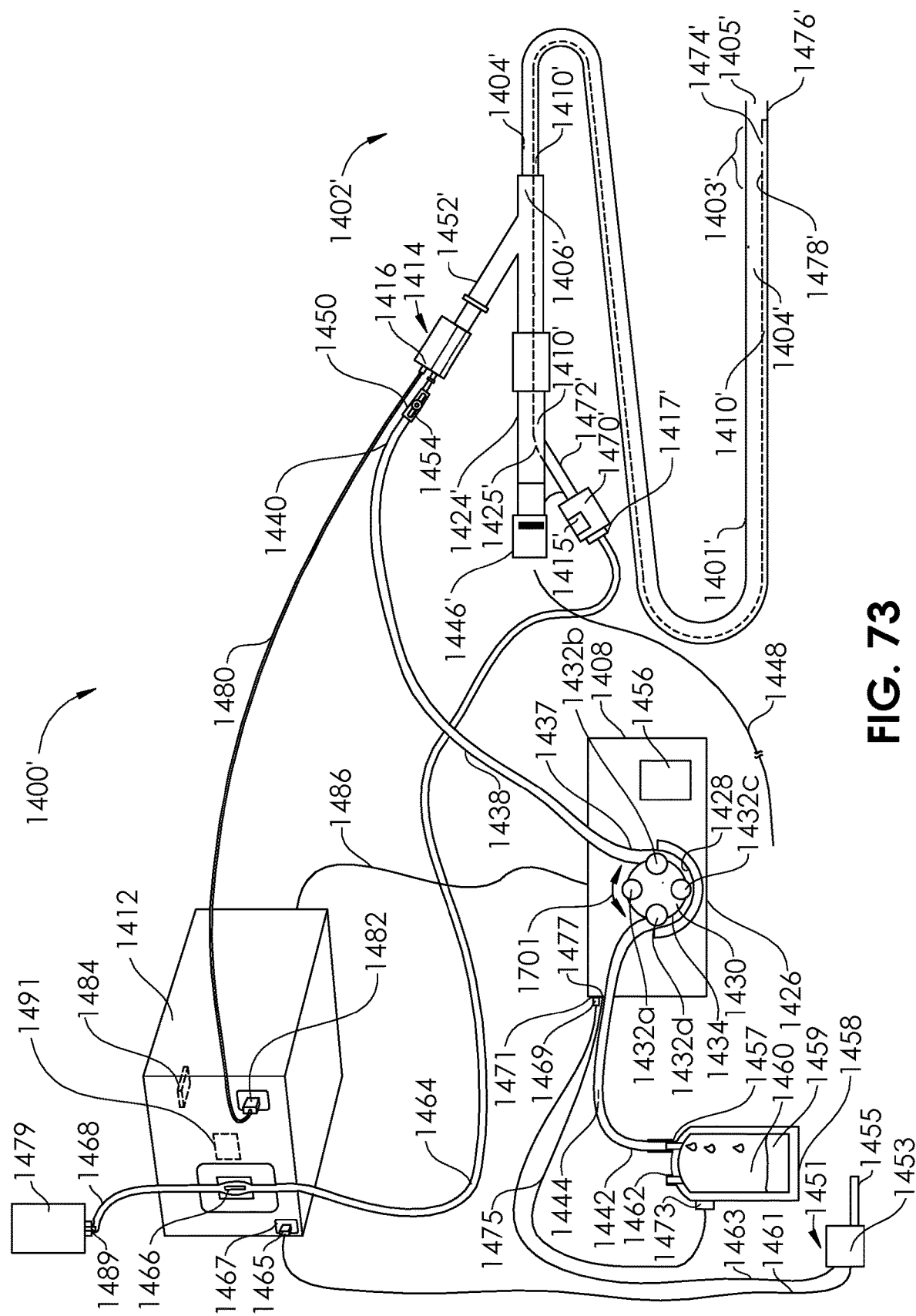
FIG. 73 is a perspective view of an aspiration system according to an embodiment of the present disclosure.

An alternative mode of using the aspiration system 1400' of FIG. 38 is shown in FIG. 73. The controller 1484 is programmed or programmable to command the peristaltic pump 1408 to operate bidirectionally, such that the rotatable head 1430 rotates in a back-and-forth manner, as shown in double-ended, curved arrow 1701. The back-and-forth rotation can create a "regurgitate" mode for thrombus that has been pulled into the aspiration lumen 1404' of the aspiration catheter 1402'. The controller 1484 may also be configured to shut down the pump 1412 while the peristaltic pump 1408 is in the "regurgitate" mode. The automatic cycling, by continual reversal of the motor, for example, allows the thrombus to be further macerated by the repetitive pulling and pushing cycles. The controller 1484 can be configured to perform a certain number of cycles and then to switch back to the aspiration direction (first rotational direction 1436 of FIG. 38) to fully remove the thrombus.

Using FIG. 36 as an example, but applying the description globally, in any of the embodiments described utilizing the peristaltic pump 1408, an alternative operation mode is possible, wherein the peristaltic pump 1408 may be run backwards (opposite of the first rotational direction 1436), so that it is causing at least some of the fluid within the extension tubing lumen 1444 and/or the aspiration lumen 1404 of the aspiration catheter 1402 to be injected out of the open distal end 1405 of the aspiration lumen 1404. For example, if the aspiration catheter 1402 is removed from the patient, material (thrombus, emboli, other clogged material) may be emptied out the open distal end 1405, prior to reusing the aspiration catheter 1402. In another use, with the aspiration catheter 1402 inside the vasculature, the proximal end 1442 of the extension tube 1438 may be placed into a container filled with contrast media or a lytic drug, or other drug, the peristaltic pump 1408 may then be run backwards to inject the contrast media, or drug into the vasculature of the patient. Thus, an additional injection site or the detaching of a luer connection is not required.

In another alternative operation mode, the peristaltic pump 1408 is stopped, or caused to be stopped by the controller 1484, and a lytic drug is used as the fluid source 1479. The pump 1412 is then used for pulsing lytic into the patient's vasculature (e.g., at or near a thrombus) through the open distal end 1405 of the aspiration lumen 1404, via the high pressure injection lumen 1410 of the tube 1478. By shutting off the peristaltic pump 1408, the injection through the injection lumen 1410 (and out the orifice 1474) allows the lytic drug to be sent out the open distal end 1405, into the vasculature of the patient.

Any of the aspiration systems 1400, 1400', 1400", 400, 600, 2100 utilizing the peristaltic pump 1408, 408, 608, 2102/2108 or the centrifugal pump 1409 together with an aspiration catheter 1402, 1402', 402, 602 having both an aspiration lumen and an injection lumen can alternatively also be used with an aspiration catheter 202 having an aspiration lumen 204 and no injection lumen, or with an aspiration catheter 1402, 1402', 402, 602 without injecting through the injection lumen. The peristaltic pump 1408, 408, 608, 2102/2108 or the centrifugal pump 1409 alone can be used for the aspiration of thrombus.

Using any of the aspiration systems described herein, a distal blood pressure may be measured in a diseased coronary artery, peripheral artery, or other artery by the open distal end of the aspiration lumen 1404 of the aspiration catheter 1402, with the pumps 1408, 1412 turned off or uncoupled, in order to determine a value for Fractional Flow Reserve (FFR), as disclosed in U.S. Pat. No. 6,565,514, Method and System for Determining Physiological Variables, to Svanerudh et al., which is incorporated herein by reference in its entirety for all purposes. The pressure sensor 1416 may be used to measure the pressure in the aspiration lumen 1404. For example, in a first step, the user assures that the pump 1412 is not actively pumping saline through the injection lumen 1410 and assures that the peristaltic pump 1408 is not actively aspirating through the aspiration lumen 1404. In a second step, the user places the open distal end 1405 of the aspiration lumen 1404 distal to an atherosclerotic lesion, stenosis, or partial blockage of interest in an artery, or a partial blockage or stenosis caused significantly by thrombus, or by a combination of atherosclerosis and thrombus. The user then in a third step measures a pressure at the open distal end 1405 of the aspiration lumen 1404 using the aspiration monitoring system 1414 while also measuring a pressure proximal to the lesion, for example, with a pressure transducer coupled to a guiding catheter. In a fourth step, the user obtains or calculates the Fractional Flow Reserve (FFR), to help determine the significance of the stenosis of partial blockage.

While the foregoing is directed to embodiments of the present disclosure, other and further embodiments may be devised without departing from the basic scope thereof.

The ranges disclosed herein also encompass any and all overlap, sub-ranges, and combinations thereof. Language such as "up to," "at least," "greater than," "less than,"

"between," and the like includes the number recited. Numbers preceded by a term such as "approximately", "about", and "substantially" as used herein include the recited numbers (e.g., about 10%=10%), and also represent an amount close to the stated amount that still performs a desired function or achieves a desired result. For example, the terms "approximately", "about", and "substantially" may refer to an amount that is within less than 10% of, within less than 5% of, within less than 1% of, within less than 0.1% of, and within less than 0.01% of the stated amount.

What is claimed is:

1. A system for catheter-based aspiration, comprising:
an aspiration catheter comprising an elongate shaft configured for placement within a blood vessel of a subject, the shaft comprising an aspiration lumen having a proximal end and an open distal end;
an extension tube having a distal end and a proximal end and a lumen extending therebetween, the distal end of the lumen of the extension tube configured to be hydraulically coupled to the aspiration lumen of the aspiration catheter at or adjacent the proximal end of the aspiration lumen of the aspiration catheter;
a peristaltic pump configured for driving fluid through the extension tube and comprising a pump base having a pressure shoe, and a rotatable head, the rotatable head including two or more compression elements arrayed therearound;
a compressible tubular portion disposed between the distal end and the proximal end of the extension tube, the compressible tubular portion configured to be coupled to the pressure shoe and the rotatable head of the peristaltic pump, such that operation of the peristaltic pump causes the rotatable head to rotate such that the two or more compression elements drive fluid from the aspiration lumen of the aspiration catheter through the extension tube from the distal end of the extension tube to the proximal end of the extension tube;
a first sensor configured to sense a location between the peristaltic pump and the open distal end of the aspiration lumen when the compressible tubular portion is coupled to the pressure shoe and the rotatable head of the peristaltic pump, such that the first sensor directly measures a characteristic of flow through at least one of the aspiration lumen or the lumen of the extension tube, wherein the characteristic of flow comprises at least one of a pressure, a flow rate, or a flow velocity; and
a controller configured to receive a first signal from the first sensor and configured to vary the operation of the peristaltic pump based at least in part on the first signal received from the first sensor related to a change in the characteristic of flow.

2. The system of claim 1, wherein the controller is configured to vary rotation speed of the rotatable head of the peristaltic pump based at least in part on the first signal received from the first sensor related to a change in the characteristic of flow.

3. The system of claim 1, wherein the controller is configured to stop rotation of the rotatable head of the peristaltic pump based at least in part on the first signal received from the first sensor related to a change in the characteristic of flow.

4. The system of claim 3, wherein the controller is configured to stop rotation of the rotatable head of the peristaltic pump such that a first compression element of the two or more compression elements occludes the extension tube at the compressible tubular portion.

5. The system of claim 1, wherein the two or more compression elements comprise two or more rollers.

6. The system of claim 1, wherein the first sensor comprises a pressure transducer.

7. The system of claim 1, wherein the first sensor comprises an ultrasound sensor.

8. The system of claim 7, wherein the controller is configured to count the number of times during a predetermined time period that a signal output by the ultrasound sensor surpasses a predetermined threshold amplitude.

9. The system of claim 8, wherein the controller is further configured to determine whether the number of times during the predetermined time period is less than, or less than or equal to, a predetermined value, or greater than, or greater than or equal to, the predetermined value.

10. The system of claim 9, further comprising a communication device coupled to the controller and configured to be in a first communication mode if the number of times during the predetermined time period is less than or less than or equal to the predetermined value and to be in a second communication mode if the number of times during the predetermined time period is greater than or greater than or equal to the predetermined value.

11. The system of claim 1, further comprising a collection receptacle having an interior, wherein the proximal end of the extension tube is configured to deliver the fluid into the interior of the collection receptacle.

12. The system of claim 11, further comprising a level sensor coupled to the collection receptacle and configured to send a signal to the controller when a predetermined fluid height or fluid volume is reached.

13. The system of claim 12, wherein the controller is configured to stop rotation of the rotatable head of the peristaltic pump based at least in part on the signal from the level sensor.

14. The system of claim 1, further comprising a return conduit hydraulically coupled to the extension tube and configured to return to a vasculature of the subject, fluid that has passed through the extension tube from the distal end to the proximal end.

15. The system of claim 14, further comprising a filter disposed between the extension tube and the return conduit.

16. The system of claim 1, wherein the aspiration catheter further comprises an injection lumen extending within the aspiration lumen and having a distal end and a proximal end, and an orifice at or near the distal end of the injection lumen, the orifice configured to create one or more jets into the aspiration lumen when pressurized fluid is injected through the injection lumen.

17. The system of claim 16, further comprising an injection pump configured to pressurize fluid through the injection lumen, wherein the controller is configured to cause the injection pump to inject in a pulsatile manner.

18. The system of claim 16, further comprising an injection pump configured to pressurize fluid through the injection lumen, wherein the controller is configured to control a time interval between initiation of operation of the peristaltic pump and initiation of operation of the injection pump.

19. The system of claim 18, wherein the controller is configured to initiate the operation of the peristaltic pump and the injection pump at substantially the same time.

20. The system of claim 16, further comprising an injection pump configured to pressurize fluid through the injection lumen, wherein the controller is configured to control a time interval between stoppage of operation of the peristaltic pump and stoppage of operation of the injection pump.

21. The system of claim 20, wherein the controller is configured to stop operation of the peristaltic pump and the injection pump at substantially the same time.

22. The system of claim 16, further comprising an injection pump configured to pressurize fluid through the injection lumen, wherein the controller is further configured to vary the operation of the injection pump based at least in part on the first signal received from the first sensor related to a change in the characteristic of flow.

23. The system of claim 16, further comprising an injection pump configured to pressurize fluid through the injection lumen, and further comprising a second sensor coupled to the controller, the controller configured to receive a second signal from the second sensor, wherein the second sensor is configured to sense the presence of air within the pressurized fluid injected through the injection lumen.

24. The system of claim 23, wherein the controller is configured to stop operation of the injection pump based at least in part on changes in the second signal received from the second sensor.

25. The system of claim 23, wherein the second sensor comprises a pressure transducer.

26. The system of claim 23, wherein the second sensor comprises an optical sensor.

27. The system of claim 23, wherein the second sensor is configured to measure electrical current driving the injection pump.

28. The system of claim 16, further comprising an injection pump configured to pressurize fluid through the injection lumen, and further comprising a foot pedal configured to cause the controller to initiate the operation of the peristaltic pump and the injection pump at substantially the same time.

29. The system of claim 1, wherein the proximal end of the extension tube includes a plurality of sideholes.

30. The system of claim 1, further comprising a foot pedal configured to signal the controller to vary the operation of the peristaltic pump.

* * * * *

UNITED STATES PATENT AND TRADEMARK OFFICE
CERTIFICATE OF CORRECTION

| | |
|---|---|
| PATENT NO. | : 10,716,880 B2 |
| APPLICATION NO. | : 16/440955 |
| DATED | : July 21, 2020 |
| INVENTOR(S) | : Bradley S. Culbert et al. |

It is certified that error appears in the above-identified patent and that said Letters Patent is hereby corrected as shown below:

On the Title Page

Column 2, Item (56): replace:
"DE 3387858 C2 9/1986"
With:
-- DE 3338758 C2 9/1986 --

Signed and Sealed this
Third Day of September, 2024

Katherine Kelly Vidal
*Director of the United States Patent and Trademark Office*